(12) United States Patent
Zhang et al.

(10) Patent No.: US 11,905,284 B2
(45) Date of Patent: Feb. 20, 2024

(54) 5,7-DIHYDRO-PYRROLO-PYRIDINE DERIVATIVES

(71) Applicant: PFIZER INC., New York, NY (US)

(72) Inventors: Lei Zhang, Auburndale, MA (US); Christopher Ryan Butler, Canton, MA (US); Elizabeth Mary Beck, Oxford (GB); Michael Aaron Brodney, Newton, MA (US); Matthew Frank Brown, Stonington, CT (US); Laura Ann McAllister, Arlington, MA (US); Erik Alphie LaChapelle, Uncasville, CT (US); Adam Matthew Gilbert, Guilford, CT (US)

(73) Assignee: PFIZER INC., New York, NY (US)

(*) Notice: Subject to any disclaimer, the term of this patent is extended or adjusted under 35 U.S.C. 154(b) by 0 days.

(21) Appl. No.: 17/335,666

(22) Filed: Jun. 1, 2021

(65) Prior Publication Data
US 2021/0309659 A1 Oct. 7, 2021

Related U.S. Application Data

(60) Continuation of application No. 16/797,966, filed on Feb. 21, 2020, now abandoned, which is a division of application No. 15/637,071, filed on Jun. 29, 2017, now Pat. No. 10,604,519.

(60) Provisional application No. 62/372,421, filed on Aug. 9, 2016, provisional application No. 62/357,624, filed on Jul. 1, 2016.

(51) Int. Cl.
| | |
|---|---|
| C07D 471/04 | (2006.01) |
| A61P 25/00 | (2006.01) |
| A61P 25/16 | (2006.01) |
| A61P 25/18 | (2006.01) |
| A61P 25/28 | (2006.01) |
| A61K 31/437 | (2006.01) |

(52) U.S. Cl.
CPC .......... *C07D 471/04* (2013.01); *A61K 31/437* (2013.01); *A61P 25/00* (2018.01); *A61P 25/16* (2018.01); *A61P 25/18* (2018.01); *A61P 25/28* (2018.01)

(58) Field of Classification Search
CPC .................................................. C07D 471/04
See application file for complete search history.

(56) References Cited

U.S. PATENT DOCUMENTS

2012/0122842 A1  5/2012  Curtin

FOREIGN PATENT DOCUMENTS

| CN | 1869036 A | 11/2006 |
|---|---|---|
| WO | WO2012067965 | 5/2012 |
| WO | WO2012138845 | 10/2012 |
| WO | WO2012149540 | 11/2012 |
| WO | WO2013074388 | 5/2013 |
| WO | WO2013083591 | 6/2013 |
| WO | WO2013083741 | 6/2013 |
| WO | WO2013126856 | 8/2013 |
| WO | WO2015027204 | 2/2015 |
| WO | 2015118342 A1 | 8/2015 |

OTHER PUBLICATIONS

Staskin, "Pharmacologic Management of Overactive Bladder: Practical Options for the Primary Care Physician" The American Journal of Medicine (2006) vol. 119 (3A), 24S-28S.*
Ono "Therapeutic effect of cevimeline on dry eye in patients with Sjogren's syndrome: a randomized, double-blind clinical study" American Journal of Ophthalmology (2004), 138(1), 6-17.*
Lahoti "A prospective, double-blind trial of L-hyoscyamine versus glucagon for the inhibition of small intestinal motility during ERCP" Gastrointestinal endoscopy (1997), 46(2), 139-42.*
Prat Journal of Medicinal Chemistry (2009), 52(16), 5076-5092.*
Montuschi, Inhaled muscarinic acetylcholine receptor antagonists for treatment of COPD Current Medicinal Chemistry (2013), 20(12), 1464-1476.*
Pera "Tiotropium inhibits pulmonary inflammation and remodelling in a guinea pig model of COPD" European Respiratory Journal 2011, 38(4), 789-796.*
Adam et al., "Symptomatic treatment of Huntington disease," Journal of the American Society for Experimental Neurotherapeutics, 5(2):181-197 (2008).
Brady et al., "Centrally active allosteric potentiators of the M4 muscarinic acetylcholine receptor reverse amphetamine-induced hyperlocomotor activity in rats," Journal of Pharmacology and Experimental Therapeutics, 327(3):941-953 (2008).
Carruthers et al., "The muscarinic system, cognition and schizophrenia," Neuroscience and Biobehavioral Reviews, 55:393-402 (2015).
Church et al., "Poststreptoccal movement disorders," Neuroimmunology in Clinical Practice, Eds. Bernadette Kalman and Thomas Brannagan, III, Blackwell, Chapter 21:240-250 (2008).

(Continued)

*Primary Examiner* — David K O'Dell
(74) *Attorney, Agent, or Firm* — HALEY GUILIANO LLP; James F. Haley, Jr.; Jacob E. Dander

(57) ABSTRACT

The present invention provides, in part, compounds of Formula I:

I

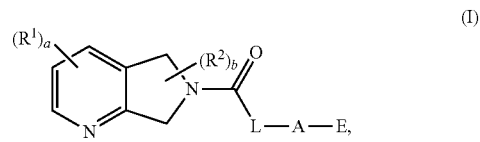

(I)

or an N-oxide thereof, or a pharmaceutically acceptable salt of the compound or the N-oxide, wherein: $R^1$, $R^2$, L, A, and E are as described herein; processes for the preparation of; intermediates used in the preparation of; and compositions containing such compounds, N-oxides, or salts, and their uses for treating M4-mediated (or M4-associated) disorders including, e.g., Alzheimer's Disease, schizophrenia (e.g., its cognitive and negative symptoms), pain, addiction, and a sleep disorder.

18 Claims, No Drawings

(56) References Cited

OTHER PUBLICATIONS

Conn et al., "Activation of metabotropic glutamate receptors as a novel approach for the treatment of schizophrenia," Trends in Pharmacological Sciences, 30(1):25-31 (2008).
Costigan et al., "Neuropathic pain: a maladaptive response ofthe nervous system to damage," Annual Review of Neuroscience, 32:1-32 (2009).
Cowie, "Sleep apnea: State of the art," Trends in Cardiovascular Medicine, 27:280-289 (2017).
Dall et al., "Muscarinic receptor M4 positive allosteric modulators attenuate central effects of cocaine," Drug and Alcohol Dependence, 176:154-161 (2017) (21 pages).
De Godoy et al., "Treatment of upper airway resistance syndrome in adults: Where do we stand?," Sleep Science, 8(1):42-28 (2015).
Etscheid et al., "N-Ethylmaleimide differentiates between the M 2- and M 4-autoreceptor-mediated inhibition of acetylcholine release in the mouse brain," Naunyn-Schmiedeberg's Archives of Pharmacology, 391(11):1295-1299 (2018).
Filippini et al., "Distinct patterns of brain activity in young carriers of the APOE-є4 allele," PNAS, 106(17):7209-7214 (2009).
Fodstad et al., Intractable singultus: a diagnostic and therapeutic challenge, British Journal of Neurosurgery, 7:255-262 (1993).
Foster et al., "Antipsychotic-like Effects of M4 Positive Allosteric Modulators Are Mediated by CB2 Receptor-Dependent Inhibition of Dopamine Release," Neuron, 91(6):1244-1252 (2016).
Hook, "Neuroproteases in peptide neurotransmission and neurodegenerative diseases: applications to drug discovery research," Biodrugs, 20(2):105-119 (2006).
Le Bars et al., "Animal models of nociception," Pharmacological Reviews, 53(4):597-652 (2001).
Lutz, "Mouse models of ALS: Past, present and future," Brian Research, 1693:1-10 (2018).
Makrilakis, "Pathophyisology of Type 2 Diabetes," Diabetes in Clinical Practice, 3:43-58 (2006) (16 pages).
Marcotte et al., "Animal models of schizophrenia: a critical review," Journal of Psychiatry Neuroscience, 26(5):395-410 (2001).
Mason, "Drug therapy for obstructive sleep apnoea in adults (Review)," Cochrane Database of Systemic Reviews, Issue 5, Art. No. CD003002 (2013) (106 pages).
Naumann et al., "Narcolepsy: pathophysiology and neuropsychological changes," Behavioural Neurology, 14:89-98 (2003).
PCT International Search Report and Written Opinion for International Patent Application No. PCT/IB2017/053565, dated Sep. 13, 2017 (18 pages).
Petrov et al., "ALS Clinical Trials Review: 20 Years of Failure. Are We Any Closer to Registeringa New Treatment?," Fontiers in Aging Neuroscience, 9:1-11 (2017).
Pochampally et al., "Design, novel synthesis and docking studies of N,N'-substituted urea analogues and evaluation of their antimicrobial activity", World Journal of Pharmacy and Pharmaceutical Sciences, 3(4):1494-1519 (2014).
Quiroz et al., "Hippocampal hyperactivation in presymptomatic familial Alzheimer's disease," Annals of Neurology, 68(6):865-875 (2010).
Reid et al., "Epilepsy, energy deficiency and new therapeutic approaches including diet," Pharmacology and Therapeutics, 144(2):192-201 (2014).
Scarr, "Muscarinic receptors: their roles in disorders of the central nervous system and potential as therapeutic targets," CNS Neuroscience and Therapeutics, 18(5):369-379 (2012).
The Van Nostrand Chemist's Dictionary, entry for "aryl", p. 44 (1953).
Touitou et al., "Promoting adjustment of the sleep-wake cycle by chronobiotics," Physiology and Behavior, 90(2-3):294-300 (2007).
Walker et al., "Acetylcholine Muscarinic M4 Receptors as a Therapeutic Target for Alcohol Use Disorder: Converging Evidence From Humans and Rodents," Biological Psychiatry, 88(12):898-909 (2020).
Yang et al., "Discovery of Selective M4 Muscarinic Acetylcholine Receptor Agonists with Novel Carbamate Isosteres," ACS Medicinal Chemistry Letters, 10:941-948 (2019).
Zhu et al., "Allosteric modulation of ß-cell M3 muscarinic acetylcholine receptors greatly improves glucose homeostasis in lean and obese mice," PNAS, 116(37):18684-18690 (2019).
Zlotos et al., "Muscarinic Receptor Agonists and Antagonists", Expert Opinion on Therapeutic Patents, 9(8):1029-1053 (1999).
Cookson et al., "A new cholinergic mechanism for antipsychotics: emraclidine and M4 muscarinic receptors," Lancet, 400(10369):p. 2159-2161 (2022).
Krystal et al., "Emraclidine, a novel positive allosteric modulator of cholinergic M4 receptors, for the treatment of schizophrenia: a two-part, randomised, double-blind, placebo-controlled, phase 1b trial," Lancet, 400(10369):2210-2020 (2022).

* cited by examiner

5,7-DIHYDRO-PYRROLO-PYRIDINE DERIVATIVES

CROSS-REFERENCE TO RELATED APPLICATIONS

This application is a continuation of U.S. patent application Ser. No. 16/797,966, filed Feb. 21, 2020, which is a division of U.S. patent application Ser. No. 15/637,071, filed Jun. 29, 2017, now U.S. Pat. No. 10,604,519, which claims the benefit of U.S. Provisional Patent Application No. 62/372,421, filed on Aug. 9, 2016, and U.S. Provisional Patent Application No. 62/357,624, filed on Jul. 1, 2016, the disclosures of each of which are hereby incorporated by reference in their entireties.

FIELD OF THE INVENTION

The present invention generally relates to novel 5,7-dihydro-pyrrolo-pyridine derivatives, which are activators of the muscarinic M4 receptor, salts thereof, pharmaceutical compositions thereof, and uses thereof in the treatment of M4-mediated diseases and disorders such as Schizophrenia, Alzheimer's Disease, Dementia with Lewy Bodies, Parkinson's Disease and related memory and executive dysfunction, agitation, and psychosis associated therewith.

BACKGROUND OF THE INVENTION

Patients with Schizophrenia, Alzheimer's Disease, Parkinson's Disease, Huntington's Disease, depression and various other neurological/neurodegenerative diseases frequently suffer from behavioral and cognitive impairments resulting in debilitating disruption to their daily lives. Over the years many pharmacological treatments have been discovered that provide some improvement in behavior and cognitive function. However, the improvement is modest at best, and as is often the case, the underlying dose-limiting adverse effects associated with these treatments, including extrapyramidal and metabolic side-effects, lead to partial responsiveness, and non-compliance.

In an effort to discover new and improved pharmacological treatments, researchers began to look at the muscarinic acetylcholine receptor (mAChR) as a viable mechanism. There are five mAChRs subtypes (M1-M5) that have been identified and are part of the G protein-coupled receptor (GPCR) superfamily. These subtypes are distributed widely throughout the periphery and the central nervous system, with the M1 and M4 subtypes being predominantly expressed in the CNS.

Researchers have since focused on identifying subtype selective M4 muscarinic acetylcholine receptor activators. For example, positive allosteric modulators (PAMs) of the M4 muscarinic acetylcholine receptor have gained attention as a further method of treating the behavioral impairments associated with schizophrenia and other neuropsychiatric disorders, e.g., Alzheimer's Disease. [See: Bubser, Michael, et al., "Selective Activation of M4 Muscarinic Acetylcholine Receptors reverses MK-801-Induced Behavioral Impairments and Enhances Associative Learning in Rodents", American Chemical Society, Chemical Neuroscience (2014); and Bynum, Nellie E., et al., "Antipsychotic Drug-Like Effects of the Selective M4 Muscarinic Acetylcholine Receptor Positive Allosteric Modulator VU0152100", Neuropsychopharmacology (2014) 1-16]. While the etiology of schizophrenia is unclear, it is believed that an imbalance in the dopaminergic system plays a major role. mAChR receptors are known for their regulation of dopamine levels in critical regions of the brain involved with psychosis, with M4 being the primary subtype for dopamine regulation. (See: Chan, W. Y., et al., "Allosteric Modulation of the Muscarinic M4 receptor as an Approach to Treating Schizophrenia", PNAS, August 2008, Vol. 105 No. 31 p. 10978; and Byun, Nellie, et al., "Antipsychotic Drug-Like Effects of the Selective M4 Muscarinic Acetylcholine Receptor Positive Allosteric Modulator VU0152100", Neuropsychopharmacology (2014) 1-16). Another hypothesis for M4 in schizophrenia is its ability to affect hippocampal circuitry (Shirley, Jana K., et al., An allosteric potentiator of M4 mAChR modulates hippocampal synaptic transmission", Nature Chemical Biology, Vol. 4, No. 1, January 2008; and Dasari, Sameera, et. al., "M1 and M4 Receptors Modulate Hippocampal Pyramidal Neurons", J. Neurophysiology 105: 779-792, 2011) through modulation of the hippocampal trisynaptic pathway which has been reported to be disregulated in Schizophrenic (Tamminga, Carol A., et. al., "Glutamate Dysfunction in Hippocampus: Relevance of Dentate Gyrus and CA3 Signaling", Schizophrenia Bulletin Vol. 38, no. 5, pp. 927-935, 2012), Alzheimer's Disease (Quiroz et al 2010 Ann Neurol, Filipini et al 2009 PNAS) and aMCI patients (Bakker, A., et. al., "Response of the medial temporal lobe network in amnestic mild cognitive impairment to therapeutic intervention assessed by fMRI and memory task performance", Neuromalge: Clinical 7 (2015) 688-698). Hyperactivity in the hippocampal trisynaptic pathway has been proposed as a likely cause for psychosis in schizophrenics (Tamminga, et al.).

Vanderbilt University has published several International Patent Applications directed to positive allosteric modulators (PAMs) of the muscarinic M4 acetylcholine receptor some of which include: WO2013/126856A1 (substituted 5-aminothieno[2,3-C]pyridazine-6-carboxamide analogs); WO2014/035829A1 (substituted 3-aminothieno[2,3-C]pyridine-2-carboxaminde analogs); WO2015/027204A1 (substituted thieno[2,3-B]pyridine-2-carboxamide analogs); and WO2015/027214 (substituted thieno[2,3-C]pyridazine-6-carboxamide analogs).

WO2006/047124A1 (Lilly) discloses thienopyridines as allosteric potentiators of the M4 muscarinic receptor.

New or improved activators, including positive allosteric modulators, of the muscarinic M4 receptors are needed for providing new and improved therapies to treat M4-mediated diseases and disorders such as Schizophrenia, Alzheimer's Disease and others described herein.

SUMMARY OF THE INVENTION

The present invention provides, in part, a compound of Formula I:

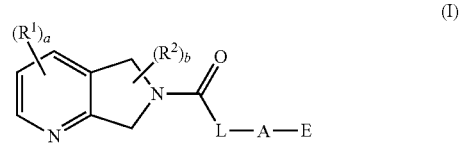

(I)

or an N-oxide thereof, or a pharmaceutically acceptable salt of the compound or the N-oxide, wherein:
  each $R^1$, when present, is independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-

$C_6$)alkynyl, optionally substituted ($C_1$-$C_6$)alkylthio, optionally substituted ($C_1$-$C_6$)alkoxy, optionally substituted ($C_3$-$C_6$)cycloalkyl, optionally substituted —O—($C_3$-$C_6$)cycloalkyl, —N($R^3$)($R^4$), —N($R^3$)(C(=O)($R^4$), —C(=O)N($R^3$)($R^4$), —O—C(=O)—N($R^3$)($R^4$), —C(=O)—$R^3$, and —C(=O)—$OR^3$;

a is an integer selected from 0, 1, 2, and 3;

each $R^2$, when present, is independently selected from the group consisting of hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkylthio, optionally substituted ($C_1$-$C_6$)alkoxy, —N($R^3$)($R^4$), —N($R^3$)(C(=O)($R^4$), —C(=O)N($R^3$)($R^4$), —O—C(=O)—N($R^3$)($R^4$), —C(=O)—$R^3$, and —C(=O)—$OR^3$;

b is an integer selected from 0, 1, 2, 3, and 4;

L is selected from —$(CH_2)_m$—, —O—, and —NH—, wherein m is an integer selected from 1 and 2;

A is absent or selected from the group consisting of ($C_3$-$C_6$)cycloalkyl and (4- to 10-membered)heterocycloalkyl, wherein said cycloalkyl and heterocycloalkyl are each optionally substituted with one to five substituents independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkylthio, optionally substituted ($C_1$-$C_6$)alkoxy, —N($R^3$)($R^4$), —N($R^3$)(C(=O)($R^4$), —C(=O)N($R^3$)($R^4$), —O—C(=O)—N($R^3$)($R^4$), —C(=O)—$R^3$, and —C(=O)—$OR^3$;

E is selected from ($C_3$-$C_{12}$)cycloalkyl, ($C_6$-$C_{10}$)aryl and (5- to 10-membered)heteroaryl, wherein said cycloalkyl, aryl, and heteroaryl are optionally substituted with one to five substituents independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkylthio, optionally substituted ($C_1$-$C_6$)alkoxy, optionally substituted ($C_3$-$C_6$)cycloalkyl, methyloxetanyl, —N($R^3$)($R^4$), —N($R^3$)(C(=O)$R^4$), —C(=O)N($R^3$)($R^4$), —O—C(=O)—N($R^3$)($R^4$), —C(=O)—$R^3$, and —C(=O)—$OR^3$; and $R^3$ and $R^4$ at each occurrence are each independently selected from hydrogen and optionally substituted ($C_1$-$C_6$)alkyl; or $R^3$ and $R^4$ taken together with the nitrogen to which they are attached form an optionally substituted (4- to 6-membered)heterocycloalkyl.

In some embodiments, the invention also provides one or more of the compounds or an N-oxide thereof, or a pharmaceutically acceptable salt of the compound or the N-oxide, described in Examples 1-78.

The compounds of Formula I are useful for treating or preventing M4-mediated diseases and/or disorders such as Schizophrenia, Alzheimer's Disease, Dementia with Lewy Bodies, Parkinson's disease and related memory and executive dysfunction, agitation, and behavioral and cognitive impairment associated with the above, as well as pain, trauma, cardiologic, thrombotic, metabolic, autoimmune and inflammatory diseases or disorders, and disorders associated with enhanced endothelial activity/impaired endothelial barrier function.

The present invention is also directed to the use of the compounds described herein, or an N-oxide thereof, or a pharmaceutically acceptable salt of the compound or the N-oxide, in the preparation of a medicament for the treatment or prevention of a condition amenable to activation (e.g., modulation of the allosteric binding site) of the M4 muscarinic acetylcholine receptor (mAChR).

The present invention is also directed to pharmaceutically acceptable formulations containing an admixture of a compound(s) of the present invention or an N-oxide thereof, or a pharmaceutically acceptable salt of the compound or the N-oxide, and at least one excipient formulated into a pharmaceutical dosage form. Examples of such dosage forms include tablets, capsules, suppositories, gels, creams, ointments, lotions, solutions/suspensions for injection (e.g., depot), aerosols for inhalation and solutions/suspensions for oral ingestion.

DETAILED DESCRIPTION OF THE INVENTION

The headings within this document are being utilized only to expedite its review by the reader. They should not be construed as limiting the invention or claims in any manner.

Definitions and Exemplifications

As used throughout this application, including the claims, the following terms have the meanings defined below, unless specifically indicated otherwise. The plural and singular should be treated as interchangeable, other than the indication of number:

As used herein, the term "activator(s) of the muscarinic M4 receptor" means the compounds of the present invention are: i) agonists, where the compound induces an effect on the M4 receptor absent the presence of a native ligand (e.g. acetylcholine); ii) a positive allosteric modulator (PAM), wherein the compound induces an effect on the receptor in the presence of a suboptimal concentration of native ligand; or iii) the compounds of the present invention possess both agonist and PAM activity.

As used herein, the term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl ring.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 10-membered heteroaryl group" is specifically intended to include any 5-, 6-, 7-, 8-, 9- or 10-membered heteroaryl group.

The term "($C_1$-$C_6$)alkyl", as used herein, refers to a saturated, branched- or straight-chain alkyl group containing from 1 to 6 carbon atoms, such as, but not limited to, methyl, ethyl, n-propyl, isopropyl, n-butyl, sec-butyl, isobutyl, tert-butyl, n-pentyl, isopentyl, neopentyl, and n-hexyl.

The term "optionally substituted ($C_1$-$C_6$)alkyl", as used herein, refers to a ($C_1$-$C_6$)alkyl as defined above, in which one or more hydrogen atoms are replaced by a substituent selected from the group consisting of halogen, oxo, cyano, hydroxy, —$SF_5$, nitro, —($C_1$-$C_6$)alkoxy, —N($R^3$)($R^4$), —N($R^3$)(C(=O)$R^4$), —N($R^3$)C(=O)—$OR^4$, —C(=O)—N($R^3$)($R^4$), —O—C(=O)—N($R^3$)($R^4$), —C(=O)—$R^3$, —C(=O)—$OR^3$, and optionally substituted ($C_3$-$C_8$)cycloalkyl, in which $R^3$ and $R^4$ are each independently selected from hydrogen and optionally substituted $(C_1-C_6)$alkyl. For example, a $(C_1-C_6)$alkyl moiety can be substituted with one or more halogen atoms to form a "halo$(C_1-C_6)$alkyl". Representative examples of a halo$(C_1-C_6)$alkyl include, but are not limited to, fluoromethyl, 2-fluoroethyl, difluoromethyl, trifluoromethyl, and pentafluoroethyl. Other examples of optionally substituted $(C_1-C_6)$alkyl include, but are not limited to, methanol and methoxymethyl.

The term "$(C_2-C_6)$alkenyl" refers to an aliphatic hydrocarbon having from 2 to 6 carbon atoms and having at least one carbon-carbon double bond, including straight chain or branched chain groups having at least one carbon-carbon double bond. Representative examples include, but are not limited to, ethenyl, 1-propenyl, 2-propenyl (allyl), isopropenyl, 2-methyl-1-propenyl, 1-butenyl, 2-butenyl, and the like. When the compounds of the invention contain a $(C_2-C_6)$alkenyl group, the compound may exist as the pure E (entgegen) form, the pure Z (zusammen) form, or any mixture thereof.

The term "optionally substituted $(C_2-C_6)$alkenyl" refers to a $(C_2-C_6)$alkenyl as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-C_6)$alkoxy, —$N(R^3)(R^4)$, —$N(R^3)(C(=O)R^4)$, —$N(R^3)C(=O)$—$OR^4$, —$C(=O)$—$N(R^3)(R^4)$, —O—$C(=O)$—$N(R^3)(R^4)$, —$C(=O)$—$R^3$, —$C(=O)$—$OR^3$, and optionally substituted $(C_3-C_8)$cycloalkyl, in which $R^3$ and $R^4$ are each independently selected from hydrogen and optionally substituted $(C_1-C_6)$alkyl.

The term "$(C_2-C_6)$alkynyl" refers to an aliphatic hydrocarbon having two to six carbon atoms and at least one carbon-carbon triple bond, including straight chains and branched chains having at least one carbon-carbon triple bond. Representative examples include, but are not limited to, ethynyl, propynyl, butynyl, pentynyl, and hexynyl.

The term "optionally substituted $(C_2-C_6)$alkynyl" refers to a $(C_2-C_6)$alkynyl as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-C_6)$alkoxy, —$N(R^3)(R^4)$, —$N(R^3)(C(=O)R^4)$, —$N(R^3)C(=O)$—$OR^4$, —$C(=O)$—$N(R^3)(R^4)$, —O—$C(=O)$—$N(R^3)(R^4)$, —$C(=O)$—$R^3$, —$C(=O)$—$OR^3$, and optionally substituted $(C_3-C_8)$cycloalkyl, in which $R^3$ and $R^4$ are each independently selected from hydrogen and optionally substituted $(C_1-C_6)$alkyl.

The term "$(C_1-C_6)$alkoxy" as used herein, refers to a $(C_1-C_6)$alkyl group, as defined above, attached to the parent molecular moiety through an oxygen atom. Representative examples of a $(C_1-C_6)$alkoxy include, but are not limited to, methoxy, ethoxy, propoxy, 2-propoxy, butoxy, tert-butoxy, pentyloxy, and hexyloxy.

The term "optionally substituted $(C_1-C_6)$alkoxy" as used herein, refers to a $(C_1-C_6)$alkoxy group, as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-C_6)$alkoxy, —$N(R^3)(R^4)$, —$N(R^3)(C(=O)R^4)$, —$N(R^3)C(=O)$—$OR^4$, —$C(=O)$—$N(R^3)(R^4)$, —O—$C(=O)$—$N(R^3)(R^4)$, —$C(=O)$—$R^3$, —$C(=O)$—$OR^3$, and optionally substituted $(C_3-C_8)$cycloalkyl, in which $R^3$ and $R^4$ are each independently selected from hydrogen and optionally substituted $(C_1-C_6)$alkyl. For example, a $(C_1-C_6)$alkoxy can be substituted with one or more halogen atoms to form a "halo$(C_1-C_6)$alkoxy". Representative examples of a halo $(C_1-C_6)$alkoxy include, but are not limited to, fluoromethoxy, difluoromethoxy, 2-fluoroethoxy, trifluoromethoxy, and pentafluoroethoxy.

The term "$(C_1-C_6)$alkythio", as used herein, refers to a $(C_1-C_6)$alkyl group, as defined above, attached to the parent molecular moiety through a sulfur atom. Representative examples of a $(C_1-C_6)$alkylthio include, but are not limited to, methylthio, ethylthio, propylthio, and the like.

The term "optionally substituted $(C_1-C_6)$alkythio", as used herein, refers to a $(C_1-C_6)$alkylthio group, as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-C_6)$alkoxy, —$N(R^3)(R^4)$, —$N(R^3)(C(=O)R^4)$, —$N(R^3)C(=O)$—$OR^4$, —$C(=O)$—$N(R^3)(R^4)$, —O—$C(=O)$—$N(R^3)(R^4)$, —$C(=O)$—$R^3$, —$C(=O)$—$OR^3$, and optionally substituted $(C_3-C_8)$cycloalkyl, in which $R^3$ and $R^4$ are each independently selected from hydrogen and optionally substituted $(C_1-C_6)$alkyl.

As used herein, the term "$(C_3-C_{12})$cycloalkyl" refers to a carbocyclic substituent obtained by removing hydrogen from a saturated carbocyclic molecule wherein the cyclic framework has 3 to 12 carbons. A "$(C_3-C_8)$cycloalkyl" refers to a carbocyclic substituent obtained by removing hydrogen from a saturated carbocyclic molecule wherein the cyclic framework has 3 to 8 carbons. A "$(C_3-C_6)$cycloalkyl" refers to a carbocyclic substituent obtained by removing hydrogen from a saturated carbocyclic molecule having from 3 to 6 carbon atoms. A "cycloalkyl" may be a monocyclic ring, examples of which include cyclopropyl, cyclobutyl, cyclopentyl, cyclohexyl, cycloheptyl, and cyclooctyl. Also included in the definition of cycloalkyl are unsaturated non-aromatic cycloalkyls such as, but not limited to, cyclohexenyl, cyclohexadienyl, cyclopentenyl, cycloheptenyl, and cyclooctenyl. Alternatively, a cycloalkyl may contain more than one ring such as a "$(C_4-C_8)$bicycloalkyl". The term "$(C_4-C_8)$bicycloalkyl" refers to a bicyclic ring system containing from 4 to 8 carbon atoms. The bicycloalkyl may be fused, such as bicyclo[1.1.0]butanyl, bicyclo[2.1.0]pentanyl, bicyclo[2.2.0]hexanyl, bicyclo[3.1.0]hexanyl, bicyclo[3.2.0]heptanyl, and bicyclo[3.3.0]-octanyl. The term "bicycloalkyl" also includes bridged bicycloalkyl systems such as, but not limited to, bicyclo[2.2.1]heptanyl and bicyclo[1.1.1]pentanyl. Other bicyclic cycloalkyl rings systems include "$(C_3-C_{12})$cycloalkyls", wherein a 3-, 4-, 5- or 6-carbon cycloalkyl ring is fused together with another ring, such another cycloalkyl ring, or an aromatic ring. For example, a dihydroindenyl ring is a cycloalkyl ring wherein a cyclopentyl ring is fused together with a phenyl ring.

The term "optionally substituted $(C_3-C_8)$cycloalkyl" or "optionally substituted $(C_3-C_6)$cycloalkyl" refers to a $(C_3-C_8)$cycloalkyl or $(C_3-C_6)$cycloalkyl, as defined above, in which one or more hydrogen atoms are replaced by a substituent selected from the group consisting of halogen, oxo, cyano, hydroxy, —$SF_5$, nitro, —$(C_1-C_6)$alkyl, —$(C_1-C_6)$alkoxy, —$N(R^3)(R^4)$, —$N(R^3)(C(=O)R^4)$, —$N(R^3)C(=O)$—$OR^4$, —$C(=O)$—$N(R^3)(R^4)$, —O—$C(=O)$—$N(R^3)(R^4)$, —$C(=O)$—$R^3$, —$C(=O)$—$OR^3$, and optionally substituted $(C_3-C_8)$cycloalkyl, in which $R^3$ and $R^4$ are each independently selected from hydrogen and optionally substituted $(C_1-C_6)$alkyl.

The term "—O—$(C_3-C_6)$cycloalkyl" refers to a $(C_3-C_6)$ cycloalkyl as described above, attached to the parent molecular moiety through an oxygen atom. Representative examples of a —O—$(C_3-C_6)$cycloalkyl include, but are not limited to, cyclopropoxy, cyclobutoxy, and the like.

The term "optionally substituted —O—$(C_3-C_6)$cycloalkyl" refers to a —O—$(C_3-C_6)$cycloalkyl as described above, in which one or more hydrogen atoms are replaced by a substituent selected from the group consisting of halogen, oxo, cyano, hydroxy, —SF$_5$, nitro, —(C$_1$-C$_6$)alkyl, —(C$_1$-C$_6$)alkoxy, —N(R$^3$)(R$^4$), —N(R$^3$)(C(=O)R$^4$), —N(R$^3$)C(=O)—OR$^4$, —C(=O)—N(R$^3$)(R$^4$), —O—C(=O)—N(R$^3$)(R$^4$), —C(=O)—R$^3$, —C(=O)—OR$^3$, and optionally substituted (C$_3$-C$_8$)cycloalkyl, in which R$^3$ and R$^4$ are each independently selected from hydrogen and optionally substituted (C$_1$-C$_6$)alkyl.

A "heterocycloalkyl," as used herein, refers to a cycloalkyl as defined above, wherein at least one of the ring carbon atoms is replaced with a heteroatom selected from nitrogen, oxygen or sulfur. The term "(4- to 6-membered)heterocycloalkyl" means the heterocycloalkyl substituent contains a total of 4 to 6 ring atoms, at least one of which is a heteroatom. The term "(4- to 8-membered)heterocycloalkyl" means the heterocycloalkyl substituent contains a total of 4 to 8 ring atoms, at least one of which is a heteroatom. A "(4- to 10-membered)heterocycloalkyl" means the heterocycloalkyl substituent contains a total of 4 to 10 ring atoms. A "(6-membered)heterocycloalkyl" means the heterocycloalkyl substituent contains a total of 6 ring atoms, at least one of which is a heteroatom. A "(5-membered)heterocycloalkyl" means the heterocycloalkyl substituent contains a total of 5 ring atoms at least one of which is a heteroatom. A heterocycloalkyl may be a single ring with up to 10 total members. Alternatively, a heterocycloalkyl as defined above may comprise 2 or 3 rings fused together, wherein at least one such ring contains a heteroatom as a ring atom (i.e., nitrogen, oxygen, or sulfur). The heterocycloalkyl substituent may be attached to the dihydropyrrolopyridine core of the compounds of the present invention via a nitrogen atom having the appropriate valence, or via any ring carbon atom. The heterocycloalkyl moiety may be optionally substituted with one or more substituents at a nitrogen atom having the appropriate valence, or at any available carbon atom.

Also included in the definition of "heterocycloalkyl" are heterocycloalkyls that are fused to a phenyl or naphthyl ring or to a heteroaryl ring such as, but not limited to, a pyridinyl ring or a pyrimidinyl ring.

Examples of heterocycloalkyl rings include, but are not limited to, azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, octahydro-benzofuranyl, octahydrobenzimidazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydro-oxazolyl, morpholinyl, oxetanyl, tetrahydrodiazinyl, oxazinyl, oxathiazinyl, quinuclidinyl, chromanyl, isochromanyl, dihydrobenzodioxinyl, benzodioxolyl, benzoxazinyl, indolinyl, dihydrobenzofuranyl, tetrahydroquinolyl, isochromyl, dihydro-1H-isoindolyl, 2-azabicyclo[2.2.1]heptanonyl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), and the like.

The term "optionally substituted heterocycloalkyl" [e.g., optionally substituted (4- to 10-membered)heterocycloalkyl] refers to a heterocycloalkyl, as defined above, in which one or more hydrogen atoms, where chemically permissible, are replaced by a substituent selected from the group consisting of halogen, oxo, cyano, hydroxy, —SF$_5$, nitro, —(C$_1$-C$_6$)alkyl, —(C$_1$-C$_6$)alkoxy, —N(R$^3$)(R$^4$), —N(R$^3$)(C(=O)R$^4$), —N(R$^3$)C(=O)—OR$^4$, —C(=O)—N(R$^3$)(R$^4$), —O—C(=O)—N(R$^3$)(R$^4$), —C(=O)—R$^3$, —C(=O)—OR$^3$, and optionally substituted (C$_3$-C$_8$)cycloalkyl, in which R$^3$ and R$^4$ are each independently selected from hydrogen and optionally substituted (C$_1$-C$_6$)alkyl.

A "(C$_6$-C$_{10}$)aryl" refers to an all-carbon monocyclic or fused-ring polycyclic aromatic group having a conjugated pi-electron system containing from 6 to 10 carbon atoms, such as phenyl or naphthyl.

The term "optionally substituted (C$_6$-C$_{10}$)aryl" refers to a (C$_6$-C$_{10}$)aryl, as defined above, in which one or more hydrogen atoms are replaced by a substituent selected from the group consisting of halogen, oxo, cyano, hydroxy, —SF$_5$, nitro, —(C$_1$-C$_6$)alkyl, —(C$_1$-C$_6$)alkoxy, —N(R$^3$)(R$^4$), —N(R$^3$)(C(=O)R$^4$), —N(R$^3$)C(=O)—OR$^4$, —C(=O)—N(R$^3$)(R$^4$), —O—C(=O)—N(R$^3$)(R$^4$), —C(=O)—R$^3$, —C(=O)—OR$^3$, and optionally substituted (C$_3$-C$_8$)cycloalkyl, in which R$^3$ and R$^4$ are each independently selected from hydrogen and optionally substituted (C$_1$-C$_6$)alkyl.

As used herein, the term "heteroaryl" refers to monocyclic or fused-ring polycyclic aromatic heterocyclic groups with one or more heteroatom ring members (ring-forming atoms) each independently selected from oxygen (O), sulfur (S) and nitrogen (N) in at least one ring. A "(5- to 14-membered) heteroaryl" ring refers to a heteroaryl ring having from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 10-membered)heteroaryl" ring refers to a heteroaryl ring having from 5 to 10 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 10-membered)nitrogen-containing heteroaryl" ring refers to a heteroaryl ring having from 5 to 10 ring atoms in which at least one of the ring atoms is nitrogen, with the remaining ring atoms being independently selected from the group consisting of carbon, oxygen, sulfur, and nitrogen. A "(5- to 6-membered)heteroaryl" refers to a heteroaryl ring having from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 6-membered)nitrogen-containing heteroaryl" refers to a heteroaryl ring having from 5 to 6 ring atoms in which one of the heteroatoms in the ring is a nitrogen. A "(6-membered)nitrogen-containing heteroaryl" refers to a heteroaryl ring having 6 ring atoms in which one of the heteroatoms in the ring is a nitrogen. A "(5-membered)nitrogen-containing heteroaryl" refers to a heteroaryl ring having 5 ring atoms in which one of the heteroatoms in the ring is a nitrogen. A heteroaryl may consist of a single ring or 2 or 3 fused rings. Examples of heteroaryls include, but are not limited to, 6-membered ring substituents such as pyridinyl, pyrazinyl, pyrimidinyl and pyridazinyl; 5-membered heteroaryls such as triazolyl, imidazolyl, furanyl, isoxazolyl, isothiazolyl, 1,2,3-, 1,2,4, 1,2, 5-, or 1,3,4-oxadiazolyl, oxazolyl, thiophenyl, thiazolyl, thiadiazolyl, isothiazolyl, and pyrazolyl; 6/5-membered fused ring substituents such as indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl (e.g., [1,2,4]triazolo[1,5-a]pyridin-2-yl), and anthranilyl; and 6/6-membered fused ring substituents such as quinolinyl, isoquinolinyl, cinnolinyl, quinazolinyl, oxochromanyl, and 1,4-benzoxazinyl.

It is to be understood that the heteroaryl may be optionally fused to a cycloalkyl group, or to a heterocycloalkyl group, as defined herein.

The heteroaryl substituent may be attached to the dihydropyrrolopyridine core of the compounds of the present invention via a nitrogen atom having the appropriate valence, or via any carbon atom. The heteroaryl moiety may be optionally substituted with one or more substituents at a nitrogen atom having the appropriate valence, or at any available carbon atom.

The terms "optionally substituted (5- to 10-membered) heteroaryl", "optionally substituted (5- to 6-membered)heteroaryl" and "optionally substituted (5- to 6-membered) nitrogen-containing heteroaryl" refer to a (5- to 14-membered)heteroaryl, a (5- to 6-membered)heteroaryl, and a (5- to 6-membered)nitrogen-containing heteroaryl, as defined above, in which one or more hydrogen atoms are replaced, where chemically permissible, by a substituent selected from the group consisting of halogen, oxo, cyano, hydroxy, —SF$_5$, nitro, —(C$_1$-C$_6$)alkyl, —(C$_1$-C$_6$)alkoxy, —N(R$^3$)(R$^4$), —N(R$^3$)(C(=O)R$^4$), —N(R$^3$)C(=O)—OR$^4$, —C(=O)—N(R$^3$)(R$^4$), —O—C(=O)—N(R$^3$)(R$^4$), —C(=O)—R$^3$, —C(=O)—OR$^3$, and optionally substituted (C$_3$-C$_8$)cycloalkyl, in which R$^3$ and R$^4$ are each independently selected from hydrogen and optionally substituted (C$_1$-C$_6$)alkyl.

The substituent can be attached to the heteroaryl moiety at any available carbon atom or to a heteroatom when the heteroatom is nitrogen having the appropriate valence.

"halo" or "halogen", as used herein, refers to a chlorine, fluorine, bromine, or iodine atom.

"hydroxy" or "hydroxyl", as used herein, means an —OH group.

"cyano", as used herein, means a —CN group, which also may be depicted:

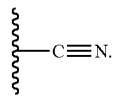

"nitro", as used herein, means an —NO$_2$ group.

"oxo", as used herein, means a =O moiety. When an oxo is substituted on a carbon atom, they together form a carbonyl moiety [—C(=O)—]. When an oxo is substituted on a sulfur atom, they together form a sulfoxide moiety [—S(=O)—]; when two oxo groups are substituted on a sulfur atom, they together form a sulfonyl moiety [—S(=O)$_2$—].

"Optionally substituted", as used herein, means that substitution is optional and therefore includes both unsubstituted and substituted atoms and moieties. A "substituted" atom or moiety indicates that any hydrogen on the designated atom or moiety can be replaced with a selection from the indicated substituent group (up to and including that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., —CH$_3$) is optionally substituted, then up to 3 hydrogen atoms on the carbon atom can be replaced with substituent groups.

"Patient" refers to warm-blooded animals such as, for example, pigs, cows, chickens, horses, guinea pigs, mice, rats, gerbils, cats, rabbits, dogs, monkeys, chimpanzees, and humans.

"Pharmaceutically acceptable" indicates that the substance or composition must be compatible, chemically and/or toxicologically, with the other ingredients comprising a formulation, and/or the mammal being treated therewith.

The term "therapeutically effective amount" as used herein refers to that amount of the compound (including an N-oxide thereof or a pharmaceutically acceptable salt of the compound or the N-oxide) being administered which will relieve to some extent one or more of the symptoms of the disorder being treated. In reference to the treatment of an M4-mediated disorder (e.g., Alzheimer's Disease or schizophrenia), a therapeutically effective amount refers to that amount which has the effect of relieving to some extent (or, for example, eliminating) one or more symptoms associated with the M4-mediated disorder (e.g., positive, negative, or cognitive symptom of schizophrenia; or psychotic symptom of Alzheimer's Disease).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

"Isoform" means any of several different forms of the same protein.

"Isozyme" or "isoenzyme" means a closely related variant of an enzyme that differs in amino acid sequence but catalyzes the same chemical reaction.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

As used herein, unless specified, the point of attachment of a substituent can be from any suitable position of the substituent. For example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms in that ring that are substitutable (i.e., bonded to one or more hydrogen atoms), unless otherwise specified or otherwise implicit from the context. For example, as shown in Formula I below, one R$^1$ (wherein a is 1, 2 or 3) may be bonded, valency permitting, to any one of the ring carbon atoms of the 6-membered ring, and R$^2$ (wherein b is 1, 2, 3, or 4) may be bonded, valency permitting, to any one of the ring carbon atoms of the 5-membered ring as shown below:

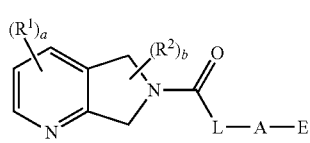

When a substituted or optionally substituted moiety is described without indicating the atom via which such moiety is bonded to a substituent, then the substituent may be bonded via any appropriate atom in such moiety. For example in an optionally substituted (5- to 10-membered) heteroaryl, a substituent on the heteroaryl can be bonded to any carbon atom on the heteroaryl part or on the heteroatom of the heteroaryl, valency permitting. Combinations of substituents and/or variables are permissible only if such combinations result in stable compounds.

This specification uses the terms "substituent," "radical," and "group" interchangeably.

If substituents are described as being "independently selected" from a group, each instance of a substituent is selected independent of any other. Each substituent therefore may be identical to or different from the other substituent(s).

As used herein the term "Formula I", "Formula Ia" and "Formula Ib" may be hereinafter referred to as a "compound (s) of the invention." Such terms are also defined to include all forms of the compounds of the invention including, but not limited to, hydrates, solvates, isomers (including for example rotational stereoisomers), crystalline and non-crystalline forms, isomorphs, polymorphs, metabolites, prodrugs thereof. For example, the compounds of the invention, or pharmaceutically acceptable salts thereof, may exist in unsolvated and solvated forms with pharmaceutically acceptable solvents such as water, ethanol and the like. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. In general, the solvated forms are considered equivalent to the unsolvated forms for the purposes of the present invention.

The compounds of the invention may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975). Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, Chem. Commun. 2004, 17, 1889-1896. For a general review of multi-component complexes, see J. K. Haleblian, J. Pharm. Sci. 1975, 64, 1269-1288.

The compounds of the invention may exist as geometric isomers, wherein the compounds have asymmetric carbon atoms, and thus may exist as two or more stereoisomeric forms. The present invention includes all the individual stereoisomers and geometric isomers of the compounds of the invention and mixtures thereof. Individual enantiomers can be obtained by chiral separation or using the relevant enantiomer in the synthesis. The carbon-carbon bonds of the compounds of the invention may be depicted herein using a solid line ( —— ), a solid wedge ( ▬■ ), or a dotted wedge ( ·····IIIII ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry may be marked with (+/−). For example, unless stated otherwise, it is intended that the compounds of the invention can exist as stereoisomers, which include cis and trans isomers, optical isomers such as R and S enantiomers, diastereomers, geometric isomers, rotational isomers, conformational isomers, atropisomers, and mixtures thereof (such as racemates and diastereomeric pairs). The compounds of the invention may exhibit more than one type of isomerism. Also included are acid addition or base addition salts wherein the counterion is optically active, for example, D-lactate or L-lysine, or racemic, for example, DL-tartrate or DL-arginine.

In some embodiments, the compounds of the present invention may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al., Absolute Configuration Determination of Chiral Molecules in the Solution State Using Vibrational Circular Dichroism. Chirality 2003, 15, 743-758; and Bringmann, G. et al., Atroposelective Synthesis of Axially Chiral Biaryl Compounds. Angew. Chem., Int. Ed. 2005, 44, 5384-5427.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the present invention may also exist as an N-oxide thereof, or a pharmaceutically acceptable salt of the compound or N-oxide.

As it is known to the person skilled in the art, amine compounds (i.e., those comprising one or more nitrogen atoms), for example tertiary amines, can form N-oxides (also known as amine oxides or amine N-oxides). An N-oxide has the formula of $(R^{100}R^{200}R^{300})N^+$—$O^-$ wherein the parent amine $(R^{100}R^{200}R^{300})N$ can be for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100}R^{200}R^{300})N$ together forms 1-alkylpiperidine, 1-alkylpyrrolidine, 1-benzylpyrrolidine, or pyridine]. For instance, an imine nitrogen, especially heterocyclic or heteroaromatic imine nitrogen

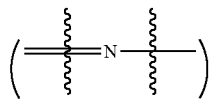

atom [such as a nitrogen atom in pyridine, pyridazine, or pyrazine], can be N-oxidized to form the N-oxide comprising the group

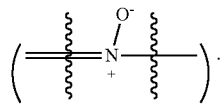

Thus, a compound according to the present invention comprising one or more nitrogen atoms (e.g., an imine nitrogen atom) may be capable of forming an N-oxide thereof (e.g., mono-N-oxides, bis-N-oxides or multi-N-oxides, or mixtures thereof depending on the number of nitrogen atoms suitable to form stable N-oxides).

As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono-N-oxide) or multi-N-oxides (e.g., bis-N-oxides), or mixtures thereof in any ratio.

As noted above, the compounds of the invention (or N-oxides thereof) may exist in the form of pharmaceutically acceptable salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the present invention with an acid whose anion, or a base whose cation, is generally considered suitable for human consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as, but not limited to, hydrochloric, hydrobromic, hydrofluoric, boric, fluoroboric, phosphoric, meta-phosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, aralipathic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylamino-sulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalene-sulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanol-amine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of the invention are known to one of skill in the art.

Compounds of the invention may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3$$^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

The invention also relates to prodrugs of the compounds of the present invention. Thus certain derivatives of compounds of the invention which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of the invention with certain moieties known to those skilled in the art as 'pro-moieties' as described, for example, in Design of Prodrugs by H. Bundgaard (Elsevier, 1985), or in Prodrugs: Challenges and Reward, 2007 edition, edited by Valentino Stella, Ronald Borchardt, Michael Hageman, Reza Oliyai, Hans Maag, Jefferson Tilley, pages 134-175 (Springer, 2007).

Moreover, certain compounds of the invention may themselves act as prodrugs of other compounds of the invention.

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

Also included within the scope of the invention are metabolites of compounds of the invention, that is, compounds formed in vivo upon administration of the drug.

The present invention also includes all pharmaceutically acceptable isotopically labeled compounds, which are identical to those recited herein, wherein one or more atoms are replaced by an atom having the same atomic number, but an atomic mass or mass number different from the atomic mass or mass number which predominates in nature. Examples of isotopes suitable for inclusion in the compounds of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically-labeled compounds of the present invention, for example, those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements and, hence, may be preferred in some circumstances. Substitution with positron-emitting isotopes, such as $^{11}$C, $^{15}$F, $^{18}$F, $^{15}$O and $^{13}$N, can be useful in positron emission tomography (PET) studies for examining substrate receptor occupancy. Isotopically labeled compounds of the present invention can generally be prepared by conventional techniques known to those skilled in the art or by processes analogous to those described in the accompanying Schemes and/or in the Examples and Preparations using an appropriate isotopically labeled reagent in place of the non-labeled reagent previously employed. Pharmaceutically acceptable solvates in accordance with the invention include those wherein the solvent of crystallization may be isotopically substituted, e.g., D$_2$O, acetone-d$_6$, or DMSO-d$_6$. Compounds of the invention, which include compounds exemplified in Examples 1-67 described below, include isotopically labeled versions of these compounds, such as, but not limited to, the deuterated and tritiated isotopes and all other isotopes discussed above.

In certain embodiments, the present invention is directed to novel, selective, radiolabelled M4 positive allosteric modulators which are useful for imaging and quantifying distribution of M4 compounds in tissues (e.g., brain), using positron-emission tomography (PET).

Compounds

The compounds of Formula I, as described above, contain a 5,7-dihydro-pyrrolo-pyridine core wherein the core is optionally substituted on the pyridine ring with up to three R$^1$; optionally substituted on the pyrrole ring with up to four R$^2$; and L, A, and E are as defined above, and hereinafter.

In one embodiment, in Formula I as described above, each R$^1$, when present, is selected from the group consisting of halogen, optionally substituted (C$_1$-C$_6$)alkyl, optionally substituted (C$_1$-C$_6$)alkoxy, and —N(R$^3$)(R$^4$); and a is an integer selected from 1, 2 and 3.

In certain embodiments, R$^1$ is a halogen, and the halogen is selected from chloro and fluoro.

In certain embodiments, R$^1$ is an optionally substituted (C$_1$-C$_6$)alkyl, and the (C$_1$-C$_6$)alkyl is selected from methyl and ethyl. Examples of optionally substituted (C$_1$-C$_6$)alkyl include, but are not limited to, fluoromethyl, difluoromethyl, trifluoromethyl, fluoroethyl, difluoroethyl, trifluoroethyl, methanol, and methoxymethyl.

In certain embodiments, R$^1$ is an optionally substituted (C$_1$-C$_6$)alkoxy, and the (C$_1$-C$_6$)alkoxy is selected from methoxy and ethoxy. Examples of optionally substituted (C$_1$-C$_6$)alkoxy include, but are not limited to, fluoromethoxy, difluoromethoxy, trifluoromethoxy, fluoroethoxy, difluoroethoxy and trifluoroethoxy.

In certain embodiments, R$^1$ is —N(R$^3$)(R$^4$), wherein R$^3$ and R$^4$ are each independently selected from hydrogen and optionally substituted (C$_1$-C$_6$)alkyl, wherein the (C$_1$-C$_6$) alkyl is selected from methyl, ethyl, and propyl. In certain embodiments, one of R$^3$ and R$^4$ is hydrogen and the other is an optionally substituted (C$_1$-C$_6$)alkyl. In another embodiment both R$^3$ and R$^4$ can be hydrogen. In yet another embodiment both R$^3$ and R$^4$ can be an optionally substituted (C$_1$-C$_6$)alkyl. For example, when R$^3$ and R$^4$ are each an optionally substituted (C$_1$-C$_6$)alkyl, the (C$_1$-C$_6$)alkyl is methyl.

It is to be understood that any of the above-mentioned subgenuses (embodiments) of $R^1$ can be combined together with any of the subgenuses for $R^2$, L, A, and E as described above and hereinafter.

In certain other embodiments, in Formula I as described above, each $R^2$, when present, is an optionally substituted $(C_1-C_6)$alkyl; and b is an integer selected from 0 and 1.

In certain embodiments, b is 1 and the optionally substituted $(C_1-C_6)$alkyl is methyl.

In certain embodiments, b is 0 (i.e., $R^2$ is absent).

It is to be understood that any of the above-mentioned subgenuses (embodiments) of $R^2$ can be combined together with any of the subgenuses for $R^1$, L, A, and E as described above and hereinafter.

In certain other embodiments, in Formula I as described above, L is oxygen.

In certain other embodiments, in Formula I as described above, L is —NH—.

In certain embodiments, L is —(CH$_2$)$_m$— and m is an integer selected from 1 and 2.

In certain embodiments, L is —(CH$_2$)$_m$— and m is 2.
In certain embodiments, L is —(CH$_2$)$_m$— and m is 1.

It is to be understood that any of the above-mentioned subgenuses (embodiments) of L can be combined together with any of the subgenuses for $R^1$, $R^2$, A, and E as described above and hereinafter.

In certain other embodiments, in Formula I as described above, A is a $(C_3-C_6)$cycloalkyl selected from the group consisting of cyclopropyl, cyclobutyl, cyclopentyl, and cyclohexyl, wherein said cycloalkyl is optionally substituted with one to three substituents independently selected from the group consisting of halogen, cyano, —N(R$^3$)(R$^4$), optionally substituted $(C_1-C_6)$alkyl, and optionally substituted $(C_1-C_6)$alkoxy.

In certain embodiments A is cyclopropyl.

In certain other embodiments, A is a (4- to 6-membered) heterocycloalkyl selected from the group consisting of azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, imidazolidinyl, pyrrolidinyl, piperidinyl, piperazinyl, oxazolidinyl, thiazolidinyl, pyrazolidinyl, tetrahydropyranyl, tetrahydrothiazinyl, tetrahydrothiadiazinyl, tetrahydrooxazolyl, oxetanyl, dioxetanyl, dioxolanyl, dioxanyl, oxazinyl, and oxathiazinyl, wherein said heterocycloalkyl is optionally substituted with one to three substituents independently selected from the group consisting of halogen, cyano, —N(R$^3$)(R$^4$), optionally substituted $(C_1-C_6)$alkyl, and optionally substituted $(C_1-C_6)$alkoxy.

In certain embodiments A is a (4- to 6-membered)heterocycloalkyl and the heterocycloalkyl is azetidinyl.

It is to be understood that any of the above-mentioned subgenuses (embodiments) of A can be combined together with any of the subgenuses for $R^1$, $R^2$, L, and E as described above and hereinafter.

In certain embodiments, in Formula I as described above, E is a (5- to 10-membered)heteroaryl selected from the group consisting of triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, isothiazolyl, pyrazolyl, pyridinyl, pyrazinyl, pyrimidinyl, pyridazinyl, indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl, anthranilyl, quinolinyl, isoquinolinyl, cinnolinyl, quinazolinyl, oxochromanyl, and 1,4-benzoxazinyl, wherein said heteroaryl is optionally substituted with one to three substituents independently selected from the group consisting of halogen, cyano, —N(R$^3$)(R$^4$), optionally substituted $(C_1-C_6)$alkyl, and optionally substituted $(C_1-C_6)$alkoxy.

In certain other embodiments, E is a (5- to 6-membered) nitrogen-containing heteroaryl selected from the group consisting of triazolyl, imidazolyl, pyrazolyl, pyridinyl, pyrazinyl, pyrimidinyl, and pyridazinyl, wherein said nitrogen-containing heteroaryl is optionally substituted with one to three substituents independently selected from the group consisting of halogen, cyano, —N(R$^3$)(R$^4$), optionally substituted $(C_1-C_6)$alkyl, and optionally substituted $(C_1-C_6)$alkoxy.

In certain other embodiments, E is pyridinyl optionally substituted with one to two substituents independently selected from the group consisting of halogen, cyano, —N(R$^3$)(R$^4$), optionally substituted $(C_1-C_6)$alkyl, and optionally substituted $(C_1-C_6)$alkoxy.

In certain other embodiments, E is pyrimidinyl optionally substituted with one to two substituents independently selected from the group consisting of halogen, cyano, —N(R$^3$)(R$^4$), optionally substituted $(C_1-C_6)$alkyl, and optionally substituted $(C_1-C_6)$alkoxy.

It is to be understood that any of the above-mentioned subgenuses (embodiments) of E can be combined together with any of the subgenuses for $R^1$, $R^2$, L, and A as described above and hereinafter.

In certain other embodiments, the present invention is a compound of Formula Ia:

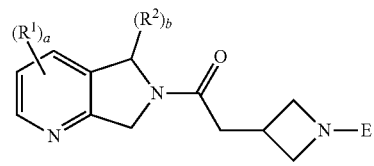

or an N-oxide thereof, or a pharmaceutically acceptable salt of the compound or the N-oxide, wherein:
  each $R^1$, when present, is independently selected from the group consisting of halogen, optionally substituted $(C_1-C_6)$alkyl, and optionally substituted $(C_1-C_6)$alkoxy;
  a is an integer selected from 1, 2 and 3;
  $R^2$, when present, is an optionally substituted $(C_1-C_6)$alkyl;
  b is an integer selected from 0 and 1;
  E is a (5- to 6-membered)heteroaryl, wherein said heteroaryl is optionally substituted with one to three substituents independently selected from the group consisting of halogen, cyano, optionally substituted $(C_1-C_6)$alkyl, optionally substituted $(C_1-C_6)$alkoxy, and —N(R$^3$)(R$^4$), wherein R$^3$ and R$^4$ at each occurrence are each independently selected from hydrogen and optionally substituted $(C_1-C_6)$alkyl.

In another embodiment, in Formula Ia, as described above, b is 1 and $R^2$ is methyl.

In another embodiment, b is 0 (i.e., $R^2$ is absent).

In another embodiment, in Formula Ia as described above, E is a (5- to 6-membered)nitrogen-containing heteroaryl selected from the group consisting of pyrazolyl, thiazolyl, thiadiazolyl, pyridinyl, pyrimidinyl, and pyrazinyl, wherein said nitrogen-containing heteroaryl is optionally substituted with one to three substituents independently selected from the group consisting of halogen, cyano, —N(R$^3$)(R$^4$), optionally substituted (C$_1$-C$_6$)alkyl, and optionally substituted (C$_1$-C$_6$)alkoxy.

In certain other embodiments, E is pyridinyl optionally substituted with one to two substituents independently selected from the group consisting of halogen, cyano, —N(R$^3$)(R$^4$), optionally substituted (C$_1$-C$_6$)alkyl, and optionally substituted (C$_1$-C$_6$)alkoxy.

In certain other embodiments, E is pyrimidinyl optionally substituted with one to two substituents independently selected from the group consisting of halogen, cyano, —N(R$^3$)(R$^4$), optionally substituted (C$_1$-C$_6$)alkyl, and optionally substituted (C$_1$-C$_6$)alkoxy.

In certain other embodiments, the present invention is a compound of Formula Ib:

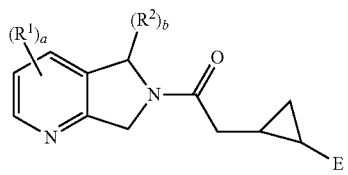

Ib or an N-oxide thereof, or a pharmaceutically acceptable salt of the compound or the N-oxide, wherein:
  each R$^1$, when present, is independently selected from the group consisting of halogen, optionally substituted (C$_1$-C$_6$)alkyl, and optionally substituted (C$_1$-C$_6$)alkoxy;
  a is an integer selected from 1, 2 and 3;
  R$^2$, when present, is an optionally substituted (C$_1$-C$_6$)alkyl;
  b is an integer selected from 0 and 1;
  E is a (5- to 6-membered)heteroaryl, wherein said heteroaryl is optionally substituted with one to three substituents independently selected from the group consisting of halogen, cyano, hydroxy, optionally substituted (C$_1$-C$_6$)alkyl, optionally substituted (C$_1$-C$_6$)alkoxy, and —N(R$^3$)(R$^4$), wherein R$^3$ and R$^4$ at each occurrence are each independently selected from hydrogen and optionally substituted (C$_1$-C$_6$)alkyl.

In another embodiment, in Formula Ib, as described above, b is 1 and R$^2$ is methyl.

In another embodiment, b is 0 (i.e., R$^2$ is absent).

In another embodiment, in Formula Ib as described above, E is a (5- to 6-membered)nitrogen-containing heteroaryl selected from the group consisting of pyrazolyl, thiazolyl, thiadiazolyl, pyridinyl, pyrimidinyl, and pyrazinyl, wherein said nitrogen-containing heteroaryl is optionally substituted with one to three substituents independently selected from the group consisting of halogen, cyano, —N(R$^3$)(R$^4$), optionally substituted (C$_1$-C$_6$)alkyl, and optionally substituted (C$_1$-C$_6$)alkoxy.

In certain other embodiments, E is pyridinyl optionally substituted with one to two substituents independently selected from the group consisting of halogen, cyano, —N(R$^3$)(R$^4$), optionally substituted (C$_1$-C$_6$)alkyl, and optionally substituted (C$_1$-C$_6$)alkoxy.

In certain other embodiments, E is pyrimidinyl optionally substituted with one to two substituents independently selected from the group consisting of halogen, cyano, —N(R$^3$)(R$^4$), optionally substituted (C$_1$-C$_6$)alkyl, and optionally substituted (C$_1$-C$_6$)alkoxy.

In certain other embodiments, the present invention is directed to a compound selected from the group consisting of:
1-(2,4-dimethyl-5,7-dihydro-6H-pyrrolo[3,4-b]pyridin-6-yl)-2-[1-(pyridin-3-yl)azetidin-3-yl]ethanone,
2-{1-[2-(difluoromethyl)pyridin-4-yl]azetidin-3-yl}-1-(2,4-dimethyl-5,7-dihydro-6H-pyrrolo[3,4-b]pyridin-6-yl)ethanone,
1-(2,4-dimethyl-5,7-dihydro-6H-pyrrolo[3,4-b]pyridin-6-yl)-2-[1-(pyrimidin-4-yl)azetidin-3-yl]ethanone,
2-{1-[2-(difluoromethoxy)pyridin-4-yl]azetidin-3-yl}-1-(2,4-dimethyl-5,7-dihydro-6H-pyrrolo[3,4-b]pyridin-6-yl)ethanone,
2-[1-(1,2,4-thiadiazol-5-yl)azetidin-3-yl]-1-(2,3,4-trimethyl-5,7-dihydro-6H-pyrrolo[3,4-b]pyridin-6-yl)ethanone,
1-[2-(difluoromethyl)-4-methyl-5,7-dihydro-6H-pyrrolo[3,4-b]pyridin-6-yl]-2-{1-[2-(trifluoromethyl)pyridin-4-yl]azetidin-3-yl}ethanone,
1-[2-(methoxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone,
2-{1-[2-(difluoromethoxy)pyridin-4-yl]azetidin-3-yl}-1-[2-(methoxymethyl)-4-methyl-5,7-dihydro-6H-pyrrolo[3,4-b]pyridin-6-yl]ethanone,
1-[2-(hydroxymethyl)-4-methyl-5,7-dihydro-6H-pyrrolo[3,4-b]pyridin-6-yl]-2-[1-(pyridin-3-yl)azetidin-3-yl]ethanone,
2-{1-[2-(difluoromethoxy)pyridin-4-yl]azetidin-3-yl}-1-[2-(difluoromethyl)-3,4-dimethyl-5,7-dihydro-6H-pyrrolo[3,4-b]pyridin-6-yl]ethanone,
1-(2,4-dimethyl-5,7-dihydro-6H-pyrrolo[3,4-b]pyridin-6-yl)-2-{1-[2-(trifluoromethyl)pyridin-4-yl]azetidin-3-yl}ethanone,
1-(3-chloro-2,4-dimethyl-5,7-dihydro-6H-pyrrolo[3,4-b]pyridin-6-yl)-2-{1-[2-(difluoromethyl)pyridin-4-yl]azetidin-3-yl}ethanone,
1-(3-chloro-2,4-dimethyl-5,7-dihydro-6H-pyrrolo[3,4-b]pyridin-6-yl)-2-[1-(pyridin-3-yl)azetidin-3-yl]ethanone,
2-[1-(pyridin-3-yl)azetidin-3-yl]-1-(2,4,5-trimethyl-5,7-dihydro-6H-pyrrolo[3,4-b]pyridin-6-yl)ethanone ENT-1,
2-[1-(pyridin-3-yl)azetidin-3-yl]-1-(2,4,5-trimethyl-5,7-dihydro-6H-pyrrolo[3,4-b]pyridin-6-yl)ethanone, ENT-2,
1-(2,4-dimethyl-5,7-dihydro-6H-pyrrolo[3,4-b]pyridin-6-yl)-2-[(1S,2R)-2-(6-methylpyridin-3-yl)cyclopropyl]ethanone,
1-(2,4-dimethyl-5,7-dihydro-6H-pyrrolo[3,4-b]pyridin-6-yl)-2-[(1R,2S)-2-(6-methylpyridin-3-yl)cyclopropyl]ethanone,
1-[2-(difluoromethyl)-4-methyl-5,7-dihydro-6H-pyrrolo[3,4-b]pyridin-6-yl]-2-[(1R,2S)-2-(6-methylpyridin-3-yl)cyclopropyl]ethanone,
2,4-dimethyl-N-[1-(pyridin-3-yl)azetidin-3-yl]-5,7-dihydro-6H-pyrrolo[3,4-b]pyridine-6-carboxamide,
1-(pyridin-3-yl)azetidin-3-yl 2,4-dimethyl-5,7-dihydro-6H-pyrrolo[3,4-b]pyridine-6-carboxylate,
1-(2-methoxy-4-methyl-5,7-dihydro-6H-pyrrolo[3,4-b]pyridin-6-yl)-2-[1-(pyridin-3-yl)azetidin-3-yl]ethanone,
1-(3-chloro-2-methoxy-4-methyl-5,7-dihydro-6H-pyrrolo[3,4-b]pyridin-6-yl)-2-[1-(pyridin-3-yl)azetidin-3-yl]ethanone,
2-[1-(pyridin-3-yl)azetidin-3-yl]-1-(2,3,4-trimethyl-5,7-dihydro-6H-pyrrolo[3,4-b]pyridin-6-yl)ethanone, 1-[2-(hydroxymethyl)-4-methyl-5,7-dihydro-6H-pyrrolo[3,4-b]pyridin-6-yl]-2-[1-(pyrimidin-4-yl)azetidin-3-yl]ethanone, 2-{1-[2-(difluoromethoxy)pyridin-4-yl]azetidin-3-yl}-1-[2-(difluoromethyl)-4-methyl-5,7-dihydro-6H-pyrrolo[3,4-b]pyridin-6-yl]ethanone, 1-(3-chloro-2-methoxy-4-methyl-5,7-dihydro-6H-pyrrolo[3,4-b]pyridin-6-yl)-2-[1-(pyrimidin-5-yl)azetidin-3-yl]ethanone, 1-[2-(methoxymethyl)-4-methyl-5,7-dihydro-6H-pyrrolo[3,4-b]pyridin-6-yl]-2-[1-(pyridin-3-yl)azetidin-3-yl]ethanone, 1-(2-methoxy-3,4-dimethyl-5,7-dihydro-6H-pyrrolo[3,4-b]pyridin-6-yl)-2-[1-(pyridin-3-yl)azetidin-3-yl]ethanone, 1-(2-methoxy-3,4-dimethyl-5,7-dihydro-6H-pyrrolo[3,4-b]pyridin-6-yl)-2-[1-(pyrimidin-5-yl)azetidin-3-yl]ethanone, 1-(2,4-dimethyl-5,7-dihydro-6H-pyrrolo[3,4-b]pyridin-6-yl)-2-[1-(pyridazin-4-yl)azetidin-3-yl]ethanone, 1-[2-(methoxymethyl)-4-methyl-5,7-dihydro-6H-pyrrolo[3,4-b]pyridin-6-yl]-2-[1-(pyrimidin-5-yl)azetidin-3-yl]ethanone, 1-[3-chloro-2-(difluoromethoxy)-4-methyl-5,7-dihydro-6H-pyrrolo[3,4-b]pyridin-6-yl]-2-[1-(pyrimidin-5-yl)azetidin-3-yl]ethanone, 1-[2-(hydroxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone, 1-[2-(difluoromethyl)-4-methyl-5,7-dihydro-6H-pyrrolo[3,4-b]pyridin-6-yl]-2-[1-(pyrimidin-5-yl)azetidin-3-yl]ethanone, 2-[1-(pyrimidin-4-yl)azetidin-3-yl]-1-(2,3,4-trimethyl-5,7-dihydro-6H-pyrrolo[3,4-b]pyridin-6-yl)ethanone, 1-(pyridin-3-yl)azetidin-3-yl 2,3,4-trimethyl-5,7-dihydro-6H-pyrrolo[3,4-b]pyridine-6-carboxylate, 2-[trans-2-(pyridin-3-yl)cyclopropyl]-1-(2,3,4-trimethyl-5,7-dihydro-6H-pyrrolo[3,4-b]pyridin-6-yl)ethanone, ENT-1, 2-[trans-2-(pyridin-3-yl)cyclopropyl]-1-(2,3,4-trimethyl-5,7-dihydro-6H-pyrrolo[3,4-b]pyridin-6-yl)ethanone, ENT-2, 1-(3-chloro-2,4-dimethyl-5,7-dihydro-6H-pyrrolo[3,4-b]pyridin-6-yl)-2-[1-(pyrimidin-4-yl)azetidin-3-yl]ethanone, 1-[2-(methoxymethyl)-3,4-dimethyl-5,7-dihydro-6H-pyrrolo[3,4-b]pyridin-6-yl]-2-[1-(pyrimidin-5-yl)azetidin-3-yl]ethanone, 1-(2,4-dimethyl-5,7-dihydro-6H-pyrrolo[3,4-b]pyridin-6-yl)-2-{1-[2-(ethylamino)pyrimidin-4-yl]azetidin-3-yl}ethanone, 1-(2,4-dimethyl-5,7-dihydro-6H-pyrrolo[3,4-b]pyridin-6-yl)-2-{1-[6-(propan-2-ylamino)pyrimidin-4-yl]azetidin-3-yl}ethanone, 1-(2,4-dimethyl-5,7-dihydro-6H-pyrrolo[3,4-b]pyridin-6-yl)-2-[1-(2-methylimidazo[1,2-b]pyridazin-6-yl)azetidin-3-yl]ethanone, 1-(3-chloro-2,4-dimethyl-5,7-dihydro-6H-pyrrolo[3,4-b]pyridin-6-yl)-2-[1-(1,3,4-thiadiazol-2-yl)azetidin-3-yl]ethanone, 1-[2-(difluoromethyl)-4-methyl-5,7-dihydro-6H-pyrrolo[3,4-b]pyridin-6-yl]-2-{1-[2-(difluoromethyl)pyridin-4-yl]azetidin-3-yl}ethanone, 2-{1-[2-(difluoromethyl)pyridin-4-yl]azetidin-3-yl}-1-(2,3,4-trimethyl-5,7-dihydro-6H-pyrrolo[3,4-b]pyridin-6-yl)ethanone, 1-[3-chloro-2-(methoxymethyl)-4-methyl-5,7-dihydro-6H-pyrrolo[3,4-b]pyridin-6-yl]-2-{1-[2-(difluoromethyl)pyridin-4-yl]azetidin-3-yl}ethanone, 1-[3-chloro-2-(methoxymethyl)-4-methyl-5,7-dihydro-6H-pyrrolo[3,4-b]pyridin-6-yl]-2-[1-(pyridin-3-yl)azetidin-3-yl]ethanone, 1-[3-chloro-2-(methoxymethyl)-4-methyl-5,7-dihydro-6H-pyrrolo[3,4-b]pyridin-6-yl]-2-[1-(6-fluoropyridin-3-yl)azetidin-3-yl]ethanone, 2-{1-[2-(difluoromethyl)pyridin-4-yl]azetidin-3-yl}-1-[2-(methoxymethyl)-4-methyl-5,7-dihydro-6H-pyrrolo[3,4-b]pyridin-6-yl]ethanone, 1-(3-chloro-2,4-dimethyl-5,7-dihydro-6H-pyrrolo[3,4-b]pyridin-6-yl)-2-[trans-2-(pyrimidin-5-yl)cyclopropyl]ethanone, from ENT-2 in footnote 23, Table 6, 1-[3-chloro-2-(methoxymethyl)-4-methyl-5,7-dihydro-6H-pyrrolo[3,4-b]pyridin-6-yl]-2-{1-[2-(difluoromethoxy)pyridin-4-yl]azetidin-3-yl}ethanone, 1-[2-(difluoromethyl)-3,4-dimethyl-5,7-dihydro-6H-pyrrolo[3,4-b]pyridin-6-yl]-2-{1-[2-(difluoromethyl)pyridin-4-yl]azetidin-3-yl}ethanone, (−)-1-(2,4-dimethyl-5,7-dihydro-6H-pyrrolo[3,4-b]pyridin-6-yl)-2-[trans-2-(pyridin-3-yl)cyclopropyl]ethanone, ENT-1, (+)-1-(2,4-dimethyl-5,7-dihydro-6H-pyrrolo[3,4-b]pyridin-6-yl)-2-[trans-2-(pyridin-3-yl)cyclopropyl]ethanone, ENT-2, 2-(2,3-dihydro-1H-inden-2-yl)-1-(2,4-dimethyl-5,7-dihydro-6H-pyrrolo[3,4-b]pyridin-6-yl)ethanone, 4-{3-[2-(2,4-dimethyl-5,7-dihydro-6H-pyrrolo[3,4-b]pyridin-6-yl)-2-oxoethyl]azetidin-1-yl}pyridine-2-carbonitrile, 1-(2,4-dimethyl-5,7-dihydro-6H-pyrrolo[3,4-b]pyridin-6-yl)-2-[1-(2-methoxypyridin-4-yl)azetidin-3-yl]ethanone, 2-cyclopropyl-1-(2,4-dimethyl-5,7-dihydro-6H-pyrrolo[3,4-b]pyridin-6-yl)ethanone, formate salt, 1-(2,4-dimethyl-5,7-dihydro-6H-pyrrolo[3,4-b]pyridin-6-yl)-2-[1-(pyridin-4-yl)azetidin-3-yl]ethanone, 1-(2,4-dimethyl-5,7-dihydro-6H-pyrrolo[3,4-b]pyridin-6-yl)-2-[1-(pyrimidin-5-yl)azetidin-3-yl]ethanone, 1-(1,3,4-thiadiazol-2-yl)azetidin-3-yl 2,4-dimethyl-5,7-dihydro-6H-pyrrolo[3,4-b]pyridine-6-carboxylate, 1-(1,2,4-thiadiazol-5-yl)azetidin-3-yl 2-(difluoromethyl)-3,4-dimethyl-5,7-dihydro-6H-pyrrolo[3,4-b]pyridine-6-carboxylate, 1-(1,2,4-thiadiazol-5-yl)azetidin-3-yl 2,3,4-trimethyl-5,7-dihydro-6H-pyrrolo[3,4-b]pyridine-6-carboxylate, 1-(1,3,4-thiadiazol-2-yl)azetidin-3-yl 2,3,4-trimethyl-5,7-dihydro-6H-pyrrolo[3,4-b]pyridine-6-carboxylate, 1-(pyridin-3-yl)azetidin-3-yl 3-chloro-2-(methoxymethyl)-4-methyl-5,7-dihydro-6H-pyrrolo[3,4-b]pyridine-6-carboxylate, 1-(1,2,4-thiadiazol-5-yl)azetidin-3-yl 3-chloro-2,4-dimethyl-5,7-dihydro-6H-pyrrolo[3,4-b]pyridine-6-carboxylate;

1-(2,4-dimethyl-5,7-dihydro-6H-pyrrolo[3,4-b]pyridin-6-yl)-2-{1-[4-(3-methyloxetan-3-yl)phenyl]azetidin-3-yl}ethanone;

3-{3-[2-(2,4-dimethyl-5,7-dihydro-6H-pyrrolo[3,4-b]pyridin-6-yl)-2-oxoethyl]azetidin-1-yl}-4-methoxybenzonitrile;

4-{3-[2-(2,4-dimethyl-5,7-dihydro-6H-pyrrolo[3,4-b]pyridin-6-yl)-2-oxoethyl]azetidin-1-yl}-N,N-dimethylbenzamide;

1-(2,4-dimethyl-5,7-dihydro-6H-pyrrolo[3,4-b]pyridin-6-yl)-2-{1-[4-(hydroxymethyl)phenyl]azetidin-3-yl}ethanone;

2-[1-(4-cyclopropylphenyl)azetidin-3-yl]-1-(2,4-dimethyl-5,7-dihydro-6H-pyrrolo[3,4-b]pyridin-6-yl)ethanone;
2-(1-{4-[cyclopropyl(hydroxy)methyl]phenyl}azetidin-3-yl)-1-(2,4-dimethyl-5,7-dihydro-6H-pyrrolo[3,4-b]pyridin-6-yl)ethanone;
(5-{3-[2-(2,4-dimethyl-5,7-dihydro-6H-pyrrolo[3,4-b]pyridin-6-yl)-2-oxoethyl]azetidin-1-yl}-2-methoxyphenyl) acetonitrile;
4-{3-[2-(2,4-dimethyl-5,7-dihydro-6H-pyrrolo[3,4-b]pyridin-6-yl)-2-oxoethyl]azetidin-1-yl}-A/-methylbenzamide;
1-(2,4-dimethyl-5,7-dihydro-6H-pyrrolo[3,4-b]pyridin-6-yl)-2-[trans-2-(quinazolin-7-yl)cyclopropyl]ethanone;
1-(2,4-dimethyl-5,7-dihydro-6H-pyrrolo[3,4-b]pyridin-6-yl)-2-[trans-2-phenylcyclopropyl]ethanone;
1-(2,4-dimethyl-5,7-dihydro-6H-pyrrolo[3,4-b]pyridin-6-yl)-2-(1-phenyl azetidin-3-yl)ethanone; and
an N-oxide thereof, or a pharmaceutically acceptable salt thereof or pharmaceutically acceptable salt of the N-oxide.

In certain other embodiments, the present invention is directed to the use of the compounds, or N-oxide, or pharmaceutically acceptable salt of any one the compounds of the present invention in the treatment of an M4-mediated (or M4-associated) disease or disorder.

In certain other embodiments, the present invention is directed to a method for treating an M4-mediated (or M4-associated) disease or disorder in a patient, said method comprising administering to the patient a therapeutically effective amount of a compound, or N-oxide, or pharmaceutically acceptable salt of any one the compounds of the present invention.

In certain embodiments, the compounds of the present invention are M4 receptor agonists, wherein the compound has a binding affinity for and induces an effect on the M4 receptor absent the presence of a native ligand (e.g. acetylcholine).

In certain other embodiments, the compounds of the present invention are positive allosteric modulators (PAM) of the M4 receptor, wherein the compound has a binding affinity for and induces an effect on the receptor in the presence of a suboptimal concentration of native ligand (e.g., acetylcholine).

In another embodiment, the compounds of the present invention induce M4 agonist and M4 PAM activity.

In certain other embodiments, the present invention is directed to the use mentioned above wherein the M4-mediated (or M4-associated) disease or disorder is a disease or disorder selected from the group consisting of Alzheimer's Disease, schizophrenia, pain, addiction, a sleep disorder, a cognitive disorder (e.g. mild cognitive impairment, age-related mild cognitive impairment, and amnestic mild cognitive impairment), Parkinson's Disease, Huntington's Disease, dyskinesia, dry mouth, pulmonary hypertension, chronic obstructive pulmonary disease (COPD), asthma, urinary incontinence, glaucoma, Trisomy 21 (Down Syndrome), cerebral amyloid angiopathy, dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, and atherosclerosis.

In certain embodiments, the M4-mediated (or M4-associated) disease or disorder is a disease or disorder selected from the group consisting of Alzheimer's Disease, Parkinson's Disease, Huntington's Disease, schizophrenia, pain, addiction, and a sleep disorder.

The present invention also provides compositions (e.g., pharmaceutical compositions) comprising a novel compound of the present invention. Accordingly, in one embodiment, the invention provides a pharmaceutical composition comprising (a therapeutically effective amount of) a novel compound of the present invention and optionally comprising a pharmaceutically acceptable carrier. In one further embodiment, the invention provides a pharmaceutical composition comprising (a therapeutically effective amount of) a compound of the invention, optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

Pharmacology

The muscarinic acetylcholine receptor M4 (also known as muscarinic 4 or CHRM4) is a protein in humans that is encoded for the CHRM4 gene. M4 receptors are predominantly expressed in the brain. Key regions of the brain where M4 receptor expression occurs are the striatum, cortex, and hippocampus with the highest expression occurring in the striatum (approx. 46%) where M4 is the major muscarinic subtype. M4 is sporadically expressed in the periphery (e.g., testis, skin and colon).

M4 receptors are coupled to $G_{q/i}$ proteins and function as inhibitory autoreceptors in the striatum and midbrain (Zhang et al. 2002; Tzavara et al. 2004), and as postsynaptic modulatory receptors in the striatum, neocortex and hippocampus (Levy et al. 1991; Zhang et al. 1997). M4 receptors are also found presynaptically on glutamatergic synapses from cortex to striatum (Pancani, T., et al., "Allosteric activation of M4 improve behavioral and physiological alterations in early symptomatic YAC128 mice", Proceedings of the National Academy of the Sciences of the United States of America, 2015 Nov. 10; 112(45):14078-83), and on hippocampal glutamate neurons (where presynaptic M4 modulates glutamate release. The highest expression of M4 receptors is found in the striatum, M4 receptors also possess a regulatory effect on dopaminergic neurotransmission, and are coexpressed with D1 dopamine receptors in a subset of striatal medium spiny neurons which contain GABA as a major neurotransmitter (Bernard et al. 1992; Di Chiara et al. 1994; Ince et al. 1997).

It has been hypothesized that administration of a selective M4 agonist would provide antipsychotic activity for the treatment of schizophrenia (Felder et al. "Elucidating the Role of Muscarinic Receptors in Psychosis", Life Sci. 68:2605-2613, 2001). This belief was further supported by studies that demonstrated M4 receptors modulate the dynamics of dopaminergic and cholinergic neurotransmission and that a state of dopamine hyperfunctions results with a loss of M4 function (Tzavara et al., "M4 Muscarinic Receptors Regulate the Dynamics of Cholinergic and Dopaminergic Neurotransmission: relevance to the pathophysiology and treatment of related CNS pathologies" FASEB J. 18:1410-1412, 2004).

More recently, work conducted on the discovery of highly selective M4 positive allosteric modulators has helped support the hypothesis that selective activation of the M4 receptors may provide a novel approach for treating some of the symptoms associated with schizophrenia, and this work also raises the possibility that M4 selective modulators may also provide a treatment for other disorders where dopaminergic function is altered in the basal ganglia (e.g., Parkinson's Disease and dystonia) (Brady, et al., "Centrally Active Allosteric Potentiators of the M4 Muscarinic Acetylcholine Receptor Reverse Amphetamine-Induced Hyperlocomotor Activity in Rats", The Journal of Pharmacology and Experimental Therapeutics, Vol. 327, No. 3). Additional work with M1- and M4-selective modulators also suggests that selective activation of M4 receptors can provide viable therapeutic agents for safely and effectively treating Alzheimer's Disease and Schizophrenia.

The compounds of the present invention may also be useful for treating/alleviating the neuropsychiatric symptoms (i.e., behavioral symptoms) associated with Alzheimer's Disease and Schizophrenia (Foster, Daniel J. et. al., "Activation of M1 and M4 muscarinic receptors as potential treatments for Alzheimer's disease and schizophrenia", Neuropsychiatric Disease and Treatment, Volume 2014:10, pp. 183-191). These behavioral symptoms include, but are not limited to, agitation, anxiety, irritability, combativeness, disorientation, illusion, delusion, apathy, depression, disinhibition, aberrant motor and obsessive-compulsive behaviors, as well as sleep disorders (Dillon, Carol, et. al. "Behavioral symptoms related to cognitive impairment", Neuropsychiatric Disease and Treatment 2013:9 1443-1455). By treating/alleviating the above-mentioned behavioral symptoms, it is believed that the compounds of the present invention will also enhance cognition.

In view of the above, the compounds of the present invention may be useful for the treatment of schizophrenia and Alzheimer's Disease. The compounds of the present invention may also be useful for the treatment of Parkinson's Disease, Huntington's Disease, addiction, depression and epilepsy.

It is believed the M4 selective activators of the present invention may also have a wide range of other therapeutic applications for the treatment of conditions or diseases of the central nervous system which include neurologic, neurodegenerative and/or psychiatric disorders. Neurologic, neurodegenerative and/or psychiatric disorders include but are not limited to, (1) mood [affective] disorders; (2) neurotic, stress-related and somatoform disorders including anxiety disorders; (3) disorders comprising the symptom of cognitive deficiency in a mammal, including a human; (4) disorders comprising attention deficits, executive function deficits (working memory deficits), dysfunction of impulse control, extrapyramidal symptoms, disorders that are based on a malfunction of basal ganglia, hippocampus and prefrontal cortex; (5) behavioral and emotional disorders with onset usually occurring in childhood and adolescence; (6) disorders of psychological development; (7) systemic atrophies primarily affecting the central nervous system; (8) extrapyramidal and movement disorders; (9) behavioral syndromes associated with physiological disturbances and physical factors; (10) disorders of adult personality and behavior; (11) schizophrenia and other psychotic disorders; (12) mental and behavioral disorders due to psychoactive substance use; (13) sexual dysfunction comprising excessive sexual drive; (14) mental retardation; (15) factitious disorders, e.g., acute hallucinatory mania; (16) episodic and paroxysmal disorders, epilepsy; (17) narcolepsy; (18) dementia, and (19) amyotrophic lateral sclerosis.

Examples of mood [affective] disorders that can be treated according to the present invention include, but are not limited to, bipolar disorder I, hypomania (manic and mixed form), bipolar disorder II; depressive disorders such as single depressive episode or recurrent major depressive disorder, chronic depression, psychotic depression, minor depressive disorder, depressive disorder with postpartum onset, depressive disorders with psychotic symptoms; persistent mood [affective] disorders such as cyclothymia, dysthymia, euthymia; premenstrual syndrome (PMS) and premenstrual dysphoric disorder.

Examples of neurotic, stress-related and somatoform disorders that can be treated according to the present invention include, but are not limited to, anxiety disorders, social anxiety disorder, general anxiety disorder, panic disorder with or without agoraphobia, specific phobia, social phobia, chronic anxiety disorders; obsessive compulsive disorder; reaction to severe stress and adjustment disorders, such as post-traumatic stress disorder (PTSD), acute stress disorder; other neurotic disorders such as depersonalization-derealization syndrome.

The phrase "cognitive deficiency" as used herein and "disorders comprising the symptom of cognitive deficiency" refers to a subnormal functioning or a suboptimal functioning in one or more cognitive aspects such as memory, intellect, learning and logic ability, or attention and executive function (working memory) in a particular individual comparative to other individuals within the same general age population.

Examples of "disorders comprising the symptom of cognitive deficiency" that can be treated according to the present invention include, but are not limited to, cognitive deficits primarily but not exclusively related to amnesia, psychosis (schizophrenia), Parkinson's disease, Alzheimer's Disease, multi-infarct dementia, senile dementia, Lewis body dementia, stroke, frontotemporal dementia, progressive supranuclear palsy, Huntington's disease, HIV disease (HIV-associated dementia), cerebral trauma and drug abuse; mild cognitive disorder ADHD, Asperger's syndrome, and age-associated memory impairment; cognitive decline or delerium post-operative or in association with intensive care therapy.

Examples of disorders usually first diagnosed in infancy, childhood and adolescence that can be treated according to the present invention include, but are not limited to, hyperkinetic disorders including disturbance of activity and attention, attention deficit/hyperactivity disorder (ADHD), hyperkinetic conduct disorder; attention deficit disorder (ADD); conduct disorders, including but not limited to depressive conduct disorder; tic disorders including transient tic disorder, chronic motor or vocal tic disorder, combined vocal and multiple motor tic disorder (Gilles de la Tourette's syndrome), substance-induced tic disorders; autistic disorders; Batten disease, excessive masturbation, nail-biting, nose-picking and thumb-sucking.

Examples of disorders of psychological development that can be treated according to the present invention include, but are not limited to pervasive developmental disorders, including but not limited to Asperger's syndrome and Rett syndrome, autistic disorders, childhood autism and overactive disorder associated with mental retardation and stereotyped movements, specific developmental disorder of motor function, specific developmental disorders of scholastic skills.

Examples of systemic atrophies primarily affecting the central nervous system that can be treated according to the present invention include, but are not limited to, multiple sclerosis systemic atrophies primarily affecting the basal ganglia including Huntington's disease, and amyotrophic lateral sclerosis.

Examples of extrapyramidal and movement disorders with malfunction and/or degeneration of basal ganglia that can be treated according to the present invention include, but are not limited to, Huntington's disease; Parkinson's disease; second Parkinsonism such as postencephalitic Parkinsonism; Parkinsonism comprised in other disorders; Niemann-Pick disease, Lewy body disease; degenerative diseases of the basal ganglia; other extrapyramidal and movement disorders including tremor, essential tremor and drug-induced tremor, myoclonus, chorea and drug-induced chorea, drug-induced tics and tics of organic origin, drug-induced acute dystonia, drug-induced tardive dyskinesia, muscular spasms and disorders associated with muscular spasticity or weakness including tremors; mental deficiency (including spasticity, Down syndrome and fragile X syndrome), L-dopa-induced dyskinesia; restless leg syndrome and Stiffman syndrome.

Further examples of movement disorders with malfunction and/or degeneration of basal ganglia that can be treated according to the present invention include, but are not limited to, dystonia including but not limited to focal dystonia, multiple-focal or segmental dystonia, torsion dystonia, hemispheric, generalized and tardive dystonia (induced by psychopharmacological drugs). Focal dystonia include cervical dystonia (torticolli), blepharospasm (cramp of the eyelid), appendicular dystonia (cramp in the extremities, like the writer's cramp), or mandibular dystonia and spasmodic dysphonia (cramp of the vocal cord); neuroleptic-induced movement disorders including but not limited to neuroleptic malignant syndrome (NMS), neuroleptic-induced Parkinsonism, neuroleptic-induced early onset or acute dyskinesia, neuroleptic-induced acute dystonia, neuroleptic-induced acute akathisia, neuroleptic-induced tardive dyskinesia, and neuroleptic-induced tremor.

Examples of behavioral syndromes associated with physiological disturbances and physical factors according to the present invention include, but are not limited to, nonorganic sleep disorders, including but not limited to nonorganic hypersomnia, nonorganic disorder of the sleep-wake schedule (circadian rhythm sleep disorder), insomnia, parasomnia and sleep deprivation; mental and behavioral disorders associated with the puerperium including postnatal and postpartum depression; eating disorders, including but not limited to anorexia nervosa, bulimia nervosa, binge eating disorder, hyperphagia, obesity, compulsive eating disorders and pagophagia.

Examples of disorders of adult personality and behavior that can be treated according to the present invention include, but are not limited to, personality disorders, including but not limited to emotionally unstable, borderline, obsessive-compulsive, anankastic, dependent and passive-aggressive personality disorder; habit and impulse disorders (impulse-control disorder) including intermittent explosive disorder, pathological gambling, pathological fire-setting (pyromania), pathological stealing (kleptomania), trichotillomania; Munchausen syndrome.

Examples of schizophrenia and other psychotic disorders that can be treated according to the present invention include, but are not limited to, continuous or episodic schizophrenia of different types (for instance paranoid, hebephrenic, catatonic, undifferentiated, residual, and schizophreniform disorders); schizotypal disorders (such as borderline, latent, prepsychotic, prodromal, pseudoneurotic pseudopsychopathic schizophrenia and schizotypal personality disorder); persistent delusional disorders; acute, transient and persistent psychotic disorders; induced delusional disorders; schizoaffective disorders of different type (for instance manic depressive or mixed type); puerperal psychosis and other and unspecified nonorganic psychosis such as social withdrawal in schizophrenia.

Examples of mental and behavioral disorders due to psychoactive substance use that can be treated according to the present invention include, but are not limited to, mental and behavioral disorders due to use of alcohol, opioids, cannabinoids, sedatives or hypnotics, cocaine; mental and behavioral disorders due to the use of other stimulants including caffeine, mental and behavioral disorders due to drug dependence and abuse (e.g., narcotic dependence, alcoholism, amphetamine and methamphetamine dependence, opioid dependence, cocaine addiction, nicotine dependence, and drug withdrawal syndrome, and relapse prevention), use of hallucinogens, tobacco (nicotine), volatile solvents and mental and behavioral disorders due to multiple drug use and use of other psychoactive substances including the following subtype symptoms: harmful use, dependence syndrome, withdrawal state, and withdrawal state with delirium.

Examples of dementia that can be treated according to the present invention include, but are not limited to, vascular dementia, dementia due to Creutzfeld-Jacob disease, HIV, head trauma, Parkinson's, Huntington's, Pick's disease, dementia of the Alzheimer's type.

In certain embodiments, the present invention is directed to the use of the compounds of the present invention for the treatment of schizophrenia by administration of a therapeutically effective amount of a compound of the present invention to a patient in need thereof.

In certain other embodiments, the invention is further directed to the use of the compounds of the present invention for the treatment of cognitive impairment associated with schizophrenia by administration of a therapeutically effective amount of a compound of the present invention to a patient in need thereof.

Schizophrenia or psychosis for which the compounds, N-oxide thereof, and pharmaceutically acceptable salts of the foregoing of the invention may be useful includes one or more of the following conditions: schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthesia, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's Disease and post-traumatic stress syndrome), including both the positive and the negative symptoms of schizophrenia and other psychoses; cognitive disorders including dementia (associated with Alzheimer's Disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders, or age related cognitive decline.

In addition to the central nervous system disorders mentioned above, the compounds of the present invention may be used to treat other M4-mediated (or M4-associated) disorders such as, but not limited to, addiction (e.g. substance addiction such as addiction to opioids, cocaine, or alcohol), pain (e.g. acute pain, inflammatory pain, and neuropathic pain), and a sleep disorder (such as those related to REM sleep regulation, for example, those related to REM sleep onset). Additional M4-mediated (or M4-associated) disorders or conditions that may be treated by the compounds of the invention include, dry mouth, a cognitive disorder (e.g. mild cognitive impairment), dyskinesia, pulmonary hypertension, chronic obstructive pulmonary disease (COPD), asthma, urinary incontinence, glaucoma, Trisomy 21 (Down Syndrome), cerebral amyloid angiopathy, dementia (e.g. degenerative dementia), Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, and atherosclerosis. See e.g. U.S. Pat. No. 8,664,234.

Potential sleep disorders for which the compounds, N-oxide thereof, and pharmaceutically acceptable salts of the foregoing of the invention may be useful include: enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds, N-oxide thereof, and pharmaceutically acceptable salts of the foregoing of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, tenosynovitis and gout), headache, migraine and cluster headache, headache, primary hyperalgesia, secondary hyperalgesia, primary allodynia, secondary allodynia, or other pain caused by central sensitization.

The compounds, N-oxides thereof, and pharmaceutically acceptable salts of the foregoing of the invention may be used to decrease tolerance and/or dependence to opioid treatment of pain, and for treatment of withdrawal syndrome of e.g., alcohol, opioids, and cocaine.

Formulations

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be formulated such that administration topically to the skin or mucosa (i.e., dermally or transdermally) leads to systemic absorption of the compound. In another embodiment, the compounds of the invention can also be formulated such that administration intranasally or by inhalation leads to systemic absorption of the compound. In another embodiment, the compounds of the invention may be formulated such that administration rectally or vaginally leads to systemic absorption of the compound.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically (e.g., intranasal or ophthalmic).

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of the present invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents, and include depot formulations.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of an M4 activator compound of the present invention and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the present invention or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of the present invention, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-ß (or fragments thereof), such as $Aß_{1-15}$ conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the *Gingko biloba* extract EGb-761 (ROKAN, TEBONIN), tramiprosate (CEREBRIL, ALZHEMED), eprodisate (FIBRILLEX, KIACTA), compound W [3,5-bis(4-nitrophenoxy)benzoic acid], NGX-96992, neprilysin (also known as neutral endopeptidase (NEP)), scylloinositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANS-DERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxapine, risperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN); (xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-N-ethyl-3-fluoro-3-[3-fluoro-4-(pyrrolidin-1-ylmethyl)phenyl]-cyclobutanecarboxamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURINETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-(benzyloxy)-5-[(5-undecyl-2H-pyrrol-2-ylidene)methyl]-1H,1'H-2,2'-bipyrrole (also known as PNU-156804);

(xxi) interferons, including interferon beta-1a (AVONEX, REBIF) and interferon beta-1 b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERES0TAT), gavestinel, and remacimide;

(xxiv) monoamine oxidase (MAO) inhibitors, such as selegiline (EMSAM), selegiline hydrochloride (l-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, riluzole, N-hydroxy-1,2,4,9-tetrahydro-3H-carbazol-3-imine, desmoteplase, anatibant, astaxanthin, neuropeptide NAP (e.g., AL-108 and AL-208; both Allon Therapeutics), neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-ß-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, $R^{3487}$ (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEGUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors; (h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitors such as 2-({4-[1-methyl-4-(pyridin-4-yl)-1H-pyrazol-3-yl]phenoxy}methyl)quinolin-3(4H)-one and SCH-1518291; and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSI- PHEN), LSN-2434074 (also known as LY-2434074), KMI-574, SCH-745966, Ac-rER ($N^2$-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[(2S)-3-ethyl-1-hydroxypentan-2-yl]benzenesulfonamide;

(xxxiii) serotonin (5-hydroxytryptamine) 1A ($5\text{-}HT_{1A}$) receptor antagonists, such as spiperone, levo-pindolol, BMY 7378, NAD-299, S-(–)-UH-301, NAN 190, lecozotan; (xxxiv) serotonin (5-hydroxytryptamine) 2C ($5\text{-}HT_2c$) receptor agonists, such as vabicaserin and zicronapine;

(xxxv) serotonin (5-hydroxytryptamine) 4 ($5\text{-}HT_4$) receptor agonists, such as PRX-03140 (Epix);

(xxxvi) serotonin (5-hydroxytryptamine) 6 ($5\text{-}HT_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, N-{(3S,4S)-4-[4-(5-cyanothiophen-2-yl)phenoxy]tetrahydro-furan-3-yl}propane-2-sulfonamide, and the like.

(xli) Janus kinase inhibitors (JAK) such as, but not limited to, tofacitinib, ruxolitinib, baricitinib, CYT387, GLPG0634, lestaurtinib, pacritinib, and TG101348.

(xlii) Interleukin-1 receptor-associated kinase 4 inhibitors (IRAK4) such as, but not limited to, PF-06650833.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

As noted above, the compounds of the present invention may be used in combination with one or more additional anti-schizophrenia agents which are described herein. When a combination therapy is used, the one or more additional anti-schizophrenia agents may be administered sequentially or simultaneously with the compound of the invention. In one embodiment, the additional anti-schizophrenia agent is administered to a mammal (e.g., a human) prior to administration of the compound of the invention. In another embodiment, the additional anti-schizophrenia agent is administered to the mammal after administration of the compound of the invention. In another embodiment, the additional anti-schizophrenia agent is administered to the mammal (e.g., a human) simultaneously with the administration of the compound of the invention (or an N-oxide thereof or a pharmaceutically acceptable salt of the foregoing).

The invention also provides a pharmaceutical composition for the treatment of schizophrenia in a mammal, including a human, which comprises an amount of a compound of the present invention (including an N-oxide thereof or a salt of the compound or the N-oxide), as defined above (including hydrates, solvates and polymorphs of said compound or pharmaceutically acceptable salts thereof), in combination with one or more (for example one to three) anti-schizophrenia agents such as ziprasidone, risperidone, olanzapine, quetiapine, aripiprazole, asenapine, blonanserin, or iloperidone, wherein the amounts of the active agent and the combination when taken as a whole are therapeutically effective for treating schizophrenia.

The invention also provides a pharmaceutical composition for treating an M4-mediated (or M4-associated) disease or disorder in a mammal, including a human, which comprises an amount of a compound of the present invention (including an N-oxide thereof or a salt of the compound or the N-oxide), as defined above (including hydrates, solvates and polymorphs of said compound N-oxide or a pharmaceutically acceptable salt of the foregoing), in combination with one or more (for example one to three) other agents for treating the M4-mediated (or M4-associated) disease or disorder, wherein the amount of the active agents and the combination when taken as a whole are therapeutically effective for treating the M4-mediated (or M4-associated) disease or disorder.

It will be understood that the compounds of the present invention depicted above (Formula I, Formula Ia and Formula Ib) are not limited to a particular stereoisomer (e.g. enantiomer or atropisomer) shown, but also include all stereoisomers and mixtures thereof.

General Schemes

The compounds of the invention, or their pharmaceutically acceptable salts, OR tautomers and radioisotopes may be prepared by a variety of methods that are analogously known in the art. The reaction schemes described below, together with synthetic methods known in the art of organic chemistry, or modifications and derivatizations that are familiar to those of ordinary skill in the art, illustrate a method for preparing the compounds. Others, including modifications thereof, will be readily apparent to one skilled in the art. Unless otherwise indicated, the substituents in the Schemes are defined as above. Isolation and purification of the products is accomplished by standard procedures, which are known to a chemist of ordinary skill.

The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999; and T. W. Greene and P. G. M. Wuts, Protective Groups in Organic Chemistry, John Wiley & Sons, 2006, which are hereby incorporated by reference.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high-performance liquid chromatography (HPLC) or thin-layer chromatography (TLC).

One skilled in the art will recognize that in some cases, the compounds in Schemes 1-9 will be generated as a mixture of diastereomers and/or enantiomers; these may be separated at various stages of the synthetic Scheme using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the Scheme, methods and examples are used for convenience of representation and/or to reflect the order in which they are introduced in the Scheme, and are not intended to necessarily correspond to the symbols, superscripts or subscripts in the appended claims. The Scheme is representative of methods useful in synthesizing the compounds of the present invention. They are not to constrain the scope of the invention in any way.

Compounds of the invention and intermediates thereof may be prepared according to the following reaction schemes and accompanying discussion. Unless otherwise indicated, $R^1$, $R^2$, L, A, E and structural Formula I in the reaction schemes and discussion that follow are as defined above. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

Scheme 1

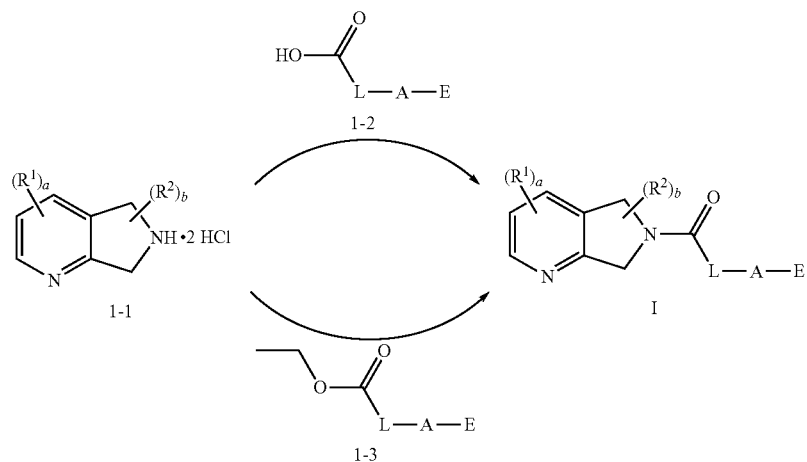

Scheme 1 refers to one synthetic sequence for the preparation of compounds of Formula I, as depicted above. Referring to Scheme 1, amines of Formula 1-1, carboxylic acids of Formula 1-2 and esters of Formula 1-3, wherein $R^1$, $R^2$, a, b, L, A, and E are as described above, are either commercially available or can be obtained by the methods described herein in subsequent schemes.

A compound of Formula I can be prepared by reacting an amine of Formula 1-1 with a carboxylic acid of Formula 1-2 under amide coupling conditions well known in the art, typically involving a suitable activating reagent, such as O-(7-azabenzotriazol-1-yl)-N,N,N',N'-tetramethyluronium hexafluorophosphate (HATU) or 1,1'-carbonyldiimidazole, with or without a suitable base, e.g., N,N-diisopropylethylamine, and in a suitable solvent, such as N,N-dimethylformamide (DMF) and tetrahydrofuran (THF). Alternatively, a compound of Formula I can be prepared by direct coupling of an amine of Formula 1-1 and an ester of Formula 1-3, under reaction conditions such as heating with 1,3,4,6,7,8-hexahydro-2H-pyrimido[1,2-a]pyrimidine in a suitable solvent, such as DMF, or treatment with trimethylaluminum in a suitable solvent, such as 1,2-dichloroethane, at reaction temperatures ranging from 50° C. to 100° C. During either of these amide formation reaction steps, the $R^1$, $R^2$, a and b substituents of the amine of Formula 1-1, and the L, A and E substituents of the carboxylic acids of Formula 1-2 and the esters of Formula 1-3 should be represented by the same moiety as is desired in the final product, Formula I, or a protected variation thereof.

Scheme 2

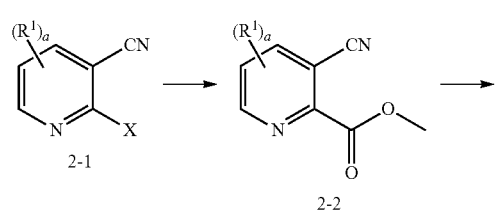

Scheme 2 refers to preparation of intermediates of Formula 2-5 that can be used in the amide formation reaction described in Scheme 1. Referring to Scheme 2, compounds of Formula 2-1, wherein $R^1$ and a are as described above and X is Cl, Br, or I, are either commercially available or can be obtained by methods well known in the art. An ester of Formula 2-2 can be prepared via carbonylation of a compound of Formula 2-1 in methanol under a pressure of carbon monoxide (e.g., 50 psi), in the presence of a suitable transition metal catalyst, such as [1,1'-bis(diphenylphosphino)ferrocene]dichloropalladium(II) [Pd(dppf)Cl₂], and a suitable base, such as triethylamine. During this step $R^1$ and a of Formula 2-1 should be represented by the same moiety as is desired in the final product, Formula I of Scheme I, or a protected variation thereof.

The nitrile group of a compound of Formula 2-2 can be converted to the corresponding primary amine, under conditions such as hydrogenation catalyzed by Raney nickel, which can react with the ester moiety in situ to give a lactam of Formula 2-3. A compound of Formula 2-4 can then be prepared in 2 steps involving a reduction of the lactam carbonyl group using a suitable reducing reagent, such as borane-dimethyl sulfide complex, in a suitable solvent, such as THF, and subsequent Boc-protection using di-tert-butyl dicarbonate in the presence of a suitable base, such as sodium hydroxide. An intermediate of Formula 2-5 can then be prepared via removal of the Boc protecting group using an excess of hydrogen chloride in a suitable solvent, such as methanol.

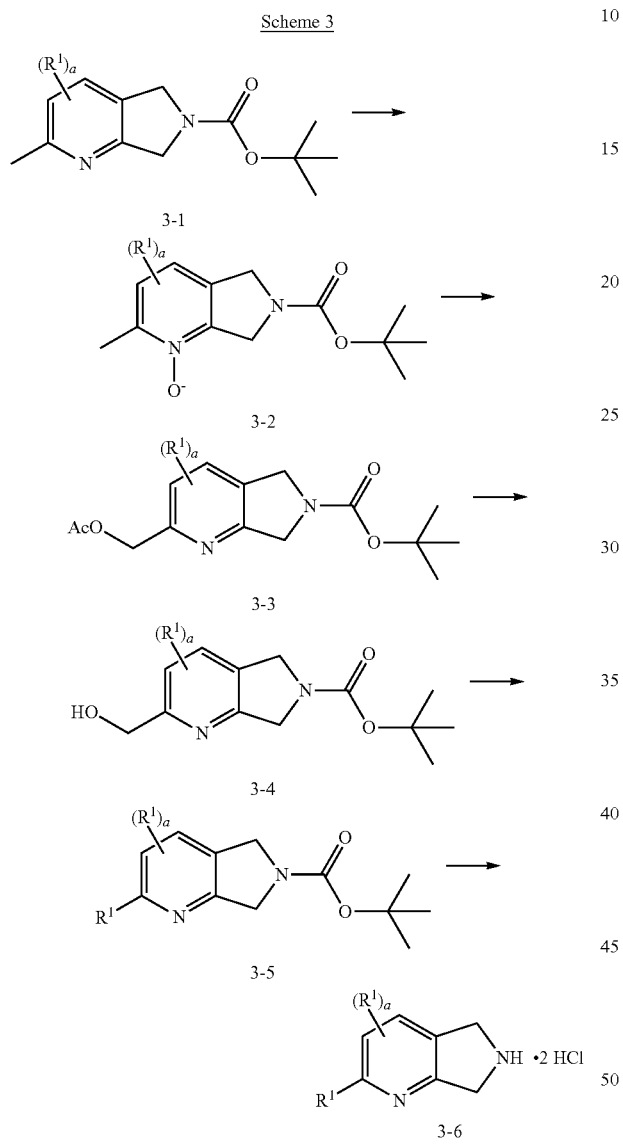

converted to the corresponding N-oxide of Formula 3-2 using a suitable oxidizing reagent, such as 3-chloroperoxybenzoic acid (m-CPBA) in a suitable solvent, such as dichloromethane. A compound of Formula 3-3 can be obtained by treating an N-oxide of Formula 3-2 with acetic anhydride at reaction temperatures ranging from 50° C. to 100° C.; the compound of Formula 3-3 can then be converted to the corresponding alcohol of Formula 3-4 under ester hydrolysis conditions well known in the art, such as exposure to an aqueous solution of sodium hydroxide. The primary alcohol moiety of a compound of Formula 3-4 can then be used as a synthetic handle to introduce substituent $R^1$ at the benzylic position via methods well known in the art to yield a compound of Formula 3-5. Finally, an intermediate of Formula 3-6 can then be prepared via removal of the Boc protecting group using an excess of hydrogen chloride in a suitable solvent, such as methanol.

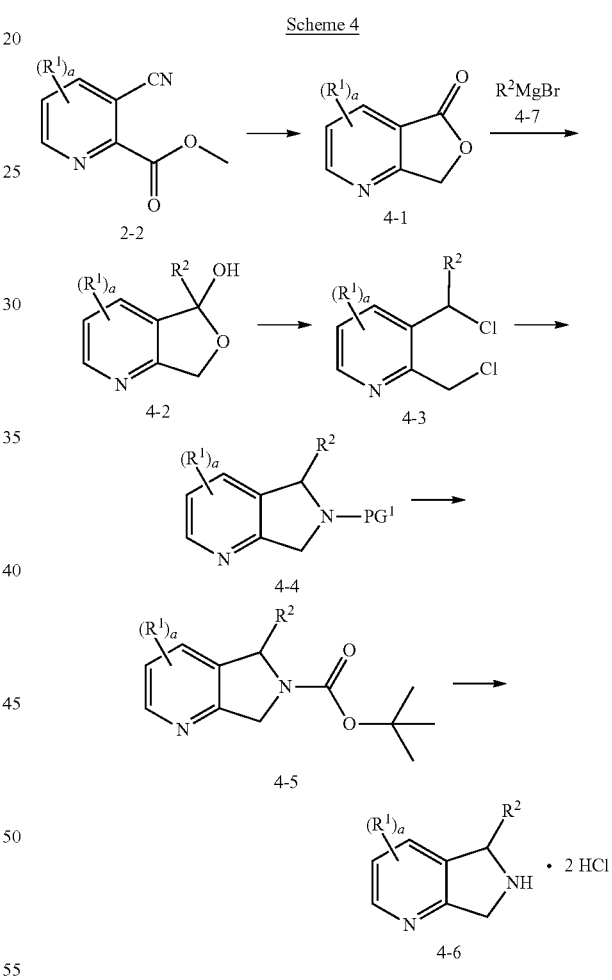

Scheme 3 refers to preparation of intermediates of Formula 3-6 that can be used in the amide formation reactions described in Scheme 1, wherein $R^1$ and a are as described above. For example, during this step $R^1$ and a of Formula 3-1 should be represented by the same moiety as is desired in the final product, Formula I of Scheme I, or a protected variation thereof. $R^1$ at the benzylic position of Formula 3-5 and Formula 3-6 represent substituents that can be easily derived from an alcohol at the benzylic position using methods well known in the art, such as, but not limited to, alkoxymethyl groups, aldehyde, carboxylic acid, esters, and fluorinated alkyl groups, such as fluoromethyl or difluoromethyl groups. Referring to Scheme 3, a compound of Formula 3-1 can be Scheme 4 refers to preparation of intermediates of Formula 4-6 that can be used in the amide formation reactions described in Scheme 1. Referring to Scheme 4, a compound of Formula 2-2 can be converted to a lactone of Formula 4-1 via reduction of the methyl ester moiety to the corresponding alcohol, using a suitable reducing reagent, such as sodium borohydride (NaBH$_4$), followed by lactone formation in the presence of concentrated sulfuric acid. During this step $R^1$ and a of Formula 2-2 should be represented by the same moiety as is desired in the final product, Formula I of Scheme I, or a protected variation thereof.

A lactol of Formula 4-2 can then be obtained via nucleophilic addition of a Grignard reagent of Formula 4-7, wherein $R^2$ is as described above, in a suitable solvent, such as THF. During this step $R^2$ of Formula 4-7 should be represented by the same moiety as is desired in the final product, Formula I of Scheme I, or a protected variation thereof.

A dichloro intermediate of Formula 4-3 can be prepared in two steps from a lactol of Formula 4-2 involving a reduction to the corresponding diol using a suitable reducing reagent, such as lithium aluminum hydride (LiAlH$_4$), and subsequent chlorination, using a suitable chlorination reagent such as thionyl chloride, in a suitable solvent, such as dichloromethane. A compound of Formula 4-4 can be obtained by condensation of a dichloro intermediate of Formula 4-3 with a suitable protected amine source (NH$_2$-PG$^1$) wherein PG$^1$ is a benzyl-based protecting group, such as 2,4-dimethoxyphenylmethyl amine. A compound of Formula 4-5 can be obtained via removal of PG$^1$ using conditions well known in the art and subsequent Boc protection using di-tert-butyl dicarbonate. Finally, an intermediate of Formula 4-6 can be obtained by removal of the Boc protecting group in the presence of an excess of hydrogen chloride in a suitable solvent, such as dichloromethane.

Scheme 5

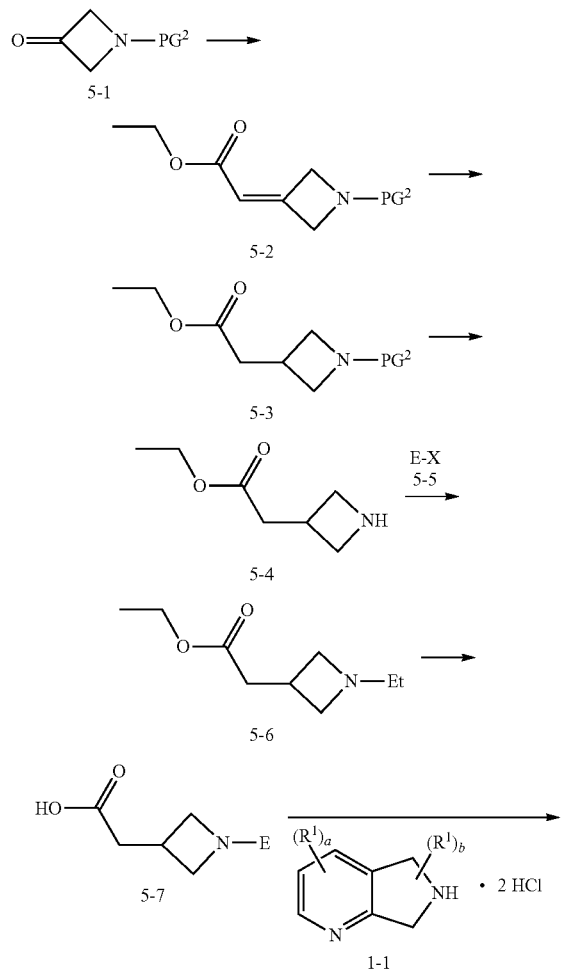

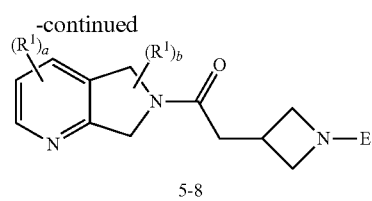

5-8

Scheme 5 refers to preparation of a compound of Formula 5-8. Referring to Scheme 5, a compound of Formula 5-1 is either commercially available or can be obtained by methods well known in the art, wherein PG$^2$ is a suitable protecting group such as Boc. A compound of Formula 5-1 can be converted to a compound of Formula 5-2 via Wittig olefination using a suitable reagent, such as (carboethoxymethylene)-triphenylphosphorane. A compound of Formula 5-3 can then be obtained via hydrogenation in the presence of a suitable catalyst, such as 10% palladium on carbon, in a suitable solvent, such as tert-butyl methyl ether. Upon removal of PG$^2$ using methods well known in the art, an azetidine intermediate of Formula 5-4 can be obtained. Suitable terminal substituents (E as described above) can be introduced via suitable coupling conditions well known in the art with a reagent of Formula 5-5, wherein E is as described above and X is Cl, Br, or I, to give compounds of Formula 5-6. During this step E of Formula 5-5 should be represented by the same moiety as is desired in the final product, Formula I of Scheme I, or a protected variation thereof. For example, when E is a heteroaryl and X is ortho- or para- to a heteroaryl nitrogen atom, the coupling reaction can be achieved via an S$_N$Ar reaction well known in the art, in the presence of a suitable base, such as triethylamine, and a suitable salt, such as cesium fluoride, in a suitable solvent, such as dimethyl sulfoxide (DMSO). In another example, wherein E is an aryl or heteroaryl and X is Cl, Br, or I not activated by a heteroaryl nitrogen, the coupling reaction can be achieved in the presence of a suitable catalyst, such as tris(dibenzylideneacetone)dipalladium(0) [Pd$_2$(dba)$_3$], a suitable ligand, such as 1,1'-binaphthalene-2,2'-diylbis(diphenylphosphane) (BINAP) and 4,5-bis(diphenylphosphino)-9,9-dimethylxanthene (Xantphos®), and a suitable base, such as cesium carbonate, in a suitable solvent, such as toluene and 1,4-dioxane. A compound of Formula 5-6 can then be converted to the corresponding carboxylic acid of Formula 5-7 via ester hydrolysis, using a suitable base such as sodium hydroxide or lithium hydroxide. A compound of Formula 5-8 can then be prepared from a carboxylic acid of Formula 5-7 and an amine of Formula 1-1 via amide formation as described in Scheme 1. During this step $R^1 \cdot R^2$, a and b of Formula 1-1 should be represented by the same moiety as is desired in the final product, Formula I of Scheme I, or a protected variation thereof.

Scheme 6

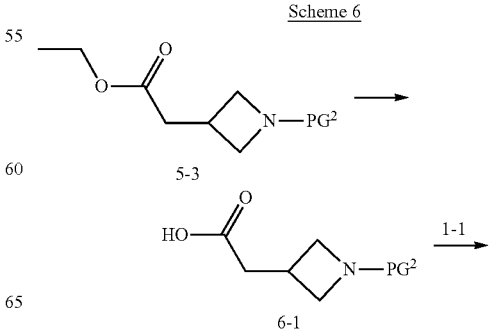

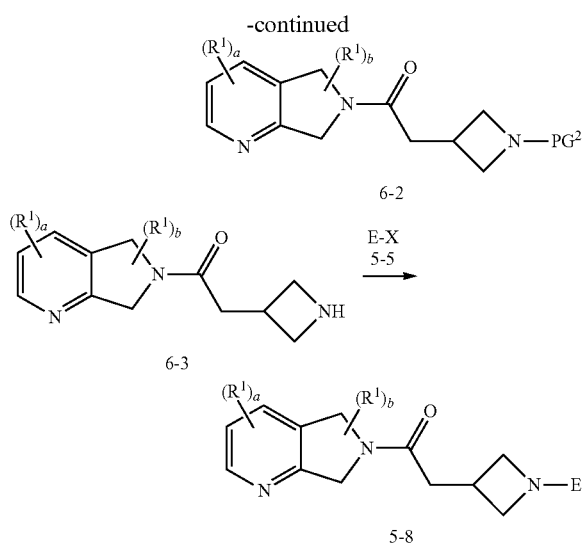

Scheme 6 refers to an alternative preparation of a compound of Formula 5-8. Referring to Scheme 6, a compound of Formula 5-3, wherein PG² is as described above, can be converted to the corresponding carboxylic acid of Formula 6-1, which can be coupled with an amine of Formula 1-1 using the conditions described in Scheme 1 to give a compound of Formula 6-2. During this step $R^1 \cdot R^2$, a and b of Formula 1-1 (see Scheme 1 above) should be represented by the same moiety as is desired in the final product, Formula I of Scheme I, or a protected variation thereof.

Protecting group PG² can be removed using methods well known in the art, to afford a compound of Formula 6-3, which can be converted to a compound of Formula 5-8 under the coupling conditions described in Scheme 5. During this step E of Formula 5-5 (see Scheme 5 above) should be represented by the same moiety as is desired in the final product, Formula I of Scheme I, or a protected variation thereof.

Scheme 7 refers to preparation of a compound of Formula 7-5, wherein R¹, R², a, b, and E are as described above. The compounds in this scheme are depicted as single enantiomers for illustration purposes only and they can be the racemate, or either enantiomer, or a mixture thereof. Referring to Scheme 7, a compound of Formula 7-1, wherein PG is a suitable silyl-based protecting group, such as a tert-butyl(dimethyl)silyl (TBDMS) group, and Z¹ is a boronic ester B(OR)₂ wherein each R is independently H or $C_{1-6}$ alkyl, or wherein the two OR groups, together with the B atom to which they are attached, form an optionally substituted 5- to 10-membered heterocycloalkyl, is either commercially available or can be obtained by methods well known in the art. A compound of Formula 7-1 can be converted to a compound of Formula 7-2 via a cyclopropanation reaction well known in the art. A typical procedure involves treating an alkene with a zincate species derived from diiodomethane and diethylzinc in the presence of a suitable acid such as trichloroacetic acid, in a suitable solvent, such as dichloromethane. A compound of Formula 7-3 can be prepared via a Suzuki coupling of a compound of Formula 7-2 and a reagent of Formula 5-5 (see Scheme 5 above), wherein E is an aryl or heteroaryl and X is Cl, Br, or I, in the presence of a suitable catalyst, such as palladium (II) acetate, and a suitable ligand, such as di(1-adamantyl)-n-butylphosphine (CataCXium® A), in the presence of a suitable base, such as cesium carbonate, and in a suitable solvent, such as 2-methylbutan-2-ol. During this step E of Formula 5-5 should be represented by the same moiety as is desired in the final product, Formula I of Scheme I, or a protected variation thereof.

Upon oxidation with a suitable reagent, such as sodium periodate, in the presence of a suitable catalyst, such as ruthenium(III) chloride, a compound of Formula 7-3 can be converted to the corresponding carboxylic acid of Formula 7-4, which in turn can be coupled with an amine of Formula 1-1 to give a compound of Formula 7-5 using the amide formation conditions described in Scheme 1. During this step $R^1 \cdot R^2$, a and b of Formula 1-1 (see Scheme 1 above)

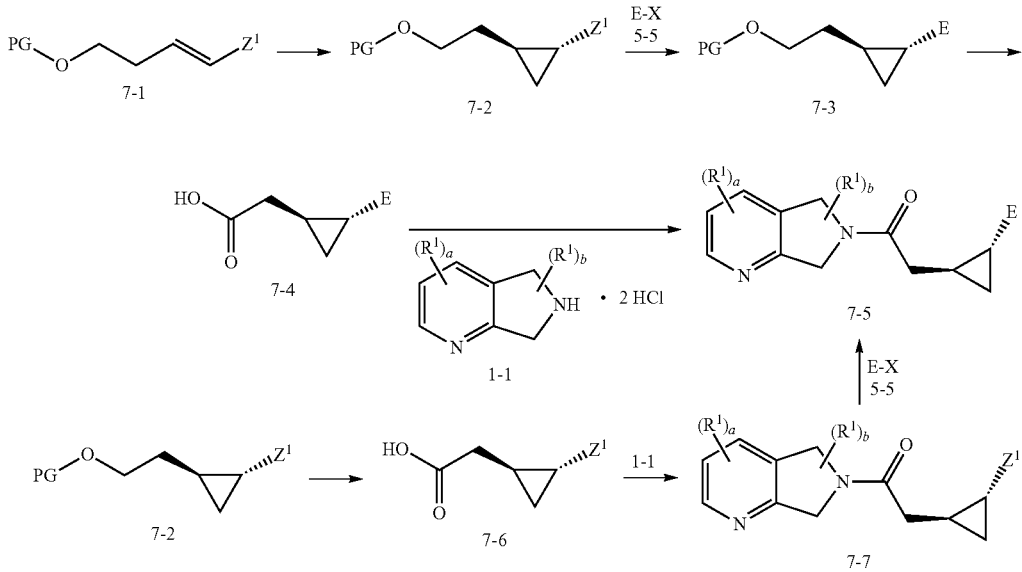

Scheme 7 should be represented by the same moiety as is desired in the final product, Formula I of Scheme I, or a protected variation thereof.

Alternatively, a compound of Formula 7-2 can be converted to the corresponding carboxylic acid 7-6 using the conditions described above, which can then be coupled with an amine of Formula 1-1 to afford a compound of Formula 7-7 via amide formation. During this step $R^1 \cdot R^2$, a and b of Formula 1-1 (see Scheme 1 above) should be represented by the same moiety as is desired in the final product, Formula I of Scheme I, or a protected variation thereof.

A compound of Formula 7-5 can then be obtained via coupling reaction of a compound of Formula 7-7 with a reagent of Formula 5-5 using the conditions described above.

carbonate, in a suitable solvent, such as toluene and 1,4-dioxane. During this step E of Formula 5-5 should be represented by the same moiety as is desired in the final product, Formula I of Scheme I, or a protected variation thereof.

The Boc protecting group can be removed using a suitable acid, such as trifluoroacetic acid, in a suitable solvent, such as dichloromethane, to give a compound of Formula 8-3, which can be converted to a compound of Formula 8-4 upon amide formation with an amine of Formula 1-1 using the conditions described in Scheme 1. During this step $R^1 \cdot R^2$, a and b of Formula 1-1 (see Scheme 1 above) should be represented by the same moiety as is desired in the final product, Formula I of Scheme I, or a protected variation thereof.

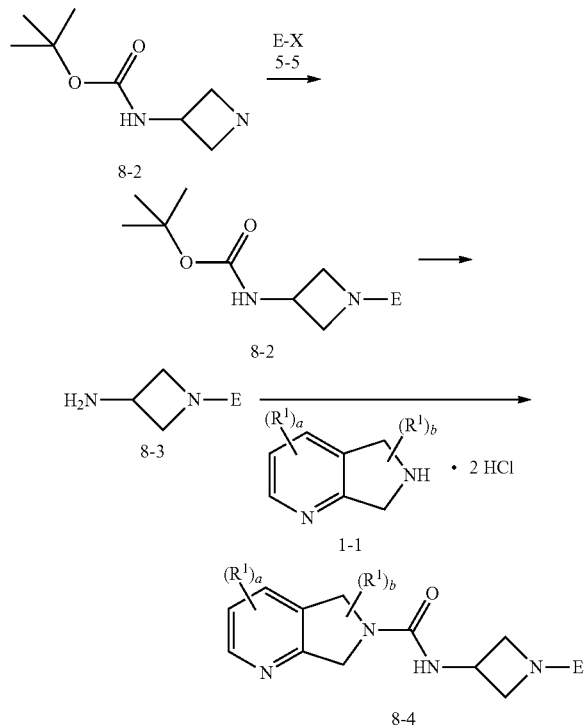

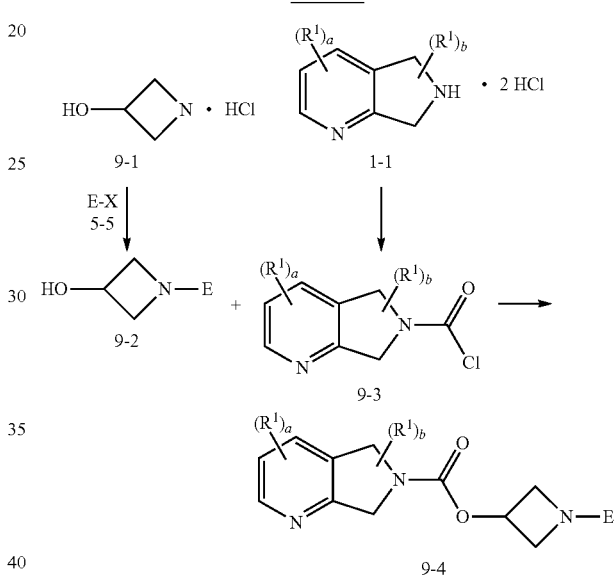

Scheme 8 refers to preparation of a compound of Formula 8-4, wherein $R^1$, $R^2$, a, b, and E are as described above. Referring to Scheme 8, a compound of Formula 8-2 can be prepared via coupling of tert-butyl azetidin-3-ylcarbamate (8-1) with a reagent of Formula 5-5 (see Scheme 5) wherein E is an aryl or heteroaryl and X is Cl, Br, or I. For example, when E is a heteroaryl and X is ortho- or para- to a heteroaryl nitrogen, the coupling reaction can be achieved via an $S_NAr$ reaction well known in the art, in the presence of a suitable base, such as triethylamine, and a suitable salt, such as cesium fluoride, in a suitable solvent, such as dimethyl sulfoxide (DMSO). In another example, wherein E is an aryl or heteroaryl and X is Cl, Br, or I not activated by a heteroaryl nitrogen, the coupling reaction can be achieved in the presence of a suitable catalyst, such as tris(dibenzylideneacetone)dipalladium(0) [Pd$_2$(dba)$_3$], a suitable ligand, such as 1,1'-binaphthalene-2,2'-diylbis(diphenylphosphane) (BINAP) and 4,5-bis(diphenylphosphino)-9,9-dimethylxanthene (Xantphos), and a suitable base, such as cesium Scheme 9 refers to preparation of a compound of Formula 9-4, wherein $R^1$, $R^2$, a, b, and E are as described above. Referring to Scheme 9, a compound of Formula 9-2 can be prepared via coupling of azetidin-3-ol, hydrochloride salt (9-1) with a reagent of Formula 5-5 (see Scheme 5 above) wherein E is an aryl or heteroaryl and X is Cl, Br, or I. For example, when E is a heteroaryl and X is ortho- or para- to a heteroaryl nitrogen atom, the coupling reaction can be achieved via an $S_NAr$ reaction well known in the art, in the presence of a suitable base, such as triethylamine, and a suitable salt, such as cesium fluoride, in a suitable solvent, such as dimethyl sulfoxide (DMSO). In another example, wherein E is an aryl or heteroaryl and X is Cl, Br, or I not activated by a heteroaryl nitrogen, the coupling reaction can be achieved in the presence of a suitable catalyst, such as tris(dibenzylideneacetone)dipalladium(0) [Pd$_2$(dba)$_3$], a suitable ligand, such as 1,1'-binaphthalene-2,2'-diylbis(diphenylphosphane) (BINAP) and 4,5-bis(diphenylphosphino)-9,9-dimethylxanthene (Xantphos), and a suitable base, such as cesium carbonate, in a suitable solvent, such as toluene and 1,4-dioxane. During this step E of Formula 5-5 should be represented by the same moiety as is desired in the final product, Formula I of Scheme I, or a protected variation thereof.

A compound of Formula 9-3 can be prepared from an amine of Formula 1-1 using bis(trichloromethyl) carbonate in the presence of a suitable base, such as pyridine, in a suitable solvent, such as dichloromethane. During this step $R^1 \cdot R^2$, a and b of Formula 1-1 (see Scheme 1 above) should be represented by the same moiety as is desired in the final product, Formula I of Scheme I, or a protected variation thereof.

A compound of Formula 9-4 can then be prepared via carbamate formation from an alcohol of Formula 9-2 and a compound of Formula 9-3 in the presence of a suitable base, such as sodium hydride, in a suitable solvent, such as THF.

Additional starting materials and intermediates useful for making the compounds of the present invention can be obtained from chemical vendors such as Sigma-Aldrich or can be made according to methods described in the chemical art.

Those skilled in the art can recognize that in all of the Schemes described herein, if there are functional (reactive) groups present on a part of the compound structure such as a substituent group, for example $R^1$, $R^2$, L, A, and E etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion (CN$^-$). For another example, an —S— can be oxidized to —S(=O)— and/or —S(=O)$_2$—. For yet another example, an unsaturated bond such as C=C or C≡C can be reduced to a saturated bond by hydrogenation. In some embodiments, a primary amine or a secondary amine moiety (present on a substituent group such as $R^1$, $R^2$, L, A, E, etc.) can be converted to an amide, sulfonamide, urea, or thiourea moiety by reacting it with an appropriate reagent such as an acid chloride, a sulfonyl chloride, an isocyanate, or a thioisocyanate compound. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^1$, $R^2$, L, A, and E, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an NH$_2$ group can be protected by a benzyloxycarbonyl (Cbz) or Boc group; conversion back to the NH$_2$ group can be carried out at a later stage of the synthetic process via deprotection.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, with mixed solvent systems, such as but limited to aqueous plus acetonitrile, either or both of which may contain additives such as trifluoroacetic acid, formic acid, concentrated ammonium hydroxide, or with supercritical fluid chromatography, carried out using a combination of carbon dioxide and an organic solvent such as methanol or acetonitrile, optionally containing an additive such as diethylamine or ammonium hydroxide, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well known to those of ordinary skill in the art.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art. In the following Examples and Preparations, "DMSO" means dimethyl sulfoxide, "N" where referring to concentration means Normal, "M" means molar, "ml." means milliliter, "mmol" means millimoles, "µmol" means micromoles, "eq." means equivalent, "° C." means degrees Celsius, "MHz" means megahertz, "HPLC" means high-performance liquid chromatography.

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich® Sure/Seal™ from Sigma-Aldrich, or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein. The following are abbreviations which may appear in the experimental procedures described herein:

9-BBN=9-borabicyclo[3.3.1]nonane; $BF_3 \cdot Et_2O$=boron trifluoride diethyl etherate; BINAP=1,1'-binaphthalene-2,2'-diylbis(diphenylphosphane); Boc=tert-butoxycarbonyl; br=broad; n-BuLi=n-butyllithium; t-BuONa=sodium tert-butoxide; t-ButylXPhos=di-tert-butyl[2',4',6'-tri(propan-2-yl)biphenyl-2-yl]phosphane; Bz=benzoyl; cataCXium® A=di(1-adamantyl)-n-butylphosphine; CDCl$_3$=deuterochloroform; CD$_3$OD=deuteromethanol; CF$_3$COOH=trifluoroacetic acid; d=doublet; dd=doublet of doublets; ddd=doublet of doublet of doublets; DBU=1,8-diazabicyclo[5.4.0]undec-7-ene; DCM=dichloromethane; DEPT=distortionless enhancement of polarization transfer; DMB=(2,4-dimethoxyphenyl)methyl; dppf=1,1'-bis(diphenylphosphino)ferrocene; EDC or EDCI=1-[3-(dimethylamino)propyl]-3-ethylcarbodiimide hydrochloride; EtOAc=ethyl acetate; EtOH=ethanol; g=gram; GCMS=gas chromatography-mass spectrometry; h=hour; H$_2$O=water; HATU=O-(7-azabenzotriazol-1-yl)-N,N,N',N'-tetramethyluronium hexafluorophosphate; HCl=hydrochloric acid; HPLC=high-performance liquid chromatography; Hz=hertz; K$_2$CO$_3$=potassium carbonate; KF=potassium fluoride; L=liter; LCMS=liquid chromatography mass spectrometry; m=multiplet; M=molar; m-CPBA=3-chloroperoxybenzoic acid; MeOH=methanol; mg=milligram; MHz=megahertz; min=minutes; mL=milliliter; μL=microliter; mmol=millimole; μmol=micromole; Mo(CO)$_6$=molybdenum hexacarbonyl; mol=mole; MPa=megapascal; N=normal; N$_2$=nitrogen; NaH=sodium hydride; NaHCO$_3$=sodium bicarbonate; NaOAc=sodium acetate; NaOt-Bu=sodium tert-butoxide; NaOCl=sodium hypochlorite; NaOH=sodium hydroxide; NaOMe=sodium methoxide; Na$_2$SO$_4$=sodium sulfate; NEt$_3$=triethylamine; NH$_4$Cl=ammonium chloride; NH$_2$OH·HCl=hydroxylamine hydrochloride; NMR=nuclear magnetic resonance; NOE=Nuclear Overhauser effect; Pd(Amphos)$_2$Cl$_2$=bis[di-tert-butyl(4-dimethylaminophenyl)phosphine]dichloropalladium(II); Pd$_2$(dba)$_3$=tris(dibenzylideneacetone)dipalladium(0); Pd(dppf)Cl$_2$=[1,1'-bis(diphenylphosphino)ferrocene]dichloropalladium(II); Pd(dtbpf)Cl$_2$=[1,1'-bis(di-tert-butylphosphino)-ferrocene]dichloropalladium(II); Pd(PCy$_3$)$_2$Cl$_2$=dichlorobis(tricyclohexyl-phosphine)palladium(II); PPh$_3$=triphenylphosphine; psi=pounds per square inch; q=quartet; rt=room temperature; s=singlet; T3P=2,4,6-tripropyl-1,3,5,2,4,6-trioxatriphosphinane 2,4,6-trioxide; TBAF=tetrabutylammonium fluoride; TEA=triethylamine; TEA·3HF=triethylamine trihydrofluoride; TFA=trifluoroacetic acid; THF=tetrahydrofuran; TLC=thin-layer chromatography; t=triplet; Xantphos=4,5-bis(diphenylphosphino)-9,9-dimethylxanthene.

Preparation P1

2,4-Dimethyl-6,7-dihydro-5H-pyrrolo[3,4-b]pyridine, Dihydrochloride Salt (P1)

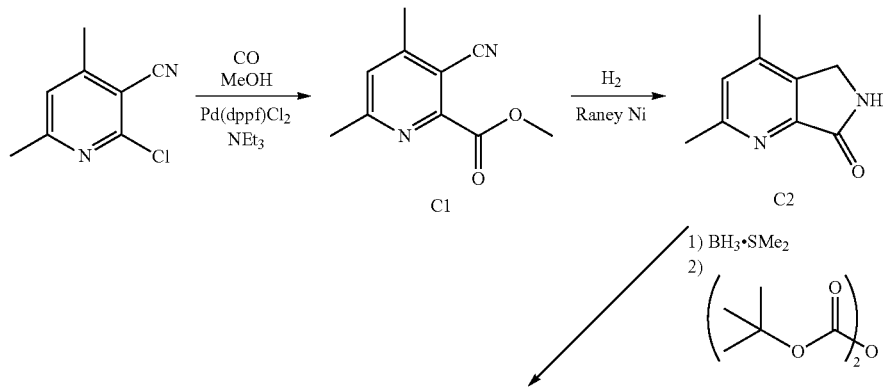

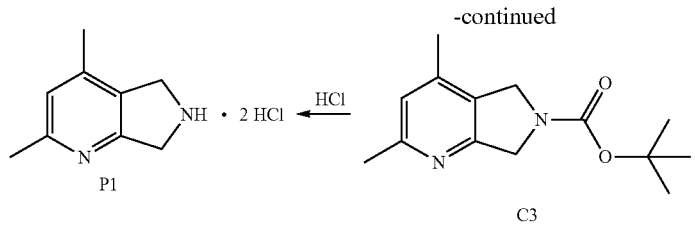

Step 1. Synthesis of methyl 3-cyano-4,6-dimethylpyridine-2-carboxylate (C1)

Triethylamine (547 g, 5.41 mol) and [1,1'-bis(diphenylphosphino)ferrocene]dichloropalladium(II) [Pd(dppf)Cl$_2$; 66 g, 90 mmol] were added to a solution of 2-chloro-4,6-dimethylpyridine-3-carbonitrile (300 g, 1.80 mol) in methanol (3.5 L). Carbon monoxide gas was bubbled into the reaction mixture, which was then pressurized to 50 psi with carbon monoxide and heated at 70° C. for 28 hours. After the reaction mixture had been filtered, the filtrate was concentrated in vacuo. Silica gel chromatography (Gradient: 25% to 50% ethyl acetate in petroleum ether) provided the product as a pale brown solid. Yield: 300 g, 1.6 mol, 89%. $^1$H NMR (400 MHz, CDCl$_3$) δ 7.34 (s, 1H), 4.06 (s, 3H), 2.68 (s, 3H), 2.61 (s, 3H).

Step 2. Synthesis of 2,4-dimethyl-5,6-dihydro-7H-pyrrolo[3,4-b]pyridin-7-one (C2)

Raney nickel (150 g, 1.75 mol) was added to a solution of C1 (300 g, 1.6 mol) in methanol (9 L), and the reaction mixture was stirred at 10° C. for 72 hours under 15 psi of hydrogen. The catalyst was removed via filtration, and the filtrate was concentrated in vacuo; the residue was purified by chromatography on silica gel (Eluents: 1:1 petroleum ether/ethyl acetate, followed by 20:1 dichloromethane/methanol) to afford the product as an off-white solid. Yield: 190 g, 1.17 mol, 73%. $^1$H NMR (400 MHz, CDCl$_3$) δ 7.86 (br s, 1H), 7.14 (s, 1H), 4.38 (s, 2H), 2.66 (s, 3H), 2.36 (s, 3H).

Step 3. Synthesis of tert-butyl 2,4-dimethyl-5,7-dihydro-6H-pyrrolo[3,4-b]pyridine-6-carboxylate (C3)

Borane-dimethyl sulfide complex (10 M solution in dimethyl sulfide; 92.5 mL, 925 mol) was added in a drop-wise manner to a 0° C. solution of C2 (30.0 g, 185 mmol) in tetrahydrofuran (500 mL). The reaction mixture was stirred at reflux (75° C.) for 18 hours, whereupon it was cooled to 0° C. and quenched via slow addition of methanol (200 mL), followed by aqueous hydrochloric acid (6 M, 500 mL). The resulting mixture was allowed to stir at reflux (70° C.) for 3 hours and was then cooled to room temperature. The pH of the solution was adjusted to 9-10 via addition of 2 M aqueous sodium hydroxide solution. Di-tert-butyl dicarbonate (80.7 g, 370 mmol) was then added, and the reaction mixture was stirred at room temperature for 16 hours. Solvent was removed in vacuo, and the residue was extracted with ethyl acetate (3×300 mL). The combined organic layers were washed with saturated aqueous sodium chloride solution (200 mL), dried over sodium sulfate, filtered, and concentrated under reduced pressure; silica gel chromatography (Gradient: 11% to 50% ethyl acetate in petroleum ether) afforded the product as an off-white solid, which contained a tetrahydrofuran-derived contaminant. From analysis of the $^1$H NMR, the product was presumed to exist as a mixture of rotamers. Yield: 36.0 g, 145 mmol, 78%. $^1$H NMR (400 MHz, CDCl$_3$), product peaks only: δ 6.84 (s, 1H), 4.65 (br s, 1H), 4.59 (s, 2H), 4.55 (br s, 1H), 2.48 (s, 3H), 2.21 (s, 3H), [1.50 (s) and 1.49 (s), total 9H].

Step 4. Synthesis of 2,4-dimethyl-6,7-dihydro-5H-pyrrolo[3,4-b]pyridine, Dihydrochloride Salt (P1)

A solution of hydrogen chloride in ethyl acetate (4.0 M, 141 mL, 564 mmol) was added drop-wise to a 0° C. solution of C3 (35.0 g, 141 mmol) in methanol (300 mL), and the reaction mixture was stirred at room temperature for 16 hours. It was then combined with two similar reactions (these reactions were carried out using a total of 11.6 g, 46.7 mmol, of C3) and concentrated in vacuo. The residue was treated with ethyl acetate (200 mL), stirred for 10 minutes, and filtered. The filter cake provided the product as a yellow solid. Combined yield: 27.9 g, 126 mmol, 67%. LCMS m/z 149.2 [M+H]$^+$. $^1$H NMR (400 MHz, CD$_3$OD) δ 7.76 (s, 1H), 5.01 (s, 2H), 4.88 (s, 2H), 2.80 (s, 3H), 2.61 (s, 3H).

Preparation P2

2,3,4-Trimethyl-6,7-dihydro-5H-pyrrolo[3,4-b]pyridine, Dihydrochloride Salt (P2)

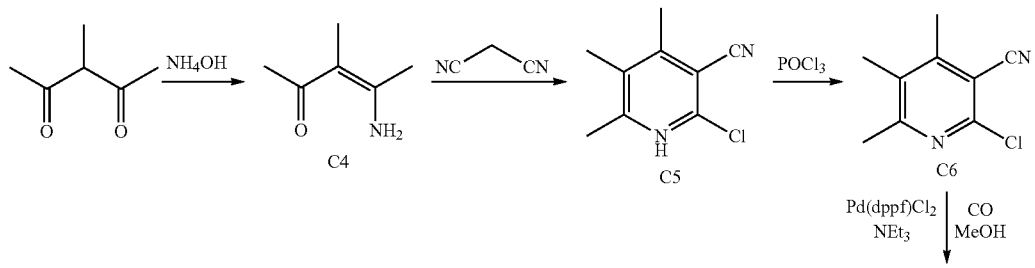

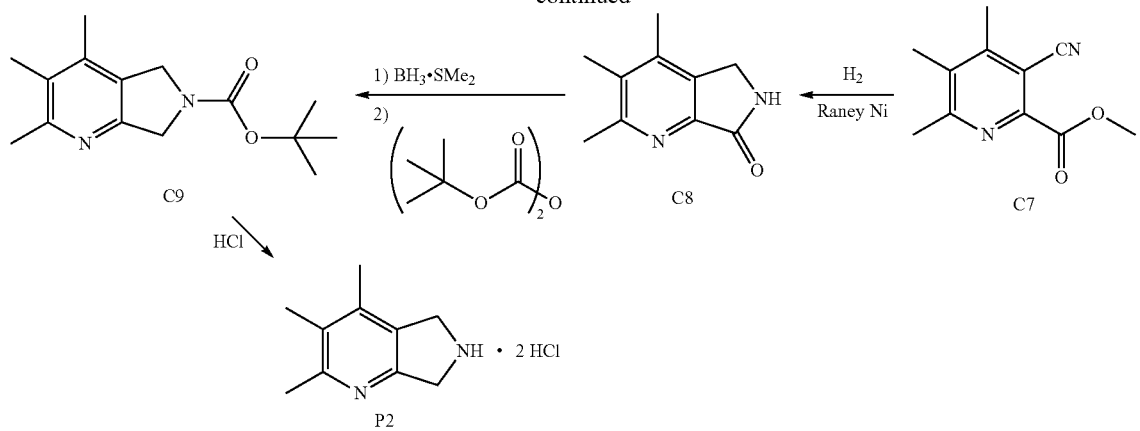

Step 1. Synthesis of 4-amino-3-methylpent-3-en-2-one (C4)

A mixture of 3-methylpentane-2,4-dione (60.0 g, 526 mmol), silica gel (2 g), and aqueous ammonium hydroxide solution (25-28%, 180 mL) was stirred at room temperature (20° C.) for 2 hours. The reaction mixture became a solid mass, which was triturated with petroleum ether (100 mL). The resulting solid was treated with methanol (200 mL) and the mixture was heated until most of the material had dissolved. After the hot mixture had been filtered, the filtrate was concentrated in vacuo, affording the product as a pale yellow solid. Yield: 43.9 g, 388 mmol, 74%. $^1$H NMR (400 MHz, CDCl$_3$) δ 2.15 (s, 3H), 1.96 (s, 3H), 1.83 (s, 3H).

Step 2. Synthesis of 4,5,6-trimethyl-2-oxo-1,2-dihydropyridine-3-carbonitrile (C5)

A solution of propanedinitrile (25.6 g, 388 mmol) in tetrahydrofuran (100 mL) was added drop-wise to a 0° C. solution of C4 (43.9 g, 388 mmol) in tetrahydrofuran (300 mL). The reaction mixture was stirred at room temperature (20° C.) for 16 hours, whereupon the solid was collected via filtration. The filter cake was washed with ethyl acetate (300 mL) to provide the product as a white solid. Yield: 48.0 g, 296 mmol, 76%. $^1$H NMR (400 MHz, DMSO-d$_6$) δ 11.19-10.76 (br s, 1H), 2.32 (s, 3H), 2.25 (s, 3H), 1.93 (s, 3H).

Step 3. Synthesis of 2-chloro-4,5,6-trimethylpyridine-3-carbonitrile (C6)

A mixture of C5 (28.0 g, 173 mmol) in phosphorus oxychloride (100 mL) was heated at 110° C. for 16 hours, whereupon it was cooled to room temperature (20° C.). Most of the solvent was removed via concentration in vacuo, and the residue was added to water (1.5 L) drop-wise at room temperature (20° C.). The pH of the mixture was adjusted to approximately 7 by addition of solid sodium carbonate, and the resulting precipitate was collected via filtration, affording the product as a pale yellow solid. Yield: 29 g, 160 mmol, 92%. $^1$H NMR (400 MHz, CDCl$_3$) δ 2.57 (s, 3H), 2.52 (s, 3H), 2.25 (s, 3H).

Step 4. Synthesis of methyl 3-cyano-4,5,6-trimethylpyridine-2-carboxylate (C7)

Conversion of C6 to C7 was carried out using the method described for synthesis of C1 from 2-chloro-4,6-dimethylpyridine-3-carbonitrile in Preparation P1. The product was obtained as a pale yellow solid. Yield: 13.0 g, 63.6 mmol, 77%. $^1$H NMR (400 MHz, CDCl$_3$) δ 4.05 (s, 3H), 2.67 (s, 3H), 2.59 (s, 3H), 2.35 (s, 3H).

Step 5. Synthesis of 2,3,4-trimethyl-5,6-dihydro-7H-pyrrolo[3,4-b]pyridin-7-one (C8)

Raney nickel (67 g, 0.78 mol) was added to a solution of C7 (40.0 g, 196 mmol) in methanol (2.5 L), and the reaction mixture was stirred at 20° C. for 3 days under 40 psi of hydrogen. It was then filtered, and the filtrate was concentrated in vacuo. The residue was washed with ethyl acetate (200 mL) to provide the product as a pale yellow solid. Yield: 33 g, 190 mmol, 97%. $^1$H NMR (400 MHz, CD$_3$OD) δ 4.38 (s, 2H), 2.59 (s, 3H), 2.34 (s, 6H).

Step 6. Synthesis of tert-butyl 2,3,4-trimethyl-5,7-dihydro-6H-pyrrolo[3,4-b]pyridine-6-carboxylate (C9)

Borane-dimethyl sulfide complex (10 M solution in dimethyl sulfide; 93.6 mL, 936 mmol) was added in a drop-wise manner to a 0° C. suspension of C8 (33 g, 190 mmol) in tetrahydrofuran (500 mL). The reaction mixture was stirred at 80° C. for 16 hours, whereupon it was cooled to 0° C. and quenched via slow addition of methanol (120 mL), followed by aqueous hydrochloric acid (6 M, 250 mL). The resulting mixture was allowed to stir at 90° C. for 3 hours and was then cooled to room temperature. The pH of the solution was adjusted to 9-10 via addition of 8 M aqueous sodium hydroxide solution. Di-tert-butyl dicarbonate (61.3 g, 281 mmol) was then added, and the reaction mixture was stirred at room temperature (20° C.) for 2 hours. Most of the solvent was removed under reduced pressure; the residue was diluted with water (200 mL) and extracted with ethyl acetate (3×200 mL). The combined organic layers were washed with saturated aqueous sodium chloride solution (500 mL), dried over sodium sulfate, filtered, and concentrated in vacuo. Silica gel chromatography (Eluent: 3:1 petroleum ether/ethyl acetate) afforded the product as a white solid, which contained a small amount of a tetrahydrofuran-derived contaminant. From analysis of the $^1$H NMR, this material was presumed to exist as a mixture of rotamers. Yield: 36 g, 137 mmol, 72%. $^1$H NMR (400 MHz, CDCl$_3$), product peaks only: δ 4.66 (s, 1H), 4.63 (s, 1H), 4.60 (s, 1H), 4.58 (s, 1H), [2.51 (s) and 2.51 (s), total 3H], 2.20 (s, 3H), 2.19 (s, 3H), [1.53 (s) and 1.51 (s), total 9H].

Step 7. Synthesis of 2,3,4-trimethyl-6,7-dihydro-5H-pyrrolo[3,4-b]pyridine, Dihydrochloride Salt (P2)

A solution of hydrogen chloride in methanol (20 mL) was added drop-wise to a 0° C. solution of C9 (15.0 g, 57.2 mmol) in methanol (100 mL), and the reaction mixture was stirred at room temperature (20° C.) for 2 hours. Removal of solvent in vacuo provided a solid, which was treated with ethyl acetate (50 mL) and stirred at room temperature (20° C.) for 30 minutes. The solid was collected via filtration and washed with ethyl acetate to provide the product as a pale yellow solid. Yield: 10.4 g, 44.2 mmol, 77%. LCMS m/z 163.1 [M+H]+. 1H NMR (400 MHz, DMSO-d6) δ 10.65-10.52 (br s, 2H), 4.65 (br s, 2H), 4.62 (br s, 2H), 2.63 (s, 3H), 2.36 (s, 3H), 2.26 (s, 3H).

Preparation P3

2-(Difluoromethyl)-4-methyl-6,7-dihydro-5H-pyrrolo[3,4-b]pyridine, Dihydrochloride Salt (P3)

quenched via slow addition of methanol (250 mL), followed by aqueous hydrochloric acid (6 M, 500 mL). The resulting mixture was allowed to stir at reflux (80° C.) for 16 hours and was then cooled to room temperature. The pH of the solution was adjusted to 9-10 via addition of 2 M sodium hydroxide solution. Di-tert-butyl dicarbonate (60.6 g, 278 mmol) was then added, and the reaction mixture was stirred at room temperature for 12 hours. Solvent was removed under reduced pressure; the residue was diluted with water (500 mL) and extracted with ethyl acetate (3×300 mL). The combined organic layers were washed with saturated aqueous sodium chloride solution (200 mL), dried over sodium sulfate, filtered, and concentrated in vacuo. Chromatography on silica gel (Gradient: 9% to 25% ethyl acetate in petroleum ether) provided the product (58 g) as a white solid, which contained a tetrahydrofuran-derived contaminant; this material was used directly in the following step. From analysis of the 1H NMR, this material was presumed to exist as a mixture of rotamers. LCMS m/z 249.1 [M+H]+. 1H NMR (400 MHz, CDCl3), product peaks only: δ 6.86 (s, 1H), 4.69 (br s, 1H), 4.63 (s, 2H), 4.58 (br s, 1H), 2.51 (s, 3H), 2.24 (s, 3H), [1.53 (s) and 1.52 (s), total 9H].

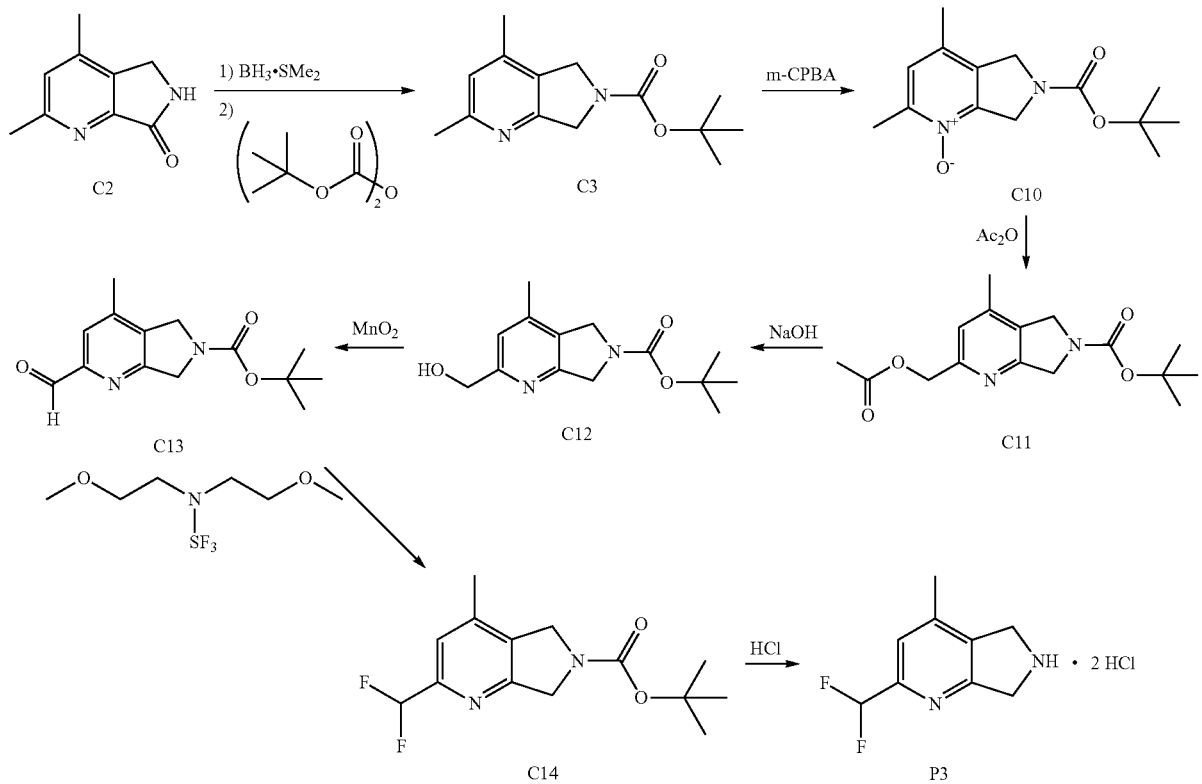

Step 1. Synthesis of tert-butyl 2,4-dimethyl-5,7-dihydro-6H-pyrrolo[3,4-b]pyridine-6-carboxylate (C3)

Borane-dimethyl sulfide complex (10 M solution in dimethyl sulfide; 92.5 mL, 925 mmol) was added in a drop-wise manner to a 0° C. suspension of C2 (30.0 g, 185 mmol) in tetrahydrofuran (600 mL). The reaction mixture was heated at reflux for 24 hours, whereupon it was cooled to 0° C. and

Step 2. Synthesis of tert-butyl 2,4-dimethyl-5,7-dihydro-6H-pyrrolo[3,4-b]pyridine-6-carboxylate 1-oxide (C10)

To a solution of C3 (from the previous step; 58 g, <185 mmol) in dichloromethane (500 mL) was added 3-chloroperoxybenzoic acid (m-CPBA; 85%, 48.4 g, 238 mmol) in portions at 0° C., and the reaction mixture was allowed to stir and warm to room temperature over 16 hours, whereupon the reaction was quenched by addition of saturated aqueous sodium thiosulfate solution (300 mL). The resulting mixture was extracted with dichloromethane (3×200 mL), and the combined organic layers were washed sequentially with saturated aqueous sodium bicarbonate solution (300 mL) and saturated aqueous sodium chloride solution (300 mL), dried over sodium sulfate, filtered, and concentrated in vacuo. Silica gel chromatography (Eluent: 2:1 petroleum ether/ethyl acetate, followed by 20:1 dichloromethane/methanol) afforded the product as a yellow solid. From analysis of the $^1$H NMR, this material was presumed to exist as a mixture of rotamers. Yield: 29.0 g, 110 mmol, 59% over 2 steps. $^1$H NMR (400 MHz, CDCl$_3$) δ 7.01 (s, 1H), 4.87-4.80 (m, 2H), 4.70-4.61 (m, 2H), 2.51 (s, 3H), 2.23 (s, 3H), [1.53 (s) and 1.52 (s), total 9H].

Step 3. Synthesis of tert-butyl 2-[(acetyloxy)methyl]-4-methyl-5,7-dihydro-6H-pyrrolo[3,4-b]pyridine-6-carboxylate (C11)

A solution of C10 (29.0 g, 110 mmol) in acetic anhydride (170 mL) was heated at 90° C. for 4 hours, whereupon the reaction mixture was concentrated in vacuo and treated with saturated aqueous sodium bicarbonate solution until no additional gas evolution was observed. The resulting mixture was extracted with ethyl acetate (3×200 mL), and the combined organic layers were washed sequentially with saturated aqueous sodium chloride solution (200 mL) and water (200 mL), dried over sodium sulfate, and filtered. The filtrate was concentrated under reduced pressure to afford the product (30 g) as a black oil; this material was used directly in the next step. Major component in LCMS: m/z 306.9 [M+H]$^+$.

Step 4. Synthesis of tert-butyl 2-(hydroxymethyl)-4-methyl-5,7-dihydro-6H-pyrrolo[3,4-b]pyridine-6-carboxylate (C12)

To an aqueous solution of sodium hydroxide (2 M, 250 mL) was added C11 (from the previous step; 30 g), and the reaction mixture was heated for 2 hours at 80° C. After the reaction mixture had cooled, it was extracted with dichloromethane (3×100 mL), and the combined organic layers were washed with saturated aqueous sodium chloride solution (100 mL), dried over sodium sulfate, filtered, and concentrated in vacuo. Silica gel column chromatography (Eluent: 25:1 dichloromethane/methanol) afforded the product (12.0 g) as a brown solid, which was used directly in the following step. Major component in LCMS: m/z 264.9 [M+H]$^+$.

Step 5. Synthesis of tert-butyl 2-formyl-4-methyl-5,7-dihydro-6H-pyrrolo[3,4-b]pyridine-6-carboxylate (C13)

To a solution of C12 (from the previous step; 12.0 g) in 1,4-dioxane (200 mL) was added manganese(IV) oxide (27.6 g, 317 mmol), and the reaction mixture was heated at 80° C. for 2 hours. The reaction mixture was filtered, and the filter cake was washed with dichloromethane (3×100 mL); the combined filtrates were concentrated in vacuo and purified by silica gel chromatography (Eluent: 6:1 petroleum ether/ethyl acetate), affording the product as a yellow solid. From analysis of the $^1$H NMR, this material was presumed to exist as a mixture of rotamers. Yield: 4.36 g, 16.6 mmol, 15% over 3 steps. $^1$H NMR (400 MHz, CDCl$_3$) δ [10.04 (s) and 10.03 (s), total 1H], 7.71 (s, 1H), 4.83-4.68 (m, 4H), 2.38 (s, 3H), [1.55 (s) and 1.54 (s), total 9H].

Step 6. Synthesis of tert-butyl 2-(difluoromethyl)-4-methyl-5,7-dihydro-6H-pyrrolo[3,4-b]pyridine-6-carboxylate (C14)

A solution of [bis(2-methoxyethyl)amino]sulfur trifluoride (7.35 g, 33.2 mmol) in dichloromethane (20 mL) was added drop-wise over 5 minutes to a −20° C. solution of C13 (4.36 g, 16.6 mmol) in dichloromethane (80 mL), and the reaction mixture was allowed to stir and warm from −20° C. to room temperature (10° C. to 15° C.) over 4 hours. Saturated aqueous sodium bicarbonate solution (50 mL) was then added, and the resulting mixture was extracted with dichloromethane (3×100 mL). The combined organic layers were washed with saturated aqueous sodium chloride solution (100 mL), dried over sodium sulfate, filtered, and concentrated in vacuo. Silica gel chromatography (Eluent: 7:1 petroleum ether/ethyl acetate, followed by 6:1 petroleum ether/ethyl acetate) provided the product as a yellow solid. From analysis of the $^1$H NMR, this material was presumed to exist as a mixture of rotamers. Yield: 2.1 g, 7.4 mmol, 45%. $^1$H NMR (400 MHz, CDCl$_3$) δ 7.35 (s, 1H), [6.61 (t, $J_{HF}$=55.6 HZ) and 6.60 (t, $J_{HF}$=55.5 HZ), total 1H], 4.75 (br s, 1H), 4.70 (s, 2H), 4.66 (br s, 1H), 2.36 (s, 3H), [1.54 (s) and 1.53 (s), total 9H].

Step 1. Synthesis of 2-(difluoromethyl)-4-methyl-6,7-dihydro-5H-pyrrolo[3,4-b]pyridine, Dihydrochloride Salt (P3)

A solution of hydrogen chloride in methanol (4 M, 7 mL) was added drop-wise to a 0° C. solution of C14 (2.1 g, 7.4 mmol) in dichloromethane (35 mL). The reaction mixture was stirred at room temperature for 2 hours, whereupon it was concentrated in vacuo, providing the product as a brown solid. Yield: 1.62 g, 6.30 mmol, 85%. LCMS m/z 185.1 [M+H]$^+$. $^1$H NMR (400 MHz, CD$_3$OD) δ 7.54 (s, 1H), 6.71 (t, $J_{HF}$=55.1 HZ, 1H), 4.76 (s, 2H), 4.64 (s, 2H), 2.45 (s, 3H).

Preparation P4 tert-Butyl 2-(difluoromethyl)-3,4-dimethyl-5,7-dihydro-6H-pyrrolo[3,4-b]pyridine-6-carboxylate (P4)

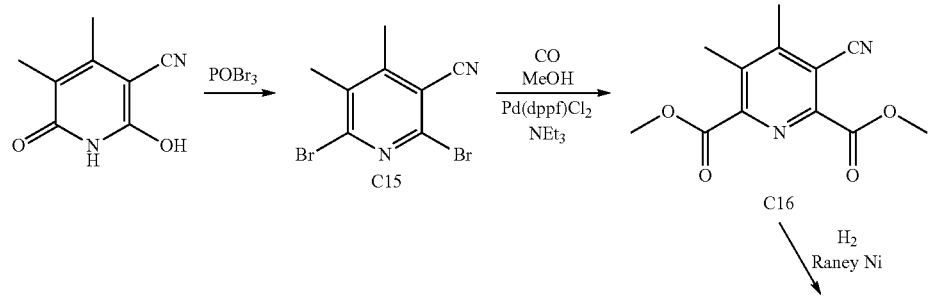

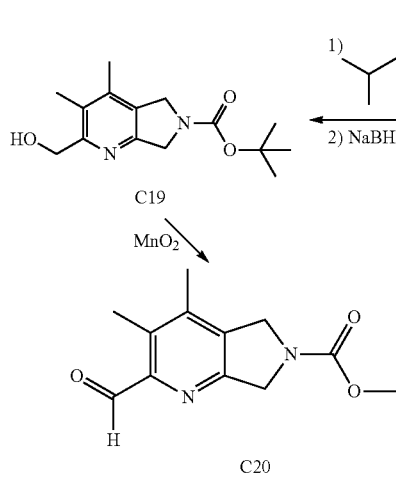
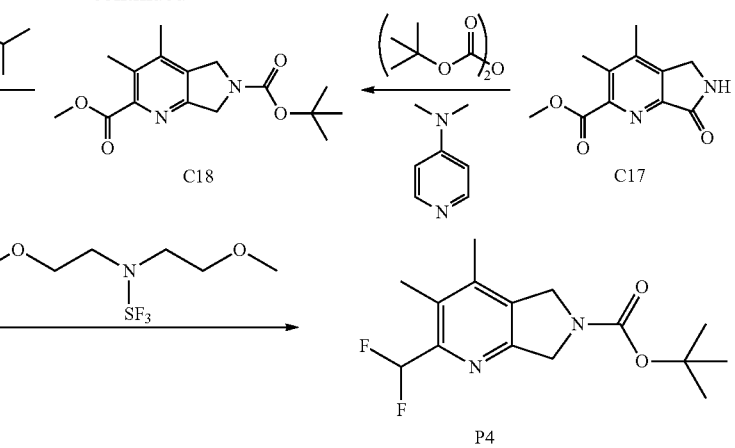

Step 1. Synthesis of 2,6-dibromo-4,5-dimethylpyridine-3-carbonitrile (C15)

A mixture of 2-hydroxy-4,5-dimethyl-6-oxo-1,6-dihydropyridine-3-carbonitrile (28 g, 170 mmol) and phosphorus oxybromide (97.8 g, 341 mmol) was heated at 190° C. for 1 hour. The reaction mixture was cooled to room temperature and quenched by addition of ice water, and the pH was then adjusted to approximately 7 via addition of aqueous sodium bicarbonate solution. The resulting suspension was extracted with dichloromethane (4×100 mL), and the combined organic layers were dried over sodium sulfate, filtered, and evaporated under reduced pressure. Silica gel chromatography (Eluent: 20:1 petroleum ether/ethyl acetate) afforded the product as a white solid. Yield: 25 g, 86 mmol, 51%. $^1$H NMR (400 MHz, CDCl$_3$) δ 2.60 (s, 3H), 2.41 (s, 3H).

Step 2. Synthesis of dimethyl 3-cyano-4,5-dimethylpyridine-2,6-dicarboxylate (C16)

Conversion of C15 to C16 was carried out using the method described for synthesis of C1 from 2-chloro-4,6-dimethylpyridine-3-carbonitrile in Preparation P1. The product was obtained as an off-white solid. Yield: 22 g, 89 mmol, 78%. $^1$H NMR (400 MHz, CDCl$_3$) δ 4.06 (s, 3H), 4.01 (s, 3H), 2.68 (s, 3H), 2.53 (s, 3H).

Step 3. Synthesis of methyl 3,4-dimethyl-7-oxo-6,7-dihydro-5H-pyrrolo[3,4-b]pyridine-2-carboxylate (C17)

Raney nickel (15.2 g. 177 mmol) was added to a solution of C16 (22.0 g, 88.6 mmol) in methanol (1.8 L), and the reaction mixture was stirred at 20° C. for 72 hours under 15 psi of hydrogen. The catalyst was removed via filtration, and the filter cake was washed with dichloromethane (3×150 mL). The combined filtrates were concentrated in vacuo, and the residue was triturated with tert-butyl methyl ether (500 mL) to afford the product as an off-white solid. Yield: 18.0 g, 81.7 mmol, 92%. $^1$H NMR (400 MHz, CDCl$_3$) δ 7.35-7.28 (br s, 1H), 4.46 (s, 2H), 3.98 (s, 3H), 2.51 (s, 3H), 2.37 (s, 3H).

Step 4. Synthesis of 6-tert-butyl 2-methyl 3,4-dimethyl-7-oxo-5,7-dihydro-6H-pyrrolo[3,4-b]pyridine-2,6-dicarboxylate (C18)

To a mixture of C17 (18.0 g, 81.7 mmol) and di-tert-butyl dicarbonate (18.8 g, 86.1 mmol) in dichloromethane (800 mL) was added 4-(dimethylamino)pyridine (1.5 g, 12.3 mmol) in one portion. The reaction mixture was stirred at 20° C. to 25° C. for 3 hours, whereupon the solvent was removed under reduced pressure and the residue was purified by silica gel chromatography (Eluent: 2:1 petroleum ether/ethyl acetate), affording the product as a white solid. Yield: 23 g, 72 mmol, 88%. $^1$H NMR (400 MHz, CDCl$_3$) δ 4.72 (s, 2H), 3.97 (s, 3H), 2.49 (s, 3H), 2.38 (s, 3H), 1.61 (s, 9H).

Step 5. Synthesis of tert-butyl 2-(hydroxymethyl)-3,4-dimethyl-5,7-dihydro-6H-pyrrolo[3,4-b]pyridine-6-carboxylate (C19)

Diisobutylaluminum hydride (1 M solution in toluene; 47 mL, 47 mmol) was added drop-wise over 5 minutes to a −10° C. solution of C18 (7.50 g, 23.4 mmol) in tetrahydrofuran (250 mL), and the reaction mixture was stirred at −10° C. to −5° C. for 50 minutes. Diisobutylaluminum hydride (1 M solution in toluene; 47 mL, 47 mmol) was again added drop-wise, and stirring was continued at −5° C. for 3.5 hours. The reaction was quenched via addition of sodium sulfate decahydrate (10.0 g, 31.0 mmol), and the resulting mixture was stirred at room temperature for 30 minutes, whereupon it was filtered. The filter cake was washed with a mixture of dichloromethane and methanol (15:1, 4 L), and the combined filtrates were concentrated in vacuo to afford a pale red solid (4 g). This material was dissolved in acetic acid (100 mL) and treated with sodium cyanoborohydride (3.0 g, 47.7 mmol) in 5 portions at room temperature. After the reaction mixture had been stirred at 20° C. to 25° C. for 18 hours, it was poured into saturated aqueous sodium carbonate solution (200 mL), stirred for 20 minutes, and extracted with ethyl acetate (3×150 mL). The combined organic layers were washed with saturated aqueous sodium chloride solution (3×100 mL), dried over sodium sulfate, filtered, and concentrated under reduced pressure. Silica gel chromatography (Gradient: 17% to 50% ethyl acetate in petroleum ether) afforded the product as a white solid. From analysis of the $^1$H NMR, this material was presumed to exist as a mixture of rotamers. Yield: 3.30 g, 11.8 mmol, 50%. LCMS m/z 278.9 [M+H]+. 1H NMR (400 MHz, CD3OD) δ 4.71 (s, 2H), 4.67 (br s, 1H), 4.64 (br s, 1H), 4.63-4.59 (m, 2H), 2.30 (s, 3H), [2.27 (s) and 2.26 (s), total 3H], [1.54 (s) and 1.53 (s), total 9H].

Step 6. Synthesis of tert-butyl 2-formyl-3,4-dimethyl-5,7-dihydro-6H-pyrrolo[3,4-b]pyridine-6-carboxylate (C20)

This reaction was carried out in two identical batches. To a solution of C19 (500 mg, 1.80 mmol) in 1,4-dioxane (20 solid. From analysis of the 1H NMR, this material was presumed to exist as a mixture of rotamers. Yield: 380 mg, 1.27 mmol, 84%. 1H NMR (400 MHz, CDCl3) δ [6.71 (t, J$_{HF}$=54.8 HZ) and 6.69 (t, J$_{HF}$=54.7 HZ), total 1H], 4.73-4.68 (br s, 2H), 4.68-4.63 (br s, 2H), 2.42 (br s, 3H), 2.25 (s, 3H), [1.54 (s) and 1.53 (s), total 9H].

Preparation P5 tert-Butyl 2-(methoxymethyl)-4-methyl-5,7-dihydro-6H-pyrrolo[3,4-b]pyridine-6-carboxylate (P5)

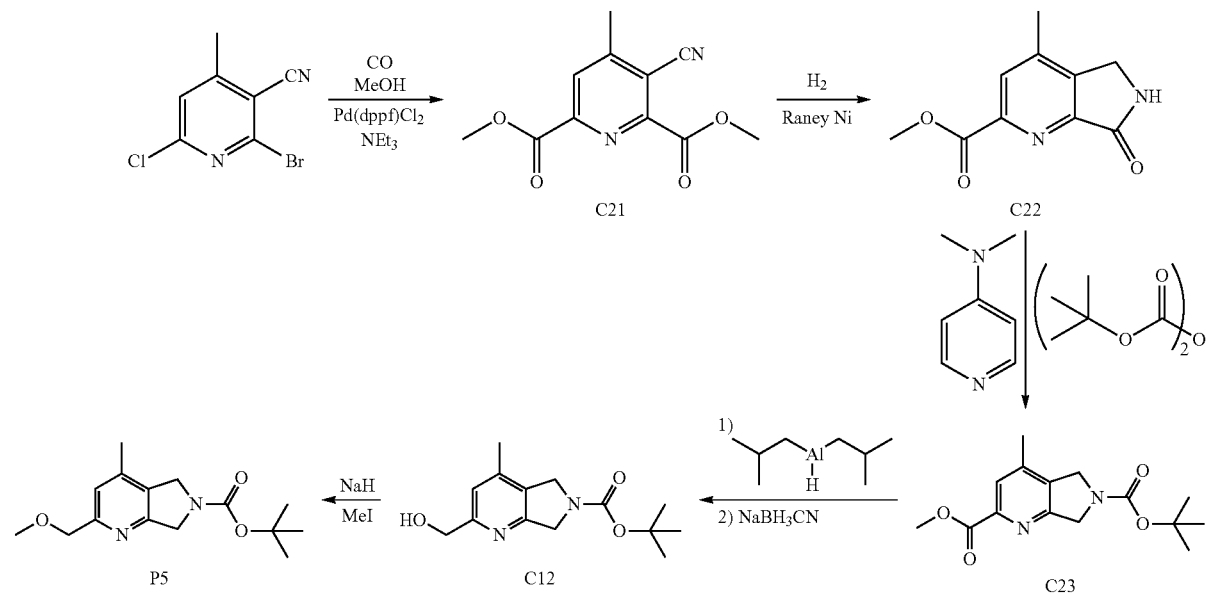

mL) was added manganese(IV) oxide (1.56 g, 17.9 mmol), and the reaction mixture was stirred at 70° C. for 2 hours. Solids were removed via filtration and the filter cake was washed with ethyl acetate (100 mL). The filtrates from the two reactions were combined and concentrated in vacuo to afford the product as a pale yellow solid. From analysis of the 1H NMR, this material was presumed to exist as a mixture of rotamers. Yield: 650 mg, 2.35 mmol, 65%. 1H NMR (400 MHz, CDCl3) δ [10.18 (s) and 10.17 (s), total 1H], 4.80-4.67 (m, 4H), 2.62 (s, 3H), 2.28 (s, 3H), [1.55 (s) and 1.54 (s), total 9H].

Step 8. Synthesis of tert-butyl 2-(difluoromethyl)-3,4-dimethyl-5,7-dihydro-6H-pyrrolo[3,4-b]pyridine-6-carboxylate (P4)

A solution of [bis(2-methoxyethyl)amino]sulfur trifluoride (841 mg, 3.80 mmol) in dichloromethane (3 mL) was added drop-wise to a −20° C. solution of C20 (420 mg, 1.52 mmol) in dichloromethane (15 mL). The reaction mixture was allowed to warm to room temperature and stir for 72 hours, whereupon water (10 mL) was added, and the pH was adjusted to 7-8 via addition of aqueous sodium bicarbonate solution. The resulting mixture was extracted with dichloromethane (2×15 mL); the combined organic layers were washed with saturated aqueous sodium chloride solution (20 mL), dried over sodium sulfate, filtered, and concentrated in vacuo. Silica gel chromatography (Eluent: 5:1 petroleum ether/ethyl acetate) provided the product as a pale yellow Step 1. Synthesis of dimethyl 3-cyano-4-methylpyridine-2,6-dicarboxylate (C21)

[1,1'-Bis(diphenylphosphino)ferrocene]dichloropalladium(II) (97.7 g, 134 mmol) was added to a solution of 2,6-dichloro-4-methylpyridine-3-carbonitrile (500 g, 2.67 mol) and triethylamine (810 g, 8.0 mol) in methanol (5.0 L). The reaction mixture was stirred at 100° C. under carbon monoxide (4 MPa) for 14 hours, whereupon it was cooled to 25° C. and filtered through diatomaceous earth. The filtrate was concentrated in vacuo, and the residue was pulped with a mixture of tert-butyl methyl ether, dichloromethane, and methanol (10:1:1, 3 L). The resulting material was partitioned between water (2.5 L) and dichloromethane (2.5 L). The organic layer was washed with saturated aqueous sodium chloride solution, dried, filtered, and concentrated under reduced pressure to provide the product as a brown solid. Yield: 273 g, 1.17 mol, 44%. 1H NMR (400 MHz, CDCl3) δ 8.28 (br q, J=0.7 Hz, 1H), 4.09 (s, 3H), 4.05 (s, 3H), 2.76 (d, J=0.6 Hz, 3H).

Step 2. Synthesis of methyl 4-methyl-7-oxo-6,7-dihydro-5H-pyrrolo[3,4-b]pyridine-2-carboxylate (C22)

Raney nickel (270 g, 3.15 mol) was added to a solution of C21 (290 g, 1.24 mmol) in methanol (3 L). The reaction mixture was heated to 50° C. and stirred under hydrogen (3 MPa) for 48 hours, whereupon it was cooled to 25° C. and dissolved in a mixture of dichloromethane and methanol (1:1, 6 L) at 70° C. The resulting solution was filtered and the filtrate was concentrated in vacuo. Pulping of the residue with methanol (500 mL) afforded the product as a red-white solid. Yield: 230 g, 1.12 mol, 90%. $^1$H NMR (400 MHz, CDCl$_3$) δ 8.15 (s, 1H), 7.25-7.19 (br s, 1H), 4.51 (s, 2H), 4.02 (s, 3H), 2.50 (s, 3H).

Step 3. Synthesis of 6-tert-butyl 2-methyl 4-methyl-7-oxo-5,7-dihydro-6H-pyrrolo[3,4-b]pyridine-2,6-dicarboxylate (C23)

Di-tert-butyl dicarbonate (254 g, 1.16 mol) and 4-(dimethylamino)pyridine (11.6 g, 95.0 mmol) were added to a solution of C22 (233 g, 1.13 mol) in dichloromethane (2 L). The reaction mixture was stirred at 25° C. for 16 hours, whereupon additional di-tert-butyl dicarbonate (125 g, 573 mmol) was added and stirring was continued at 25° C. for 2 hours. The reaction mixture was then washed with 10% aqueous citric acid solution and extracted with dichloromethane (2×1 L). The combined organic layers were washed with saturated aqueous sodium chloride solution, dried, filtered, and concentrated in vacuo. The residue was pulped with tert-butyl methyl ether (2 L) to provide the product as a gray-white solid. Yield: 300 g, 0.98 mol, 87%. $^1$H NMR (400 MHz, CDCl$_3$) δ 8.16 (s, 1H), 4.76 (s, 2H), 4.01 (s, 3H), 2.51 (s, 3H), 1.61 (s, 9H).

Step 4. Synthesis of tert-butyl 2-(hydroxymethyl)-4-methyl-5,7-dihydro-6H-pyrrolo[3,4-b]pyridine-6-carboxylate (C12)

This reaction was run in two identical batches. To a −10° C. solution of C23 (30.00 g, 97.94 mmol) in tetrahydrofuran (1.0 L) was added diisobutylaluminum hydride (1 M solution in toluene; 114 mL, 114 mmol) drop-wise over about 5 minutes. The reaction mixture was stirred at −10° C. to −5° C. for 50 minutes, whereupon another charge of diisobutylaluminum hydride (1 M solution in toluene, 285 mL, 285 mmol) was added drop-wise. Stirring was continued at −10° C. to −5° C. for 2.5 hours. The reaction was then quenched via addition of sodium sulfate decahydrate until no more bubbling was observed. After the mixture had been stirred at 25° C. for 30 minutes, magnesium sulfate was added, and the resulting mixture was filtered through a pad of diatomaceous earth. The filter pad was washed with a mixture of dichloromethane and methanol (10:1, 25×300 mL), and the combined organic filtrates were dried over sodium sulfate, filtered, and concentrated in vacuo to provide a red oil (21.0 g). This material was dissolved in acetic acid (200 mL) and treated with sodium cyanoborohydride (12.9 g, 205 mmol) in 5 portions at 25° C. {Caution; gas evolution.} The reaction mixture was stirred at 20° C. to 35° C. for 18 hours, and then poured into saturated aqueous sodium bicarbonate solution (1.2 L). After the resulting mixture had stirred for 20 minutes, it was extracted with ethyl acetate (3×500 mL), and the combined organic layers were washed with saturated aqueous sodium chloride solution (3×300 mL), dried over sodium sulfate, filtered, and concentrated in vacuo. The two reaction batches were combined at this point, and purified using silica gel chromatography (Gradient: 33% to 66% ethyl acetate in petroleum ether), affording the product as a yellow gum. Yield: 20.8 g, 78.7 mmol, 40%. LCMS m/z 264.9 [M+H]$^+$. $^1$H NMR (400 MHz, CDCl$_3$) δ 6.97 (br s, 1H), [4.74 (s) and 4.73 (s), total 2H], [4.72 (br s) and 4.62 (br s), total 2H], 4.67 (s, 2H), 2.30 (s, 3H), [1.54 (s) and 1.53 (s), total 9H].

Step 5. Synthesis of tert-butyl 2-(methoxymethyl)-4-methyl-5,7-dihydro-6H-pyrrolo[3,4-b]pyridine-6-carboxylate (P5)

To a 5° C. solution of C12 (21.0 g, 79.4 mmol) in tetrahydrofuran (500 mL) was added sodium hydride (60% in mineral oil; 6.16 g, 154 mmol) portion-wise over 20 minutes. The resulting suspension was stirred at 20° C. for 1 hour, whereupon iodomethane (24.0 mL, 385 mmol) was added drop-wise. The reaction mixture was stirred at 20° C. for 2 hours, cooled to 0° C., and quenched via drop-wise addition of saturated aqueous ammonium chloride solution (100 mL). The resulting mixture was extracted with ethyl acetate (3×500 mL), and the combined organic layers were dried over sodium sulfate, filtered, and concentrated in vacuo. Chromatography on silica gel (Gradient: 0% to 30% ethyl acetate in petroleum ether) provided the product as an off-white solid. From analysis of the $^1$H NMR, the product was presumed to exist as a mixture of rotamers. Yield: 21 g, 75 mmol, 94%. LCMS m/z 278.9 [M+H]$^+$. $^1$H NMR (400 MHz, CDCl$_3$) δ 7.11 (s, 1H), 4.72-4.57 (m, 4H), [4.53 (s) and 4.52 (s), total 2H], 3.46 (s, 3H), 2.27 (s, 3H), [1.52 (s) and 1.50 (s), total 9H].

Preparation P6

3-Chloro-2,4-dimethyl-6,7-dihydro-5H-pyrrolo[3,4-b]pyridine, Dihydrochloride Salt (P6)

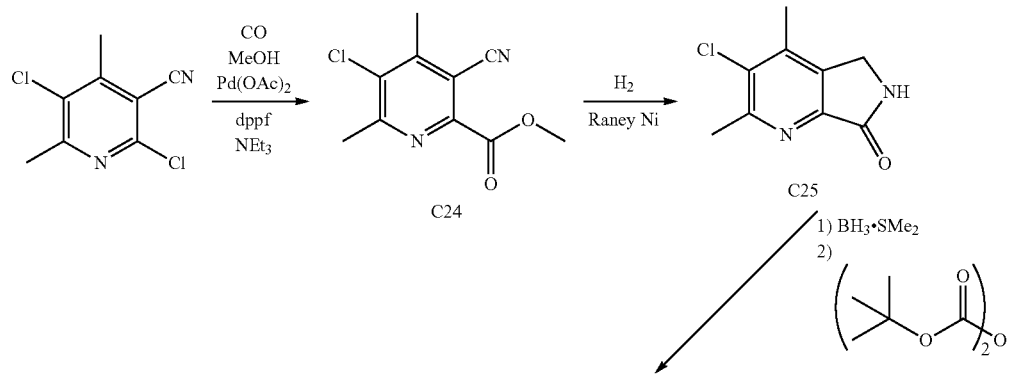

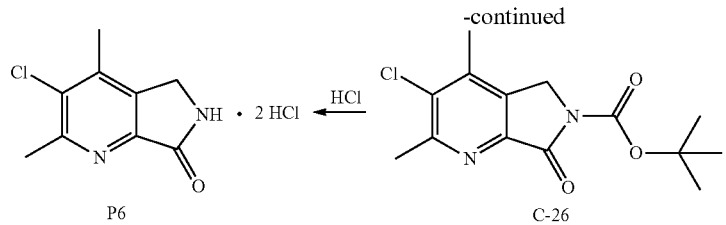

Step 1. Synthesis of methyl 5-chloro-3-cyano-4,6-dimethylpyridine-2-carboxylate (C24)

Triethylamine (20.4 mL, 146 mmol), palladium(II) acetate (837 mg, 3.73 mmol), and 1,1'-bis(diphenylphosphino)ferrocene (dppf; 4.14 g, 7.47 mmol) were added to a solution of 2,5-dichloro-4,6-dimethylpyridine-3-carbonitrile (15.0 g, 74.6 mmol) in methanol (600 mL). Carbon monoxide was bubbled in, and the reaction mixture was heated at 70° C. for 24 hours under 50 psi of carbon monoxide. After the reaction mixture had cooled to room temperature, it was filtered, and the filtrate was concentrated under reduced pressure. Silica gel chromatography (Eluent: 5:1 petroleum ether/ethyl acetate) afforded the product as a white solid. Yield: 15.3 g, 68.1 mmol, 91%. $^1$H NMR (400 MHz, CDCl$_3$) δ 4.06 (s, 3H), 2.78 (s, 3H), 2.71 (s, 3H).

Step 2. Synthesis of 3-chloro-2,4-dimethyl-5,6-dihydro-7H-pyrrolo[3,4-b]pyridin-7-one (C25)

Conversion of C24 to the product was carried out using the method described for synthesis of C17 from C16 in Preparation P4. The product was isolated as a yellow solid. Yield: 12.5 g, 63.6 mmol, 93%. LCMS m/z 197.0 (chlorine isotope pattern observed) [M+H]$^+$. $^1$H NMR (400 MHz, CDCl$_3$) δ 7.51-7.42 (br s, 1H), 4.41 (s, 2H), 2.77 (s, 3H), 2.42 (s, 3H).

Step 3. Synthesis of tert-butyl 3-chloro-2,4-dimethyl-5,7-dihydro-6H-pyrrolo[3,4-b]pyridine-6-carboxylate (C26)

To a 0° C. solution of C25 (12.5 g, 63.6 mmol) in tetrahydrofuran (500 mL) was added borane-dimethyl sulfide complex (10 M in dimethyl sulfide; 50.9 mL, 509 mmol), in a drop-wise manner. The reaction mixture was stirred at reflux for 16 hours, whereupon it was cooled to 0° C. The reaction was quenched by slow addition of methanol (200 mL), followed by aqueous hydrochloric acid solution (6 M; 400 mL); the resulting mixture was stirred at reflux (80° C.) for 3 hours, cooled to room temperature, and treated with 2 M aqueous sodium hydroxide solution until the pH of the solution was approximately 9-10. At this point, di-tert-butyl dicarbonate (20.8 g, 95.3 mmol) was added and the mixture was stirred at room temperature for 16 hours. After removal of organic solvents under reduced pressure, the residue was diluted with saturated aqueous ammonium chloride solution (1 L) and extracted with ethyl acetate (3×1 L). The combined organic layers were washed with saturated aqueous sodium chloride solution (2×1 L), dried over sodium sulfate, filtered, and concentrated in vacuo. Chromatography on silica gel (Eluent: 20:1 petroleum ether/ethyl acetate) afforded the product as a white solid. From analysis of the $^1$H NMR, this material was presumed to exist as a mixture of rotamers. Yield: 8.02 g, 28.4 mmol, 45%. LCMS m/z 282.9 (chlorine isotope pattern observed) [M+H]$^+$. $^1$H NMR (400 MHz, CDCl$_3$) δ 4.69-4.57 (m, 4H), [2.62 (s) and 2.61 (s), total 3H], 2.30 (s, 3H), [1.53 (s) and 1.51 (s), total 9H].

Step 4. Synthesis of 3-chloro-2,4-dimethyl-6,7-dihydro-5H-pyrrolo[3,4-b]pyridine, Dihydrochloride Salt (P6)

To a solution of C26 (2.30 g, 8.13 mmol) in dichloromethane (30 mL) was added a solution of hydrogen chloride in 1,4-dioxane (4 M, 6.0 mL, 24 mmol) at room temperature (~13° C.). The reaction mixture was stirred at room temperature for 16 hours, whereupon it was concentrated in vacuo, affording the product as a pink solid. Yield: 1.70 g, 6.65 mmol, 82%. LCMS m/z 182.9 (chlorine isotope pattern observed) [M+H]$^+$. $^1$H NMR (400 MHz, CD$_3$OD) δ 4.81 (s, 2H), 4.77 (s, 2H), 2.74 (s, 3H), 2.52 (s, 3H).

Preparation P7

2,4,5-Trimethyl-6,7-dihydro-5H-pyrrolo[3,4-b]pyridine, Dihydrochloride Salt (P7)

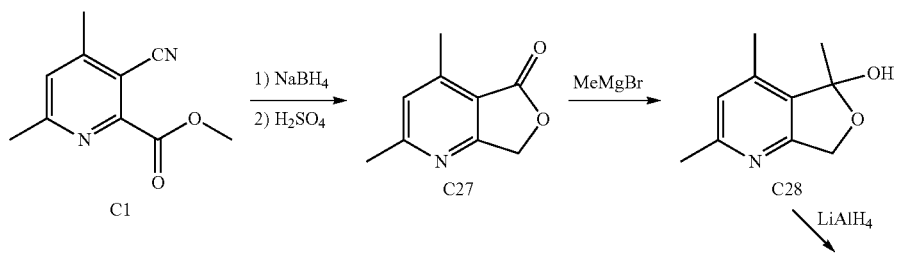

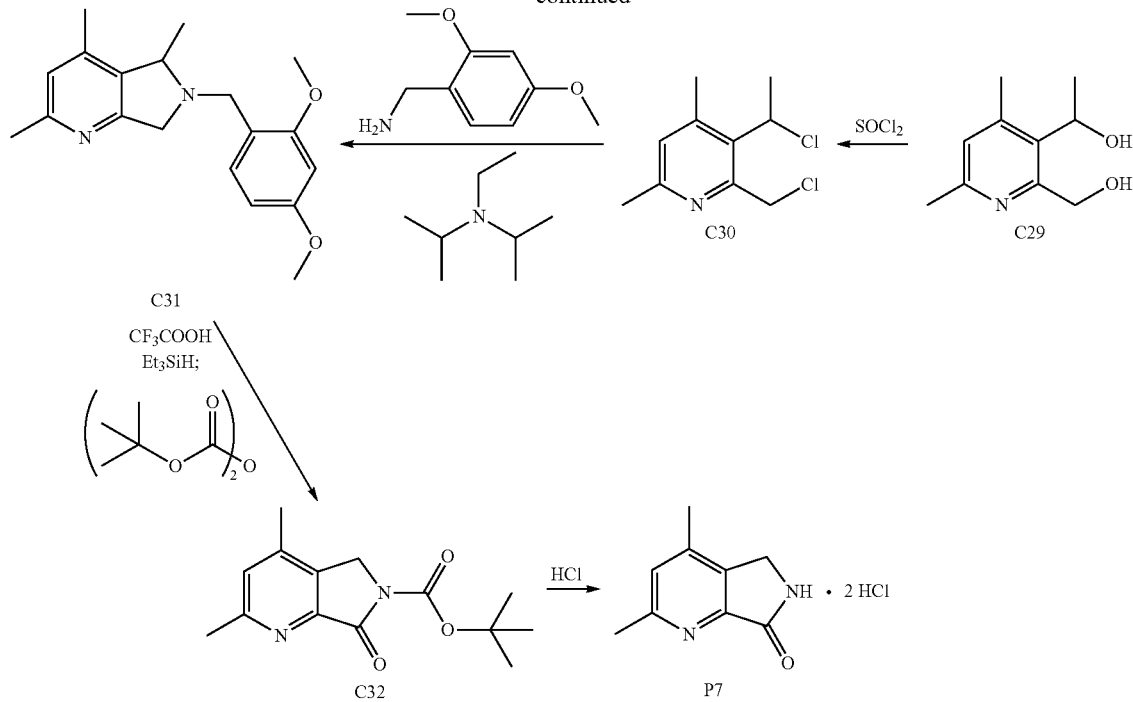

Step 1. Synthesis of 2,4-dimethylfuro[3,4-b]pyridin-5(7H)-one (C27)

Sodium borohydride (59.7 g, 1.58 mol) was added in portions to a 0° C. solution of C1 (100 g, 526 mmol) in a mixture of tetrahydrofuran (900 mL) and methanol (2.5 L). The reaction mixture was stirred at 25° C. for 36 hours, whereupon water (500 mL) was added, and the organic solvents were removed in vacuo. The aqueous residue was diluted with saturated aqueous ammonium chloride solution (500 mL) and extracted with ethyl acetate (3×150 mL). The combined organic layers were washed with saturated aqueous sodium chloride solution (150 mL), dried over sodium sulfate, filtered, and concentrated under reduced pressure to provide a brown oil (79.5 g). A portion of this material (50.0 g, <331 mmol) was dissolved in ethanol (500 mL), cooled to 0° C., and treated in a drop-wise manner with concentrated sulfuric acid (98%, 400 mL). The reaction mixture was then heated at 90° C. for 16 hours, whereupon it was cooled to room temperature and added drop-wise to stirring ice water (3.0 L). After the resulting mixture had been adjusted to a pH of 7-8 via addition of solid sodium bicarbonate, most of the ethanol was removed in vacuo, and the resulting mixture was extracted with ethyl acetate (3×1 L). The combined organic layers were washed with saturated aqueous sodium chloride solution (1.5 L), dried over sodium sulfate, filtered, and concentrated under reduced pressure. Silica gel chromatography (Eluent: 2:1 petroleum ether/ethyl acetate) afforded the product as a pale yellow solid. Yield: 42.0 g, 257 mmol, 78%. $^1$H NMR (400 MHz, CDCl$_3$) δ 7.10 (s, 1H), 5.22 (s, 2H), 2.66 (s, 3H), 2.65 (s, 3H).

Step 2. Synthesis of 2,4,5-trimethyl-5,7-dihydrofuro[3,4-b]pyridin-5-ol (C28)

Methylmagnesium bromide (3.0 M solution in diethyl ether; 51.1 mL, 153 mmol) was added drop-wise to a 0° C. solution of C27 (5.00 g, 30.6 mmol) in tetrahydrofuran (150 mL). The reaction mixture was stirred at room temperature for 3 hours, whereupon it was quenched with saturated aqueous ammonium chloride solution (150 mL) and extracted with ethyl acetate (3×150 mL). The combined organic layers were washed with saturated aqueous sodium chloride solution (150 mL), dried over sodium sulfate, filtered, and concentrated in vacuo to provide the product as a pale yellow solid. Yield: 4.3 g, 24 mmol, 78%. $^1$H NMR (400 MHz, CDCl$_3$) δ 6.89 (s, 1H), 5.05-4.85 (m, 2H), 2.52 (s, 3H), 2.43 (s, 3H), 1.80 (s, 3H).

Step 3. Synthesis of 1-[2-(hydroxymethyl)-4,6-dimethylpyridin-3-yl]ethanol (C29)

To a 0° C. solution of C28 (2.10 g, 11.7 mmol) in tetrahydrofuran (100 mL) was added lithium aluminum hydride (1.33 g, 35.0 mmol) in a portion-wise manner. The reaction mixture was stirred at room temperature (20° C.) for 16 hours, whereupon it was treated with water (10 mL) and stirred at room temperature for 10 minutes. Aqueous sodium hydroxide solution (15%, 10 mL) was added drop-wise, and stirring was continued for 20 minutes, at which time additional water (30 mL) was added drop-wise. The resulting mixture was stirred for 30 minutes and filtered; the filter cake was washed with ethyl acetate (100 mL). The combined filtrates were concentrated in vacuo to remove tetrahydrofuran, and the residue was diluted with water (100 mL) and extracted with ethyl acetate (3×100 mL). The combined organic layers were washed with saturated aqueous sodium chloride solution (100 mL), dried over sodium sulfate, filtered, and concentrated under reduced pressure to afford the product as a brown oil. Yield: 1.70 g, 9.38 mmol, 80%. $^1$H NMR (400 MHz, CDCl$_3$) δ 6.87 (s, 1H), 5.21 (q, J=6.8 Hz, 1H), 4.80 (AB quartet, J$_{AB}$=15.1 HZ, Δ$_{\nu AB}$=5.6 HZ, 2H), 2.47 (s, 3H), 2.41 (s, 3H), 1.50 (d, J=6.8 Hz, 3H).

Step 4. Synthesis of 3-(1-chloroethyl)-2-(chloromethyl)-4,6-dimethylpyridine (C30)

Thionyl chloride (33.5 g, 282 mmol) was added drop-wise to a 0° C. solution of C29 (1.70 g, 9.38 mmol) in dichloromethane (100 mL), and the reaction mixture was stirred at room temperature for 4 hours. Concentration in vacuo afforded the product as a dark brown solid. Yield: 2.00 g, 7.86 mmol, 98%. $^1$H NMR (400 MHz, CDCl$_3$) δ 7.46 (s, 1H), 5.63-5.52 (m, 2H), 5.28-5.16 (m, 1H), 2.95 (s, 3H), 2.84 (br s, 3H), 1.99 (d, J=7.0 Hz, 3H).

Step 5. Synthesis of 6-(2,4-dimethoxybenzyl)-2,4,5-trimethyl-6,7-dihydro-5H-pyrrolo[3,4-b]pyridine (C31)

N,N-Diisopropylethylamine (3.56 g, 27.5 mmol) was added drop-wise to a solution of C30 (2.00 g, 9.17 mmol) in a mixture of dichloromethane (20 mL) and acetonitrile (100 mL). After the resulting mixture had been stirred at room temperature (25° C.) for 10 minutes, a solution of 1-(2,4-dimethoxyphenyl)methanamine (1.69 g, 10.1 mmol) in dichloromethane (5 mL) was added drop-wise, and the reaction mixture was stirred at 75° C. for 3 hours. It was then cooled to room temperature, diluted with water (100 mL), and concentrated in vacuo to remove most of the acetonitrile. The resulting mixture was extracted with ethyl acetate (3×100 mL), and the combined organic layers were washed with saturated aqueous sodium chloride solution (1 L), dried over sodium sulfate, and filtered. The filtrate was concentrated under reduced pressure and purified via silica gel chromatography (Eluents: 5:1, then 2:1, then 1:1 petroleum ether/ethyl acetate) to provide the product as a brown oil. Yield: 900 mg, 2.88 mmol, 31%. LCMS m/z 312.9 [M+H]$^+$. $^1$H NMR (400 MHz, CDCl$_3$) δ 7.29 (d, J=9.0 Hz, 1H), 6.75 (s, 1H), 6.50-6.45 (m, 2H), 4.24-4.17 (m, 1H), 4.14 (br d, J=14.6 Hz, 1H), 3.99 (d, J=13.6 Hz, 1H), 3.87-3.75 (m, 2H), 3.82 (s, 3H), 3.82 (s, 3H), 2.46 (s, 3H), 2.26 (s, 3H), 1.43 (d, J=6.3 Hz, 3H).

Step 6. Synthesis of tert-butyl 2,4,5-trimethyl-5,7-dihydro-6H-pyrrolo[3,4-b]pyridine-6-carboxylate (C32)

A mixture of C31 (385 mg, 1.23 mmol), trifluoroacetic acid (5 mL), and triethylsilane (1.0 mL, 6.3 mmol) was stirred at 70° C. for 6 hours. After cooling to room temperature, the reaction mixture was diluted with tetrahydrofuran (10 mL) and water (2 mL), and then carefully treated with aqueous sodium hydroxide solution (15%, 5 mL) until the pH was 9-10. Di-tert-butyl dicarbonate (323 mg, 1.48 mmol) was added, and the reaction mixture was stirred at room temperature for 16 hours. After addition of water (10 mL), the mixture was extracted with ethyl acetate (3×20 mL), and the combined organic layers were washed with saturated aqueous sodium chloride solution (20 mL), dried over sodium sulfate, filtered, and concentrated in vacuo. Silica gel chromatography (Eluents: 10:1, then 8:1, then 6:1 petroleum ether/ethyl acetate) afforded the product as a yellow oil. From analysis of the $^1$H NMR, this material was presumed to exist as a mixture of rotamers. Yield: 170 mg, 0.648 mmol, 53%. LCMS m/z 263.0 [M+H]$^+$. $^1$H NMR (400 MHz, CDCl$_3$) δ 6.85 (s, 1H), [5.21-5.14 (m) and 5.09-5.02 (m), total 1H], 4.75-4.54 (m, 2H), 2.51 (s, 3H), 2.28 (s, 3H), [1.54 (s) and 1.51 (s), total 9H], [1.48 (d, J=6.0 Hz) and 1.45 (d, J=6.0 Hz), total 3H].

Step 7. Synthesis of 2,4,5-trimethyl-6,7-dihydro-5H-pyrrolo[3,4-b]pyridine, Dihydrochloride Salt (P7)

A solution of hydrogen chloride in ethyl acetate (4.0 M, 0.81 mL, 3.2 mmol) was added drop-wise to a 0° C. solution of C32 (170 mg, 0.648 mmol) in dichloromethane (0.5 mL), and the reaction mixture was stirred at room temperature for 1 hour. After removal of solvents in vacuo, the solid residue was triturated with tert-butyl methyl ether (3×20 mL) to provide the product as an off-white solid. Yield: 130 mg, 0.553 mmol, 85%. LCMS m/z 163.1 [M+H]$^+$. $^1$H NMR (400 MHz, DMSO-d$_6$) δ 10.77-10.55 (br s, 1H), 10.05-9.86 (br s, 1H), 7.29 (s, 1H), 5.19-5.08 (m, 1H), 4.67 (brd, J=15 Hz, 1H), 4.45 (br d, J=15 Hz, 1H), 2.52 (s, 3H), 2.37 (s, 3H), 1.55 (d, J=6.5 Hz, 3H).

Preparation P8

2-Methoxy-4-methyl-6,7-dihydro-5H-pyrrolo[3,4-b]pyridine, dihydrochloride salt (P8)

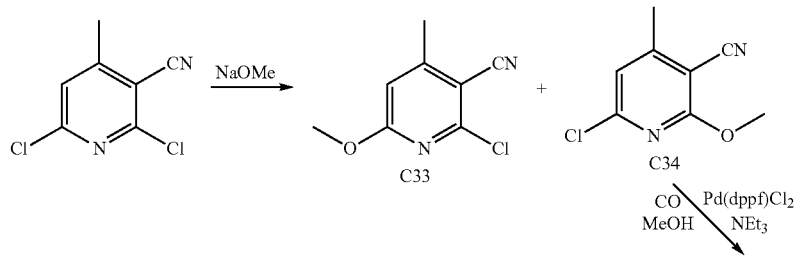

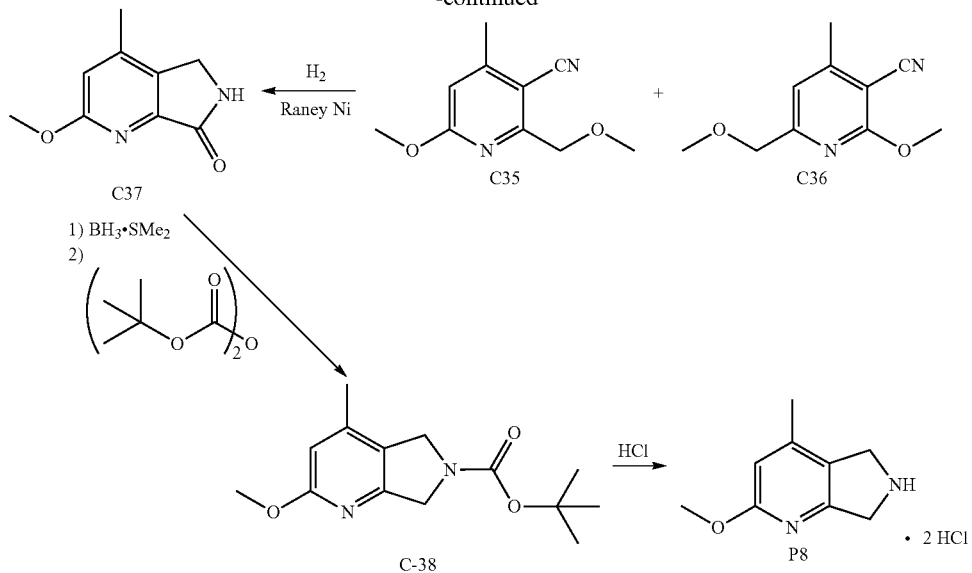

Step 1. Synthesis of 2-chloro-6-methoxy-4-methylpyridine-3-carbonitrile (C33) and 6-chloro-2-methoxy-4-methylpyridine-3-carbonitrile (C34)

A solution of 2,6-dichloro-4-methylpyridine-3-carbonitrile (10.0 g, 53.5 mmol) in methanol (50 mL) was cooled to 0° C. and treated in a drop-wise manner with a solution of sodium methoxide in methanol (freshly prepared, 1.07 M; 75 mL, 80.2 mmol) over 30 minutes. The reaction mixture was allowed to stir until thin-layer chromatographic analysis indicated that the starting material was completely consumed, whereupon water (50 mL) was added and methanol was removed under reduced pressure. The resulting mixture was extracted with ethyl acetate (3×50 mL), and the combined organic layers were washed with saturated aqueous sodium chloride solution (50 mL), dried over sodium sulfate, filtered, and concentrated in vacuo. By $^1$H NMR, the product consisted of a roughly equimolar mixture of C33 and C34. This material was used directly in the following step. Yield: 9.3 g, 51 mmol, 95%. $^1$H NMR (400 MHz, CDCl$_3$) δ 6.90 (s, 1H), 6.60 (s, 1H), 4.06 (s, 3H), 3.99 (s, 3H), 2.50 (s, 6H).

Step 2. Synthesis of methyl 3-cyano-6-methoxy-4-methylpyridine-2-carboxylate (C35) and methyl 5-cyano-6-methoxy-4-methylpyridine-2-carboxylate (C36)

Triethylamine (20.9 mL, 150 mmol) and [1,1'-bis(diphenylphosphino)ferrocene]-dichloropalladium(II) (3.73 g, 5.10 mmol) were added to a mixture of C33 and C34 (from the previous step, roughly 1:1 mixture; 9.3 g, 51 mmol) in methanol (200 mL). Carbon monoxide gas was bubbled into the reaction mixture, which was then pressurized to 50 psi with carbon monoxide and heated at 70° C. for 19 hours. After the reaction mixture had been filtered, the filtrate was concentrated in vacuo. Silica gel chromatography (Eluent: 10:1 petroleum ether/ethyl acetate) afforded the product as a white solid; by $^1$H NMR analysis, this material was composed of a roughly 3:1 mixture of C35 and C36. This material was used directly in the following step. Yield: 6.9 g, 33 mmol, 65%. $^1$H NMR (400 MHz, CDCl$_3$) δ Peaks attributed to C35: 6.85 (s, 1H), 4.05 (s, 3H), 4.04 (s, 3H), 2.56 (s, 3H); Peaks attributed to C36: 7.65 (s, 1H), 4.14 (s, 3H), 3.99 (s, 3H), 2.59 (s, 3H).

Step 3. Synthesis of 2-methoxy-4-methyl-5,6-dihydro-7H-pyrrolo[3,4-b]pyridin-7-one (C37)

To a solution of C35 and C36 (from the previous step, roughly 3:1 mixture; 6.9 g, 33 mmol) in methanol (200 mL) was added Raney nickel (2.46 g, 28.7 mmol). Hydrogen was bubbled into the reaction mixture, which was then pressurized to 40 psi with hydrogen and stirred at 40° C. for 48 hours. The catalyst was removed via filtration, and the filtrate was concentrated in vacuo. Silica gel chromatography (Gradient: 0% to 17% methanol in ethyl acetate) afforded the product as an off-white solid. Yield: 3.2 g, 18 mmol, 34% over 3 steps. LCMS m/z 178.9 [M+H]$^+$. $^1$H NMR (400 MHz, CDCl$_3$) δ 7.69-7.59 (br s, 1H), 6.74 (s, 1H), 4.33 (br s, 2H), 4.05 (s, 3H), 2.34 (s, 3H).

Step 4. Synthesis of tert-butyl 2-methoxy-4-methyl-5,7-dihydro-6H-pyrrolo[3,4-b]pyridine-6-carboxylate (C38)

Conversion of C37 to the product was carried out using the method described for synthesis of C3 from C2 in Preparation P1. The product was obtained as a white solid. From analysis of the $^1$H NMR, this material was presumed to exist as a mixture of rotamers. Yield: 2.2 g, 8.3 mmol, 46%. LCMS m/z 264.8 [M+H]$^+$. $^1$H NMR (400 MHz, CDCl$_3$) δ 6.45 (s, 1H), 4.65-4.50 (m, 4H), [3.91 (s) and 3.90 (s), total 3H], 2.22 (s, 3H), [1.53 (s) and 1.52 (s), total 9H].

Step 5. Synthesis of 2-methoxy-4-methyl-6,7-dihydro-5H-pyrrolo[3,4-b]pyridine, Dihydrochloride Salt (P8)

A solution of hydrogen chloride in methanol (4 M, 2 mL) was added drop-wise to a 0° C. solution of C38 (100 mg, 0.378 mmol) in dichloromethane (10 mL), and the reaction mixture was stirred at room temperature for 1 hour. Concentration in vacuo afforded the product as an off-white solid. Yield: 74 mg, 0.31 mmol, 82%. $^1$H NMR (400 MHz, CD$_3$OD) δ 6.63 (s, 1H), 4.59 (s, 2H), 4.48 (s, 2H), 3.90 (s, 3H), 2.30 (s, 3H).

Example 1

1-(2,4-Dimethyl-5,7-dihydro-6H-pyrrolo[3,4-b]pyridin-6-yl)-2-[1-(pyridin-3-yl)azetidin-3-yl]ethanone (1)

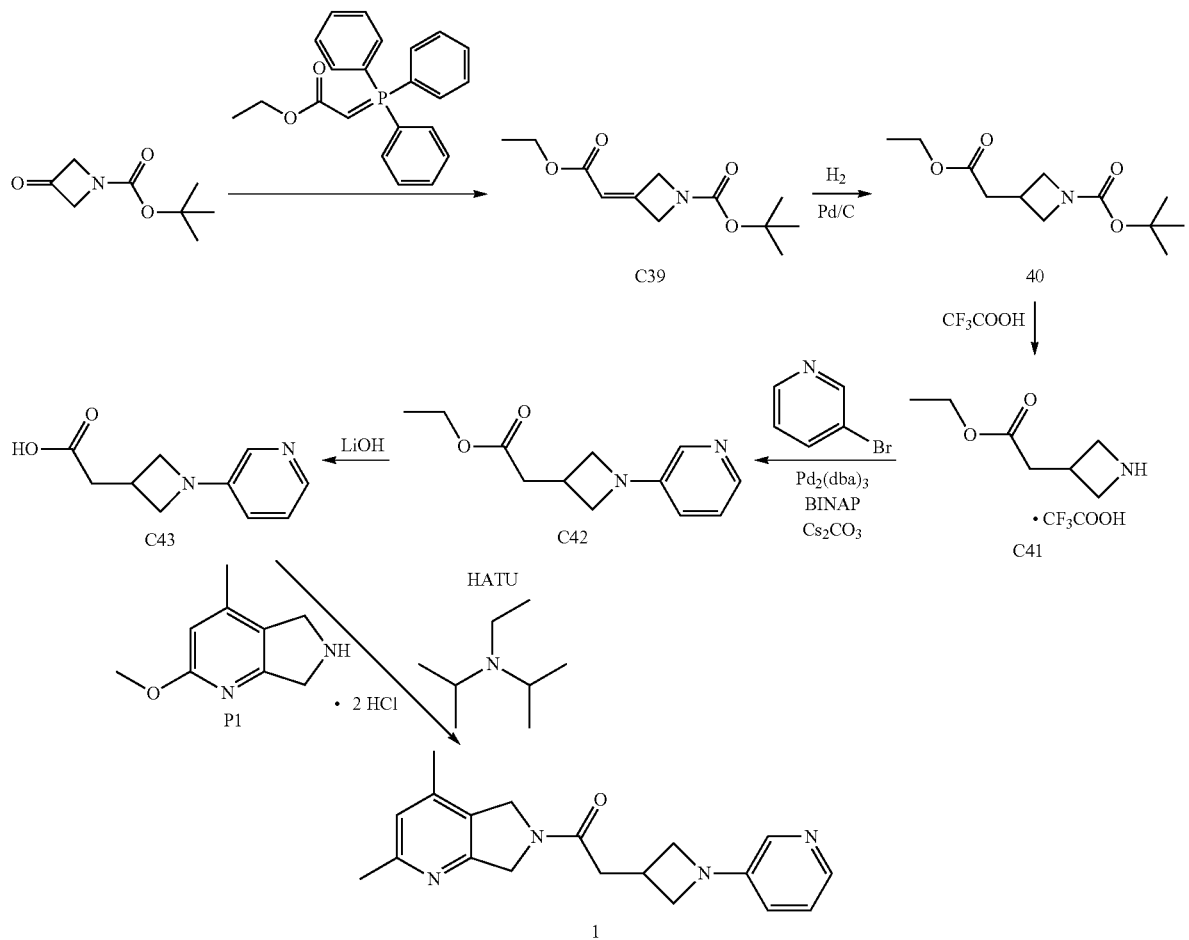

Step 1. Synthesis of tert-butyl 3-(2-ethoxy-2-oxoethylidene)azetidine-1-carboxylate (C39)

tert-Butyl 3-oxoazetidine-1-carboxylate (100 g, 584 mmol) was dissolved in dichloromethane (750 mL), cooled in an ice bath, and vigorously stirred while (carboethoxymethylene)triphenylphosphorane (220 g, 631 mmol) was added portion-wise over 15 minutes. The reaction mixture was then heated to 40° C. for 4 hours, whereupon most of the dichloromethane was removed in vacuo. The resulting thick slurry was diluted with a mixture of hexanes and tert-butyl methyl ether (2:1, 1 L), and stirred at room temperature for 1.5 hours. Triphenylphosphine oxide was removed via filtration; the filter cake was washed with a 2:1 mixture of hexanes and tert-butyl methyl ether, and the combined filtrates were concentrated in vacuo. Silica gel chromatography (Eluent: 2:1 hexanes/tert-butyl methyl ether) afforded the product as a clear, slightly yellow oil. Yield: 141.8 g, quantitative.

Step 2. Synthesis of tert-butyl 3-(2-ethoxy-2-oxoethyl)azetidine-1-carboxylate (C40)

A solution of C39 (141 g, 584 mmol) in tert-butyl methyl ether (500 mL) was placed in a Parr bottle and treated with 10% palladium on carbon (~50% water by weight; 2.5 g). The reaction vessel was evacuated and charged with nitrogen. This evacuation cycle was repeated several times, and then the bottle was pressurized to 40 psi with hydrogen and shaken for 30 minutes, whereupon the vessel was purged with additional nitrogen/vacuum cycles. The reaction mixture was filtered through a pad of diatomaceous earth and powdered cellulose, which was subsequently rinsed with tert-butyl methyl ether. The combined filtrates were concentrated in vacuo to provide the product as a clear, colorless oil. Yield: 140.1 g, 576 mmol, 99%. $^1$H NMR (400 MHz, DMSO-$d_6$) δ 4.04 (q, J=7.0 Hz, 2H), 3.99-3.85 (m, 2H), 3.58-3.45 (m, 2H), 2.84-2.71 (m, 1H), 2.62 (d, J=7.4 Hz, 2H), 1.36 (s, 9H), 1.17 (t, J=7.0 Hz, 3H).

Step 3. Synthesis of ethyl azetidin-3-ylacetate, Trifluoroacetate Salt (C41)

Trifluoroacetic acid (60 mL) was added in a drop-wise manner to a solution of C40 (15.0 g, 61.6 mmol) in dichloromethane (200 mL) and the reaction mixture was stirred at room temperature for 2 hours. Removal of solvents in vacuo afforded the product as a pale yellow oil. Yield: 15.85 g, 61.62 mmol, quantitative. $^1$H NMR (400 MHz, CDCl$_3$) δ 8.23-7.99 (br s, 1H), 7.99-7.77 (br s, 1H), 4.41-4.27 (m, 2H), 4.16 (q, J=7.2 Hz, 2H), 4.11-3.99 (m, 2H), 3.40-3.25 (m, 1H), 2.74 (d, J=7.2 Hz, 2H), 1.26 (t, J=7.2 Hz, 3H).

Step 4. Synthesis of ethyl [1-(pyridin-3-yl)azetidin-3-yl]acetate (C42)

A mixture of C41 (10.0 g, 38.9 mmol), 3-bromopyridine (16.6 g, 105 mmol), 1,1'-binaphthalene-2,2'-diylbis(diphenylphosphane) (BINAP; 8.7 g, 14 mmol), tris(dibenzylideneacetone)dipalladium(0) (Pd$_2$(dba)$_3$; 6.4 g, 7.0 mmol), and cesium carbonate (91.0 g, 279 mmol) in toluene (300 mL) was heated at 90° C. for 16 hours. Most of the toluene was removed via concentration in vacuo, and the residue was diluted with water (3×200 mL) and extracted with ethyl acetate (3×100 mL). The combined organic layers were washed with saturated aqueous sodium chloride solution (2×100 mL), dried over sodium sulfate, filtered, and concentrated under reduced pressure. Silica gel chromatography (Gradient: 17% to 20% ethyl acetate in petroleum ether) provided the product as a brown oil. Yield: 4.0 g, 18 mmol, 46%.

LCMS m/z 220.9 [M+H]$^+$. $^1$H NMR (400 MHz, CDCl$_3$) δ 8.01 (dd, J=4.6, 1.3 Hz, 1H), 7.85 (d, J=2.9 Hz, 1H), 7.10 (dd, J=8.2, 4.7 Hz, 1H), 6.71 (ddd, J=8.3, 2.8, 1.4 Hz, 1H), 4.16 (q, J=7.2 Hz, 2H), 4.11 (dd, J=7.9, 7.5 Hz, 2H), 3.61 (dd, J=7.2, 5.6 Hz, 2H), 3.20-3.08 (m, 1H), 2.72 (d, J=7.8 Hz, 2H), 1.27 (t, J=7.2 Hz, 3H).

Step 5. Synthesis of [1-(pyridin-3-yl)azetidin-3-yl]acetic acid (C43)

Lithium hydroxide (652 mg, 27.2 mmol) was added to a solution of C42 (3.00 g, 13.6 mmol) in a mixture of methanol (20 mL) and water (5 mL). The reaction mixture was stirred at room temperature for 2 hours, whereupon it was cooled to 0° C., and concentrated hydrochloric acid was added until the pH of the reaction mixture reached 7. Concentration in vacuo afforded the product. Yield: 3.3 g, assumed quantitative. $^1$H NMR (400 MHz, DMSO-d$_6$) δ 7.91-7.82 (m, 1H), 7.75 (s, 1H), 7.17-7.07 (m, 1H), 6.80-6.71 (m, 1H), 3.97 (dd, J=7, 7 Hz, 2H), 3.48 (dd, J=6, 6 Hz, 2H), 3.02-2.89 (m, 1H), 2.5 (2H, assumed; obscured by solvent peak).

Step 6. Synthesis of 1-(2,4-dimethyl-5,7-dihydro-6H-pyrrolo[3,4-b]pyridin-6-yl)-2-[1-(pyridin-3-yl)azetidin-3-yl]ethanone (1)

N,N-Diisopropylethylamine (7.0 g, 54 mmol) was added to a 0° C. solution of P1 (2.50 g, 13.5 mmol), C43 (2.60 g, 13.5 mmol), and O-(7-azabenzotriazol-1-yl)-N,N,N',N'-tetramethyluronium hexafluorophosphate (HATU; 7.72 g, 20.3 mmol) in N,N-dimethylformamide (50 mL). The reaction mixture was stirred and allowed to warm from 0° C. to room temperature over 1.5 hours, whereupon it was poured into water (50 mL), and the resulting mixture was extracted with ethyl acetate (3×50 mL). The combined organic layers were washed sequentially with water (2×30 mL) and with saturated aqueous sodium chloride solution (30 mL), dried over sodium sulfate, filtered, and concentrated in vacuo. Silica gel chromatography (Gradient: 2% to 5% methanol in dichloromethane) was followed by reversed-phase HPLC [Column: YMC-Actus Triart C18, 5 μm; Mobile phase: 30% acetonitrile in (water containing 0.05% ammonium hydroxide)] to afford the product as a white solid. From analysis of the $^1$H NMR, this material was presumed to exist as a mixture of rotamers. Yield: 3.80 g, 11.8 mmol, 87%. LCMS m/z 323.0 [M+H]$^+$. $^1$H NMR (400 MHz, CD$_3$OD) δ 7.85 (br d, J=5 Hz, 1H), 7.75 (d, J=2.8 Hz, 1H), 7.21 (dd, J=8.3, 4.8 Hz, 1H), 7.06 (s, 1H), 6.93-6.88 (m, 1H), 4.9-4.82 (m, 2H, assumed; partially obscured by water peak), 4.73-4.67 (m, 2H), 4.15 (dd, J=7.5, 7.5 Hz, 2H), 3.68 (br dd, J=7, 6 Hz, 2H), 3.28-3.16 (m, 1H), [2.93 (d, J=7.5 Hz) and 2.92 (d, J=7.5 Hz), total 2H], 2.49 (s, 3H), 2.31 (s, 3H).

Example 2

2-{1-[2-(Difluoromethyl)pyridin-4-yl]azetidin-3-yl}-1-(2,4-dimethyl-5,7-dihydro-6H-pyrrolo[3,4-b]pyridin-6-yl)ethanone (2)

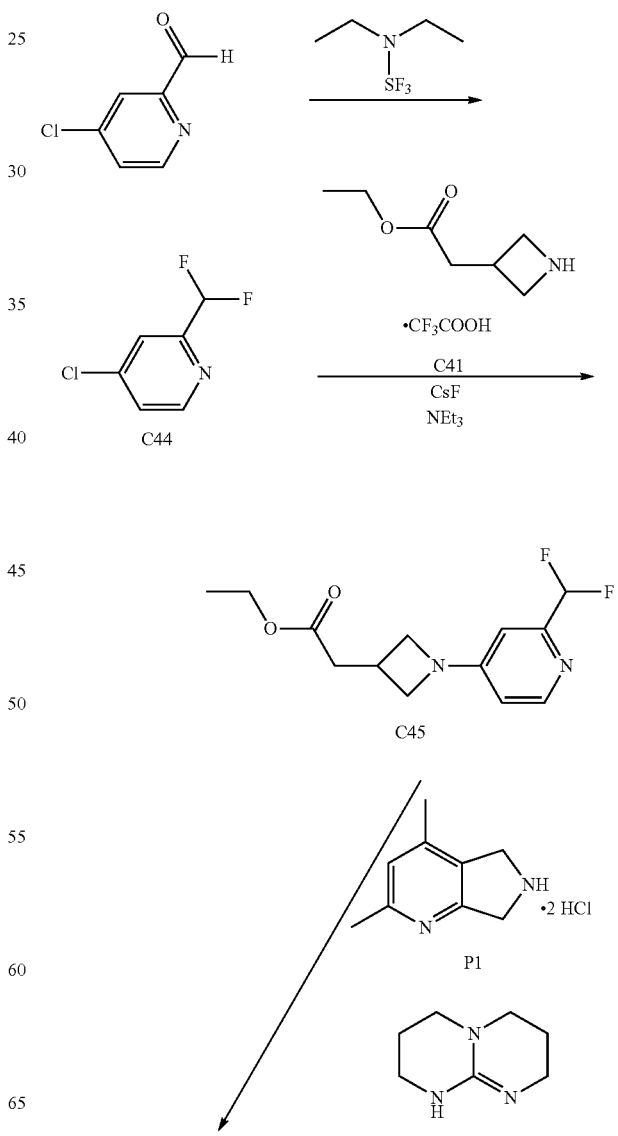

-continued

[Structure 2]

Step 1 Synthesis of 4-chloro-2-(difluoromethyl)pyridine (C44)

A solution of (diethylamino)sulfur trifluoride (854 mg, 5.30 mmol) in dichloromethane (5 mL) was added in a drop-wise manner to a −30° C. (dry ice-acetonitrile bath) solution of 4-chloropyridine-2-carbaldehyde (500 mg, 3.5 mmol) in dichloromethane (15 mL). The reaction mixture was stirred at −30° C. for 4 hours, and then allowed to warm to room temperature and stir for 16 hours. The reaction was quenched via addition of ice and was then basified to pH 8-10 by addition of saturated aqueous sodium bicarbonate solution. The resulting mixture was extracted with dichloromethane (3×50 mL), and the combined organic layers were washed with saturated aqueous sodium chloride solution (2×50 mL), dried over sodium sulfate, filtered, and concentrated in vacuo at low temperature, affording the product as a brown liquid. This was used in the following step without further purification. {Note: [Bis(2-methoxyethyl)amino]sulfur trifluoride is also a useful fluorinating agent for this transformation.} Yield: 500 mg, 3.1 mmol, 89%. $^1$H NMR (400 MHz, CDCl$_3$) δ 8.57 (d, J=5.3 Hz, 1H), 7.67 (d, J=1.9 Hz, 1H), 7.45-7.42 (m, 1H), 6.63 (t, J$_{HF}$=55.2 HZ, 1H).

Step 2. Synthesis of ethyl {1-[2-(difluoromethyl)pyridin-4-yl]azetidin-3-yl}acetate (C45)

A mixture of C44 (500 mg, 3.1 mmol), C41 (1.18 g, 4.59 mmol), cesium fluoride (464 mg, 3.05 mmol), and triethylamine (1.67 mL, 12.0 mmol) in dimethyl sulfoxide (10 mL) was stirred at 100° C. for 18 hours, whereupon the reaction mixture was poured into water (30 mL) and extracted with dichloromethane (3×100 mL). The combined organic layers were washed with water (3×100 mL) and with saturated aqueous sodium chloride solution (100 mL), dried over sodium sulfate, filtered, and concentrated in vacuo. Silica gel chromatography (Eluent: 3:1 petroleum ether/ethyl acetate) provided the product as a yellow oil. Yield: 443 mg, 1.64 mmol, 53%. $^1$H NMR (400 MHz, CDCl$_3$) δ 8.23 (d, J=5.6 Hz, 1H), 6.55 (d, J=2.3 Hz, 1H), 6.51 (t, J$_{HF}$=55.8 HZ, 1H), 6.28 (dd, J=5.6, 2.3 Hz, 1H), 4.19 (dd, J=8.2, 8.0 Hz, 2H), 4.17 (q, J=7.2 Hz, 2H), 3.70 (dd, J=8.1, 5.5 Hz, 2H), 3.23-3.12 (m, 1H), 2.72 (d, J=7.8 Hz, 2H), 1.28 (t, J=7.1 Hz, 3H).

Step 3. Synthesis of 2-{1-[2-(difluoromethyl)pyridin-4-yl]azetidin-3-yl}-1-(2,4-dimethyl-5,7-dihydro-6H-pyrrolo[3,4-b]pyridin-6-yl)ethanone (2)

A mixture of P1 (90 mg, 0.49 mmol), C45 (105 mg, 0.388 mmol), and 1,3,4,6,7,8-hexahydro-2H-pyrimido[1,2-a]pyrimidine (TBD; 203 mg, 1.46 mmol) in N,N-dimethylformamide (8 mL) was stirred at 85° C. for 16 hours. The reaction mixture was poured into water (10 mL) and extracted with ethyl acetate (3×10 mL). The combined organic layers were washed with water (3×10 mL) and with saturated aqueous sodium chloride solution (10 mL), dried over sodium sulfate, filtered and concentrated in vacuo. Reversed-phase HPLC (Column: Waters XBridge C18 OBD, 5 μm; Mobile phase A: water containing 0.05% ammonium hydroxide; Mobile phase B: acetonitrile; Gradient: 24% to 39% B) provided the product as a white solid. From analysis of the $^1$H NMR, the product was presumed to exist as a mixture of rotamers. Yield: 16.4 mg, 44 μmol, 11%. LCMS m/z 373.0 [M+H]$^+$. $^1$H NMR (400 MHz, CDCl$_3$) δ 8.23 (d, J=5.5 Hz, 1H), 6.94-6.90 (m, 1H), 6.57-6.55 (m, 1H), 6.51 (t, J$_{HF}$=55.8 HZ, 1H), 6.32-6.28 (m, 1H), 4.81-4.72 (m, 4H), [4.28 (dd, J=8.3, 8.0 Hz) and 4.27 (dd, J=8.0, 8.0 Hz), total 2H], 3.78-3.71 (m, 2H), 3.37-3.25 (m, 1H), 2.85-2.79 (m, 2H), [2.54 (s) and 2.53 (s), total 3H], [2.28 (s) and 2.27 (s), total 3H].

Example 3

1-(2,4-Dimethyl-5,7-dihydro-6H-pyrrolo[3,4-b]pyridin-6-yl)-2-[1-(pyrimidin-4-yl)azetidin-3-yl]ethanone (3)

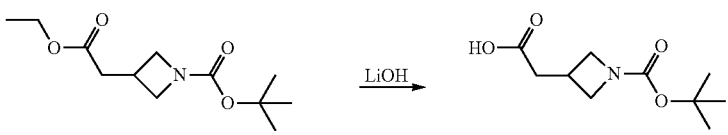

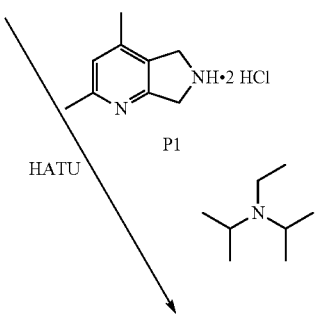

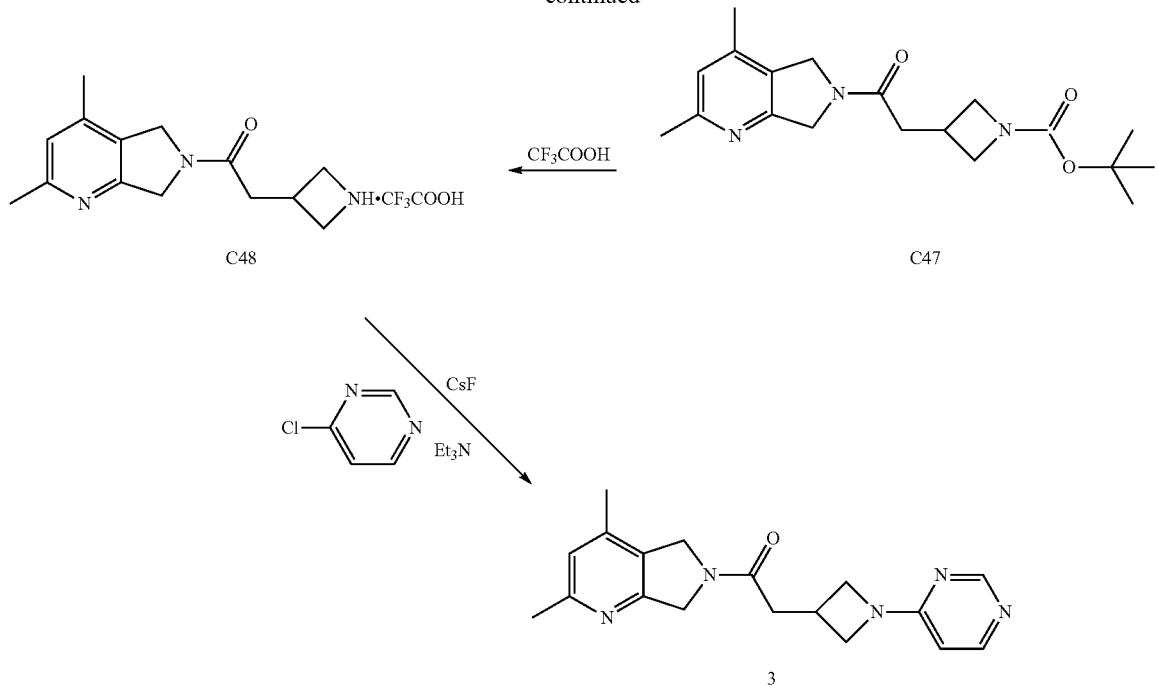

Step 1. Synthesis of [1-(tert-butoxycarbonyl)azetidin-3-yl]acetic acid (C46)

Lithium hydroxide (862 mg, 36.0 mmol) was added to a solution of C40 (7.30 g, 30.0 mmol) in a mixture of tetrahydrofuran (40 mL) and water (10 mL), and the reaction mixture was stirred at 20° C. for 2 hours. The reaction mixture was adjusted to a pH of 4 via addition of 1 M aqueous hydrochloric acid, and the resulting mixture was extracted with ethyl acetate (3×100 mL). The combined organic layers were washed sequentially with water (100 mL) and with saturated aqueous sodium chloride solution (100 mL), dried over sodium sulfate, filtered, and concentrated in vacuo to provide the product as a white solid. Yield: 6.0 g, 28 mmol, 93%. $^{1}$H NMR (400 MHz, CD$_3$OD) δ 4.06 (dd, J=8.5, 8.3 Hz, 2H), 3.61 (dd, J=8, 6 Hz, 2H), 2.94-2.82 (m, 1H), 2.62 (d, J=7.8 Hz, 2H), 1.43 (s, 9H).

Step 2. Synthesis of tert-butyl 3-[2-(2,4-dimethyl-5,7-dihydro-6H-pyrrolo[3,4-b]pyridin-6-yl)-2-oxo-ethyl]azetidine-1-carboxylate (C47)

N,N-Diisopropylethylamine (2.8 g, 21.7 mmol) was added drop-wise to a 0° C. suspension of P1 (1.0 g, 4.5 mmol), C46 (1.17 g, 5.44 mmol), and O-(7-azabenzotriazol-1-yl)-N,N,N',N'-tetramethyluronium hexafluorophosphate (2.47 g, 6.50 mmol) in N,N-dimethylformamide (10 mL). The reaction mixture was stirred at 27° C. for 15 hours, whereupon it was poured into water (100 mL), and the resulting mixture was extracted with ethyl acetate (3×60 mL). The combined organic layers were washed with water (2×60 mL) and with saturated aqueous sodium chloride solution (30 mL), dried over sodium sulfate, filtered, and concentrated in vacuo. Silica gel chromatography (Gradient: 17% to 100% ethyl acetate in petroleum ether) afforded the product as a brown oil. This material was taken directly to the following step. Yield: 1.6 g, quantitative. $^{1}$H NMR (400 MHz, CDCl$_3$) δ 6.91 (s, 1H), 4.81-4.67 (m, 4H), 4.23-4.11 (m, 2H), 3.70-3.61 (m, 2H), 3.09-2.97 (m, 1H), 2.77-2.66 (m, 2H), 2.53 (s, 3H), 2.26 (s, 3H), 1.44 (s, 9H).

Step 3. Synthesis of 2-(azetidin-3-yl)-1-(2,4-dimethyl-5,7-dihydro-6H-pyrrolo[3,4-b]pyridin-6-yl) ethanone, trifluoroacetate salt (C48)

To a solution of C47 (1.6 g, 4.5 mmol) in dichloromethane (50 mL) was added trifluoroacetic acid (15 mL) drop-wise, and the reaction mixture was stirred at room temperature for 2 hours. Removal of solvents under reduced pressure provided the product as a brown oil. Yield: 1.2 g, 3.3 mmol, 73%.

Step 4. Synthesis of 1-(2,4-dimethyl-5,7-dihydro-6H-pyrrolo[3,4-b]pyridin-6-yl)-2-[1-(pyrimidin-4-yl) azetidin-3-yl]ethanone (3)

A mixture of C48 (1.0 g, 2.8 mmol), 4-chloropyrimidine (421 mg, 3.68 mmol), cesium fluoride (372 mg, 2.45 mmol), and triethylamine (991 mg, 9.79 mmol) in dimethyl sulfoxide (15 mL) was stirred at 100° C. for 15 hours. After the reaction mixture had been poured into water (15 mL) and extracted with ethyl acetate (3×15 mL), the combined organic layers were washed with water (15 mL) and with saturated aqueous sodium chloride solution (15 mL), dried over sodium sulfate, filtered, and concentrated in vacuo. Silica gel chromatography (Gradient: 2% to 5% methanol in dichloromethane) was followed by reversed-phase HPLC (Column: Waters XBridge C18 OBD, 5 µm; Mobile phase A: water containing 0.05% ammonium hydroxide; Mobile phase B: acetonitrile; Gradient: 26% to 56% B) to provide the product as a pale yellow solid.

From analysis of the $^{1}$H NMR, this material was presumed to exist as a mixture of rotamers. Yield: 450 mg, 1.39 mmol, 50%. LCMS m/z 323.9 [M+H]$^{+}$. $^{1}$H NMR (400 MHz, CD₃OD), characteristic peaks: δ 8.39 (s, 1H), 8.07 (d, J=6.0 Hz, 1H), 7.06 (s, 1H), 6.39 (br d, J=6.5 Hz, 1H), [4.88 (s), 4.70 (s), and 4.68 (s), total 3H], 4.34 (dd, J=9.0, 8.5 Hz, 2H), 3.92-3.85 (m, 2H), 3.30-3.18 (m, 1H), [2.94 (d, J=7.5 Hz) and 2.93 (d, J=7.5 Hz), total 2H], 2.49 (s, 3H), [2.31 (s) and 2.31 (s), total 3H].

Example 4

2-{1-[2-(Difluoromethoxy)pyridin-4-yl]azetidin-3-yl}-1-(2,4-dimethyl-5,7-dihydro-6H-pyrrolo[3,4-b]pyridin-6-yl)ethanone (4)

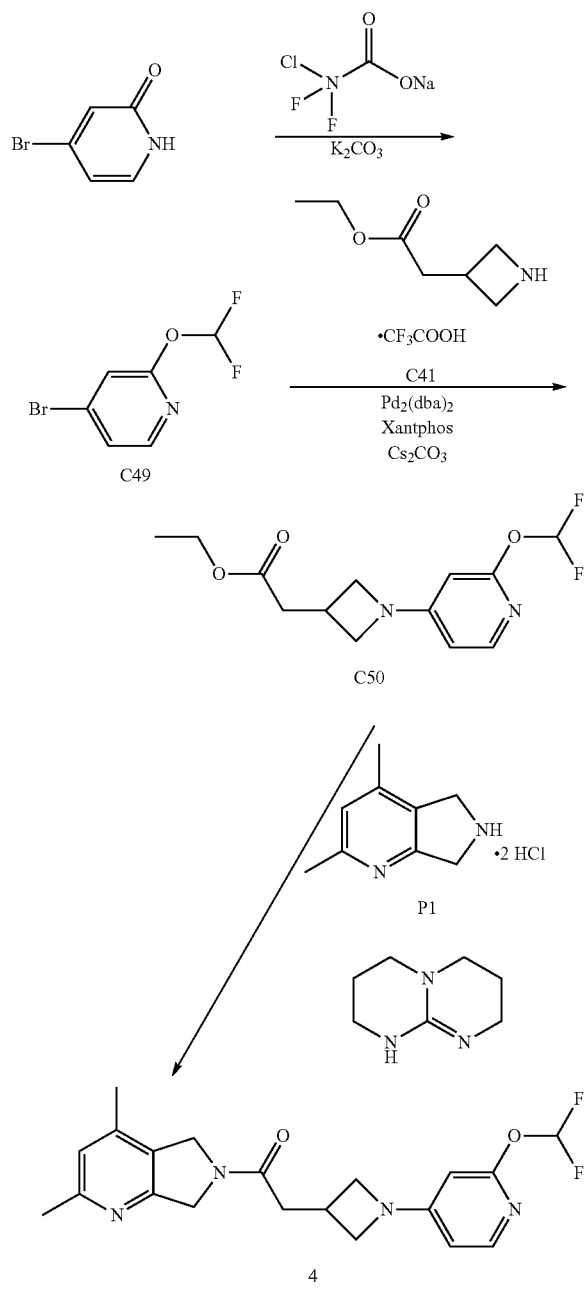

Step 1. Synthesis of 4-bromo-2-(difluoromethoxy)pyridine (C49)

Sodium chloro(difluoro)acetate (5.26 g, 34.5 mmol) and potassium carbonate (3.57 g, 25.8 mmol) were added to a solution of 4-bromopyridin-2(1H)-one (3.00 g, 17.2 mmol) in N,N-dimethylformamide (30 mL), and the reaction mixture was stirred at 95° C. for 2 hours. Water (100 mL) was added, and the resulting mixture was extracted with ethyl acetate (3×50 mL). The combined organic layers were washed sequentially with water (200 mL) and with saturated aqueous sodium chloride solution (150 mL), dried over sodium sulfate, filtered, and concentrated in vacuo. Silica gel chromatography (Eluent: 15:1 petroleum ether/ethyl acetate) afforded the product as a pale yellow oil. Yield: 1.5 g, 6.7 mmol, 39%. ¹H NMR (400 MHz, CDCl₃) δ 8.04 (d, J=5.5 Hz, 1H), 7.44 (t, $J_{HF}$=72.6 HZ, 1H), 7.27 (dd, J=5.4, 1.6 Hz, 1H), 7.12 (brd, J=1.5 Hz, 1H).

Step 2. Synthesis of ethyl {1-[2-(difluoromethoxy)pyridin-4-yl]azetidin-3-yl}acetate (C50)

A mixture of C41 (120 mg, 0.467 mmol), C49 (105 mg, 0.469 mmol), tris(dibenzylideneacetone)dipalladium(0) (12.8 mg, 14.0 μmol), 4,5-bis(diphenylphosphino)-9,9-dimethylxanthene (Xantphos; 17.8 mg, 30.8 μmol), and cesium carbonate (608 mg, 1.87 mmol) in 1,4-dioxane (5 mL) was stirred at 100° C. for 16 hours. After cooling to room temperature, the reaction mixture was filtered, and the filtrate was concentrated in vacuo. The residue was purified using silica gel chromatography (Eluent: 20:1 petroleum ether/ethyl acetate) to provide the product as a yellow oil. Yield: 50 mg, 0.17 mmol, 36%. ¹H NMR (400 MHz, CDCl₃) δ 7.81 (d, J=5.9 Hz, 1H), 7.42 (t, $J_{HF}$=73.7 HZ, 1H), 6.08 (dd, J=5.8, 2.1 Hz, 1H), 5.75 (d, J=2.0 Hz, 1H), 4.20-4.11 (m, 4H), 3.66 (dd, J=8.0, 5.5 Hz, 2H), 3.20-3.09 (m, 1H), 2.71 (d, J=7.9 Hz, 2H), 1.28 (t, J=7.1 Hz, 3H).

Step 3. Synthesis of 2-{1-[2-(difluoromethoxy)pyridin-4-yl]azetidin-3-yl}-1-(2,4-dimethyl-5,7-dihydro-6H-pyrrolo[3,4-b]pyridin-6-yl)ethanone (4)

A mixture of C50 (50 mg, 0.17 mmol), P1 (32.3 mg, 0.146 mmol), and 1,3,4,6,7,8-hexahydro-2H-pyrimido[1,2-a]pyrimidine (97.2 mg, 0.698 mmol) in N,N-dimethylformamide (3 mL) was heated at 80° C. for 16 hours. The reaction mixture was directly purified by reversed-phase HPLC (Column: Waters XBridge C18 OBD, 5 μm; Mobile phase A: water containing 0.05% ammonium hydroxide; Mobile phase B: acetonitrile; Gradient: 25% to 55% B) to afford the product as a white solid. From analysis of the ¹H NMR, this material was presumed to exist as a mixture of rotamers. Yield: 14.4 mg, 37.1 μmol, 25%. LCMS m/z 389.0 [M+H]⁺. ¹H NMR (400 MHz, CDCl₃) δ 7.81 (d, J=5.8 Hz, 1H), [7.43 (t, $J_{HF}$=73.8 HZ) and 7.42 (t, $J_{HF}$=73.8 HZ), total 1H], [6.92 (s) and 6.91 (s), total 1H], 6.11-6.07 (m, 1H), 5.78-5.75 (m, 1H), 4.80-4.71 (m, 4H), 4.25-4.18 (m, 2H), 3.73-3.65 (m, 2H), 3.35-3.24 (m, 1H), 2.84-2.77 (m, 2H), [2.54 (s) and 2.53 (s), total 3H], [2.27 (s) and 2.27 (s), total 3H].

Example 5

2-[1-(1,2,4-Thiadiazol-5-yl)azetidin-3-yl]-1-(2,3,4-trimethyl-5,7-dihydro-6H-pyrrolo[3,4-b]pyridin-6-yl)ethanone (5)

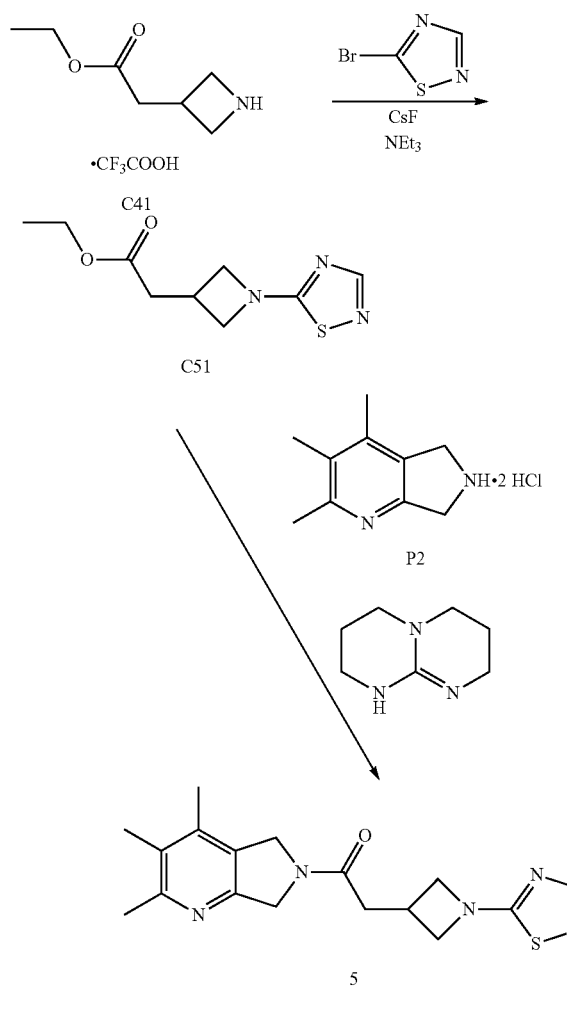

Step 1. Synthesis of ethyl [1-(1,2,4-thiadiazol-5-yl)azetidin-3-yl]acetate (C51)

[5-Bromo-1,2,4-thiadiazole was reacted with C41 using the method described for synthesis of C45 from C44 and C41 in Example 2. The product was obtained as a yellow oil. Yield: 1.10 g, 4.84 mmol, 76%. $^1$H NMR (400 MHz, CDCl$_3$) δ 7.93 (s, 1H), 4.37-4.31 (m, 2H), 4.15 (q, J=7.2 Hz, 2H), 3.89 (dd, J=9.1, 5.6 Hz, 2H), 3.32-3.21 (m, 1H), 2.74 (d, J=7.9 Hz, 2H), 1.26 (t, J=7.2 Hz, 3H).

Step 2. Synthesis of 2-[1-(1,2,4-thiadiazol-5-yl)azetidin-3-yl]-1-(2,3,4-trimethyl-5,7-dihydro-6H-pyrrolo[3,4-b]pyridin-6-yl)ethanone (5)

This reaction was carried out in two identical batches. A mixture of P2 (100 mg, 0.425 mmol), C51 (114 mg, 0.502 mmol), and 1,3,4,6,7,8-hexahydro-2H-pyrimido[1,2-a]pyrimidine (280 mg, 2.01 mmol) in N,N-dimethylformamide (3 mL) was heated at 80° C. for 16 hours. The two reaction mixtures were combined and directly purified by reversed-phase HPLC (Column: Waters XBridge C18 OBD, 5 μm; Mobile phase A: water containing 0.05% ammonium hydroxide; Mobile phase B: acetonitrile; Gradient: 16% to 46% B), affording the product as a white solid. From analysis of the $^1$H NMR, this material was presumed to exist as a mixture of rotamers. Yield: 99.9 mg, 0.291 mmol, 34%. LCMS m/z 343.9 [M+H]$^+$. $^1$H NMR (400 MHz, CDCl$_3$) δ 7.93 (s, 1H), 4.78-4.71 (m, 4H), 4.46-4.39 (m, 2H), 3.97-3.89 (m, 2H), 3.47-3.35 (m, 1H), [2.85 (d, J=7.8 Hz) and 2.82 (d, J=7.8 Hz), total 2H], [2.54 (s) and 2.53 (s), total 3H], 2.22 (br s, 6H).

Example 6

1-[2-(Difluoromethyl)-4-methyl-5,7-dihydro-6H-pyrrolo[3,4-b]pyridin-6-yl]-2-{1-[2-(trifluoromethyl)pyridin-4-yl]azetidin-3-yl}ethanone (6)

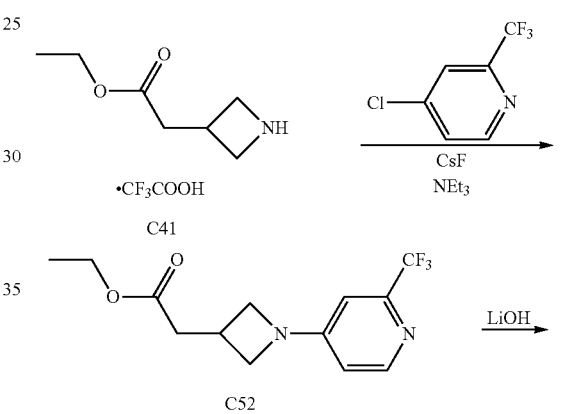

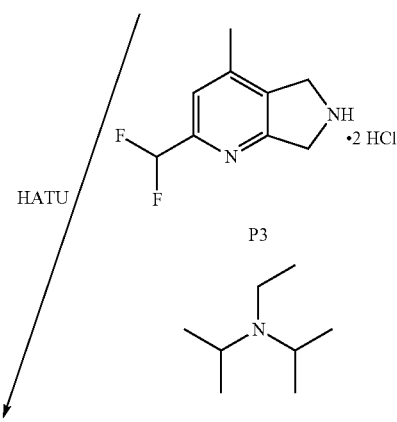

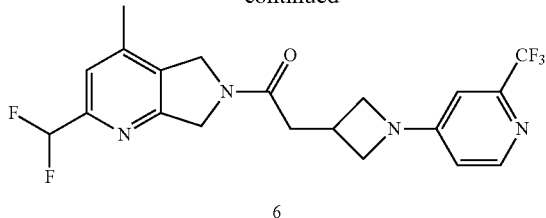

Step 1. Synthesis of ethyl {1-[2-(trifluoromethyl)pyridin-4-yl]azetidin-3-yl}acetate (C52)

4-Chloro-2-(trifluoromethyl)pyridine was reacted with C41 using the method described for synthesis of C45 from C44 and C41 in Example 2. The product was isolated as a pale yellow oil. Yield: 5.10 g, 17.7 mmol, 91%. LCMS m/z 289.1 [M+H]$^+$. $^1$H NMR (400 MHz, CDCl$_3$) δ 8.28 (d, J=5.6 Hz, 1H), 6.57 (d, J=2.3 Hz, 1H), 6.32 (dd, J=5.6, 2.3 Hz, 1H), 4.23-4.17 (m, 2H), 4.17 (q, J=7.2 Hz, 2H), 3.72 (dd, J=8.3, 5.5 Hz, 2H), 3.25-3.13 (m, 1H), 2.73 (d, J=7.9 Hz, 2H), 1.28 (t, J=7.2 Hz, 3H).

Step 2. Synthesis of {1-[2-(trifluoromethyl)pyridin-4-yl]azetidin-3-yl}acetic acid (C53)

Lithium hydroxide (498 mg, 20.8 mmol) was added to a solution of C52 (2.0 g, 6.9 mmol) in a mixture of water (4 mL) and tetrahydrofuran (20 mL), and the reaction mixture was stirred at room temperature for 2 hours, whereupon it was cooled to 0° C. After adjustment of the pH to 7 via addition of 3 M aqueous hydrochloric acid, the mixture was concentrated in vacuo to provide the product as a white solid. Yield: 1.7 g, 6.5 mmol, 94%. $^1$H NMR (400 MHz, CD$_3$OD) δ 8.13 (d, J=5.8 Hz, 1H), 6.67 (d, J=2.3 Hz, 1H), 6.48 (dd, J=5.8, 2.3 Hz, 1H), 4.20 (dd, J=8.4, 8.3 Hz, 2H), 3.74 (dd, J=8.5, 5.5 Hz, 2H), 3.21-3.09 (m, 1H), 2.64 (d, J=7.9 Hz, 2H).

Step 3. Synthesis of 1-[2-(difluoromethyl)-4-methyl-5,7-dihydro-6H-pyrrolo[3,4-b]pyridin-6-yl]-2-{1-[2-(trifluoromethyl)pyridin-4-yl]azetidin-3-yl}ethanone (6)

A mixture of C53 (177 mg, 0.680 mmol) and O-(7-azabenzotriazol-1-yl)-N,N,N',N'-tetramethyluronium hexafluorophosphate (388 mg, 1.02 mmol) in N,N-dimethylformamide (5 mL) was stirred at room temperature for 30 minutes, whereupon P3 (150 mg, 0.583 mmol) was added. N,N-Diisopropylethylamine (0.60 mL, 3.4 mmol) was added drop-wise, and the reaction mixture was stirred at room temperature for 1 hour, whereupon it was directly purified by reversed-phase HPLC (Column: Waters XBridge C18 OBD, 5 μm; Mobile phase A: water containing 0.05% ammonium hydroxide; Mobile phase B: acetonitrile; Gradient: 27% to 57% B), affording the product as a white solid. From analysis of the $^1$H NMR, this material was presumed to exist as a mixture of rotamers. Yield: 157 mg, 0.368 mmol, 63%. LCMS m/z 427.1 [M+H]$^+$. $^1$H NMR (400 MHz, CD$_3$OD) δ 8.14 (d, J=5.8 Hz, 1H), 7.47 (s, 1H), 6.72-6.68 (m, 1H), 6.69 (t, J$_{HF}$=55.2 HZ, 1H), 6.53-6.48 (m, 1H), 4.99-4.90 (m, 2H), 4.82-4.74 (m, 2H), 4.31-4.24 (m, 2H), 3.85-3.78 (m, 2H), 3.33-3.21 (m, 1H, assumed; partially obscured by solvent peak), [2.96 (d, J=7.6 Hz) and 2.95 (d, J=7.8 Hz), total 2H], 2.42 (s, 3H).

Example 7

1-[2-(Methoxymethyl)-4-methyl-5,7-dihydro-6N-pyrrolo[3,4-b]pyridin-6-yl]-2-{1-[2-(trifluoromethyl)pyridin-4-yl]azetidin-3-yl}ethanone (7)

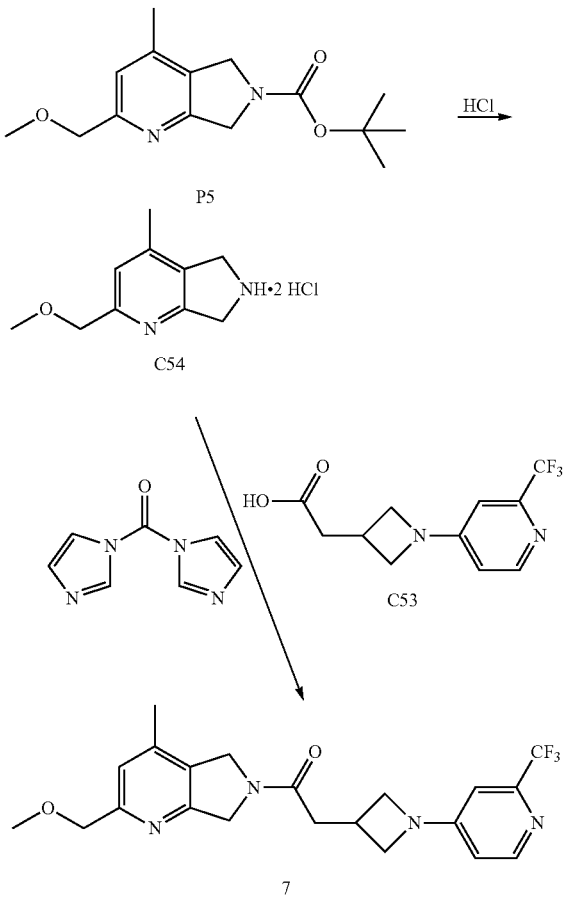

Step 1. Synthesis of 2-(methoxymethyl)-4-methyl-6,7-dihydro-5H-pyrrolo[3,4-b]pyridine, Dihydrochloride Salt (C54)

A solution of P5 (780 mg, 2.80 mmol) in dichloromethane (5.6 mL) was cooled in an ice bath and treated over 10 minutes with a solution of hydrogen chloride in 1,4-dioxane (4 M, 3.5 mL, 14 mmol). The ice bath was then removed and the reaction mixture was stirred at room temperature overnight, whereupon it was concentrated in vacuo. The resulting material was used without additional purification. Yield: 600 mg, 2.4 mmol, 86%.

Step 2. Synthesis of 1-[2-(methoxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone (7)

A mixture of C53 (584 mg, 2.24 mmol) and 1,1'-carbonyldiimidazole (423 mg, 2.61 mmol) in tetrahydrofuran (9 mL) was stirred at room temperature for 1.5 hours. This mixture was added to a flask containing C54 (600 mg, 2.4 mmol), and the reaction mixture was stirred at room temperature for 64 hours. It was then diluted with ethyl acetate and washed three times with water, once with saturated aqueous sodium bicarbonate solution, and once with saturated aqueous sodium chloride solution. The organic layer was dried over sodium sulfate, filtered, and concentrated in vacuo the resulting foam was treated with hot 2-propanol and stirred at room temperature overnight. The resulting solid was collected via filtration and dissolved in a 1:1 mixture of dichloromethane and methanol. After a scoop of activated carbon (Darco) had been added, the mixture was heated at reflux for 20 minutes, and was then filtered through diatomaceous earth. The filter pad was washed with dichloromethane, and the combined filtrates were concentrated under reduced pressure. The residue was slurried with hot 2-propanol for 2 hours, and stirred at room temperature overnight. The resulting solid was isolated via filtration to afford the product. From analysis of the $^1$H NMR, this material was presumed to exist as a mixture of rotamers. Yield: 450 mg, 1.07 mmol, 48%. LCMS m/z 421.3 [M+H]$^+$. $^1$H NMR (400 MHz, CDCl$_3$) δ 8.28 (d, J=5.7 Hz, 1H), 7.18 (s, 1H), 6.60-6.57 (m, 1H), 6.33 (dd, J=5.7, 2.2 Hz, 1H), 4.83-4.74 (m, 4H), [4.56 (s) and 4.55 (s), total 2H], [4.29 (dd, J=8.4, 8.0 Hz) and 4.28 (dd, J=8.2, 8.2 Hz), total 2H], 3.80-3.72 (m, 2H), [3.50 (s) and 3.49 (s), total 3H], 3.40-3.27 (m, 1H), [2.84 (d, J=8.0 Hz) and 2.81 (d, J=7.6 Hz), total 2H], [2.33 (s) and 2.32 (s), total 3H].

Example 8

2-{1-[2-(Difluoromethoxy)pyridin-4-yl]azetidin-3-yl}-1-[2-(methoxymethyl)-4-methyl-5,7-dihydro-6H-pyrrolo[3,4-b]pyridin-6-yl]ethanone (8)

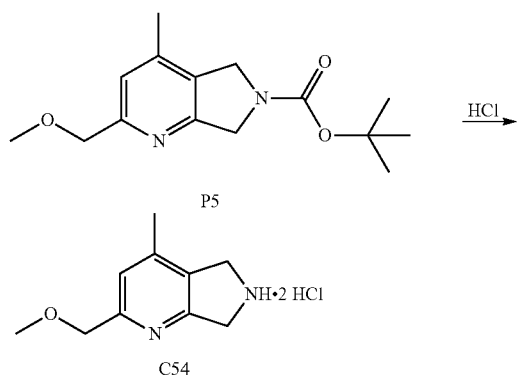

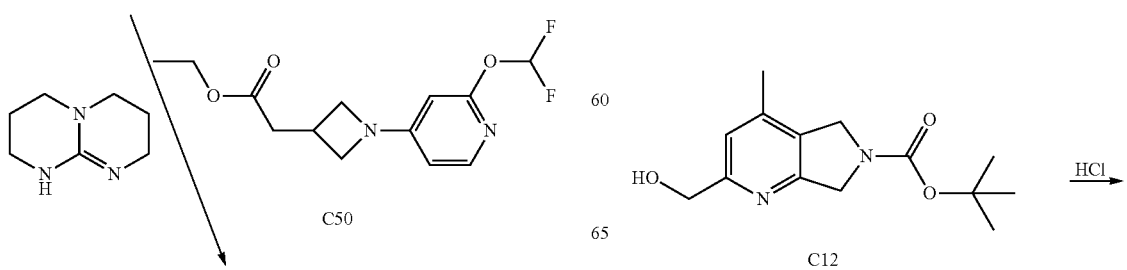

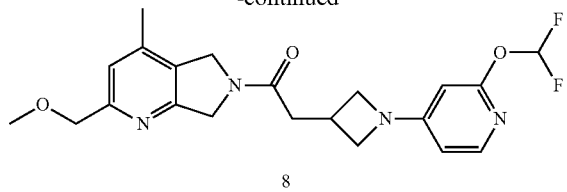

Step 1. Synthesis of 2-(methoxymethyl)-4-methyl-6,7-dihydro-5H-pyrrolo[3,4-b]pyridine, Dihydrochloride Salt (C54)

A solution of hydrogen chloride in methanol (4 M, 4.5 mL, 18 mmol) was added to a 0° C. solution of P5 (1.00 g, 3.59 mmol) in dichloromethane (15 mL). The reaction mixture was stirred at room temperature for 2 hours, whereupon it was concentrated in vacuo. The residue was triturated with tert-butyl methyl ether (3×50 mL) to provide the product as a brown solid. Yield: 700 mg, 2.79 mmol, 78%. $^1$H NMR (400 MHz, CD$_3$OD) 7.82 (br s, 1H), 5.00 (s, 2H), 4.90-4.88 (br s, 2H), 4.87-4.85 (m, 2H), 3.58 (s, 3H), 2.63 (brs, 3H).

Step 2. Synthesis of 2-{1-[2-(difluoromethoxy)pyridin-4-yl]azetidin-3-yl}-1-[2-(methoxymethyl)-4-methyl-5,7-dihydro-6H-pyrrolo[3,4-b]pyridin-6-yl]ethanone (8)

A mixture of C54 (120 mg, 0.478 mmol), C50 (160 mg, 0.559 mmol), and 1,3,4,6,7,8-hexahydro-2H-pyrimido[1,2-a]pyrimidine (311 mg, 2.23 mmol) in N,N-dimethylformamide (4 mL) was heated at 80° C. for 16 hours. The reaction mixture was directly purified via reversed-phase HPLC (Column: Waters XBridge C18 OBD, 5 μm; Mobile phase A: water containing 0.05% ammonium hydroxide; Mobile phase B: acetonitrile; Gradient: 25% to 55% B), followed by supercritical fluid chromatography [Column: Chiral Technologies Chiralpak AS, 5 μm; Mobile phase: 3:1 carbon dioxide/(methanol containing 0.1% ammonium hydroxide)], affording the product as a white solid. From analysis of the $^1$H NMR, this material was presumed to exist as a mixture of rotamers. Yield: 31.5 mg, 75.3 μmol, 16%. LCMS m/z 419.1 [M+H]$^+$. $^1$H NMR (400 MHz, CDCl$_3$) δ 7.80 (d, J=5.8 Hz, 1H), [7.42 (t, J$_{HF}$=73.7 Hz) and 7.42 (t, J$_{HF}$=73.8 HZ), total 1H], 7.17 (s, 1H), 6.11-6.06 (m, 1H), 5.78-5.74 (m, 1H), 4.83-4.73 (m, 4H), [4.56 (s) and 4.54 (s), total 2H], [4.22 (dd, J=8.0, 8.0 Hz) and 4.21 (dd, J=8.2, 8.0 Hz), total 2H], 3.73-3.65 (m, 2H), [3.49 (s) and 3.49 (s), total 3H], 3.34-3.22 (m, 1H), [2.82 (d, J=7.8 Hz) and 2.79 (d, J=7.8 Hz), total 2H], [2.32 (s) and 2.31 (s), total 3H].

Example 9

1-[2-(Hydroxymethyl)-4-methyl-5,7-dihydro-6H-pyrrolo[3,4-b]pyridin-6-yl]-2-[1-(pyridin-3-yl)azetidin-3-yl]ethanone (9)

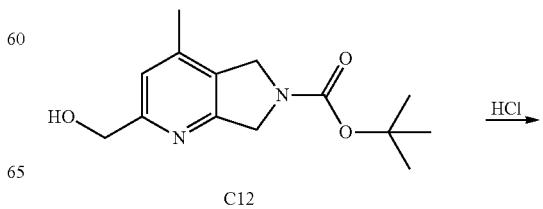

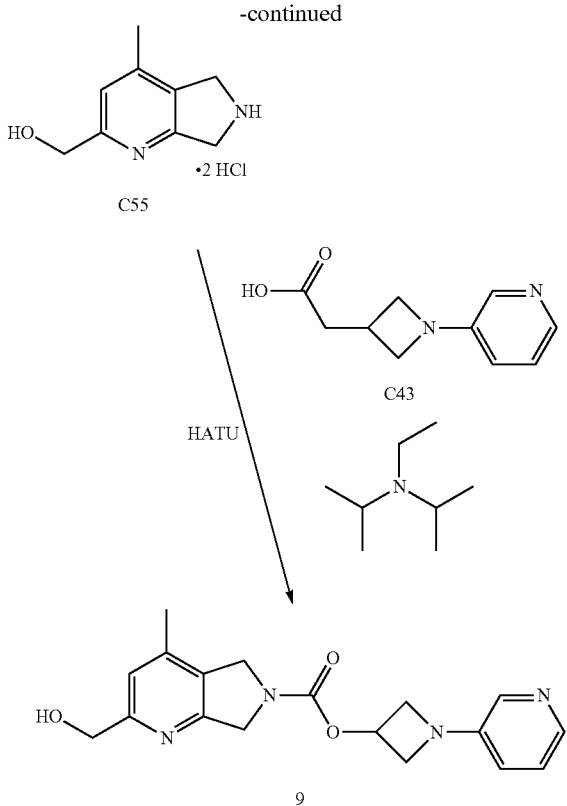

Step 1. Synthesis of (4-methyl-6,7-dihydro-5H-pyrrolo[3,4-b]pyridin-2-yl)methanol, Dihydrochloride Salt (C55)

A solution of hydrogen chloride in methanol (4 M; 2 mL, 8 mmol) was added in a drop-wise manner to a 0° C. solution of C12 (200 mg, 0.757 mmol) in dichloromethane (4 mL). After the reaction mixture had been stirred at room temperature for 1 hour, it was concentrated in vacuo to afford the product as a dark red solid. Yield: 123 mg, 0.519 mmol, 69%.

Step 2. Synthesis of 1-[2-(hydroxymethyl)-4-methyl-5,7-dihydro-6H-pyrrolo[3,4-b]pyridin-6-yl]-2-[1-(pyridin-3-yl)azetidin-3-yl]ethanone (9)

N,N-Diisopropylethylamine (0.62 mL, 3.56 mmol) was added to a 0° C. solution of C55 (123 mg, 0.519 mmol), C43 (144 mg, 0.749 mmol), and O-(7-azabenzotriazol-1-yl)-N,N,N',N'-tetramethyluronium hexafluorophosphate (427 mg, 1.12 mmol) in N,N-dimethylformamide (3 mL), and the reaction mixture was stirred at 0° C. to room temperature for 1 hour. It was then directly purified by reversed-phase HPLC (Column: YMC-Actus Triart C18, 5 μm; Mobile phase A: water containing 0.05% ammonium hydroxide; Mobile phase B: acetonitrile; Gradient: 18% to 48% B), followed by supercritical fluid chromatography [Column: Chiral Technologies Chiralpak AS, 5 μm; Mobile phase A: 7:3 carbon dioxide/(methanol containing 0.1% ammonium hydroxide]. The product was isolated as an off-white solid. From analysis of the $^1$H NMR, this material was presumed to exist as a mixture of rotamers. Yield: 33.4 mg, 98.6 μmol, 19%. LCMS m/z 339.0 [M+H]$^+$. $^1$H NMR (400 MHz, CD$_3$OD), characteristic peaks: δ 7.86 (d, J=4.5 Hz, 1H), 7.75 (br s, 1H), 7.30 (s, 1H), 7.21 (dd, J=8.3, 4.5 Hz, 1H), 6.94-6.88 (m, 1H), 4.92 (s, 1H), [4.74 (s) and 4.71 (s), total 2H], 4.66 (s, 2H), 4.16 (br dd, J=8, 8 Hz, 2H), 3.68 (dd, J=7.3, 5.8 Hz, 2H), 3.27-3.18 (m, 1H), 2.93 (dd, J=7.3, 7.0 Hz, 2H), 2.37 (s, 3H).

Example 10

2-{1-[2-(Difluoromethoxy)pyridin-4-yl]azetidin-3-yl}-1-[2-(difluoromethyl)-3,4-dimethyl-5,7-dihydro-6H-pyrrolo[3,4-b]pyridin-6-yl]ethanone (10)

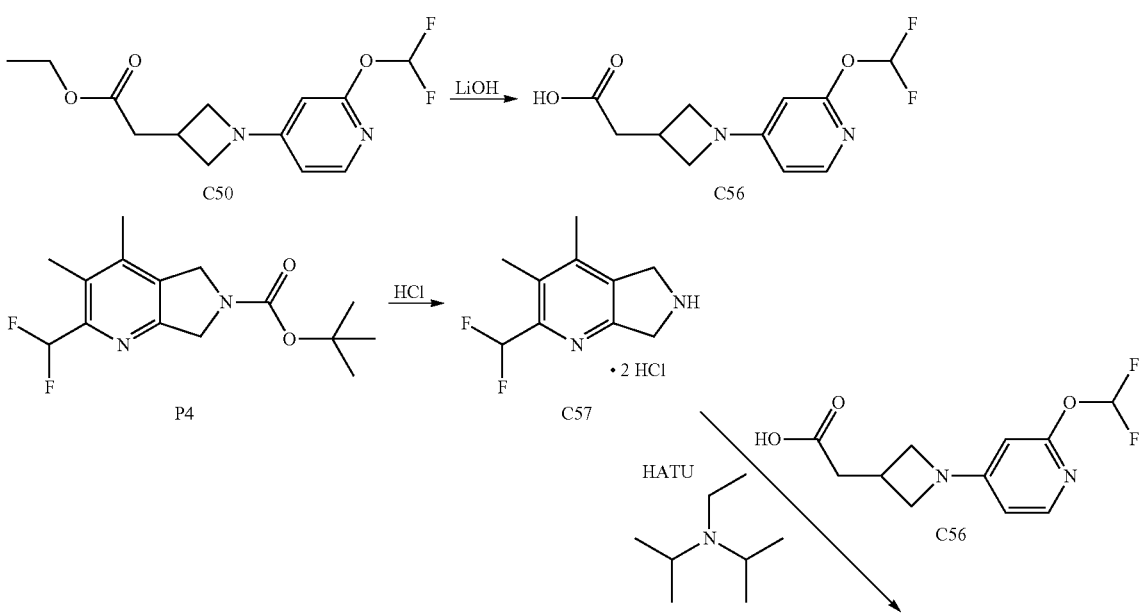

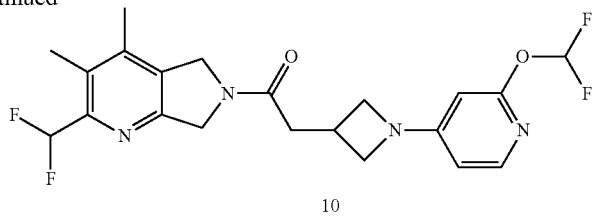

10

Step 1. Synthesis of {1-[2-(difluoromethoxy)pyridin-4-yl]azetidin-3-yl}acetic acid (C56)

Lithium hydroxide (50.2 mg, 2.10 mmol) was added to a solution of C50 (300 mg, 1.05 mmol) in tetrahydrofuran (4 mL) and water (1 mL). The reaction mixture was stirred at room temperature for 2 hours, whereupon it was cooled to 0° C. and the pH was adjusted to <7 via addition of concentrated hydrochloric acid. The resulting mixture was diluted with tetrahydrofuran (10 mL), dried over sodium sulfate, filtered, and concentrated under reduced pressure to afford the product as a white solid. Yield: 271 mg, 1.05 mmol, 100%. LCMS m/z 258.1 [M+H]$^+$. $^1$H NMR (400 MHz, DMSO-d$_6$) δ 7.75 (d, J=5.5 Hz, 1H), 7.61 (t, J$_{HF}$=73.8 HZ, 1H), 6.18 (brd, J=5.5 Hz, 1H), 5.81 (br s, 1H), 4.00 (dd, J=8.0, 7.5 Hz, 2H), 3.58-3.50 (m, 2H), 3.02-2.87 (m, 1H), 2.29 (d, J=8.0 Hz, 2H).

Step 2. Synthesis of 2-(difluoromethyl)-3,4-dimethyl-6,7-dihydro-5H-pyrrolo[3,4-b]pyridine, Dihydrochloride Salt (C57)

A solution of hydrogen chloride in methanol (4 M, 2 mL, 8 mmol) was added to a solution of P4 (300 mg, 1.01 mmol) in methanol (10 mL) and the reaction mixture was stirred at room temperature for 3 hours. Removal of solvents in vacuo provided the product as a brown oil, which was used without further purification. Yield: 275 mg. 1.01 mmol, 100%.

Step 3. Synthesis of 2-{1-[2-(difluoromethoxy)pyridin-4-yl]azetidin-3-yl}-1-[2-(difluoromethyl)-3,4-dimethyl-5,7-dihydro-6H-pyrrolo[3,4-b]pyridin-6-yl]ethanone (10)

To a mixture of C57 (90 mg, 0.33 mmol), C56 (103 mg, 0.399 mmol), and O-(7-azabenzotriazol-1-yl)-N,N,N',N'-tetramethyluronium hexafluorophosphate (151 mg, 0.397 mmol) in N,N-dimethylformamide (5 mL) was added N,N-diisopropylethylamine (172 mg, 1.33 mmol), and the reaction mixture was stirred at room temperature for 30 minutes. It was then directly purified via reversed-phase HPLC (Column: Waters XBridge C18 OBD, 5 μm; Mobile phase A: water containing 0.05% ammonium hydroxide; Mobile phase B: acetonitrile; Gradient: 33% to 63% B). The product was isolated as a white solid; from analysis of the $^1$H NMR, this material was presumed to exist as a mixture of rotamers. Yield: 84.2 mg, 0.192 mmol, 58%. LCMS m/z 439.0 [M+H]$^+$. $^1$H NMR (400 MHz, CD$_3$OD) δ [7.75 (d, J=5.9 Hz) and 7.75 (d, J=5.9 Hz), total 1H], [7.36 (t, J$_{HF}$=73.8 HZ) and 7.36 (t, J$_{HF}$=73.8 HZ), total 1H], [6.84 (t, J$_{HF}$=54.4 HZ) and 6.83 (t, J$_{HF}$=54.5 HZ), total 1H], [6.22 (dd, J=5.9, 2 Hz) and 6.21 (dd, J=5.9, 2 Hz), total 1H], 5.84-5.82 (m, 1H), 4.98-4.95 (br s, 1H), 4.89-4.86 (m, 1H, assumed; largely obscured by water peak), 4.80-4.77 (br s, 1H), 4.73-4.71 (br s, 1H), 4.23-4.16 (m, 2H), 3.73 (dd, J=8.1, 5.5 Hz, 2H), 3.27-3.18 (m, 1H), [2.94 (d, J=7.8 Hz) and 2.92 (d, J=7.8 Hz), total 2H], 2.42 (br s, 3H), 2.33 (s, 3H).

Example 11

1-(2,4-Dimethyl-5,7-dihydro-6H-pyrrolo[3,4-b]pyridin-6-yl)-2-{1-[2-(trifluoromethyl)pyridin-4-yl]azetidin-3-yl}ethanone (11)

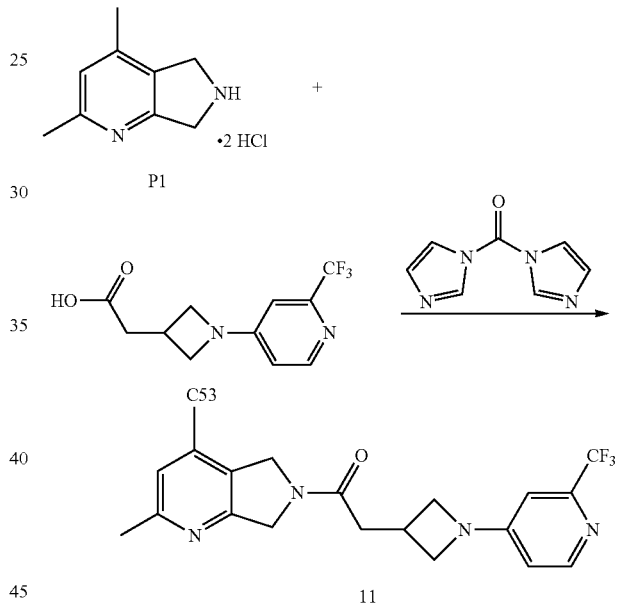

A mixture of C53 (462 mg, 1.78 mmol) and 1,1'-carbonyldiimidazole (332 mg, 2.05 mmol) in tetrahydrofuran (6.0 mL) was stirred at room temperature for 1.5 hours, whereupon additional 1,1'-carbonyldiimidazole (10 mg, 62 μmol) was introduced, and stirring was continued for 30 minutes. To the reaction mixture was added P1 (360 mg, 1.63 mmol), and stirring was continued overnight. The reaction mixture was then diluted with ethyl acetate and washed three times with water, once with saturated aqueous sodium bicarbonate solution, and once with saturated aqueous sodium chloride solution. The organic layer was dried over sodium sulfate, filtered, and concentrated in vacuo; the resulting foam was diluted with hot 2-propanol (6 mL) and stirred at room temperature overnight. The solution was then was stirred with activated carbon (Darco) for 3 minutes and filtered through diatomaceous earth using methanol. After the filtrate had been concentrated in vacuo, it was diluted with hot 2-propanol (8 mL) and allowed to stir at room temperature overnight. Filtration using diethyl ether provided the product as a white solid. From analysis of the $^1$H NMR, this material was presumed to exist as a mixture of rotamers. Yield: 353 mg, 0.904 mmol, 55%. LCMS m/z 391.3 [M+H]$^+$. $^1$H NMR (400 MHz, CDCl$_3$) δ 8.29 (d, J=5.7 Hz, 1H), [6.93 (s) and 6.91 (s), total 1H], 6.61-6.57 (m, 1H), 6.34 (dd, J=5.7, 2.2 Hz, 1H), 4.81-4.71 (m, 4H), [4.29 (dd, J=8.2, 8.2 Hz) and 4.28 (dd, J=8.2, 8.2 Hz), total 2H], 3.80-3.72 (m, 2H), 3.39-3.27 (m, 1H), 2.86-2.78 (m, 2H), [2.54 (s) and 2.53 (s), total 3H], [2.28 (s) and 2.27 (s), total 3H].

Example 12

1-(3-Chloro-2,4-dimethyl-5,7-dihydro-6H-pyrrolo[3,4-b]pyridin-6-yl)-2-{1-[2-(difluoromethyl)pyridin-4-yl]azetidin-3-yl}ethanone (12)

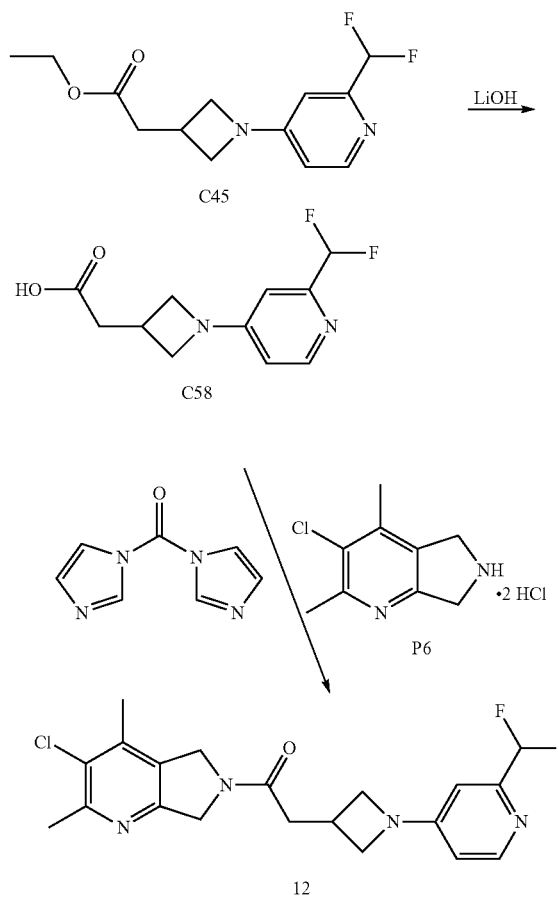

Step 1. Synthesis of {1-[2-(difluoromethyl)pyridin-4-yl]azetidin-3-yl}acetic acid (C58)

Conversion of C45 to the product was carried out using the method described for synthesis of C56 from C50 in Example 10. The product was obtained as a white solid. Yield: 890 mg, 3.67 mmol, 50%. NMR data was obtained from a reaction run on C45 under similar conditions. $^1$H NMR (400 MHz, CD$_3$OD) δ 8.10 (d, J=6.0 Hz, 1H), 6.61 (d, J=2.3 Hz, 1H), 6.57 (t, J$_{HF}$=55.2 HZ, 1H), 6.45 (dd, J=5.9, 2.4 Hz, 1H), 4.22 (dd, J=8.5, 8.3 Hz, 2H), 3.76 (dd, J=8.7, 5.6 Hz, 2H), 3.21-3.09 (m, 1H), 2.72 (d, J=7.8 Hz, 2H).

Step 2. Synthesis of 1-(3-chloro-2,4-dimethyl-5,7-dihydro-6H-pyrrolo[3,4-b]pyridin-6-yl)-2-{1-[2-(difluoromethyl)pyridin-4-yl]azetidin-3-yl}ethanone (12)

A mixture of C58 (558 mg, 2.30 mmol) and 1,1'-carbonyldiimidazole (373 mg, 2.30 mmol) in acetonitrile (4 mL) was stirred at room temperature for 75 minutes, and then added to P6 (575 mg, 2.25 mmol). After addition of acetonitrile (2 mL), the reaction mixture was stirred at room temperature for 1.25 hours, whereupon it was diluted with dichloromethane (30 mL) and saturated aqueous sodium carbonate solution (20 mL), and stirring was continued for 2 minutes. The organic layer was washed sequentially with saturated aqueous sodium carbonate solution (2×15 mL) and saturated aqueous sodium chloride solution (15 mL), then treated with activated carbon (Darco G-60; 35 mg) and stirred at room temperature overnight. Sodium sulfate and diatomaceous earth were added, and the resulting mixture was stirred for 2 minutes and filtered through a pad of diatomaceous earth using dichloromethane. The filtrate was concentrated in vacuo, treated with 2-propanol (12 mL), and heated at reflux for 15 minutes. Upon cooling to room temperature, the mixture was stirred for 30 minutes, whereupon it was filtered, and the collected solid was washed with 2-propanol (2×12 mL) and diethyl ether (12 mL), providing the product as an off-white solid. From analysis of the $^1$H NMR, this material was presumed to exist as a mixture of rotamers. Yield: 651 mg, 1.60 mmol, 71%. LCMS m/z 407.2 (chlorine isotope pattern observed) [M+H]$^+$. $^1$H NMR (400 MHz, CDCl$_3$) δ 8.22 (d, J=5.7 Hz, 1H), 6.55 (d, J=2.0 Hz, 1H), 6.51 (t, J$_{HF}$=55.8 HZ, 1H), 6.29 (dd, J=5.7, 2.2 Hz, 1H), 4.79-4.73 (m, 4H), [4.27 (dd, J=8.1, 8.1 Hz) and 4.26 (dd, J=8.1, 8.1 Hz), total 2H], 3.77-3.70 (m, 2H), 3.37-3.24 (m, 1H), 2.84-2.77 (m, 2H), [2.64 (s) and 2.63 (s), total 3H], [2.34 (s) and 2.33 (s), total 3H].

Example 13

1-(3-Chloro-2,4-dimethyl-5,7-dihydro-6H-pyrrolo[3,4-b]pyridin-6-yl)-2-[1-(pyridin-3-yl)azetidin-3-yl]ethanone (13)

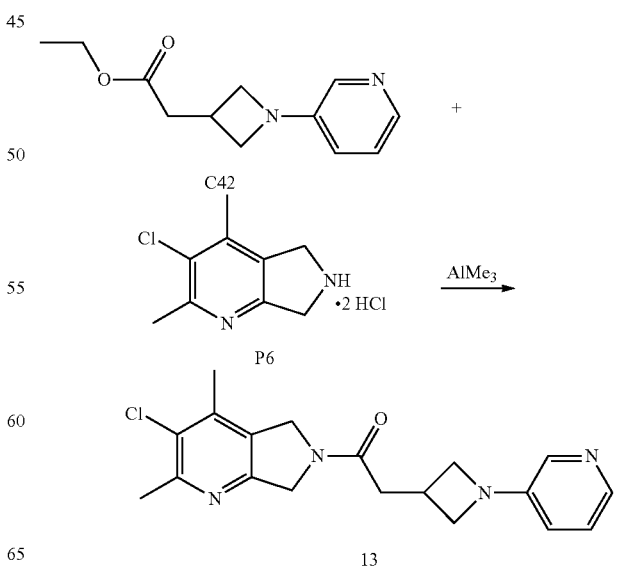

To a room temperature (14° C.) suspension of P6 (44.8 mg, 0.175 mmol) in 1,2-dichloroethane (0.5 mL) was added a solution of trimethylaluminum (2.0 M in toluene; 0.25 mL, 0.5 mmol) in one portion. After the reaction mixture had stirred at room temperature (14° C.) for 20 minutes, a solution of C42 (30 mg, 0.14 mmol) in 1,2-dichloroethane (0.5 mL) was added in one portion, and the reaction mixture was stirred at 75° C. for 4 hours, whereupon it was cooled and allowed to stand at room temperature for 16 hours. Saturated aqueous ammonium chloride solution (1 mL) was added, followed by water (5 mL) and dichloromethane (15 mL), and the aqueous layer was extracted sequentially with dichloromethane (2×15 mL) and with a mixture of dichloromethane and methanol (10:1, 10 mL). The combined organic layers were washed with saturated aqueous sodium chloride solution (10 mL), dried over sodium sulfate, filtered, and concentrated in vacuo. Purification via reversed-phase HPLC (Column: Agela Durashell, 5 μm; Mobile phase A: 0.05% ammonium hydroxide in water; Mobile phase B: acetonitrile; Gradient: 29% to 49% B) provided the product as a white solid. From analysis of the $^1$H NMR, this material was presumed to exist as a mixture of rotamers. Yield: 33 mg, 92 μmol, 66%. LCMS m/z 357.1 (chlorine isotope pattern observed) [M+H]$^+$. $^1$H NMR (400 MHz, CDCl$_3$) δ 8.01 (br d, J=4.5 Hz, 1H), 7.87 (d, J=2.5 Hz, 1H), 7.11 (dd, J=8.3, 4.8 Hz, 1H), 6.76-6.70 (m, 1H), 4.82-4.73 (m, 4H), [4.20 (dd, J=7.5, 7.5 Hz) and 4.19 (dd, J=7.5, 7.5 Hz), total 2H], 3.70-3.63 (m, 2H), 3.34-3.22 (m, 1H), [2.84 (d, J=7.5 Hz) and 2.81 (d, J=7.5 Hz), total 2H], [2.65 (s) and 2.64 (s), total 3H], [2.34 (s) and 2.34 (s), total 3H].

Examples 14 and 15

2-[1-(Pyridin-3-yl)azetidin-3-yl]-1-(2,4,5-trimethyl-5,7-dihydro-6H-pyrrolo[3,4-b]pyridin-6-yl)ethanone, ENT-1 (14) and 2-[1-(Pyridin-3-yl)azetidin-3-yl]-1-(2,4,5-trimethyl-5,7-dihydro-6H-pyrrolo[3,4-b]pyridin-6-yl)ethanone, ENT-2 (15)

triazol-1-yl)-N,N,N',N'-tetramethyluronium hexafluorophosphate (194 mg, 0.510 mmol) at room temperature, and the reaction mixture was stirred for 1 hour, whereupon N,N-diisopropylethylamine (176 mg, 1.36 mmol) was added, followed by P7 (80.0 mg, 0.340 mmol). Stirring was continued for 16 hours, at which time the reaction mixture was concentrated in vacuo and directly purified via reversed-phase HPLC (Column: YMC-Actus Triart C18, 5 μm; Mobile phase A: water containing 0.05% ammonium hydroxide; Mobile phase B: acetonitrile; Gradient: 28% to 58% B), affording the racemic product as a brown solid. Yield: 30.0 mg, 89.1 μmol, 26%. A portion of this material (25 mg) was separated into its component enantiomers via supercritical fluid chromatography (Column: Chiral Technologies Chiralpak AS, 5 μm; Mobile phase A: carbon dioxide; Mobile phase B: methanol containing 0.05% diethylamine; Gradient: 5% to 40% B). The first-eluting enantiomer was assigned as 14, and the second-eluting enantiomer as 15; both were obtained as brown solids. From analysis of the $^1$H NMR spectra, both compounds exist as a mixture of rotamers.

14—Yield: 9.0 mg, 36% for the separation. LCMS m/z 337.1 [M+H]$^+$. $^1$H NMR (400 MHz, CDCl$_3$) δ 8.05-7.95 (m, 1H), 7.92-7.81 (m, 1H), 7.15-7.06 (m, 1H), [6.89 (s) and 6.88 (s), total 1H], 6.76-6.70 (m, 1H), [5.45-5.36 (m) and 5.24-5.16 (m), total 1H], [4.73 (br AB quartet, J$_{AB}$=14.8 HZ, Δ$_{\nu AB}$=30 HZ), 4.93 (d, J=17.1 Hz), and 4.62 (d, J=17.6 Hz), total 2H], 4.23-4.13 (m, 2H), 3.73-3.60 (m, 2H), 3.33-3.20 (m, 1H), [2.97-2.80 (m) and 2.78 (d, J=8.0 Hz), total 2H], [2.53 (s) and 2.52 (s), total 3H], 2.30 (s, 3H), 1.53-1.46 (m, 3H).

15—Yield: 7.5 mg, 30% for the separation. LCMS m/z 337.1 [M+H]$^+$. $^1$H NMR (400 MHz, CDCl$_3$) δ 8.04-7.96 (m, 1H), 7.87 (br s, 1H), 7.11 (br dd, J=8.2, 4.6 Hz, 1H), [6.89 (br s) and 6.88 (br s), total 1H], 6.76-6.70 (m, 1H), [5.40 (br q, J=6 Hz) and 5.20 (br q, J=6 Hz), total 1H], [4.73 (br AB quartet, J$_{AB}$=14.6 HZ, Δ$_{\nu AB}$=30 HZ), 4.93 (d, J=17 Hz), and 4.62 (d, J=17 Hz), total 2H], 4.23-4.14 (m, 2H), 3.72-3.60 (m, 2H), 3.33-3.20 (m, 1H), [2.96-2.80 (m) and 2.78 (d,

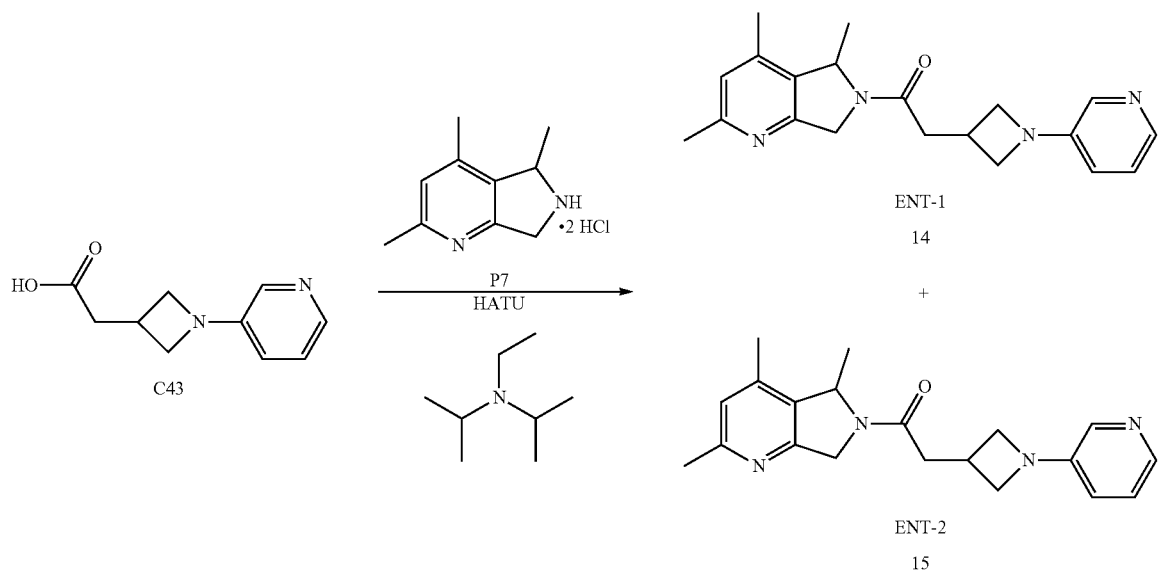

To a suspension of C43 (98.1 mg, 0.510 mmol) in N,N-dimethylformamide (3 mL) was added 0-(7-azabenzo- J=7.8 Hz), total 2H], [2.53 (s) and 2.52 (s), total 3H], 2.30 (s, 3H), [1.51 (d, J=6.5 Hz) and 1.49 (d, J=6.5 Hz), total 3H].

Example 16

1-(2,4-Dimethyl-5,7-dihydro-6H-pyrrolo[3,4-b]pyridin-6-yl)-2-[(1S,2R)-2-(6-methylpyridin-3-yl)cyclopropyl]ethanone (16)

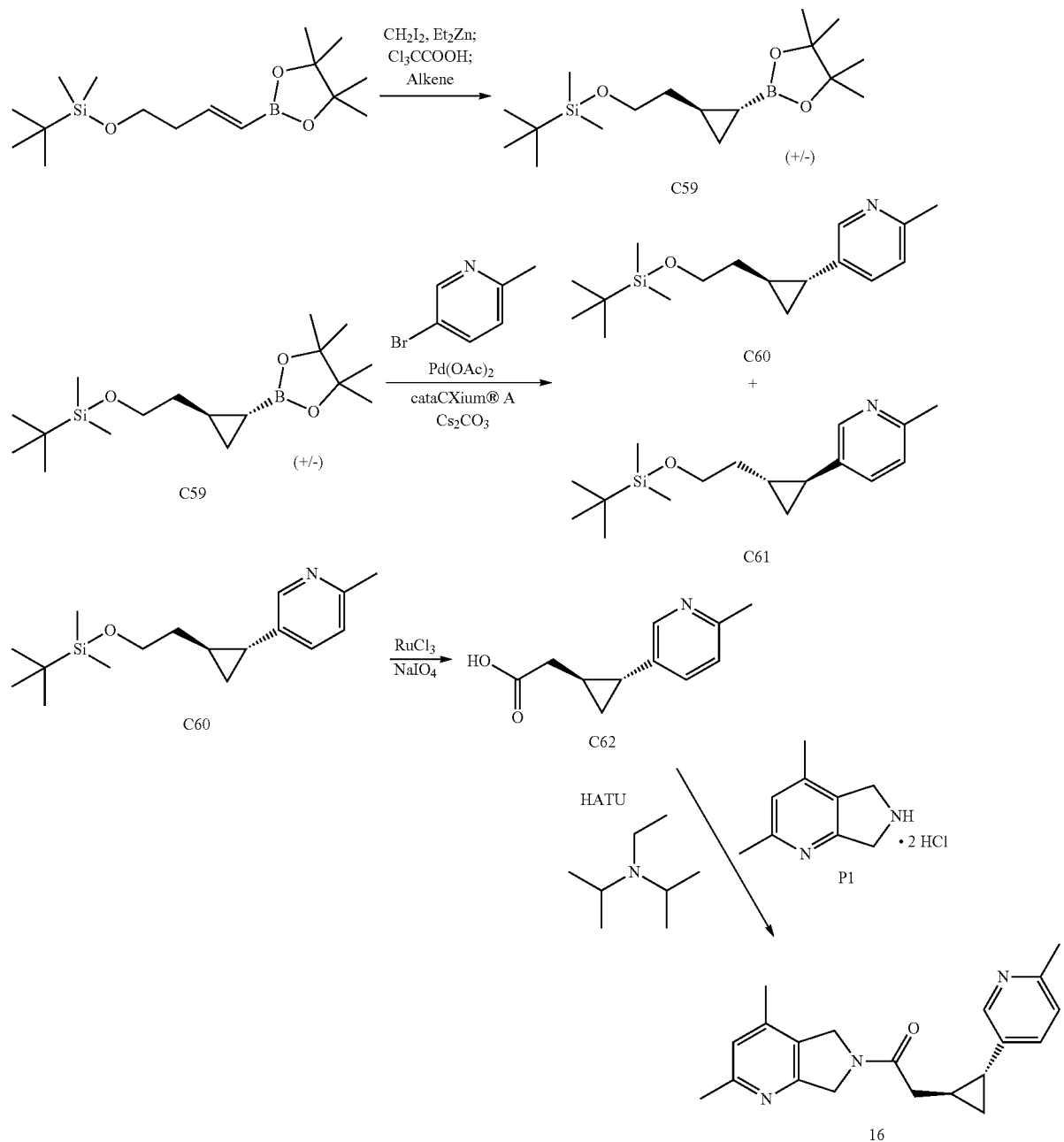

Step 1 Synthesis of tert-butyl(dimethyl){2-[trans-2-(4,4,5,5-tetramethyl-1,3,2-dioxaborolan-2-yl)cyclopropyl]ethoxy}silane (C59)

Diiodomethane (2.1 kg, 7.8 mol) was added in a drop-wise manner to a −40° C. solution of diethylzinc (1 M, 3.85 L, 3.85 mol) in dichloromethane (8 L).

After this mixture had stirred for 2 hours, a solution of trichloroacetic acid (0.628 kg, 3.84 mol) in dichloromethane (1 L) was added drop-wise, and the reaction mixture was warmed to −10° C. and allowed to stir for an additional 2 hours. A solution of tert-butyl(dimethyl){[(3E)-4-(4,4,5,5-tetramethyl-1,3,2-dioxaborolan-2-yl)but-3-en-1-yl]oxy}silane (400 g, 1.28 mol) in dichloromethane (1 L) was slowly added, and the reaction mixture was stirred at room temperature overnight, whereupon it was quenched via addition of cold aqueous citric acid solution (10%, 10 L). The organic layer was washed with saturated aqueous sodium chloride solution, and concentrated in vacuo; purification of the residue using chromatography on silica gel (Gradient: 0% to 7% ethyl acetate in petroleum ether) provided the product as a light yellow oil. Yield: 260 g, 797 mmol, 62%. $^1$H NMR (400 MHz, CDCl$_3$) δ 3.71-3.64 (m, 2H), 1.51-1.44 (m, 2H), 1.22 (s, 12H), 1.04-0.95 (m, 1H), 0.90 (s, 9H), 0.71-0.65 (m, 1H), 0.46-0.39 (m, 1H), 0.06 (s, 6H), −0.35 to −0.42 (m, 1H).

Step 2. Synthesis of 5-[(1R,2S)-2-(2-{[tert-butyl (dimethyl)silyl]oxy}ethyl)cyclopropyl]-2-methylpyridine (C60) and 5-[(1S,2R)-2-(2-{[tert-butyl (dimethyl)silyl]oxy}ethyl)cyclopropyl]-2-methylpyridine (C61)

Palladium(II) acetate (251 mg, 1.12 mmol) and di(1-adamantyl)-n-butylphosphine (cataCXium® A; 667 mg, 1.86 mmol) were dissolved in degassed 2-methylbutan-2-ol (150 mL), and the reaction vessel was evacuated and charged with nitrogen. This evacuation cycle was repeated twice, and the mixture was stirred at room temperature for one hour, whereupon degassed water (10 mL) was added, followed by cesium carbonate (18.2 g, 55.9 mmol) and 5-bromo-2-methylpyridine (3.20 g, 18.6 mmol). A solution of C59 (6.70 g, 20.5 mmol) in 2-methylbutan-2-ol (40 mL) was added via syringe, and the evacuation/nitrogen fill cycles were repeated. The reaction mixture was then heated at 75° C. for 16 hours, cooled to room temperature, and filtered through diatomaceous earth. The filter pad was washed with methanol until no additional color eluted, and the combined filtrates were concentrated in vacuo. The residue was diluted with ethyl acetate (250 mL), and the organic layer was washed with water (150 mL). The aqueous layer was extracted with ethyl acetate (2×250 mL), and the combined organic layers were dried over magnesium sulfate, filtered, and concentrated under reduced pressure. Silica gel chromatography (Gradient: 0% to 50% ethyl acetate in heptane) provided the racemic product as a light tan oil. Yield of racemic product: 3.00 g, 10.3 mmol, 55%. The component enantiomers were separated via supercritical fluid chromatography [Column: Phenomenex Lux Cellulose-1, 5 μm; Mobile phase: 95:5 carbon dioxide/(acetonitrile containing 0.2% ammonium hydroxide)]. The first-eluting enantiomer was assigned as C60, and the second-eluting enantiomer as C61; both were obtained as oils. The indicated absolute stereochemistries were established via an X-ray crystal structure determination carried out on 18, which was prepared from C61 via C63.

C60—Yield: 1.20 g, 40% for the separation. LCMS m/z 292.4 [M+H]$^+$. $^1$H NMR (500 MHz, CDCl$_3$) δ 8.28 (d, J=2.2 Hz, 1H), 7.19 (dd, J=8.0, 2.3 Hz, 1H), 7.03 (d, J=8.1 Hz, 1H), 3.73 (t, J=6.5 Hz, 2H), 2.52 (s, 3H), 1.68-1.56 (m, 3H), 1.14-1.07 (m, 1H), 0.90-0.81 (m, 2H), 0.89 (s, 9H), 0.04 (s, 3H), 0.04 (s, 3H).

C61—Yield: 1.30 g, 43% for the separation. LCMS m/z 292.4 [M+H]$^+$. $^1$H NMR (500 MHz, CDCl$_3$) δ 8.28 (d, J=2.0 Hz, 1H), 7.21 (dd, J=8.0, 2.0 Hz, 1H), 7.05 (d, J=8.0 Hz, 1H), 3.73 (t, J=6.5 Hz, 2H), 2.53 (s, 3H), 1.68-1.56 (m, 3H), 1.15-1.07 (m, 1H), 0.92-0.82 (m, 2H), 0.89 (s, 9H), 0.04 (s, 3H), 0.04 (s, 3H).

Step 3. Synthesis of [(1S,2R)-2-(6-methylpyridin-3-yl)cyclopropyl]acetic acid (C62)

Ruthenium(III) chloride (11 mg, 53 μmol) was added to a solution of C60 (500 mg, 1.72 mmol) in acetonitrile (10 mL) at room temperature. A solution of sodium periodate (1.10 g, 5.14 mmol) in water (7.5 mL) was then added to the stirring reaction mixture, and stirring was continued for 4 hours. After addition of aqueous hydrochloric acid (1 M, 5 mL), the mixture was concentrated in vacuo, and the residue was dissolved in acetonitrile (50 mL) and filtered through a pad of diatomaceous earth. The filter pad was washed with additional acetonitrile (60 mL), and the combined filtrates were concentrated under reduced pressure to afford the product as a gum. Yield: 310 mg, 1.62 mmol, 94%. $^1$H NMR (500 MHz, CD$_3$OD), characteristic peaks: δ 8.53 (d, J=2.0 Hz, 1H), 8.22 (dd, J=8.4, 2.1 Hz, 1H), 7.79 (d, J=8.6 Hz, 1H), 2.73 (s, 3H), 2.61 (dd, half of ABX pattern, J=16.9, 5.9 Hz, 1H), 2.36 (dd, half of ABX pattern, J=16.9, 8.1 Hz, 1H).

Step 4. Synthesis of 1-(2,4-dimethyl-5,7-dihydro-6H-pyrrolo[3,4-b]pyridin-6-yl)-2-[(1S,2R)-2-(6-methylpyridin-3-yl)cyclopropyl]ethanone (16)

Compound C62 (130 mg, 0.680 mmol) and P1 (115 mg, 0.520 mmol) were dissolved in N,N-dimethylformamide (6 mL) and treated with N,N-diisopropylethylamine (0.43 mL, 2.47 mmol). O-(7-Azabenzotriazol-1-yl)-N,N,N',N'-tetramethyluronium hexafluorophosphate (284 mg, 0.747 mmol) was added, and the reaction mixture was stirred at room temperature for 16 hours. After addition of half-saturated aqueous sodium chloride solution (10 mL), the mixture was extracted with ethyl acetate (3×150 mL). The combined organic layers were washed three times with saturated aqueous sodium chloride solution, dried over magnesium sulfate, filtered, and concentrated in vacuo. Purification via reversed-phase HPLC (Column: Waters XBridge C18, 5 μm; Mobile phase A: water containing 0.03% ammonium hydroxide; Mobile phase B: acetonitrile containing 0.03% ammonium hydroxide; Gradient: 20% to 40% B) afforded the product as a glass. From analysis of the $^1$H NMR, this material was presumed to exist as a mixture of rotamers. Yield: 15.0 mg, 46.6 μmol, 9%. LCMS m/z 322.4 [M+H]$^+$. $^1$H NMR (500 MHz, CD$_3$OD) δ 8.26 (br s, 1H), 7.44 (dd, J=8.1, 2.4 Hz, 1H), 7.18 (d, J=8.1 Hz, 1H), 7.05 (s, 1H), [4.87 (s), 4.82 (s), 4.71 (s), and 4.70 (s), total 4H], 2.69-2.56 (m, 2H), [2.49 (s) and 2.49 (s), total 3H], 2.47 (s, 3H), [2.31 (s) and 2.30 (s), total 3H], 1.89-1.83 (m, 1H), 1.50-1.42 (m, 1H), 1.08-0.98 (m, 2H).

Example 17

1-(2,4-Dimethyl-5,7-dihydro-6H-pyrrolo[3,4-b]pyridin-6-yl)-2-[(1R,2S)-2-(6-methylpyridin-3-yl)cyclopropyl]ethanone (17)

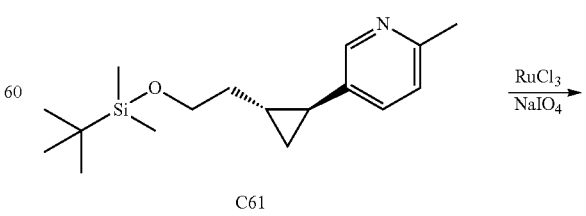

C61

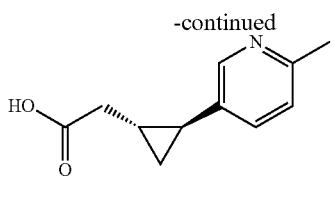

C63

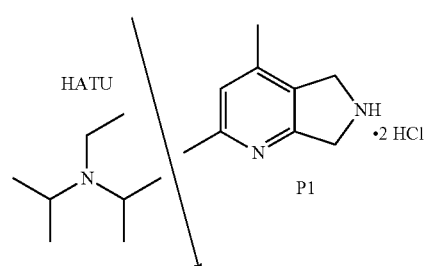

P1

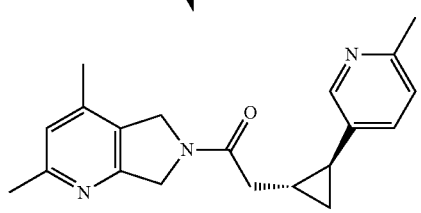

17

Step 1. Synthesis of [(1R,2S)-2-(6-methylpyridin-3-yl)cyclopropyl]acetic acid (C63)

Conversion of C61 to the product was carried out using the method described for synthesis of C62 from C60 in Example 16. In this case, purification was effected using silica gel chromatography (Gradient: 0% to 10% methanol in dichloromethane) to afford the product as an oil. Yield: 210 mg, 1.10 mmol, 64%. LCMS m/z 192.2 [M+H]$^+$. $^1$H NMR (400 MHz, CD$_3$OD) δ 8.40 (br s, 1H), 7.92 (dd, J=8.2, 2 Hz, 1H), 7.56 (d, J=8.6 Hz, 1H), 2.62 (s, 3H), 2.51 (dd, half of ABX pattern, J=16.8, 6.2 Hz, 1H), 2.33 (dd, half of ABX pattern, J=16.8, 7.8 Hz, 1H), 1.96-1.89 (m, 1H), 1.46-1.36 (m, 1H), 1.16-1.09 (m, 1H), 1.07-0.99 (m, 1H).

Step 2. Synthesis of 1-(2,4-dimethyl-5,7-dihydro-6H-pyrrolo[3,4-b]pyridin-6-yl)-2-[(1R,2S)-2-(6-methylpyridin-3-yl)cyclopropyl]ethanone (17)

Reaction of C63 with P1 was carried out using the method described for synthesis of 16 from C62 in Example 16. Purification was effected via reversed-phase HPLC (Column: Waters XBridge C18, 5 μm; Mobile phase A: water containing 0.03% ammonium hydroxide; Mobile phase B: acetonitrile containing 0.03% ammonium hydroxide; Gradient: 20% to 30% B), to afford the product as a light tan glass. From analysis of the $^1$H NMR, this material was presumed to exist as a mixture of rotamers. Yield: 35 mg, 0.11 mmol, 16%. LCMS m/z 322.4 [M+H]$^+$. $^1$H NMR (500 MHz, CD$_3$OD) δ 8.26 (br s, 1H), 7.44 (dd, J=8.1, 2.4 Hz, 1H), 7.18 (d, J=8.1 Hz, 1H), 7.05 (s, 1H), [4.87 (s, assumed; obscured by water peak), 4.82 (s), 4.71 (s), and 4.70 (s), total 4H], 2.70-2.56 (m, 2H), [2.49 (s) and 2.49 (s), total 3H], 2.47 (s, 3H), [2.31 (s) and 2.30 (s), total 3H], 1.89-1.84 (m, 1H), 1.50-1.42 (m, 1H), 1.08-0.98 (m, 2H).

Example 18

1-[2-(Difluoromethyl)-4-methyl-5,7-dihydro-6H-pyrrolo[3N-b]pyridin-6-yl]-2-[(1R,2S)-2-(6-methylpyridin-3-yl)cyclopropyl]ethanone (18)

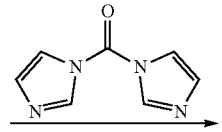

P3

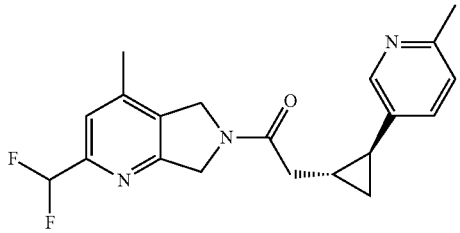

18

1,1'-Carbonyldiimidazole (17.8 mg, 0.110 mmol) and C63 (15.0 mg, 78.4 μmol) were mixed with acetonitrile (0.8 mL) and stirred at room temperature for 2 hours, whereupon P3 (33.0 mg, 0.128 mmol) was added, and the reaction mixture was stirred for an additional 2 hours. It was then diluted with ethyl acetate and washed three times with aqueous sodium bicarbonate solution; the organic layer was dried over sodium sulfate, filtered, and concentrated in vacuo. Silica gel chromatography (Gradient: 0% to 7% methanol in dichloromethane) afforded the product as a solid. From analysis of the $^1$H NMR, the product was presumed to exist as a mixture of rotamers. The crystal for X-ray structure determination (see below) was obtained via recrystallization from ethanol. Yield: 12 mg, 34 mmol, 43%. LCMS m/z 358.3 [M+H]$^+$. $^1$H NMR (400 MHz, CDCl$_3$) δ 8.34 (br s, 1H), 7.39 (s, 1H), 7.34-7.29 (m, 1H), 7.07-7.02 (m, 1H), [6.61 (t, J$_{HF}$=55.4 Hz) and 6.60 (t, J$_{HF}$=55.6 HZ), total 1H], 4.89-4.79 (m, 4H), 2.68-2.46 (m, 2H), 2.51 (s, 3H), [2.38 (s) and 2.37 (s), total 3H], 1.84-1.76 (m, 1H), 1.55-1.44 (m, 1H), 1.11-1.03 (m, 1H), 1.00-0.93 (m, 1H).

Single-Crystal X-Ray Structural Determination of 18

Single Crystal X-Ray Analysis Data collection was performed on a Bruker-AXS X8 Kappa diffractometer at 100° K, using Cu K$_a$ radiation (λ=1.54178 Å) from an IμS microsource. Data collection consisted of omega and phi scans.

Data reduction was carried out with the program SAINT[1] and semi-empirical absorption correction based on equivalents was performed with the program SADABS[2].

The structure was solved with direct methods using the program SHELXT[3] and refined against $F^2$ on all data with SHELXL[4] using established refinement techniques[5]. All non-hydrogen atoms were refined anisotropically. All hydrogen atoms were placed in geometrically calculated positions and refined using a riding model while constraining their $U_{iso}$ to 1.2 times the $U_{eq}$ of the atoms to which they bind (1.5 times for methyl groups). No restraints were used in the refinement of the structure of 18.

The compound crystallizes in the orthorhombic chiral space group $P2_12_12_1$ with one target molecule per asymmetric unit.

The molecule is chiral and the absolute structure was determined by both the methods of Parsons[6] and Hooft[7].

Pertinent crystal, data collection and refinement information is summarized in Table 1. Atomic coordinates, bond lengths, bond angles, and displacement parameters are listed in Tables 2-5.

SOFTWARE AND REFERENCES

1. Bruker (2011). SAINT, Bruker-AXS Inc., Madison, Wis., USA.
2. Sheldrick, G. M., (2009). SADABS, University of Göttingen, Germany.
3. Sheldrick, G. M., *Acta Cryst.* 2015, A71, 3-8.
4. Sheldrick, G. M., *Acta Cryst.* 2015, C77, 3-8.
5. Müller, P., *Crystallography Reviews* 2009, 15, 57-83.
6. Parsons, S. & Flack, H. D., *Acta Cryst.* 2004, A60, s61.
7. Hooft, R. W. W., Straver, L. H., Spek, A. L., *J. Appl. Cryst.* 2008, 41, 96-103.

TABLE 2

Atomic coordinates ($\times 10^4$) and equivalent isotropic displacement parameters ($Å^2 \times 10^3$) for 18. U(eq) is defined as one-third of the trace of the orthogonalized $U^{ij}$ tensor.

| | x | y | z | U(eq) |
|---|---|---|---|---|
| F(1) | 1635(1) | −1567(1) | 5371(1) | 34(1) |
| F(2) | 3530(1) | −2097(1) | 5968(1) | 36(1) |
| O(1) | 5050(1) | 5192(1) | 3195(1) | 25(1) |
| N(1) | 310(2) | 11243(2) | 3712(1) | 29(1) |
| N(2) | 4222(2) | 3741(2) | 4050(1) | 21(1) |
| N(3) | 3072(2) | 1086(2) | 5251(1) | 22(1) |
| C(1) | 4252(2) | 4940(2) | 3725(1) | 20(1) |
| C(2) | 3268(2) | 5957(2) | 4053(1) | 21(1) |
| C(3) | 3060(2) | 7090(2) | 3506(1) | 21(1) |
| C(4) | 2024(2) | 6948(2) | 2865(1) | 26(1) |
| C(5) | 1702(2) | 7827(2) | 3550(1) | 21(1) |
| C(6) | 1597(2) | 9267(2) | 3436(1) | 20(1) |
| C(7) | 556(2) | 9966(2) | 3802(1) | 25(1) |
| C(8) | 2465(2) | 9972(2) | 2948(1) | 23(1) |
| C(9) | 2238(2) | 11295(2) | 2852(1) | 25(1) |
| C(10) | 1148(2) | 11904(2) | 3234(1) | 26(1) |
| C(11) | 851(3) | 13338(2) | 3123(1) | 35(1) |
| C(12) | 3329(2) | 3320(2) | 4689(1) | 22(1) |
| C(13) | 3700(2) | 1900(2) | 4763(1) | 20(1) |
| C(14) | 4753(2) | 1564(2) | 4258(1) | 21(1) |
| C(15) | 5176(2) | 2712(2) | 3779(1) | 22(1) |
| C(16) | 5242(2) | 282(2) | 4244(1) | 22(1) |
| C(17) | 4607(2) | −579(2) | 4758(1) | 22(1) |
| C(18) | 3542(2) | −146(2) | 5233(1) | 22(1) |
| C(19) | 2750(2) | −1052(2) | 5756(1) | 24(1) |
| C(20) | 6349(2) | −136(2) | 3686(1) | 27(1) |

TABLE 3

Bond lengths [Å] and angles [°] for 18.

| | |
|---|---|
| F(1)—C(19) | 1.373(2) |
| F(2)—C(19) | 1.358(2) |

TABLE 1

Crystal data and structure refinement for 18.

| | |
|---|---|
| Empirical formula | $C_{20}H_{21}F_2N_3O$ |
| Formula weight | 357.40 |
| Temperature | 100(2)K |
| Wavelength | 1.54178 Å |
| Crystal system | Orthorhombic |
| Space group | $P2_12_12_1$ |
| Unit cell dimensions | a = 9.6591(2) Å    α = 90° |
| | b = 10.2245(2) Å    β = 90° |
| | c = 17.3206(4) Å    γ = 90° |
| Volume | 1710.57(6) $Å^3$ |
| Z | 4 |
| Density (calculated) | 1.388 $Mg/m^3$ |
| Absorption coefficient | 0.849 $mm^{-1}$ |
| F(000) | 752 |
| Crystal size | 0.340 × 0.300 × 0.200 $mm^3$ |
| Theta range for data collection | 5.023 to 68.184° |
| Index ranges | −11 <= h <= 11, −10 <= k <= 12, −20 <=/<= 20 |
| Reflections collected | 18544 |
| Independent reflections | 3126 [$R_{int}$ = 0.0314] |
| Completeness to theta = 67.679° | 100.0% |
| Absorption correction | Semi-empirical from equivalents |
| Refinement method | Full-matrix least-squares on $F^2$ |
| Data/restraints/parameters | 3126/0/237 |
| Goodness-of-fit on $F^2$ | 1.030 |
| Final R indices [I > 2q(I)] | R1 = 0.0281, wR2 = 0.0755 |
| R indices (all data) | R1 = 0.0285, wR2 = 0.0759 |
| Largest diff. peak and hole | 0.255 and −0.135 $e.Å^{-3}$ |

TABLE 3-continued

Bond lengths [Å] and angles [°] for 18.

| | |
|---|---|
| O(1)—C(1) | 1.227(2) |
| N(1)—C(7) | 1.337(3) |
| N(1)—C(10) | 1.340(3) |
| N(2)—C(1) | 1.350(2) |
| N(2)—C(12) | 1.468(2) |
| N(2)—C(15) | 1.475(2) |
| N(3)—C(13) | 1.332(3) |
| N(3)—C(18) | 1.339(3) |
| C(1)—C(2) | 1.518(3) |
| C(2)—C(3) | 1.509(3) |
| C(2)—H(2A) | 0.9900 |
| C(2)—H(2B) | 0.9900 |
| C(3)—C(4) | 1.503(3) |
| O(3)—C(5) | 1.514(3) |
| C(3)—H(3) | 1.0000 |
| O(4)—C(5) | 1.520(3) |
| C(4)—H(4A) | 0.9900 |
| C(4)—H(4B) | 0.9900 |
| C(5)—C(6) | 1.488(3) |
| C(5)—H(5) | 1.0000 |
| C(6)—C(7) | 1.386(3) |
| C(6)—C(8) | 1.392(3) |
| C(7)—H(7) | 0.9500 |
| C(8)—C(9) | 1.381(3) |
| C(8)—H(8) | 0.9500 |
| C(9)—C(10) | 1.391(3) |
| C(9)—H(9) | 0.9500 |
| C(10)—C(11) | 1.507(3) |
| C(11)—H(11A) | 0.9800 |
| C(11)—H(11B) | 0.9800 |
| C(11)—H(11C) | 0.9800 |
| C(12)—C(13) | 1.501(3) |
| C(12)—H(12A) | 0.9900 |
| C(12)—H(12B) | 0.9900 |
| C(13)—C(14) | 1.385(3) |
| C(14)—C(16) | 1.393(3) |
| C(14)—C(15) | 1.495(3) |
| C(15)—H(15A) | 0.9900 |
| C(15)—H(15B) | 0.9900 |
| C(16)—C(17) | 1.395(3) |
| C(16)—C(20) | 1.504(3) |
| C(17)—C(18) | 1.389(3) |
| C(17)—H(17) | 0.9500 |
| C(18)—C(19) | 1.505(3) |
| C(19)—H(19) | 1.0000 |
| C(20)—H(20A) | 0.9800 |
| C(20)—H(20B) | 0.9800 |
| C(20)—H(20C) | 0.9800 |
| C(7)—N(1)—C(10) | 117.20(18) |
| C(1)—N(2)—C(12) | 126.41(16) |
| C(1)—N(2)—C(15) | 120.09(16) |
| C(12)—N(2)—C(15) | 113.48(15) |
| C(13)—N(3)—C(18) | 114.76(17) |
| O(1)—C(1)—N(2) | 121.10(17) |
| O(1)—C(1)—C(2) | 121.95(18) |
| N(2)—C(1)—C(2) | 116.94(16) |
| C(3)—C(2)—C(1) | 112.03(15) |
| C(3)—C(2)—H(2A) | 109.2 |
| C(1)—C(2)—H(2A) | 109.2 |
| C(3)—C(2)—H(2B) | 109.2 |
| C(1)—C(2)—H(2B) | 109.2 |
| H(2A)—C(2)—H(2B) | 107.9 |
| C(4)—C(3)—C(2) | 118.62(16) |
| C(4)—C(3)—C(5) | 60.52(13) |
| C(2)—C(3)—C(5) | 117.83(16) |
| C(4)—C(3)—H(3) | 116.1 |
| C(2)—C(3)—H(3) | 116.1 |
| C(5)—C(3)—H(3) | 116.1 |
| C(3)—C(4)—C(5) | 60.12(13) |
| C(3)—C(4)—H(4A) | 117.8 |
| C(5)—C(4)—H(4A) | 117.8 |
| C(3)—C(4)—H(4B) | 117.8 |
| C(5)—C(4)—H(4B) | 117.8 |
| H(4A)—C(4)—H(4B) | 114.9 |
| C(6)—C(5)—C(3) | 123.05(17) |
| C(6)—C(5)—C(4) | 119.72(17) |
| C(3)—C(5)—C(4) | 59.36(13) |
| O(6)—C(5)—H(5) | 114.5 |
| O(3)—C(5)—H(5) | 114.5 |
| O(4)—C(5)—H(5) | 114.5 |
| C(7)—C(6)—C(8) | 116.56(17) |
| C(7)—C(6)—C(5) | 119.94(18) |
| C(8)—C(6)—C(5) | 123.45(18) |
| N(1)—C(7)—C(6) | 125.40(19) |
| N(1)—C(7)—H(7) | 117.3 |
| C(6)—C(7)—H(7) | 117.3 |
| C(9)—C(8)—C(6) | 119.08(19) |
| C(9)—C(8)—H(8) | 120.5 |
| C(6)—C(8)—H(8) | 120.5 |
| C(8)—C(9)—C(10) | 120.03(19) |
| C(8)—C(9)—H(9) | 120.0 |
| C(10)—C(9)—H(9) | 120.0 |
| N(1)—C(10)—C(9) | 121.73(19) |
| N(1)—C(10)—C(11) | 117.0(2) |
| C(9)—C(10)—C(11) | 121.3(2) |
| C(10)—C(11)—H(11A) | 109.5 |
| C(10)—C(11)—H(11B) | 109.5 |
| H(11A)—C(11)—H(11B) | 109.5 |
| C(10)—C(11)—H(11C) | 109.5 |
| H(11A)—C(11)—H(11C) | 109.5 |
| H(11B)—C(11)—H(11C) | 109.5 |
| N(2)—C(12)—C(13) | 101.99(15) |
| N(2)—C(12)—H(12A) | 111.4 |
| C(13)—C(12)—H(12A) | 111.4 |
| N(2)—C(12)—H(12B) | 111.4 |
| C(13)—C(12)—H(12B) | 111.4 |
| H(12A)—C(12)—H(12B) | 109.2 |
| N(3)—C(13)—C(14) | 125.46(18) |
| N(3)—C(13)—C(12) | 123.37(17) |
| C(14)—C(13)—C(12) | 111.17(17) |
| C(13)—C(14)—C(16) | 119.56(18) |
| C(13)—C(14)—C(15) | 110.91(16) |
| C(16)—C(14)—C(15) | 129.52(18) |
| N(2)—C(15)—C(14) | 102.26(15) |
| N(2)—C(15)—H(15A) | 111.3 |
| C(14)—C(15)—H(15A) | 111.3 |
| N(2)—C(15)—H(15B) | 111.3 |
| C(14)—C(15)—H(15B) | 111.3 |
| H(15A)—C(15)—H(15B) | 109.2 |
| C(14)—C(16)—C(17) | 115.69(18) |
| C(14)—C(16)—C(20) | 121.33(18) |
| C(17)—C(16)—C(20) | 122.94(18) |
| C(18)—C(17)—C(16) | 120.16(17) |
| C(18)—C(17)—H(17) | 119.9 |
| C(16)—C(17)—H(17) | 119.9 |
| N(3)—C(18)—C(17) | 124.36(17) |
| N(3)—C(18)—C(19) | 113.12(17) |
| C(17)—C(18)—C(19) | 122.46(17) |
| F(2)—C(19)—F(1) | 105.38(16) |
| F(2)—C(19)—C(18) | 111.40(16) |
| F(1)—C(19)—C(18) | 109.98(16) |
| F(2)—C(19)—H(19) | 110.0 |
| F(1)—C(19)—H(19) | 110.0 |
| C(18)—C(19)—H(19) | 110.0 |
| C(16)—C(20)—H(20A) | 109.5 |
| C(16)—C(20)—H(20B) | 109.5 |
| H(20A)—C(20)—H(20B) | 109.5 |
| C(16)—C(20)—H(20C) | 109.5 |
| H(20A)—C(20)—H(20C) | 109.5 |
| H(20B)—C(20)—H(20C) | 109.5 |

Symmetry transformations used to generate equivalent atoms.

TABLE 4

Anisotropic displacement parameters (Å² × 10³) for 18. The anisotropic displacement factor exponent takes the form: $-2\pi^2[h^2 a^{*2}U^{11} + \ldots + 2 h k a^* b^* U^{12}]$.

| | U11 | U22 | U33 | U23 | U13 | U12 |
|---|---|---|---|---|---|---|
| F(1) | 30(1) | 37(1) | 35(1) | 3(1) | −3(1) | −12(1) |
| F(2) | 29(1) | 28(1) | 51(1) | 17(1) | 6(1) | 5(1) |
| O(1) | 23(1) | 25(1) | 27(1) | 3(1) | 4(1) | 4(1) |
| N(1) | 34(1) | 24(1) | 29(1) | 0(1) | 0(1) | 7(1) |
| N(2) | 19(1) | 19(1) | 24(1) | 0(1) | 2(1) | 3(1) |
| N(3) | 22(1) | 21(1) | 22(1) | 0(1) | −1(1) | 2(1) |
| C(1) | 16(1) | 22(1) | 22(1) | −2(1) | −3(1) | −1(1) |
| C(2) | 21(1) | 18(1) | 24(1) | 1(1) | 2(1) | 1(1) |
| C(3) | 21(1) | 19(1) | 23(1) | −1(1) | 1(1) | 1(1) |
| C(4) | 31(1) | 20(1) | 28(1) | −1(1) | −5(1) | 2(1) |
| C(5) | 21(1) | 20(1) | 23(1) | 1(1) | 1(1) | 0(1) |
| C(6) | 19(1) | 19(1) | 21(1) | −1(1) | −3(1) | 0(1) |
| C(7) | 27(1) | 23(1) | 26(1) | 4(1) | 3(1) | 2(1) |
| C(8) | 22(1) | 24(1) | 23(1) | −1(1) | −1(1) | 0(1) |
| C(9) | 28(1) | 24(1) | 24(1) | 4(1) | −5(1) | −6(1) |
| C(10) | 31(1) | 20(1) | 26(1) | 0(1) | −11(1) | 0(1) |
| C(11) | 41(1) | 21(1) | 43(1) | 3(1) | −14(1) | 0(1) |
| C(12) | 24(1) | 20(1) | 23(1) | 0(1) | 2(1) | 3(1) |
| C(13) | 21(1) | 20(1) | 20(1) | −1(1) | −4(1) | 1(1) |
| C(14) | 20(1) | 22(1) | 20(1) | −1(1) | −4(1) | 1(1) |
| C(15) | 20(1) | 21(1) | 25(1) | 0(1) | 0(1) | 3(1) |
| C(16) | 22(1) | 22(1) | 22(1) | −1(1) | −5(1) | 2(1) |
| C(17) | 23(1) | 19(1) | 23(1) | 0(1) | −6(1) | 2(1) |
| C(18) | 22(1) | 21(1) | 22(1) | 0(1) | −6(1) | 1(1) |
| C(19) | 23(1) | 22(1) | 28(1) | 2(1) | −2(1) | 0(1) |
| C(20) | 28(1) | 24(1) | 29(1) | 2(1) | 2(1) | 7(1) |

TABLE 5

Hydrogen coordinates (×10⁴) and isotropic displacement parameters (Å² × 10³) for 18.

| | x | y | z | U(eq) |
|---|---|---|---|---|
| H(2A) | 2363 | 5542 | 4160 | 25 |
| H(2B) | 3642 | 6289 | 4547 | 25 |
| H(3) | 3900 | 7624 | 3387 | 25 |
| H(4A) | 1515 | 6110 | 2824 | 31 |
| H(4B) | 2237 | 7373 | 2365 | 31 |
| H(5) | 1018 | 7456 | 3923 | 25 |
| H(7) | −30 | 9498 | 4145 | 30 |
| H(8) | 3203 | 9549 | 2685 | 28 |
| H(9) | 2827 | 11790 | 2524 | 30 |
| H(11A) | 228 | 13454 | 2682 | 53 |
| H(11B) | 1719 | 13806 | 3026 | 53 |
| H(11C) | 412 | 13689 | 3589 | 53 |
| H(12A) | 2337 | 3434 | 4561 | 27 |
| H(12B) | 3540 | 3806 | 5169 | 27 |
| H(15A) | 6153 | 2955 | 3876 | 26 |
| H(15B) | 5048 | 2535 | 3222 | 26 |
| H(17) | 4903 | −1464 | 4784 | 26 |
| H(19) | 2430 | −568 | 6225 | 29 |
| H(20A) | 6603 | −1048 | 3787 | 41 |
| H(20B) | 7165 | 423 | 3750 | 41 |
| H(20C) | 6000 | −56 | 3156 | 41 |

Example 19

2,4-Dimethyl-N-[1-(pyridin-3-yl)azetidin-3-yl]-5,7-dihydro-6H-pyrrolo[3,4-b]pyridine-6-carboxamide (19)

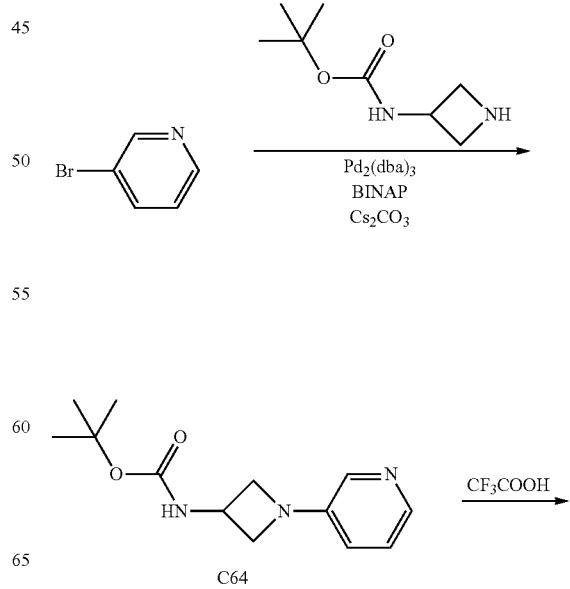

C64

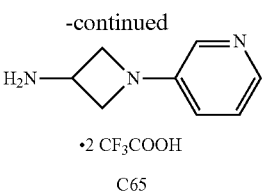

C65

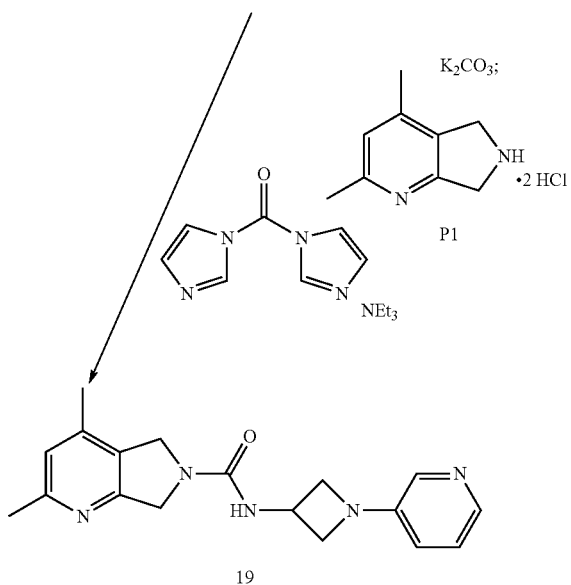

19

Step 1. Synthesis of tert-butyl [1-(pyridin-3-yl)azetidin-3-yl]carbamate (C64)

A mixture of tert-butyl azetidin-3-ylcarbamate (6.0 g, 35 mmol), 3-bromopyridine (3.8 g, 24 mmol), cesium carbonate (25.0 g, 76.7 mmol), 1,1'-binaphthalene-2,2'-diylbis(diphenylphosphane (BINAP; 900 mg, 1.45 mmol), and tris(dibenzylideneacetone)dipalladium (450 mg, 0491 mmol) in toluene (150 mL) was stirred at 90° C. for 4 hours. After the reaction mixture had cooled to room temperature, it was filtered, and the filter cake was washed with ethyl acetate (100 mL). The combined filtrates were washed sequentially with water (200 mL) and saturated aqueous sodium chloride solution (200 mL), and concentrated under reduced pressure. Chromatography on silica gel (Gradient: 17% to 50% ethyl acetate in petroleum ether) provided the product as a light yellow solid. Yield: 4.98 g, 20.0 mmol, 83%. $^1$H NMR (400 MHz, CDCl$_3$) δ 8.04 (d, J=4.5 Hz, 1H), 7.87 (d, J=3.0 Hz, 1H), 7.11 (dd, J=8.3, 4.8 Hz, 1H), 6.77-6.71 (m, 1H), 5.12-4.95 (br s, 1H), 4.74-4.59 (br s, 1H), 4.26 (dd, J=7.5, 7.5 Hz, 2H), 3.67 (dd, J=7.5, 5.5 Hz, 2H), 1.46 (s, 9H).

Step 2. Synthesis of 1-(pyridin-3-yl)azetidin-3-amine, Ditrifluoroacetate Salt (C65)

Trifluoroacetic acid (30 mL) was added to a solution of C64 (9.9 g, 40 mmol) in dichloromethane (100 mL). The reaction mixture was stirred at room temperature at 25° C. for 4 hours, whereupon it was concentrated in vacuo and triturated with tert-butyl methyl ether, affording the product as a light yellow solid. Yield: 13.9 g, 36.8 mmol, 92%. LCMS m/z 150.1 [M+H]$^+$. $^1$H NMR (400 MHz, CD$_3$OD) δ 8.11 (d, J=5.3 Hz, 1H), 8.02 (d, J=2.8 Hz, 1H), 7.75 (dd, J=8.7, 5.5 Hz, 1H), 7.58-7.52 (m, 1H), 4.44 (dd, J=8.5, 7.8 Hz, 2H), 4.35-4.27 (m, 1H), 4.13 (dd, J=9.5, 4.0 Hz, 2H).

Step 3. Synthesis of 2,4-dimethyl-N-[1-(pyridin-3-yl)azetidin-3-yl]-5,7-dihydro-6H-pyrrolo[3,4-b]pyridine-6-carboxamide (19)

Potassium carbonate (91.6 mg, 0.663 mmol) was added to a mixture of C65 (100 mg, 0.265 mmol) in tetrahydrofuran (2 mL), and the resulting mixture was stirred at room temperature for 20 minutes. The solid was filtered off and washed with tetrahydrofuran (2 mL), and the combined filtrates were added in a drop-wise manner to a suspension of P1 (49.0 mg, 0.222 mmol), triethylamine (80.5 mg, 0.796 mmol), and 1,1'-carbonyldiimidazole (86.0 mg, 0.530 mmol) in tetrahydrofuran (4 mL). The reaction mixture was stirred at room temperature for 16 hours, whereupon it was poured into water (15 mL), and extracted with ethyl acetate (3×15 mL). The combined organic layers were washed sequentially with water (10 mL) and saturated aqueous sodium chloride solution (10 mL), dried over sodium sulfate, filtered, and concentrated in vacuo. Purification using reversed-phase HPLC (Column: YMC-Actus Triart C18, 5 μm; Mobile phase A: water containing 0.05% ammonium hydroxide; Mobile phase B: acetonitrile; Gradient: 25% to 40% B) provided the product as a white solid. Yield: 34.9 mg, 0.108 mmol, 49%. LCMS m/z 323.9 [M+H]$^+$. $^1$H NMR (400 MHz, DMSO-d$_6$) δ 7.92 (dd, J=4.5, 1.2 Hz, 1H), 7.85 (d, J=2.8 Hz, 1H), 7.17 (dd, J=8.3, 4.8 Hz, 1H), 7.00 (d, J=7.5 Hz, 1H), 6.98 (s, 1H), 6.86 (ddd, J=8.2, 2.9, 1.2 Hz, 1H), 4.74-4.63 (m, 1H), 4.55 (br s, 2H), 4.52 (br s, 2H), 4.19 (dd, J=7.5, 7.5 Hz, 2H), 3.76 (dd, J=7.3, 6.5 Hz, 2H), 2.41 (s, 3H), 2.21 (s, 3H).

Example 20

1-(Pyridin-3-yl)azetidin-3-yl 2,4-dimethyl-5,7-dihydro-6H-pyrrolo[3,4-b]pyridine-6-carboxylate (20)

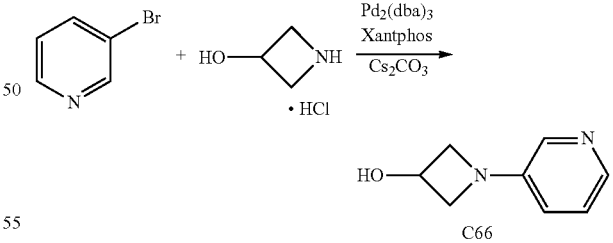

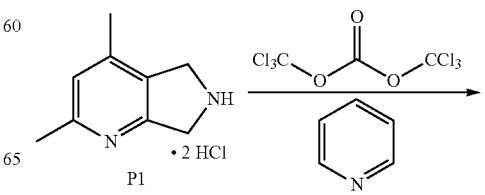

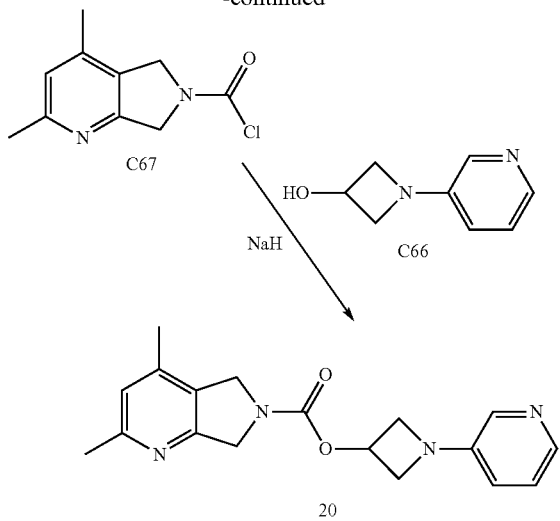

Step 1. Synthesis of 1-(pyridin-3-yl)azetidin-3-ol (C66)

A mixture of azetidin-3-ol, hydrochloride salt (347 mg, 3.17 mmol), 3-bromopyridine (500 mg, 3.16 mmol), tris(dibenzylideneacetone)dipalladium(0) (86.9 mg, 94.9 µmol), 4,5-bis(diphenylphosphino)-9,9-dimethylxanthene (Xantphos; 110 mg, 0.190 mmol), and cesium carbonate (3.09 g, 9.48 mmol) in 1,4-dioxane (20 mL) was stirred at 95° C. to 100° C. for 18 hours. After the reaction mixture had cooled to room temperature, water (50 mL) was added, and the resulting mixture was extracted with ethyl acetate (3×50 mL). The combined organic layers were washed with saturated aqueous sodium chloride solution (50 mL), dried over sodium sulfate, filtered, and concentrated in vacuo. Silica gel chromatography (Eluent: 30:1 dichloromethane/methanol) provided the product as a yellow solid. Yield: 249 mg, 1.66 mmol, 52%. $^1$H NMR (400 MHz, CDCl$_3$) δ 8.01 (dd, J=4.6, 1.3 Hz, 1H), 7.86 (d, J=2.9 Hz, 1H), 7.11 (dd, J=8.2, 4.6 Hz, 1H), 6.75 (ddd, J=8.3, 2.8, 1.3 Hz, 1H), 4.82 (tt, J=6.4, 4.6 Hz, 1H), 4.26-4.20 (m, 2H), 3.74 (br dd, J=8.7, 4.6 Hz, 2H).

Step 2. Synthesis of 2,4-dimethyl-5,7-dihydro-6H-pyrrolo[3,4-b]pyridine-6-carbonyl chloride (C67)

To a solution of P1 (125 mg, 0.565 mmol) and pyridine (214 mg, 2.71 mmol) in dichloromethane (10 mL) was added bis(trichloromethyl) carbonate (71 mg, 0.24 mmol), and the reaction mixture was stirred at room temperature (~7° C.) for 20 minutes. The reaction mixture was concentrated in vacuo to afford crude product (440 mg) as a brown solid, which was used directly in the following step.

Step 3. Synthesis of 1-(pyridin-3-yl)azetidin-3-yl 2,4-dimethyl-5,7-dihydro-6H-pyrrolo[3,4-b]pyridine-6-carboxylate (20)

Sodium hydride (60% suspension in mineral oil; 80 mg, 2 mmol) was added to a 0° C. solution of C66 (100 mg, 0.666 mmol) in tetrahydrofuran (10 mL), and the reaction mixture was stirred at room temperature (~7° C.) for 1 hour. Crude C67 (from the previous step; <0.565 mmol) was added at 0° C., and stirring was continued at room temperature for 2 days. The reaction mixture was then treated with water (20 mL) and extracted with ethyl acetate (3×20 mL); the combined organic layers were washed with saturated aqueous sodium chloride solution (30 mL), dried over sodium sulfate, filtered, and concentrated in vacuo. Purification via reversed-phase HPLC (Column: Agela Durashell C18, 5 µm; Mobile phase A: 0.05% ammonium hydroxide in water; Mobile phase B: acetonitrile; Gradient: 26% to 46% B) afforded the product as a white solid. From analysis of the $^1$H NMR, this material was presumed to exist as a mixture of rotamers. Yield: 112 mg, 0.345 mmol, 61% over 2 steps. LCMS m/z 324.8 [M+H]$^+$. $^1$H NMR (400 MHz, CDCl$_3$) δ 8.05 (d, J=4.5 Hz, 1H), 7.91 (d, J=3.0 Hz, 1H), 7.13 (dd, J=8.3, 4.8 Hz, 1H), 6.88 (s, 1H), 6.80-6.74 (m, 1H), 5.49-5.39 (m, 1H), 4.77-4.64 (m, 4H), 4.34 (dd, J=8.0, 7.0 Hz, 2H), 3.99-3.91 (m, 2H), [2.52 (s) and 2.51 (s), total 3H], [2.25 (s) and 2.24 (s), total 3H].

Using the methodology described above for Examples 1-20, Examples 21-78 were synthesized. See Table 6 for specific methods employed, as well as characterization data for these Examples.

TABLE 6

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)[1] |
|---|---|---|---|
| 21 | Example 1; P8, C43 | 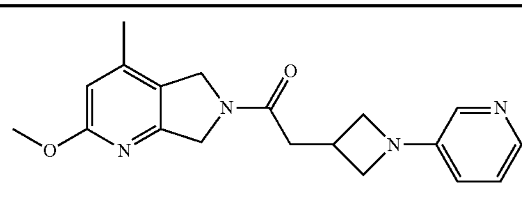 | $^1$H NMR (400 MHz, CD$_3$OD) δ 7.86 (d, J = 5 Hz, 1H), 7.75 (d, J = 2.5 Hz, 1H), 7.21 (dd, J = 8, 5 Hz, 1H), 6.94-6.88 (m, 1H), 6.56 (br s, 1H), 4.69-4.51 (m, 4H), 4.16 (dd, J = 7.5, 7.5 Hz, 2H), [3.88 (s) and 3.88 (s), total 3H], 3.68 (br dd, J = 6.5, 6.5 Hz, 2H), 3.3-3.15 (m, 1H), 2.95-2.88 (m, 2H), 2.28 (s, 3H); 339.1 |

TABLE 6-continued

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)$^1$ |
|---|---|---|---|
| 22 | Example 1$^2$; C38, C43 | 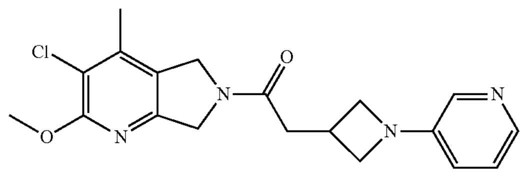 [SMILES: COc1nc2c(c(C)c1Cl)CN(C(=O)CC1CN(c3cccnc3)C1)C2] | $^1$H NMR (400 MHz, CD$_3$OD) δ 7.85 (d, J = 4.5 Hz, 1H), 7.77-7.71 (br s, 1H), 7.20 (dd, J = 8.0, 4.5 Hz, 1H), 6.89 (br d, J = 8.0 Hz, 1H), [4.81 (s) and 4.76 (s), total 2H], [4.65 (s) and 4.59 (s), total 2H], 4.14 (dd, J = 7.5, 7.5 Hz, 2H), [3.97 (s) and 3.96 (s), total 3H], 3.67 (dd, J = 7.0, 6.0 Hz, 2H), 3.27-3.15 (m, 1H), 2.95-2.85 (m, 2H), 2.31 (s, 3H); 373.0 (chlorine isotope pattern observed) |
| 23 | Example 1; P2, C43 | 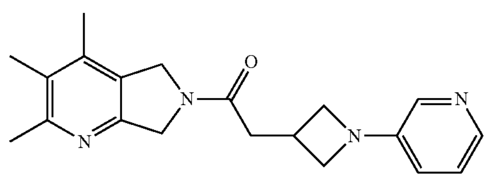 | 7.99 (br d, J = 4.5 Hz, 1H), 7.86 (d, J = 2.8 Hz, 1H), 7.10 (dd, J = 8.3, 4.5 Hz, 1H), 6.72 (ddd, J = 8.3, 2.8, 1.2 Hz, 1H), 4.78-4.71 (m, 4H), [4.19 (dd, J = 7.5, 7.5 Hz) and 4.18 (dd, J = 7.8, 7.5 Hz), total 2H], 3.69-3.63 (m, 2H), 3.34-3.21 (m, 1H), [2.83 (d, J=7.8 Hz) and 2.80 (d, J = 7.5 Hz), total 2H], [2.53 (s) and 2.52 (s), total 3H], [2.22 (s) and 2.21 (s), total 6H]; 337.2 |
| 24 | Example 3$^3$ | 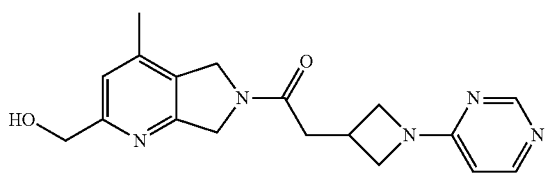 [SMILES: Cc1cc(CO)nc2c1CN(C(=O)CC1CN(c3ccncn3)C1)C2] | $^1$H NMR (600 MHz, DMSO-d$_6$), characteristic peaks: δ 8.12 (br d, J = 6 Hz, 1H), 7.22-7.19 (m, 1H), [6.37 (d, J = 6 Hz) and 6.37 (d, J = 6 Hz), total 1H], [4.84 (s) and 4.78 (s), total 2H], [4.61 (s) and 4.56 (s), total 2H], 4.53-4.50 (br s, 2H), 4.18 (dd, J = 8.5, 8.5 Hz, 2H), 3.75-3.71 (m, 2H), [2.86 (d, J = 7.5 Hz) and 2.85 (d, J = 7.5 Hz), total 2H], [2.28 (s) and 2.27 (s), total 3H]; 340.2 |
| 25 | Example 2; P3, C50 | 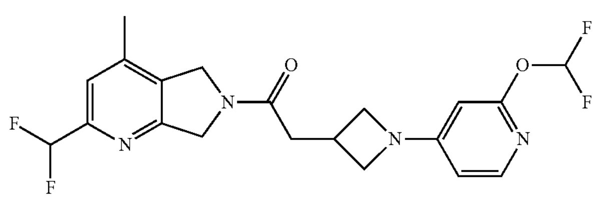 [SMILES: Cc1cc(C(F)F)nc2c1CN(C(=O)CC1CN(c3ccnc(OC(F)F)c3)C1)C2] | $^1$H NMR (400 MHz, CD$_3$OD) δ 7.75 (d, J = 5.5 Hz, 1H), 7.46 (s, 1H), 7.35 (t, J$_{HF}$ =73.8 Hz, 1H), 6.69 (t, J$_{HF}$ = 55.5 Hz, 1H), 6.20 (d, J = 5.0 Hz, 1H), 5.82 (s, 1H), [4.96 (s), 4.91 (s), 4.79 (s), and 4.75 (s), total 4H], 4.19 (dd, J = 8.0, 7.5 Hz, 2H), 3.73 (dd, J = 7.0, 6.5 Hz, 2H), 3.28-3.17 (m, 1H), 2.97-2.89 (m, 2H), 2.41 (s, 3H); 425.1 |
| 26 | Example 1$^{2,4}$; C41 | 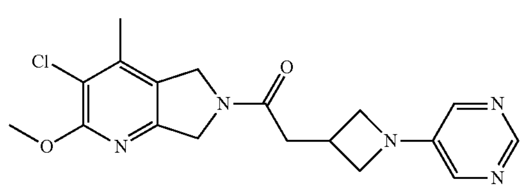 [SMILES: COc1nc2c(c(C)c1Cl)CN(C(=O)CC1CN(c3cncnc3)C1)C2] | 8.64 (s, 1H), 7.96 (s, 2H), 4.77-4.66 (m, 4H), 4.30-4.21 (m, 2H), [4.02 (s) and 4.00 (s), total 3H], 3.77-3.67 (m, 2H), 3.41-3.27 (m, 1H), 2.88-2.77 (m, 2H), [2.33 (s) and 2.32 (s), total 3H]; 373.9 (chlorine isotope pattern observed) |
| 27 | Example 1; C54, C43 | 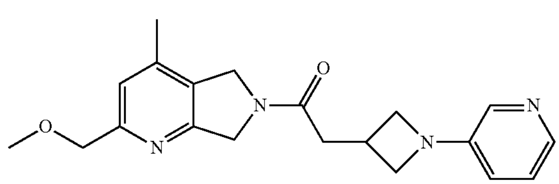 [SMILES: COCc1cc(C)c2c(n1)CN(C(=O)CC1CN(c3cccnc3)C1)C2] | 8.01 (br d, J = 4.5 Hz, 1H), 7.87 (d, J = 2.8 Hz, 1H), 7.18 (br s, 1H), 7.11 (dd, J = 8.3, 4.5 Hz, 1H), 6.73 (ddd, J = 8.3, 3.0, 1.2 Hz, 1H), 4.84-4.75 (m, 4H), [4.56 (s) and 4.55 (s), total 2H], [4.20 (dd, J = 7.8, 7.3 Hz) and 4.19 (dd, J = 7.5, 7.5 Hz), total 2H], 3.70-3.64 (m, 2H), [3.50 (s) and 3.49 (s), total 3H], 3.34-3.22 (m, 1H), |

TABLE 6-continued

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)[1] |
|---|---|---|---|
| | | | [2.85 (d, J = 7.8 Hz) and 2.82 (d, J = 7.8 Hz), total 2H], [2.33 (s) and 2.32 (s), total 3H]; 353.0 |
| 28 | Example 1[5]; C38, C43 | 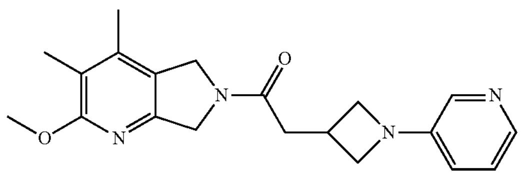 [SMILES: COc1nc2c(c(C)c1C)CN(C(=O)CC1CN(c3cccnc3)C1)C2] | $^1$H NMR (400 MHz, CD$_3$OD) δ 7.85 (br d, J = 4.3 Hz, 1H), 7.75 (d, J = 2.3 Hz, 1H), 7.21 (dd, J = 8.3, 4.8 Hz, 1H), 6.93-6.87 (m, 1H), [4.80 (s) and 4.75 (s), total 2H], [4.63 (s) and 4.60 (s), total 2H], 4.15 (dd, J = 7.8, 7.5 Hz, 2H), [3.91 (s) and 3.91 (s), total 3H], 3.68 (dd, J = 7.3, 5.8 Hz, 2H), 3.27-3.15 (m, 1H), 2.94-2.87 (m, 2H), 2.21 (s, 3H), 2.13 (s, 3H); 353.0 |
| 29 | Example 1[4,5] | 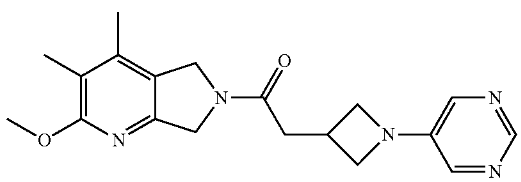 [SMILES: COc1nc2c(c(C)c1C)CN(C(=O)CC1CN(c3cncnc3)C1)C2] | $^1$H NMR (400 MHz, CD$_3$OD) δ 8.46 (s, 1H), 8.00 (s, 2H), [4.82 (s) and 4.76 (s), total 2H], [4.65 (s) and 4.60 (s), total 2H], 4.23 (dd, J = 7.5, 7.5 Hz, 2H), [3.91 (s) and 3.91 (s), total 3H], 3.77 (dd, J = 7.0, 6.0 Hz, 2H), 3.3-3.21 (m, 1H, assumed; partially obscured by solvent peak), 2.97-2.89 (m, 2H), 2.22 (s, 3H), 2.13 (s, 3H); 354.2 |
| 30 | Example 1[6]; P1, C41 | 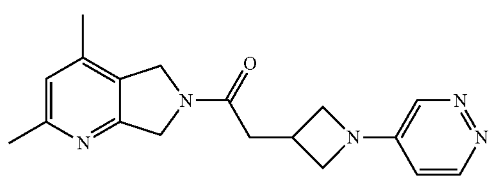 [SMILES: Cc1cc(C)c2c(n1)CN(C(=O)CC1CN(c3ccnnc3)C1)C2] | $^1$H NMR (400 MHz, CD$_3$OD) δ 8.52-8.49 (m, 1H), 8.38-8.36 (m, 1H), 7.07 (br s, 1H), 6.56-6.52 (m, 1H), 4.9-4.83 (m, 2H, assumed; partially obscured by water peak), [4.71 (s) and 4.70 (s), total 2H], 4.32 (br dd, J = 8, 8 Hz, 2H), 3.89-3.83 (m, 2H), 3.35-3.24 (m, 1H, assumed; partially obscured by solvent peak), 2.98-2.93 (m, 2H), 2.50 (s, 3H), 2.32 (s, 3H); 323.9 |
| 31 | Example 1[4]; C54 | 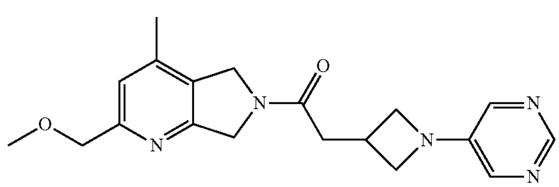 [SMILES: COCc1cc(C)c2c(n1)CN(C(=O)CC1CN(c3cncnc3)C1)C2] | $^1$H NMR (400 MHz, CD$_3$OD) δ 8.47 (s, 1H), 8.01 (br s, 2H), 7.26 (s, 1H), 4.95-4.85 (m, 2H, assumed; partially obscured by water peak), [4.75 (s) and 4.72 (s), total 2H], 4.51 (s, 2H), 4.24 (br dd, J = 8, 8 Hz, 2H), 3.77 (br dd, J = 7, 6 Hz, 2H), 3.44 (s, 3H), 3.3-3.23 (m, 1H, assumed; partially obscured by solvent peak), 2.99-2.92 (m, 2H), 2.36 (s, 3H); 353.9 |
| 32 | Example 1[4,7]; C38 | 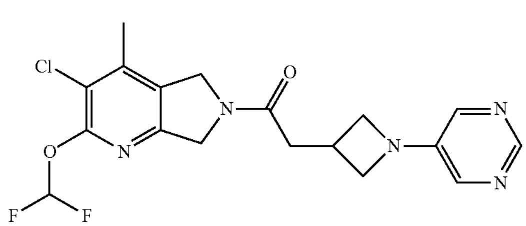 [SMILES: Cc1c(Cl)c(OC(F)F)nc2c1CN(C(=O)CC1CN(c3cncnc3)C1)C2] | 8.63 (s, 1H), 7.94 (s, 2H), [7.45 (t, J$_{HF}$ = 72.3 Hz) and 7.39 (t, J$_{HF}$ = 72.4 Hz), total 1H], 4.80-4.68 (m, 4H), [4.25 (dd, J = 7.8, 7.5 Hz) and 4.24 (dd, J = 7.8, 7.5 Hz), total 2H], 3.71 (dd, J = 6.8, 5.8 Hz, 2H), 3.39-3.26 (m, 1H), [2.84 (d, J = 7.8 Hz) and 2.81 (d, J = 7.8 Hz), total 2H], [2.37 (s) and 2.36 (s), total 3H]; 409.9 (chlorine isotope pattern observed) |

TABLE 6-continued

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)[1] |
|---|---|---|---|
| 33 | Example 1[8]; C54, C53 | 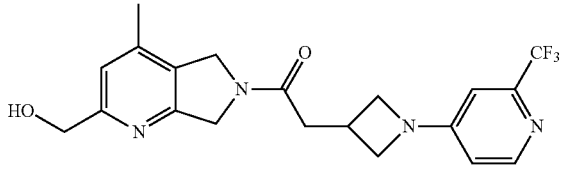 [SMILES: Cc1cc(CO)nc2c1CN(C(=O)CC1CN(c3ccnc(C(F)(F)F)c3)C1)C2] | 8.29 (d, J = 5.7 Hz, 1H), [7.04 (s) and 7.03 (s), total 1H], 6.61-6.58 (m, 1H), 6.34 (dd, J = 5.7, 2.3 Hz, 1H), 4.85-4.73 (m, 6H), [4.30 (dd, J = 8.2, 8.2 Hz) and 4.29 (dd, J = 8.2, 8.2 Hz), total 2H], 3.80-3.73 (m, 2H), 3.43-3.23 (m, 2H), [2.85 (d, J = 7.6 Hz) and 2.83 (d, J = 7.8 Hz), total 2H], [2.33 (s) and 2.32 (s), total 3H]; 407.3 |
| 34 | Example 1[4]; P3 | 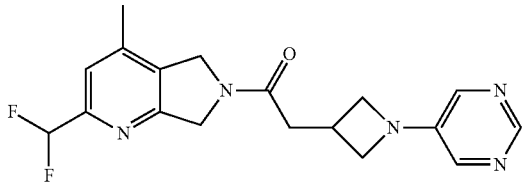 [SMILES: Cc1cc(C(F)F)nc2c1CN(C(=O)CC1CN(c3cncnc3)C1)C2] | $^1$H NMR (400 MHz, CD$_3$OD) δ 8.47 (s, 1H), 8.01 (d, J = 1.5 Hz, 2H), 7.47 (s, 1H), 6.69 (t, J$_{HF}$ = 55 Hz, 1H), [4.98 (s), 4.92 (s), 4.80 (s), and 4.76 (s), total 4H], 4.28-4.21 (m, 2H), 3.80-3.74 (m, 2H), 3.3-3.24 (m, 1H, assumed; partially obscured by solvent peak), [2.96 (d, J = 7.8 Hz) and 2.95 (d, J = 7.3 Hz), total 2H], 2.42 (s, 3H); 359.9 |
| 35 | Example 1[9]; P2, C41 | 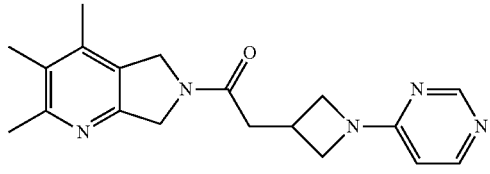 | 8.59 (s, 1H), 8.17 (d, J = 6.0 Hz, 1H), 6.18 (br d, J = 6 Hz, 1H), 4.79-4.72 (m, 4H), 4.40-4.32 (m, 2H), 3.88-3.81 (m, 2H), 3.36-3.25 (m, 1H), [2.83 (d, J = 8.0 Hz) and 2.80 (d, J = 7.8 Hz), total 2H], [2.54 (s) and 2.53 (s), total 3H], [2.23 (s) and 2.22 (s), total 6H]; 337.9 |
| 36 | P2, C66[10] | 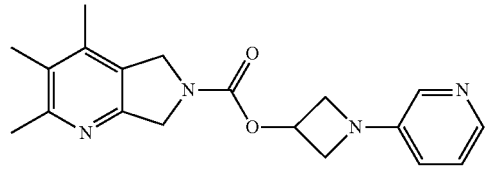 | $^1$H NMR (500 MHz, CDCl$_3$) δ 8.08-8.04 (m, 1H), 7.94-7.91 (m, 1H), 7.14 (dd, J = 8.2, 4.7 Hz, 1H), 6.80-6.76 (m, 1H), 5.49-5.40 (m, 1H), 4.73-4.68 (m, 4H), 4.38-4.33 (m, 2H), 3.98-3.93 (m, 2H), [2.53 (s) and 2.52 (s), total 3H], [2.22 (s), 2.21 (s), and 2.20 (s), total 6H]; 339.0 |
| 37 | Example 13[11,12]; P2 | 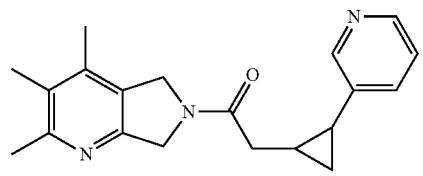 [SMILES: Cc1nc2c(c(C)c1C)CN(C(=O)CC1CC1c1cccnc1)C2]<br>trans, ENT-1 | 2.52 minutes[13]; 322.6 |
| 38 | Example 13[11,12]; P2 | 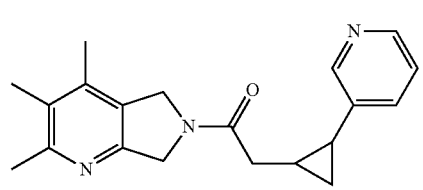 [SMILES: Cc1nc2c(c(C)c1C)CN(C(=O)CC1CC1c1cccnc1)C2]<br>trans, ENT-2 | 3.58 minutes[13]; 322.3 |

TABLE 6-continued

Method of preparation, structure, and physicochemical data for Examples 21-78

| Example Number | Method of Synthesis; Non-commercial starting materials | Structure | 1H NMR (400 MHz, CDCl3) δ; Mass spectrum, observed ion m/z [M + H]+ or HPLC retention time; Mass spectrum m/z [M+H]* (unless otherwise indicated)[1] |
|---|---|---|---|
| 39 | Example 13[14]; P6 | 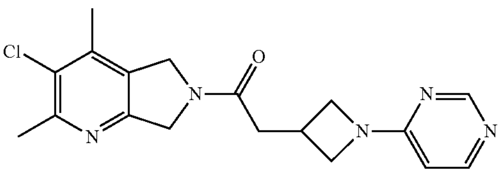 [SMILES: Cc1nc2c(c(C)c1Cl)CN(C(=O)CC1CN(c3ccncn3)C1)C2] | 8.58 (s, 1H), 8.17 (d, J = 6.0 Hz, 1H), 6.18 (br d, J = 6.0 Hz, 1H), 4.81-4.73 (m, 4H), [4.36 (dd, J = 9.0, 8.0 Hz) and 4.35 (dd, J = 8.5, 8.5 Hz), total 2H], 3.88-3.79 (m, 2H), 3.35-3.23 (m, 1H), 2.85-2.77 (m, 2H), [2.65 (s) and 2.64 (s), total 3H], 2.34 (br s, 3H); 358.1 (chlorine isotope pattern observed) |
| 40 | Example 1[4,15]; C9 | 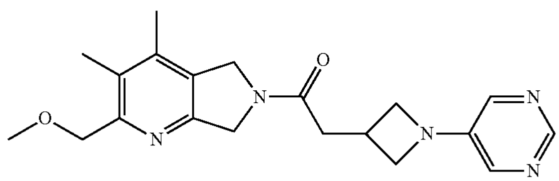 [SMILES: COCc1nc2c(c(C)c1C)CN(C(=O)CC1CN(c3cncnc3)C1)C2] | 8.64 (s, 1H), 7.96 (s, 2H), 4.83-4.73 (m, 4H), [4.62 (s) and 4.61 (s), total 2H], [4.26 (dd, J = 7.5, 7.5 Hz) and 4.25 (dd, J = 8.0, 7.5 Hz), total 2H], 3.78-3.70 (m, 2H), 3.46 (s, 3H), 3.40-3.29 (m, 1H), [2.85 (d, J = 8.0 Hz) and 2.82 (d, J = 8.0 Hz), total 2H], 2.31 (s, 3H), [2.25 (s) and 2.24 (s), total 3H]; 367.9 |
| 41 | Example 1[16]; C41, P1 | 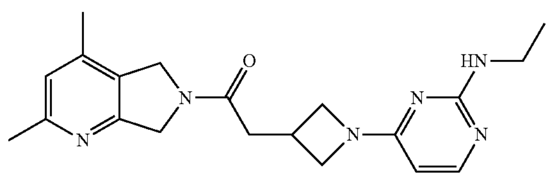 [SMILES: CCNc1nccc(N2CC(CC(=O)N3Cc4nc(C)cc(C)c4C3)C2)n1] | 1.96 minutes[17]; 367 |
| 42 | Example 1[18]; C41, P1 | 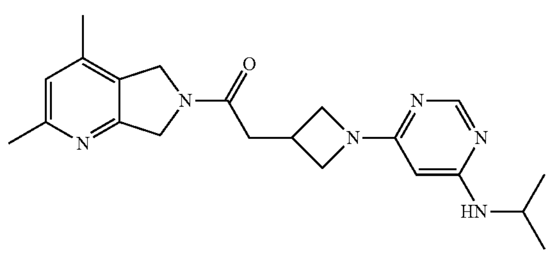 [SMILES: Cc1cc(C)c2c(n1)CN(C(=O)CC1CN(c3cc(NC(C)C)ncn3)C1)C2] | 1.98 minutes[17]; 381 |
| 43 | Example 1[19]; C41, P1 | 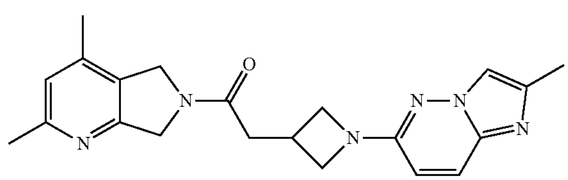 | 1.88 minutes[17]; 377 |
| 44 | Example 2[20]; C41, P6 | 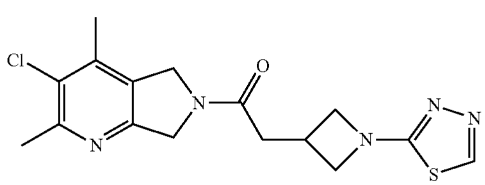 [SMILES: Cc1nc2c(c(C)c1Cl)CN(C(=O)CC1CN(c3nncs3)C1)C2] | 1H NMR (400 MHz, CD3OD) δ [8.64 (s) and 8.63 (s), total 1H], [4.92 (s), 4.85 (s, assumed; obscured by water peak), 4.74 (s), and 4.68 (s), total 4H], [4.36 (dd, J = 8, 8 Hz) and 4.36 (dd, J = 8, 8 Hz), total 2H], 3.96-3.90 (m, 2H), 3.37-3.3 (m, 1H, assumed; largely obscured by solvent peak), [2.96 (d, J = 7.5 Hz) and 2.95 (d, J = 7.5 Hz), total 2H], 2.61 (s, 3H), [2.38 (s) and 2.38 (s), total 3H]; 363.8 (chlorine isotope pattern observed) |

TABLE 6-continued

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)[1] |
|---|---|---|---|
| 45 | Example 2; P3, C45 | 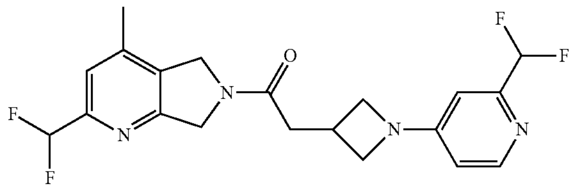 [SMILES: Cc1cc(C(F)F)nc2c1CN(C(=O)CC1CN(c3ccnc(C(F)F)c3)C1)C2] | $^1$H NMR (400 MHz, CD$_3$OD) δ 8.11 (d, J = 6.0 Hz, 1H), 7.47 (s, 1H), 6.69 (t, J$_{HF}$ = 55.2 Hz, 1H), 6.62-6.59 (m, 1H), 6.54 (t, J$_{HF}$ = 55.5 Hz, 1H), 6.47-6.42 (m, 1H), [4.97 (s), 4.92 (s), 4.80 (s), and 4.77 (s), total 4H], [4.26 (dd, J = 8.5, 8.3 Hz) and 4.26 (dd, J = 8.3, 8.3 Hz), total 2H], 3.83-3.77 (m, 2H), 3.3-3.22 (m, 1H, assumed; partially obscured by solvent peak), [2.96 (d, J = 7 Hz) and 2.95 (d, J = 8 Hz), total 2H], 2.42 (s, 3H); 409.0 |
| 46 | Example 2; P2, C45 | 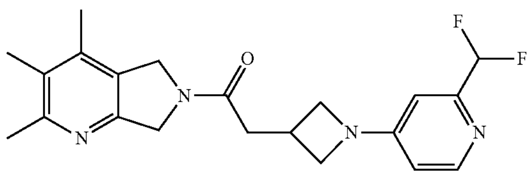 [SMILES: Cc1nc2c(c(C)c1C)CN(C(=O)CC1CN(c3ccnc(C(F)F)c3)C1)C2] | $^1$H NMR (400 MHz, CD$_3$OD) δ 8.10 (d, J = 5.8 Hz, 1H), 6.61-6.58 (m, 1H), 6.53 (t, J$_{HF}$ = 55.5 Hz, 1H), 6.44 (br d, J = 6 Hz, 1H), [4.81 (s), 4.72 (s), 4.67 (s), and 4.59 (s), total 4H], [4.25 (dd, J = 8.3, 8.3 Hz) and 4.25 (dd, J = 8.3, 8.3 Hz), total 2H], 3.82-3.76 (m, 2H), 3.30-3.21 (m, 1H), 2.97-2.91 (m, 2H), 2.51 (s, 3H), 2.28 (s, 3H), 2.26 (s, 3H); 387.1 |
| 47 | Example 1[21]; C26, C45 | 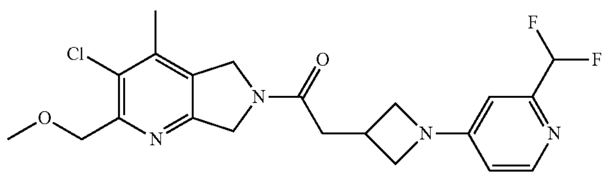 | $^1$H NMR (400 MHz, CD$_3$OD) δ 8.10 (d, J = 6.0 Hz, 1H), 6.62-6.58 (br s, 1H), 6.53 (t, J$_{HF}$ = 55.5 Hz, 1H), 6.44 (br d, J = 5.5 Hz, 1H), [4.95 (s), 4.87 (S, assumed; obscured by water peak), 4.78 (s), and 4.72 (s), total 4H], 4.68 (s, 2H), 4.25 (br dd, J = 8.5, 8.0 Hz, 2H), 3.79 (br dd, J = 7.0, 6.5 Hz, 2H), 3.45 (s, 3H), 3.30-3.20 (m, 1H), [2.95 (d, J = 7 Hz) and 2.93 (d, J = 7.5 Hz), total 2H], 2.40 (s, 3H); 437.1 (chlorine isotope pattern observed) |
| 48 | Example 1[21]; C43 | 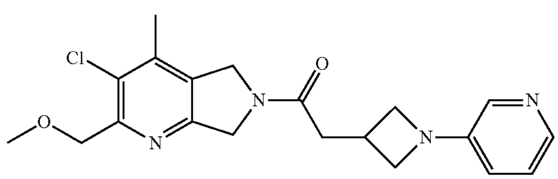 | 8.01 (dd, J = 4.8, 1.2 Hz, 1H), 7.87 (d, J = 2.8 Hz, 1H), 7.11 (dd, J = 8.3, 4.8 Hz, 1H), 6.73 (ddd, J = 8.3, 3.0, 1.5 Hz, 1H), 4.86-4.77 (m, 4H), 4.71 (s, 2H), [4.19 (dd, J = 7.8, 7.5 Hz) and 4.19 (dd, J = 7.5, 7.5 Hz), total 2H], 3.69-3.63 (m, 2H), 3.53 (s, 3H), 3.33-3.21 (m, 1H), [2.84 (d, J = 7.8 Hz) and 2.81 (d, J = 7.5 Hz), total 2H], [2.37 (s) and 2.36 (s), total 3H]; 386.9 (chlorine isotope pattern observed) |
| 49 | Example 1[21,22]; C41 | 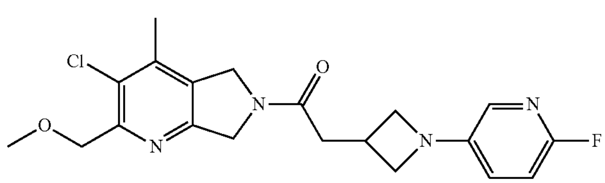 [SMILES: COCc1nc2c(c(C)c1Cl)CN(C(=O)CC1CN(c3ccc(F)nc3)C1)C2] | 7.37-7.32 (m, 1H), 6.89-6.82 (m, 1H), 6.76 (dd, half of ABX pattern, J = 8.5, 3.0 Hz, 1H), 4.85-4.76 (m, 4H), 4.71 (s, 2H), [4.15 (dd, J = 7.5, 7.5 Hz) and 4.14 (dd, J = 7.5, 7.5 Hz), total 2H], 3.66-3.59 (m, 2H), 3.53 (s, 3H), 3.31-3.19 (m, 1H), [2.83 (d, J = 7.8 Hz) and 2.80 (d, J = 7.5 Hz), total 2H], [2.36 (s) and 2.35 (s), total 3H]; 404.9 (chlorine isotope pattern observed) |

TABLE 6-continued

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)[1] |
|---|---|---|---|
| 50 | Example 2; C54, C45 | 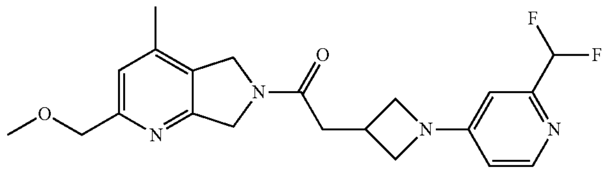 [SMILES: COCc1cc(C)c2c(n1)CN(C(=O)CC1CN(c3ccnc(C(F)F)c3)C1)C2] | 8.22 (d, J = 5.5 Hz, 1H), 7.18 (s, 1H), 6.56 (d, J = 2.0 Hz, 1H), 6.51 (t, J$_{HF}$ = 55.8 Hz, 1H), 6.29 (dd, J = 5.6, 2.1 Hz, 1H), 4.83-4.74 (m, 4H), [4.56 (s) and 4.54 (s), total 2H], [4.27 (dd, J = 8.3, 8.0 Hz) and 4.27 (dd, J = 8.3, 8.0 Hz), total 2H], 3.78-3.71 (m, 2H), [3.49 (s) and 3.49 (s), total 3H], 3.37-3.26 (m, 1H), [2.83 (d, J = 7.8 Hz) and 2.81 (d, J = 7.8 Hz), total 2H], [2.33 (s) and 2.32 (s), total 3H], 403.1 |
| 51 | Example 7[23]; C59, P6 | trans, from ENT-2 in footnote 23 | 9.03 (s, 1H), 8.56 (s, 2H), 4.78 (s, 2H), 4.75 (s, 2H), 2.68-2.58 (m, 1H), [2.64 (s) and 2.63 (s), total 3H], 2.54-2.43 (m, 1H), [2.33 (s) and 2.32 (s), total 3H], 1.83-1.76 (m, 1H), 1.65-1.53 (m, 1H), 1.19-1.11 (m, 1H), 1.10-1.02 (m, 1H); 343.3 (chlorine isotope pattern observed) |
| 52 | Example 1[21]; C56 | 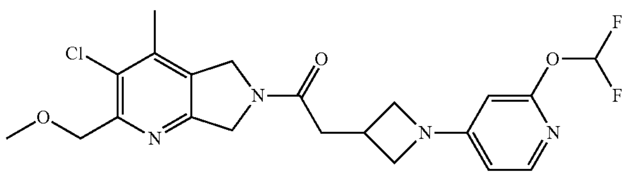 [SMILES: COCc1nc2c(c(C)c1Cl)CN(C(=O)CC1CN(c3ccnc(OC(F)F)c3)C1)C2] | 7.81 (d, J = 5.8 Hz, 1H), [7.43 (t, J$_{HF}$ = 73.5 Hz) and 7.43 (t, J$_{HF}$ = 73.8 Hz), total 1H], 6.11-6.07 (m, 1H), 5.78-5.75 (m, 1H), 4.85-4.76 (m, 4H), 4.72 (s, 2H), [4.23 (dd, J = 8.3, 8.3 Hz) and 4.22 (dd, J = 8.3, 8.0 Hz), total 2H], 3.73-3.66 (m, 2H), 3.54 (s, 3H), 3.33-3.23 (m, 1H), [2.82 (d, J = 8 Hz) and 2.79 (d, J = 8.0 Hz), total 2H], [2.37 (s) and 2.36 (s), total 3H]; 453.0 (chlorine isotope pattern observed) |
| 53 | Example 1; C57, C58 | 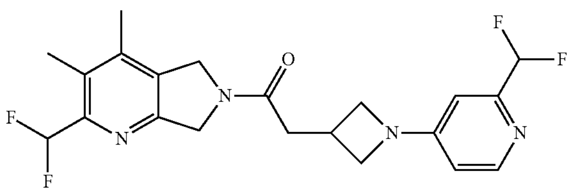 [SMILES: Cc1c(C(F)F)nc2c(c1C)CN(C(=O)CC1CN(c3ccnc(C(F)F)c3)C1)C2] | $^1$H NMR (400 MHz, CD$_3$OD) δ 8.10 (d, J = 6.0 Hz, 1H), [6.84 (t, J$_{HF}$ = 54.2 Hz) and 6.83 (t, J$_{HF}$ = 54.5 Hz), total 1H], 6.62-6.58 (br s, 1H), 6.53 (t, J$_{HF}$ = 54.5 Hz, 1H), 6.44 (br d, J = 5.5 Hz, 1H), [4.96 (s), 4.87 (s, assumed; obscured by water peak), 4.79 (s), and 4.72 (s), total 4H], [4.26 (dd, J = 8.5, 8.0 Hz) and 4.25 (dd, J = 8.5, 8.0 Hz), total 2H], 3.79 (dd, J = 8.0, 6.0 Hz, 2H), 3.31-3.20 (m, 1H), 2.98-2.91 (m, 2H), 2.42 (s, 3H), 2.33 (s, 3H); 423.0 |
| 54 | Example 16[24]; C59, P1 | trans, ENT-1 (-) | $^1$H NMR (400 MHz, CD$_3$OD) δ 8.43-8.39 (br s, 1H), 8.30 (br d, J = 5.0 Hz, 1H), 7.56 (ddd, J = 8.0, 2.0, 2.0 Hz, 1H), 7.32 (dd, J = 8.0, 5.0 Hz, 1H), 7.06 (s, 1H), [4.88 (s), 4.85 (s, assumed; obscured by water peak), 4.73 (s), and 4.71 (s), total 4H], 2.73-2.57 (m, 2H), [2.50 (s) and 2.49 (s), total 3H], 2.31 (s, 3H), 1.95-1.88 (m, 1H), 1.56-1.46 (m, 1H), 1.14-1.02 (m, 2H); 308.0 |

TABLE 6-continued

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)[1] |
|---|---|---|---|
| 55 | Example 16[24]; C59, P1 | 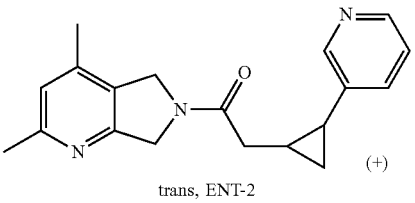 trans, ENT-2 (+) | $^1$H NMR (400 MHz, CD$_3$OD) δ 8.43-8.39 (br s, 1H), 8.30 (br d, J = 4.5 Hz, 1H), 7.56 (ddd, J = 8.0, 2, 2 Hz, 1H), 7.32 (dd, J = 8.0, 4.5 Hz, 1H), 7.06 (s, 1H), [4.88 (s), 4.84 (s), 4.73 (s) and 4.71 (s), total 4H], 2.73-2.57 (m, 2H), [2.50 (s) and 2.49 (s), total 3H], 2.31 (s, 3H), 1.95-1.88 (m, 1H), 1.56-1.46 (m, 1H), 1.14-1.02 (m, 2H); 308.1 |
| 56 | Example 1; P1 | 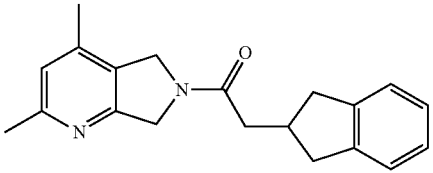 [SMILES: Cc1cc(C)c2c(n1)CN(C(=O)CC1Cc3ccccc3C1)C2] | 7.25-7.18 (m, 2H), 7.18-7.12 (m, 2H), [6.91 (s) and 6.89 (s), total 1H], 4.84-4.68 (m, 4H), 3.30-3.19 (m, 2H), 3.13-3.02 (m, 1H), 2.75-2.66 (m, 2H), 2.57 (br d, J = 7.0 Hz, 2H), [2.54 (s) and 2.52 (s), total 3H], [2.27 (s) and 2.23 (s), total 3H]; 306.9 |
| 57 | Example 4[25]; C41, P1 | 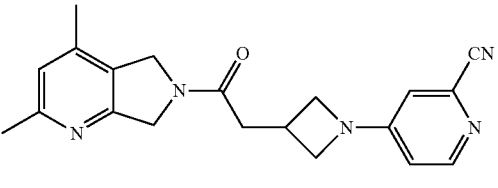 [SMILES: Cc1cc(C)c2c(n1)CN(C(=O)CC1CN(c3ccnc(C#N)c3)C1)C2] | $^1$H NMR (400 MHz, DMSO-d$_6$) δ 8.16 (d, J = 5.8 Hz, 1H), [7.00 (s) and 7.00 (s), total 1H], 6.97 (d, J = 2.5 Hz, 1H), 6.55 (dd, J = 5.8, 2.5 Hz, 1H), [4.81 (s) and 4.76 (s), total 2H], [4.58 (s) and 4.54 (s), total 2H], 4.15 (dd, J = 8.3, 8.3 Hz, 2H), 3.69 (dd, J = 8.4, 5.6 Hz, 2H), 3.16-3.06 (m, 1H), 2.85 (d, J = 7.5 Hz, 2H), 2.42 (s, 3H), [2.23 (s) and 2.22 (s), total 3H]; 347.9 |
| 58 | Example 2[26]; P1, C41 | 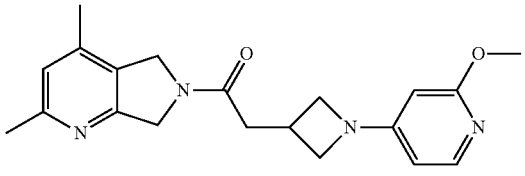 | $^1$H NMR (400 MHz, DMSO-d$_6$) δ 7.74 (d, J = 5.5 Hz, 1H), [7.00 (s) and 6.99 (s), total 1H], 6.06 (dd, J = 6.0, 2.0 Hz, 1H), 5.62 (d, J = 1.5 Hz, 1H), [4.81 (s) and 4.76 (s), total 2H], [4.58 (s) and 4.53 (s), total 2H], 4.04 (dd, J = 8.0, 8.0 Hz, 2H), 3.74 (s, 3H), 3.60-3.54 (m, 2H), 3.12-3.01 (m, 1H), 2.82 (d, J = 7.5 Hz, 2H), 2.42 (s, 3H), [2.23 (s) and 2.21 (s), total 3H]; 353.0 |
| 59 | Example 1; P1 | 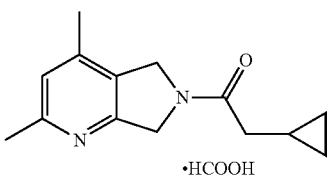 [SMILES: Cc1cc(C)c2c(n1)CN(C(=O)CC1CC1)C2 ; "·HCOOH"] ·HCOOH | 8.14 (s, 1H), [6.95 (s) and 6.92 (s), total 1H], [4.82 (s), 4.76 (s), and 4.73 (s), total 4H], 2.54 (br s, 3H), [2.37 (d, J = 6.5 Hz) and 2.36 (d, J = 6.5 Hz), total 2H], [2.29 (s) and 2.27 (s), total 3H], 1.23-1.10 (m, 1H), 0.66-0.57 (m, 2H), 0.27-0.19 (m, 2H); 230.8 |
| 60 | Example 1[27]; P1, C41 | 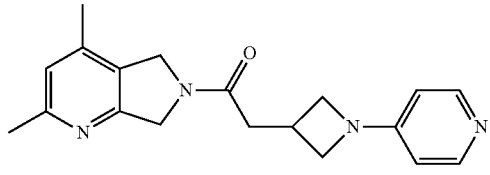 [SMILES: Cc1cc(C)c2c(n1)CN(C(=O)CC1CN(c3ccncc3)C1)C2] | 1H NMR (400 MHz, CD$_3$OD) δ 8.06-8.02 (m, 2H), 7.07 (s, 1H), 6.39-6.35 (m, 2H), [4.89 (s, assumed; obscured by water peak), 4.84 (s), 4.72 (s), and 4.70 (s), total 4H], 4.21 (dd, J = 8.0, 7.5 Hz, 2H), 3.78-3.71 (m, 2H), 3.28-3.18 (m, 1H), [2.94 (d, J = 7.8 Hz) and 2.93 (d, J = 7.8 Hz), total 2H], 2.50 (s, 3H), 2.32 (s, 3H); 322.9 |

TABLE 6-continued

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)[1] |
|---|---|---|---|
| 61 | Example 1[4]; P1, C41 | 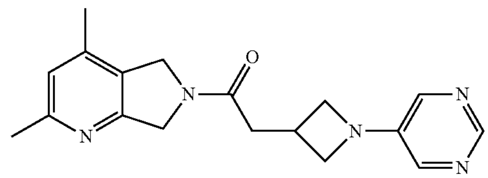 [SMILES: Cc1cc(C)c2c(n1)CN(C(=O)CC1CN(c3cncnc3)C1)C2] | $^1$H NMR (400 MHz, CD$_3$OD) δ 8.47 (s, 1H), 8.00 (s, 2H), 7.07 (s, 1H), [4.89 (s), 4.85 (s), 4.71 (s), and 4.70 (s), total 4H], 4.24 (dd, J = 7.8, 7.8 Hz, 2H), 3.80-3.73 (m, 2H), 3.33-3.23 (m, 1H, assumed; partially obscured by solvent peak), [2.95 (d, J = 7.5 Hz) and 2.94 (d, J = 7.8 Hz), total 2H], 2.50 (s, 3H), 2.32 (s, 3H); 324.0 |
| 62 | Example 36[28]; P1 | 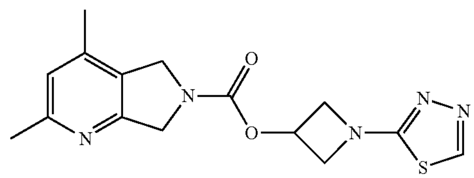 [SMILES: Cc1cc(C)c2c(n1)CN(C(=O)OC1CN(c3nncs3)C1)C2] | $^1$H NMR (400 MHz, CD$_3$OD) δ 8.69 (s, 1H), 7.04 (s, 1H), 5.48-5.40 (m, 1H), [4.76 (s), 4.71 (s), 4.66 (s), and 4.63 (s), total 4H], 4.55-4.48 (m, 2H), 4.23 (br dd, J = 9.4, 4.1 Hz, 2H), 2.48 (s, 3H), [2.29 (s) and 2.28 (s), total 3H]; 331.8 |
| 63 | Example 36[29]; C57 | 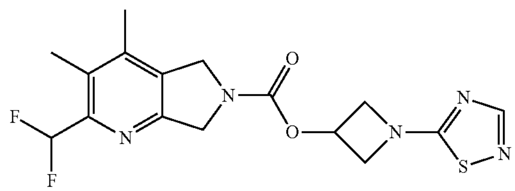 [SMILES: Cc1c(C(F)F)nc2c(c1C)CN(C(=O)OC1CN(c3ncns3)C1)C2] | 7.98 (s, 1H), [6.71 (t, $J_{HF}$ = 54.7 Hz) and 6.70 (t, $J_{HF}$ = 54.5 Hz), total 1H], 5.56-5.47 (m, 1H), 4.81-4.74 (m, 4H), 4.59-4.51 (m, 2H), 4.26 (dd, J = 10.0, 4.0 Hz, 2H), 2.43 (br s, 3H), 2.27 (s, 3H); 381.9 |
| 64 | Example 36[29]; P2 | 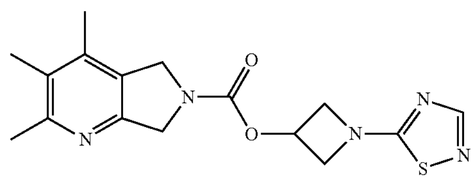 [SMILES: Cc1nc2c(c(C)c1C)CN(C(=O)OC1CN(c3ncns3)C1)C2] | 7.97 (s, 1H), 5.55-5.45 (m, 1H), 4.75-4.67 (m, 4H), 4.58-4.50 (m, 2H), 4.26 (br dd, J = 10, 4 Hz, 2H), [2.53 (s) and 2.53 (s), total 3H], 2.22 (s, 3H), 2.21 (br s, 3H); 345.9 |
| 65 | Example 36[28]; P2 | 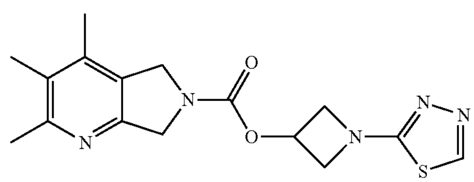 [SMILES: Cc1nc2c(c(C)c1C)CN(C(=O)OC1CN(c3nncs3)C1)C2] | $^1$H NMR (400 MHz, CD$_3$OD) δ 8.69 (s, 1H), 5.48-5.41 (m, 1H), [4.80 (s), 4.72 (s), 4.70 (s), and 4.64 (s), total 4H], 4.56-4.49 (m, 2H), 4.24 (dd, J = 9.5, 4.0 Hz, 2H), 2.50 (s, 3H), [2.27 (s) and 2.26 (s), total 6H]; 345.9 |
| 66 | Example 36[21]; C66 | 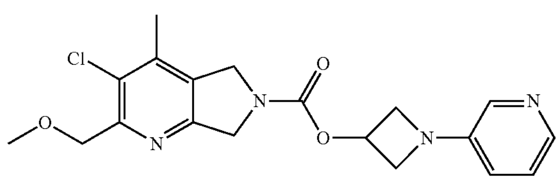 | 8.07 (br d, J = 4.5 Hz, 1H), 7.94-7.90 (m, 1H), 7.15 (dd, J = 8.5, 5.0 Hz, 1H), 6.81-6.76 (m, 1H), 5.50-5.39 (m, 1H), 4.81-4.73 (m, 4H), 4.71 (s, 2H), 4.35 (dd, J = 7.5, 7.5 Hz, 2H), 3.99-3.92 (m, 2H), [3.53 (s) and 3.53 (s) total 3H], [2.36 (s) and 2.34 (s), total 3H]; 388.8 (chlorine isotope pattern observed) |
| 67 | Example 36[29]; P6 | 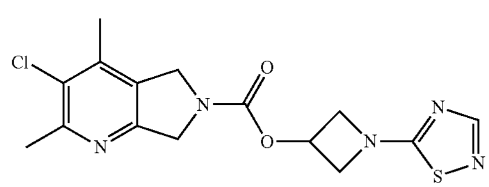 [SMILES: Cc1nc2c(c(C)c1Cl)CN(C(=O)OC1CN(c3ncns3)C1)C2] | 7.98 (br s, 1H), 5.55-5.46 (m, 1H), 4.76-4.70 (m, 4H), 4.58-4.51 (m, 2H), 4.29-4.23 (m, 2H), [2.64 (s) and 2.63 (s), total 3H], 2.33 (s, 3H); 365.9 (chlorine isotope pattern observed) |

TABLE 6-continued

Method of preparation, structure, and physicochemical data for Examples 21-78

| Example Number | Method of Synthesis; Non-commercial starting materials | Structure | ¹H NMR (400 MHz, CDCl₃) δ; Mass spectrum, observed ion m/z [M + H]⁺ or HPLC retention time; Mass spectrum m/z [M+H]* (unless otherwise indicated)[1] |
|---|---|---|---|
| 68 | Example 4[30]; C48 | 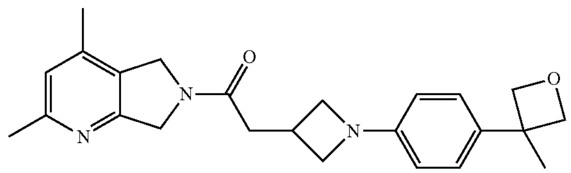 [SMILES: Cc1cc(C)c2c(n1)CN(C(=O)CC1CN(c3ccc(C4(C)COC4)cc3)C1)C2] | 1.51 minutes[31], 392.1 |
| 69 | Example 4[30]; C48 | 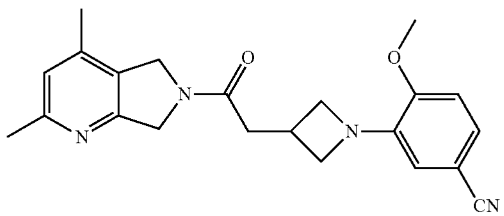 [SMILES: COc1ccc(C#N)cc1N1CC(CC(=O)N2Cc3nc(C)cc(C)c3C2)C1] | 1.82 minutes31, 377.1 |
| 70 | Example 4[30]; C48 | 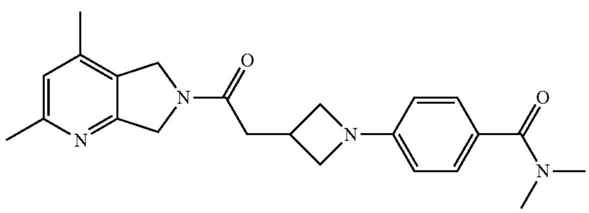 | 1.55 minutes[31], 393.1 |
| 71 | Example 4[30]: C48 | 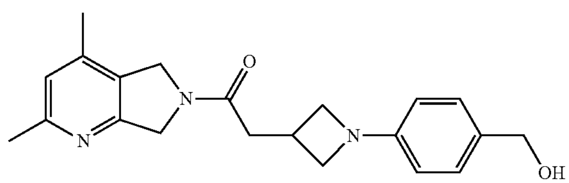 [SMILES: Cc1cc(C)c2c(n1)CN(C(=O)CC1CN(c3ccc(CO)cc3)C1)C2] | 1.12 minutes[31], 352.2 |
| 72 | Example 4[30]; C48 | 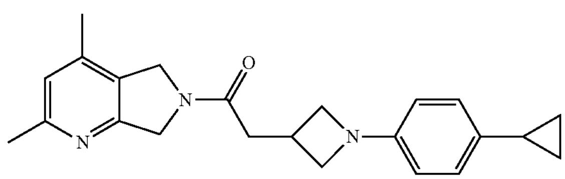 [SMILES: Cc1cc(C)c2c(n1)CN(C(=O)CC1CN(c3ccc(C4CC4)cc3)C1)C2] | 1.68 minutes[31], 362.2 |
| 73 | Example 4[30]; C48 | 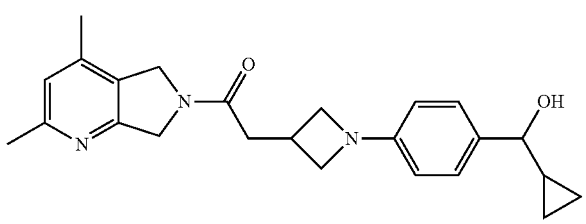 [SMILES: Cc1cc(C)c2c(n1)CN(C(=O)CC1CN(c3ccc(C(O)C4CC4)cc3)C1)C2] | 1.40 minutes[31], 392.2 |
| 74 | Example 4[30]; C48 | 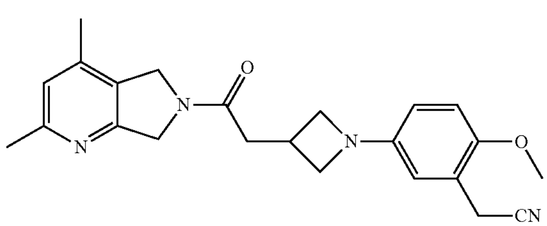 | 1.40 minutes[31], 392.2 |

TABLE 6-continued

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)[1] |
|---|---|---|---|
| 75 | Example 4[30]; C48 | 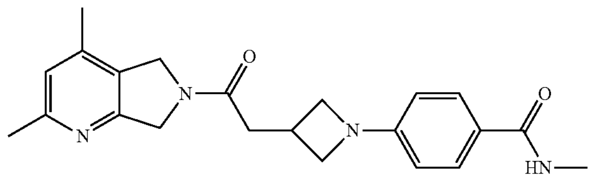 | 1.43 minutes[31], 378.1 |
| 76 | Example 16[32]; P1, C59 | (racemic) | 2.20 minutes[33], 359.3 |
| 77 | Example 16[34]; P1, C59 | (racemic) | 2.70 minutes[33], 307.3 |
| 78 | Example 4[30]; C48 | 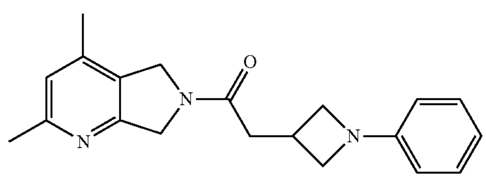 [SMILES: Cc1cc(C)c2c(n1)CN(C(=O)CC1CN(c3ccccc3)C1)C2] | $^1$H NMR (400 MHz, CD$_3$OD) δ ppm 2.31 (s, 3 H) 2.49 (s, 3 H) 2.89 (t, J = 7.03 Hz, 2 H) 3.12 (m, 1 H) 3.55-3.60 (m, 2 H) 4.06 (t, J = 7.53 Hz, 2 H) 4.70 (d, J = 4.52 Hz, 2 H) 4.81-4.88 (m, 2 H) 6.48 (d, J = 8.53 Hz, 2 H) 6.70 (t, J = 7.28 Hz, 1 H) 7.06 (s, 1 H) 7.16 (t, J = 7.78 Hz, 2 H) |

[1]Analysis of $^1$H NMR spectra indicated that these Examples may exist as a mixture of rotamers in solution.
[2]Reaction of C38 with N-chlorosuccinimide, followed by removal of the tert-butoxycarbonyl group with hydrogen chloride, afforded the requisite 3-chloro-2-methoxy-4-methyl-6,7-dihydro-5H-pyrrolo[3,4-b]pyridine.
[3]Example 3 (800 nmol) was incubated with liver microsomes (from female rabbits; 2.0 mg/mL), magnesium chloride (3.3 mM), and NADPH (1.3 mM), in 0.1 M potassium phosphate buffer (pH 7.4; total volume of incubation solution, 40 mL). The reaction mixture was shaken at 37° C. in a water bath for 45 minutes, whereupon acetonitrile (40 mL) was added and the mixture was spun at 1700g for 5 minutes. The supernatant was subjected to vacuum centrifugation to a volume of approximately 15 mL, to which was added formic acid (0.5 mL), acetonitrile (0.5 mL), and water (sufficient to reach a total volume of 50 mL). This mixture was spun at 40000g for 30 minutes. The supernatant was purified via reversed phase chromatography (Column: Agilent Polaris C18, 5 μm; Mobile phase A: 0.1% aqueous formic acid; Mobile phase B: acetonitrile; Gradient: 2% B from 0 to 5 minutes; 2% B to 20% B at 65 minutes; 20% B to 95% B at 75 minutes) to afford Example 24. Yield: 17 μg, 11 nmol, 1%.
[4][1-(Pyrimidin-5-yl)azetidin-3-yl]acetic acid was synthesized from C41 using the general method described for conversion of C41 to C43 in Example 1.
[5]Reaction of C38 with N-chlorosuccinimide provided tert-butyl 3-chloro-2-methoxy-4-methyl-5,7-dihydro-6H-pyrrolo[3,4-b]pyridine-6-carboxylate, which was reacted with trimethylboroxin in the presence of palladium(II) acetate, tricyclohexylphosphine, and cesium carbonate to afford tert-butyl 2-methoxy-3,4-dimethyl-5,7-dihydro-6H-pyrrolo[3,4-b]pyridine-6-carboxylate. Removal of the protecting group with hydrogen chloride gave the requisite 2-methoxy-3,4-dimethyl-6,7-dihydro-5H-pyrrolo[3,4-b]pyridine.
[6]Reaction of C41 with 3,5-dichloropyridazine was carried out using cesium fluoride and triethylamine, to provide ethyl [1-(6-chloropyridazin-4-yl)azetidin-3-yl]acetate. Reductive removal of the chlorine via hydrogenation over palladium on carbon, followed by ester hydrolysis with lithium hydroxide, afforded [1-(pyridazin-4-yl)azetidin-3-yl]acetic acid.
[7]Reaction of C38 with N-chlorosuccinimide provided tert-butyl 3-chloro-2-methoxy-4-methyl-5,7-dihydro-6H-pyrrolo[3,4-b]pyridine-6-carboxylate, which was subjected to methyl ether cleavage with hydrogen chloride, followed by reintroduction of the tert-butoxycarbonyl protecting group, to provide tert-butyl 3-chloro-4-methyl-2-oxo-1,2,5,7-tetrahydro-6H-pyrrolo[3,4-b]pyridine-6-carboxylate. Reaction with sodium chloro(difluoro)acetate and potassium carbonate provided tert-butyl 3-chloro-2-(difluoromethoxy)-4-methyl-5,7-dihydro-6H-pyrrolo[3,4-b]pyridine-6-carboxylate; removal of the protecting group with hydrogen chloride afforded the requisite 3-chloro-2-(difluoromethoxy)-4-methyl-6,7-dihydro-5H-pyrrolo[3,4-b]pyridine.
[8]In the final step of the synthesis, the methyl ether was cleaved via exposure to boron trichloride, to provide Example 33.
[9]Reaction of C41 with 4-chloropyrimidine was carried out using cesium fluoride and triethylamine, to provide ethyl [1-(pyrimidin-4-yl)azetidin-3-yl]acetate; ester hydrolysis with lithium hydroxide afforded [1-(pyrimidin-4-yl)azetidin-3-yl]acetic acid.
[10]Reaction of P2 and C66 with bis(pentafluorophenyl) carbonate and triethylamine provided Example 36.
[11]Cyclopropanation of ethyl (2E)-3-(pyridin-3-yl)prop-2-enoate was carried out via reaction with trimethylsulfoxonium iodide and sodium hydride, to provide ethyl trans-2-(pyridin-3-yl)cyclopropanecarboxylate. This material was reduced with lithium aluminum hydride, and the resulting primary alcohol was converted to the chloride by treatment with thionyl chloride; subsequent displacement using potassium cyanide provided [trans-2-(pyridin-3-yl)cyclopropyl]acetonitrile, which was hydrolyzed to the acid via treatment with hydrochloric acid. Exposure to sulfuric acid and methanol then afforded the requisite methyl [trans-2-(pyridin-3-yl)cyclopropyl]acetate.
[12]The racemic mixture of Examples 37 and 38 was separated into its component enantiomers via supercritical fluid chromatography (Column: Chiral Technologies Chiralcel OJ-H, 5 μm; Mobile phase: 9:1 carbon dioxide / methanol). Example 37 was the first-eluting enantiomer, and Example 38 was the second-eluting enantiomer.
[13]Conditions for analytical HPLC. Column: Chiral Technologies Chiralcel OJ-H, 4.6 × 100 mm, 5 μm; Mobile phase: 85:15 carbon dioxide / methanol; Flow rate: 1.5 mL/minute.
[14]Ethyl [1-(pyrimidin-4-yl)azetidin-3-yl]acetate was used; see footnote 9. [15]Conversion of C9 to tert-butyl 2-(hydroxymethyl)-3,4-dimethyl-5,7-dihydro-6H-pyrrolo[3,4-b]pyridine-6-carboxylate was carried out using the method described for synthesis of C12 from C3 in Preparation P3. Reaction with iodomethane and sodium hydride then provided the methyl ether, and subsequent deprotection with hydrogen chloride afforded the requisite 2-(methoxymethyl)-3,4-dimethyl-6,7-dihydro-5H-pyrrolo[3,4-b]pyridine.
[16]Reaction of C41 with 4-chloro-N-ethylpyrimidin-2-amine and cesium (ethylamino)pyrimidin-4-yl]azetidin-3-yl carbonate, followed by ester hydrolysis with lithium hydroxide, afforded {1-[2-}acetic acid.
[17]Conditions for analytical HPLC. Column: Waters XBridge C18, 2.1 × 50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.

TABLE 6-continued

Method of preparation, structure, and physicochemical data for Examples 21-78

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M+H]* (unless otherwise indicated)$^1$ |
| --- | --- | --- | --- |

[18] A Buchwald reaction using RuPhos between C41 and 6-chloro-N-(propan-2-(propan-2-ylamino)pyrimidin-4-yl]azetidin-3-yl yl)pyrimidin-4-amine, followed by ester hydrolysis with lithium hydroxide, provided {1-[6-}acetic acid.
[19] Reaction of C41 with 6-chloro-2-methylimidazo[1,2-b]pyridazine, cesium carbonate, and potassium fluoride, followed by ester hydrolysis with lithium hydroxide, provided [1-(2-methylimidazo[1,2-b]pyridazin-6-yl)azetidin-3-yl]acetic acid.
[20] Reaction of C41 with 2-bromo-1,3,4-thiadiazole was carried out using the method described for synthesis of C42 from C41 in Example 1, affording ethyl [1-(1,3,4-thiadiazol-2-yl)azetidin-3-yl]acetate.
[21] The requisite 3-chloro-2-(methoxymethyl)-4-methyl-6,7-dihydro-5H-pyrrolo[3,4-b]pyridine was synthesized as follows: C26 was converted to tert-butyl 3-chloro-2-(hydroxymethyl)-4-methyl-5,7-dihydro-6H-pyrrolo[3,4-b]pyridine-6-carboxylate using the method described for synthesis of C12 from C3 in Preparation P3. Methyl ether formation using iodomethane and sodium hydride was then followed by removal of the protecting group with hydrogen chloride.
[22] Reaction of C41 with 5-bromo-2-fluoropyridine was effected using the method described for synthesis of C50 from C41 and C49 in Example 4; ester hydrolysis with lithium hydroxide then afforded the requisite [1-(6-fluoropyridin-3-yl)azetidin-3-yl]acetic acid.
[23] 5-Bromopyrimidine was reacted with C59 using the method described for synthesis of C60 and C61 in Example 16. The component enantiomers of the product were separated via supercritical fluid chromatography [Column: Phenomenex Lux Cellulose-2, 5 μm; Mobile phase: 9:1 carbon dioxide / (acetonitrile containing 0.2% ammonium hydroxide)]. The second-eluting enantiomer (ENT-2) was oxidized to the corresponding carboxylic acid using the procedure described in Example 16 for conversion of C60 to C62, affording the single enantiomer [trans-2-(pyrimidin-5-yl)cyclopropyl]acetic acid from ENT-2.
[24] In this case, 3-bromopyridine was used, and intermediate [trans-2-(pyridin-3-yl)cyclopropyl]acetic acid was employed as the racemate. The racemic mixture of final products was separated into its component enantiomers using supercritical fluid chromatography [Column: Chiral Technologies Chiralpak AD, 10 μm; Mobile phase: 55:45 carbon dioxide / (methanol containing 0.1% ammonium hydroxide)]. The first-eluting enantiomer, which exhibited a negative (-) rotation, was assigned as Example 54 (ENT-1); the second-eluting enantiomer, which exhibited a positive (+) rotation, was assigned as Example 55 (ENT-2).
[25] Intermediate ethyl [1-(2-cyanopyridin-4-yl)azetidin-3-yl]acetate was synthesized by reaction of C41 with 4-chloropyridine-2-carbonitrile in the presence of an amine base.
[26] Reaction of C41 with 4-iodo-2-methoxypyridine was carried out using the method described for synthesis of C42 from C41 in Example 1, affording ethyl [1-(2-methoxypyridin-4-yl)azetidin-3-yl]acetate.
[27] Reaction of C41 with 4-iodopyridine was carried out using the method described for synthesis of C50 from C49 in Example 4; ester hydrolysis with lithium hydroxide then afforded [1-(pyridin-4-yl)azetidin-3-yl]acetic acid.
[28] The requisite 1-(1,3,4-thiadiazol-2-yl)azetidin-3-ol was synthesized from azetidin-3-ol and 2-bromo-1,3,4-thiadiazole in the presence of tris(dibenzylideneacetone)dipalladium(0), 1,1'-binaphthalen-2-yl(di-tert-butyl)phosphane (TrixiePhos), and cesium carbonate.
[29] Reaction of azetidin-3-ol and 5-bromo-1,2,4-thiadiazole in the presence of potassium carbonate provided 1-(1,2,4-thiadiazol-5-yl)azetidin-3-ol.
[30] Template intermediated C48 was synthesized as shown in Example 3. Examples 68-75 and example 78 were synthesized by reacting intermediate C48 with corresponding aryl bromides using the coupling condition described in example 4, step 2 [Pd$_2$(dba)$_3$, Xantphos, Cs$_2$CO$_3$, 1,4-dioxane].
[31] Conditions for analytical HPLC. Column: Waters Atlantis dC18, 4.6 × 50 mm, 5 μm; Mobile phase A: 0.05% trifluoroacetic acid in water; Mobile phase B: 0.05% trifluoroacetic acid in acetonitrile; Gradient: 5% to 95% B over 4 minutes; then hold 95% to 5 minutes; Flow rate: 2 mL/minute.
[32] The desired compound was prepared following the same procedure as example 16, wherein the coupling of Intermediate C59 was carried out with 7-bromoquinazoline.
[33] Conditions for analytical HPLC. Column: Waters Atlantis dC18, 4.6 × 50 mm, 5 μm; Mobile phase A: 0.05% trifluoroacetic acid in water; Mobile phase B: 0.05% trifluoroacetic acid in acetonitrile; Gradient: hold 5% B to 1 minute, then 5% to 95% B to 4 minutes, then hold at 95% B to 5 minutes; Flow rate: 2 mL/minute.
[34] The desired compound was prepared following the same procedure as example 16, wherein the coupling of Intermediate C59 was carried out with bromobenzene.

The M4 PAM binding affinity for the compounds of the present invention was determined utilizing the following biological assay(s):

Biological Assay

M4 Pam cAMP Assay

The M4 cAMP assay was designed to determine the potency and efficacy of muscarinic positive allosteric modulators (PAMs). Human M4 receptors were stably expressed in Human embryonic kidney (HEK293) cells expressed with the Promega GloSensor™ cAMP technology.

Cells:

HEK293 GloSensor cells expressing hM4 cells were cultured in growth media containing DMEM with 10% FBS, 1% Penicillin/Streptomycin, 500 μg/mL G418, 200 μg/mL Hygomycin B, and 1% Glutamax. When cells had grown to 80%-90% confluency, cells were harvested and seeded at a density of 25,000 cells/40 μL well, in a 384 white walled plates (Becton Dickinson 356661). Plates were incubated at 37 degrees C. and 5% $CO_2$ for use after 24 hours.

Compound Preparation for Agonist Screen:

Test compounds were initially prepared as 100% DMSO stock solutions, then transferred and serially diluted in 384-well compound plates (Matrix #4325). Each compound was tested at 10 concentrations in duplicate per experiment. Compound plates are spotted with 0.2 μL/well agonist at 400 times the final assay concentration. Positive and negative controls for the compound alone agonist response was 10 μM acetylcholine (Sigma #A2661) and DMSO, respectively. $EC_{20}$ of acetylcholine was also used to define PAM activities.

cAMP Assay:

Promega GloSensor™ reagent (Promega #E1291) had previously been aliquotted. For each experiment, a stock solution of GloSensor™ was thawed out and equilibration medium was prepared with 88% $CO_2$-independent media (Invitrogen #18045088), 10% fetal bovine serum and 2% GloSensor™ cAMP Reagent stock solution. Stock solution was mixed. Culture media in cell plates was discarded, then replaced with 40 μL/well pre-warmed equilibration media, then incubated in the dark at room temperature for 2 hours. During the incubation, stimulation media containing agonist and $EC_{20}$ acetylcholine was prepared. $CO_2$-independent media containing 50 n (nano instead of milli)M Isoproterenol representing an EC80 of b-adrenergic receptor activity (Sigma #16504, 400 times final concentration) and $EC_{20}$ acetylcholine in 1.25% DMSO was added to all columns of the compound plate, with the exception of column 12 to allow for $EC_0$ control. $EC_0$ control wells received stimulation media that does not constrain $EC_{20}$ acetylcholine. Compounds are now 5 times the final assay concentration. The plate was mixed using a plate agitator. At the end of the 2 hour GloSensor™ incubation, add 10 μL of the $CO_2$-independent media containing agonist, $EC_{20}$ acetylcholine and isoproterenol to the cell plate. Cell plate was then incubated for 10 minutes at room temperature, and then read using an EnVision plate reader (Perkin Elmer).

Data Analysis:

Data was exported from the EnVision plate reader. The percent effect for each well was determined using the mean values for the positive and negative controls on each plate for each read, specifically 100*(compound−negative control)/(positive control−negative control). Dose response curves were fitted to the compound percent effect data using a 4-parameter logistic fit model. Data was reported as $EC_{50}$ and Emax, with the Emax as the maximum asymptote of the fitted dose response curve.

TABLE 7

Biological activity of Example 1-78.

| Example Number | M4 glosensor EC$_{50}$ Mean Asymptote Maximum (%)[a] | M4 glosensor EC$_{50}$ (nM)[a] | IUPAC Name |
|---|---|---|---|
| 1 | 89.5[b] | 24.9[b] | 1-(2,4-dimethyl-5,7-dihydro-6H-pyrrolo[3,4-b]pyridin-6-yl)-2-[1-(pyridin-3-yl)azetidin-3-yl]ethanone |
| 2 | 94.4 | 19.8 | 2-{1-[2-(difluoromethyl)pyridin-4-yl]azetidin-3-yl}-1-(2,4-dimethyl-5,7-dihydro-6H-pyrrolo[3,4-b]pyridin-6-yl)ethanone |
| 3 | 95.1[b] | 36.3[b] | 1-(2,4-dimethyl-5,7-dihydro-6H-pyrrolo[3,4-b]pyridin-6-yl)-2-[1-(pyrimidin-4-yl)azetidin-3-yl]ethanone |
| 4 | 100 | 24.2 | 2-{1-[2-(difluoromethoxy)pyridin-4-yl]azetidin-3-yl}-1-(2,4-dimethyl-5,7-dihydro-6H-pyrrolo[3,4-b]pyridin-6-yl)ethanone |
| 5 | 98.2 | 8.88 | 2-[1-(1,2,4-thiadiazol-5-yl)azetidin-3-yl]-1-(2,3,4-trimethyl-5,7-dihydro-6H-pyrrolo[3,4-b]pyridin-6-yl)ethanone |
| 6 | 92.4 | 9.75 | 1-[2-(difluoromethyl)-4-methyl-5,7-dihydro-6H-pyrrolo[3,4-b]pyridin-6-yl]-2-{1-[2-(trifluoromethyl)pyridin-4-yl]azetidin-3-yl}ethanone |
| 7 | 99.8[b] | 17.4[b] | 1-[2-(methoxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone |
| 8 | 99.1 | 22.7 | 2-{1-[2-(difluoromethoxy)pyridin-4-yl]azetidin-3-yl}-1-[2-(methoxymethyl)-4-methyl-5,7-dihydro-6H-pyrrolo[3,4-b]pyridin-6-yl]ethanone |
| 9 | 86.5[b] | 17.2[b] | 1-[2-(hydroxymethyl)-4-methyl-5,7-dihydro-6H-pyrrolo[3,4-b]pyridin-6-yl]-2-[1-(pyridin-3-yl)azetidin-3-yl]ethanone |
| 10 | 99.5[c] | 28.9[c] | 2-{1-[2-(difluoromethoxy)pyridin-4-yl]azetidin-3-yl}-1-[2-(difluoromethyl)-3,4-dimethyl-5,7-dihydro-6H-pyrrolo[3,4-b]pyridin-6-yl]ethanone |
| 11 | 104[b] | 12.3[b] | 1-(2,4-dimethyl-5,7-dihydro-6H-pyrrolo[3,4-b]pyridin-6-yl)-2-{1-[2-(trifluoromethyl)pyridin-4-yl]azetidin-3-yl}ethanone |
| 12 | 119[b] | 7.10[b] | 1-(3-chloro-2,4-dimethyl-5,7-dihydro-6H-pyrrolo[3,4-b]pyridin-6-yl)-2-{1-[2-(difluoromethoxy)pyridin-4-yl]azetidin-3-yl}ethanone |
| 13 | 101[b] | 2.04[b] | 1-(3-chloro-2,4-dimethyl-5,7-dihydro-6H-pyrrolo[3,4-b]pyridin-6-yl)-2-[1-(pyridin-3-yl)azetidin-3-yl]ethanone |
| 14 | 62.5 | 9080 | 2-[1-(pyridin-3-yl)azetidin-3-yl]-1-(2,4,5-trimethyl-5,7-dihydro-6H-pyrrolo[3,4-b]pyridin-6-yl)ethanone, ENT-1 |
| 15 | 106 | 28.0 | 2-[1-(pyridin-3-yl)azetidin-3-yl]-1-(2,4,5-trimethyl-5,7-dihydro-6H-pyrrolo[3,4-b]pyridin-6-yl)ethanone, ENT-2 |
| 16 | N.D.[d] | >10000[c] | 1-(2,4-dimethyl-5,7-dihydro-6H-pyrrolo[3,4-b]pyridin-6-yl)-2-[(1S,2R)-2-(6-methylpyridin-3-yl)cyclopropyl]ethanone |
| 17 | 107[c] | 71.9[c] | 1-(2,4-dimethyl-5,7-dihydro-6H-pyrrolo[3,4-b]pyridin-6-yl)-2-[(1R,2S)-2-(6-methylpyridin-3-yl)cyclopropyl]ethanone |
| 18 | 89.0[c] | 37.7[c] | 1-[2-(difluoromethyl)-4-methyl-5,7-dihydro-6H-pyrrolo[3,4-b]pyridin-6-yl]-2-[(1R,2S)-2-(6-methylpyridin-3-yl)cyclopropyl]ethanone |
| 19 | 87.5 | 178 | 2,4-dimethyl-N-[1-(pyridin-3-yl)azetidin-3-yl]-5,7-dihydro-6H-pyrrolo[3,4-b]pyridine-6-carboxamide |
| 20 | 58.0 | 51.1 | 1-(pyridin-3-yl)azetidin-3-yl 2,4-dimethyl-5,7-dihydro-6H-pyrrolo[3,4-b]pyridine-6-carboxylate |
| 21 | 86.6[b] | 23.9[b] | 1-(2-methoxy-4-methyl-5,7-dihydro-6H-pyrrolo[3,4-b]pyridin-6-yl)-2-[1-(pyridin-3-yl)azetidin-3-yl]ethanone |
| 22 | 109[b] | 4.82[b] | 1-(3-chloro-2-methoxy-4-methyl-5,7-dihydro-6H-pyrrolo[3,4-b]pyridin-6-yl)-2-[1-(pyridin-3-yl)azetidin-3-yl]ethanone |
| 23 | 92.2[b] | 6.23[b] | 2-[1-(pyridin-3-yl)azetidin-3-yl]-1-(2,3,4-trimethyl-5,7-dihydro-6H-pyrrolo[3,4-b]pyridin-6-yl)ethanone |
| 24 | 93.8 | 31.0 | 1-[2-(hydroxymethyl)-4-methyl-5,7-dihydro-6H-pyrrolo[3,4-b]pyridin-6-yl-2-[1-(pyrimidin-4-yl)azetidin-3-yl]ethanone |
| 25 | 78.7[c] | 25.7[c] | 2-{1-[2-(difluoromethoxy)pyridin-4-yl]azetidin-3-yl}-1-[2-(difluoromethyl)-4-methyl-5,7-dihydro-6H-pyrrolo[3,4-b]pyridin-6-yl]ethanone |
| 26 | 117 | 13.9 | 1-(3-chloro-2-methoxy-4-methyl-5,7-dihydro-6H-pyrrolo[3,4-b]pyridin-6-yl-2-[1-(pyrimidin-5-yl)azetidin-3-yl]ethanone |
| 27 | 94.4 | 16.8 | 1-[2-(methoxymethyl)-4-methyl-5,7-dihydro-6H-pyrrolo[3,4-b]pyridin-6-yl-2-[1-(pyridin-3-yl)azetidin-3-yl]ethanone |
| 28 | 116 | 21.6 | 1-(2-methoxy-3,4-dimethyl-5,7-dihydro-6H-pyrrolo[3,4-b]pyridin-6-yl)-2-[1-(pyridin-3-yl)azetidin-3-yl]ethanone |
| 29 | 99.8 | 26.1 | 1-(2-methoxy-3,4-dimethyl-5,7-dihydro-6H-pyrrolo[3,4-b]pyridin-6-yl)-2-[1-(pyrimidin-5-yl)azetidin-3-yl]ethanone |
| 30 | 103 | 30.3 | 1-(2,4-dimethyl-5,7-dihydro-6H-pyrrolo[3,4-b]pyridin-6-yl)-2-[1-(pyridazin-4-yl)azetidin-3-yl]ethanone |
| 31 | 89.3 | 17.8 | 1-[2-(methoxymethyl)-4-methyl-5,7-dihydro-6H-pyrrolo[3,4-b]pyridin-6-yl-2-[1-(pyrimidin-5-yl)azetidin-3-yl]ethanone |
| 32 | 109 | 11.0 | 1-[3-chloro-2-(difluoromethoxy)-4-methyl-5,7-dihydro-6H-pyrrolo[3,4-b]pyridin-6-yl]-2-[1-(pyrimidin-5-yl)azetidin-3-yl]ethanone |

TABLE 7-continued

Biological activity of Example 1-78.

| Example Number | M4 glosensor $EC_{50}$ Mean Asymptote Maximum (%)[a] | M4 glosensor $EC_{50}$ (nM)[a] | IUPAC Name |
|---|---|---|---|
| 33 | 100[c] | 14.0[c] | 1-[2-(hydroxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone |
| 34 | 86.0[c] | 18.0[c] | 1-[2-(difluoromethyl)-4-methyl-5,7-dihydro-6H-pyrrolo[3,4-b]pyridin-6-yl-2-[1-(pyrimidin-5-yl)azetidin-3-yl]ethanone |
| 35 | 87.9 | 2.56 | 2-[1-(pyrimidin-4-yhazetidin-3-yl]-1-(2,3,4-trimethyl-5,7-dihydro-6H-pyrrolo[3,4-b]pyridin-6-yl)ethanone |
| 36 | 93.0 | 10.4 | 1-(pyridin-3-yl)azetidin-3-yl 2,3,4-trimethyl-5,7-dihydro-6H-pyrrolo[3,4-b]pyridine-6-carboxylate |
| 37 | 85.8 | 1790 | 2-[trans-2-(pyridin-3-yl)cyclopropyl]-1-(2,3,4-trimethyl-5,7-dihydro-6H-pyrrolo[3,4-b]pyridin-6-yhethanone, ENT-1 |
| 38 | 111 | 15.9 | 2-[trans-2-(pyridin-3-yl)cyclopropyl]-1-(2,3,4-trimethyl-5,7-dihydro-6H-pyrrolo[3,4-b]pyridin-6-yl)ethanone, ENT-2 |
| 39 | 96.4[b] | <1.39[b] | 1-(3-chloro-2,4-dimethyl-5,7-dihydro-6H-pyrrolo[3,4-b]pyridin-6-yl)-2-[1-(pyrimidin-4-yl)azetidin-3-yl]ethanone |
| 40 | 97.9[c] | 23.6[c] | 1-[2-(methoxymethyl)-3,4-dimethyl-5,7-dihydro-6H-pyrrolo[3,4-b]pyridin-6-yl]-2-[1-(pyrimidin-5-yl)azetidin-3-yl]ethanone |
| 41 | 95.6[b] | 7.35[b] | 1-(2,4-dimethyl-5,7-dihydro-6H-pyrrolo[3,4-b]pyridin-6-yl)-2-{1-[2-(ethylamino)pyrimidin-4-yl]azetidin-3-yl}ethanone |
| 42 | 93.9[b] | 5.05[b] | 1-(2,4-dimethyl-5,7-dihydro-6H-pyrrolo[3,4-b]pyridin-6-yl)-2-{1-[6-(propan-2-ylamino)pyrimidin-4-yl]azetidin-3-yl}ethanone |
| 43 | 88.6[c] | 25.2[c] | 1-(2,4-dimethyl-5,7-dihydro-6H-pyrrolo[3,4-b]pyridin-6-yl)-2-[1-(2-methylimidazo[1,2-b]pyridazin-6-yl]azetidin-3-yl]ethanone |
| 44 | 112 | 16.8 | 1-(3-chloro-2,4-dimethyl-5,7-dihydro-6H-pyrrolo[3,4-b]pyridin-6-yl)-2-[1-(1,3,4-thiadiazol-2-yl)azetidin-3-yl]ethanone |
| 45 | 93.5[c] | 15.6[c] | 1-[2-(difluoromethyl)-4-methyl-5,7-dihydro-6H-pyrrolo[3,4-b]pyridin-6-yl]-2-{1-[2-(difluoromethyl)pyridin-4-yl]azetidin-3-yl}ethanone |
| 46 | 106 | 9.53 | 2-{1-[2-(difluoromethyl)pyridin-4-yl]azetidin-3-yl}-1-(2,3,4-trimethyl-5,7-dihydro-6H-pyrrolo[3,4-b]pyridin-6-yl)ethanone |
| 47 | 110 | 2.19 | 1-[3-chloro-2-(methoxymethyl)-4-methyl-5,7-dihydro-6H-pyrrolo[3,4-b]pyridin-6-yl]-2-{1-[2-(difluoromethyl)pyridin-4-yl]azetidin-3-yl}ethanone |
| 48 | 105 | 2.99 | 1-[3-chloro-2-(methoxymethyl)-4-methyl-5,7-dihydro-6H-pyrrolo[3,4-b]pyridin-6-yl]-2-[1-(pyridin-3-yl)azetidin-3-yl]ethanone |
| 49 | 101[c] | 11.2[c] | 1-[3-chloro-2-(methoxymethyl)-4-methyl-5,7-dihydro-6H-pyrrolo[3,4-b]pyridin-6-yl]-2-[1-(6-fluoropyridin-3-yl)azetidin-3-yl]ethanone |
| 50 | 99.2[c] | 14.3[c] | 2-{1-[2-(difluoromethyl)pyridin-4-yl]azetidin-3-yl}-1-[2-(methoxymethyl)-4-methyl-5,7-dihydro-6H-pyrrolo[3,4-b]pyridin-6-yl]ethanone |
| 51 | 102[c] | 4.75[c] | 1-(3-chloro-2,4-dimethyl-5,7-dihydro-6H-pyrrolo[3,4-b]pyridin-6-yl)-2-[trans-2-(pyrimidin-5-yl)cyclopropyl]ethanone, from ENT-2 in footnote 23, Table 6 |
| 52 | 111[c] | 4.68[c] | 1-[3-chloro-2-(methoxymethyl)-4-methyl-5,7-dihydro-6H-pyrrolo[3,4-b]pyridin-6-yl]-2-{1-[2-(difluoromethoxy)pyridin-4-yl]azetidin-3-yl}ethanone |
| 53 | 104[c] | 38.6[c] | 1-[2-(difluoromethyl)-3,4-dimethyl-5,7-dihydro-6H-pyrrolo[3,4-b]pyridin-6-yl]-2-{1-[2-(difluoromethyl)pyridin-4-yl]azetidin-3-yl}ethanone |
| 54 | 80.0[c] | 8650[c] | (−)-1-(2,4-dimethyl-5,7-dihydro-6H-pyrrolo[3,4-b]pyridin-6-yl)-2-[trans-2-(pyridin-3-yl)cyclopropyl]ethanone, ENT 1 |
| 55 | 99.5 | 40.5 | (+)-1-(2,4-dimethyl-5,7-dihydro-6H-pyrrolo[3,4-b]pyridin-6-yl)-2-[trans-2-(pyridin-3-yl)cyclopropyl]ethanone, ENT-2 |
| 56 | 71.8[c] | 209[c] | 2-(2,3-dihydro-1H-inden-2-yl)-1-(2,4-dimethyl-5,7-dihydro-6H-pyrrolo[3,4-b]pyridin-6-yl)ethanone |
| 57 | 96.1 | 94.2 | 4-{3-[2-(2,4-dimethyl-5,7-dihydro-6H-pyrrolo[3,4-b]pyridin-6-yl)-2-oxoethyl]azetidin-1-yl}pyridine-2-carbonitrile |
| 58 | 98.8 | 88.8 | 1-(2,4-dimethyl-5,7-dihydro-6H-pyrrolo[3,4-b]pyridin-6-yl)-2-[1-(2-methoxypyridin-4-yl)azetidin-3-yl]ethanone |
| 59 | 93.5 | 816 | 2-cyclopropyl-1-(2,4-dimethyl-5,7-dihydro-6H-pyrrolo[3,4-b]pyridin-6-yl)ethanone, formate salt |
| 60 | 96.0 | 102 | 1-(2,4-dimethyl-5,7-dihydro-6H-pyrrolo[3,4-b]pyridin-6-yl)-2-[1-(pyridin-4-yl)azetidin-3-yl]ethanone |
| 61 | 90.8[b] | 60.5[b] | 1-(2,4-dimethyl-5,7-dihydro-6H-pyrrolo[3,4-b]pyridin-6-yl)-2-[1-(pyrimidin-5-yl)azetidin-3-yl]ethanone |
| 62 | 47.0 | 95.7 | 1-(1,3,4-thiadiazol-2-yl)azetidin-3-yl 2,4-dimethyl-5,7-dihydro-6H-pyrrolo[3,4-b]pyridine-6-carboxylate |
| 63 | 51.8[c] | 42.4[c] | 1-(1,2,4-thiadiazol-5-yl)azetidin-3-yl 2-(difluoromethyl)-3,4-dimethyl-5,7-dihydro-6H-pyrrolo[3,4-b]pyridine-6-carboxylate |

TABLE 7-continued

Biological activity of Example 1-78.

| Example Number | M4 glosensor EC$_{50}$ Mean Asymptote Maximum (%)[a] | M4 glosensor EC$_{50}$ (nM)[a] | IUPAC Name |
|---|---|---|---|
| 64 | 88.5[c] | 40.2[c] | 1-(1,2,4-thiadiazol-5-yl)azetidin-3-yl 2,3,4-trimethyl-5,7-dihydro-6H-pyrrolo[3,4-b]pyridine-6-carboxylate |
| 65 | 88.2[c] | 62.6[c] | 1-(1,3,4-thiadiazol-2-yl)azetidin-3-yl 2,3,4-trimethyl-5,7-dihydro-6H-pyrrolo[3,4-b]pyridine-6-carboxylate |
| 66 | 163[c] | 52.3[c] | 1-(pyridin-3-yl)azetidin-3-yl 3-chloro-2-(methoxymethyl)-4-methyl-5,7-dihydro-6H-pyrrolo[3,4-b]pyridne-6-carboxylate |
| 67 | 98.6[c] | 18.5[c] | 1-(1,2,4-thiadiazol-5-yl)azetidin-3-yl 3-chloro-2,4-dimethyl-5,7-dihydro-6H-pyrrolo[3,4-b]pyridine-6-carboxylate |
| 68 | 99.4 | 485 | 1-(2,4-dimethyl-5,7-dihydro-6H-pyrrolo[3,4-b]pyridin-6-yl)-2-{1-[4-(3-methyloxetan-3-yl)phenyl]azetidin-3-yl}ethanone |
| 69 | 41.5 | 1356 | 3-{3-[2-(2,4-dimethyl-5,7-dihydro-6H-pyrrolo[3,4-b]pyridin-6-yl)-2-oxoethyl]azetidin-1-yl}-4-methoxybenzonitrile |
| 70 | 95.0 | 184 | 4-{3-[2-(2,4-dimethyl-5,7-dihydro-6H-pyrrolo[3,4-b]pyridin-6-yl)-2-oxoethyl]azetidin-1-yl}-N,N-dimethylbenzamide |
| 71 | 90.5 | 195 | 1-(2,4-dimethyl-5,7-dihydro-6H-pyrrolo[3,4-b]pyridin-6-yl)-2-{1-[4-(hydroxyethyl)phenyl]azetidin-3-yl}ethanone |
| 72 | 90.6 | 537 | 2-[1-(4-cyclopropylphenyl)azetidin-3-yl]-1-(2,4-dimethyl-5,7-dihydro-6H-pyrrolo[3,4-b]pyridin-6-yl)ethanone |
| 73 | 95.3 | 90.5 | 2-(1-{4-[cyclopropyl(hydroxy)methyl]phenyl}azetidin-3-yl)-1-(2,4-dimethyl-5,7-dihydro-6H-pyrrolo[3,4-b]pyridin-6-yl)ethanone |
| 74 | 84.4 | 460 | (5-{3-[2-(2,4-dimethyl-5,7-dihydro-6H-pyrrolo[3,4-b]pyridin-6-yl)-2-oxoethyl]azetidin-1-yl}-2-methoxyphenyl)acetonitrile |
| 75 | 89.2 | 105 | 4-{3-[2-(2,4-dimethyl-5,7-dihydro-6H-pyrrolo[3,4-b]pyridin-6-yl)-2-oxoethyl]azetidin-1-yl}-N-methylbenzamide |
| 76 | 45 | 1397 | 1-(2,4-dimethyl-5,7-dihydro-6H-pyrrolo[3,4-b]pyridin-6-yl)-2-[trans-2-(quinazolin-7-yl)cyclopropyl]ethanone |
| 77 | 176[c] | 2884[c] | 1-(2,4-dimethyl-5,7-dihydro-6H-pyrrolo[3,4-b]pyridin-6-yl)-2-[trans-2-phenylcyclopropyl]ethanone |
| 78 | 97.3 | 88.1 | 1-(2,4-dimethyl-5,7-dihydro-6H-pyrrolo[3,4-b]pyridin-6-yl)-2-(1-phenylazetidin-3-yl)ethanone |

[a] Values represent the geometric mean of 2-4 determinations, unless otherwise indicated.
[b] Value represents the geometric mean of ≥5 determinations.
[c] Value represents a single determination.
[d] Not determined.

What is claimed is:

1. A method of treating an M4-associated disease or disorder comprising administering a compound to a subject in need thereof, wherein the compound is selected from:
   1-(2,4-Dimethyl-5,7-dihydro-6H-pyrrolo[3,4-b]pyridin-6-yl)-2-{1-[2-(trifluoromethyl)pyridin-4-yl]azetidin-3-yl}ethanone and
   1-[2-(hydroxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone,
   or an N-oxide thereof, or a pharmaceutically acceptable salt of the compound or the N-oxide,
   wherein the M4-associated disease or disorder is selected from the group consisting of schizophrenia, psychosis, and cocaine and alcohol dependence and abuse.

2. The method according to claim 1, wherein the compound is 1-(2,4-Dimethyl-5,7-dihydro-6H-pyrrolo[3,4-b]pyridin-6-yl)-2-{1-[2-(trifluoromethyl)pyridin-4-yl]azetidin-3-yl}ethanone or a pharmaceutically acceptable salt thereof.

3. The method according to claim 1, wherein the compound is 1-[2-(hydroxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone or a pharmaceutically acceptable salt of the compound thereof.

4. The method according to claim 1, wherein the compound is 1-(2,4-Dimethyl-5,7-dihydro-6H-pyrrolo[3,4-b]pyridin-6-yl)-2-{1-[2-(trifluoromethyl)pyridin-4-yl]azetidin-3-yl}ethanone.

5. The method according to claim 1, wherein the compound is a pharmaceutically acceptable salt of 1-(2,4-Dimethyl-5,7-dihydro-6H-pyrrolo[3,4-b]pyridin-6-yl)-2-{1-[2-(trifluoromethyl)pyridin-4-yl]azetidin-3-yl}ethanone.

6. The method according to claim 1, wherein the compound is an N-oxide of 1-(2,4-Dimethyl-5,7-dihydro-6H-pyrrolo[3,4-b]pyridin-6-yl)-2-{1-[2-(trifluoromethyl)pyridin-4-yl]azetidin-3-yl}ethanone.

7. The method according to claim 1, wherein the M4=associated disease or disorder is cocaine and alcohol dependence and abuse.

8. The method according to claim 1, wherein the M4-associated disease or disorder is psychosis.

9. The method according to claim 1, wherein the M4-associated disease or disorder is schizophrenia.

10. The method according to claim 4, wherein the M4=associated disease or disorder is cocaine and alcohol dependence and abuse.

11. The method according to claim 4, wherein the M4-associated disease or disorder is psychosis.

12. The method according to claim 4, wherein the M4-associated disease or disorder is schizophrenia.

13. The method according to claim 1, wherein the compound is 1-[2-(hydroxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone.

14. The method according to claim 1, wherein the compound is a pharmaceutically acceptable salt of 1-[2-(hydroxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone.

15. The method according to claim 1, wherein the compound is an N-oxide of 1-[2-(hydroxymethyl)-4-methyl-5,7-dihydro-6H-pyrrolo[3,4-b]pyridin-6-yl]-2-{1-[2-(trifluoromethyl)pyridin-4-yl]azetidin-3-yl}ethanone.

16. The method according to claim 13, wherein the M4-associated disease or disorder is cocaine and alcohol dependence and abuse.

17. The method according to claim 13, wherein the M4-associated disease or disorder is psychosis.

18. The method according to claim 13, wherein the M4-associated disease or disorder is schizophrenia.

* * * * *